(12) United States Patent
Choy et al.

(10) Patent No.: US 8,283,361 B2
(45) Date of Patent: *Oct. 9, 2012

(54) HETEROCYCLIC UREA DERIVATIVES AND METHODS OF USE THEREOF

(75) Inventors: Allison Laura Choy, Waltham, MA (US); Pamela Hill, Waltham, MA (US); John Irvin Manchester, Waltham, MA (US); Brian Sherer, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 284 days.

This patent is subject to a terminal disclaimer.

(21) Appl. No.: 12/477,781

(22) Filed: Jun. 3, 2009

(65) Prior Publication Data

US 2010/0190745 A1   Jul. 29, 2010

Related U.S. Application Data

(60) Provisional application No. 61/058,736, filed on Jun. 4, 2008.

(51) Int. Cl.
*A61K 31/04* (2006.01)
*C07D 215/38* (2006.01)

(52) U.S. Cl. .................. 514/312; 546/159; 546/163

(58) Field of Classification Search .................. 514/312; 546/159, 163
See application file for complete search history.

(56) References Cited

U.S. PATENT DOCUMENTS

| 7,674,801 B2 * | 3/2010 | Basarab et al. ............. 514/300 |
| 2010/0317624 A1 * | 12/2010 | Choy et al. .................. 514/82 |
| 2012/0101100 A1 | 4/2012 | Bist et al. | |

FOREIGN PATENT DOCUMENTS

| EP | 0519449 A1 | 12/1992 |
| WO | 2002/060879 A2 | 8/2002 |
| WO | 2005/012292 A1 | 2/2005 |
| WO | 20061022773 A1 | 3/2006 |
| WO | 20061092599 A2 | 9/2006 |
| WO | 20071071965 A2 | 6/2007 |
| WO | 20071116106 A1 | 10/2007 |
| WO | 20081068470 A1 | 6/2008 |
| WO | 20091106885 A1 | 9/2009 |

OTHER PUBLICATIONS

U.S. Appl. No. 12/392,730, filed Mar. 2009, Choy.*
Champoux, "DNA Topoisomerases: Structure, Function and Mechanism" Annual Rev. Biochem. (2001); vol. 70; pp. 369-413.
Drlica and Zhao, "DNA Gyrase, Topoisomerase IV, and the 4-Quinolones" Microbiology and Molecular Biology Reviews (1997); vol. 61; No. 3; pp. 377-392.
International Search Report for PCT/GB2007/004624; mailed Mar. 20, 2008.
International Search Report for PCT/GB2009/050187; mailed Apr. 29, 2009.
International Search Report for PCT/GB2009/050611; mailed Jul. 22, 2009.
Maxwell, "DNA Gyrase as a Drug Target" Trends in Microbiology (1997); vol. 5; No. 3; pp. 102-109.
Takagi and Ueda, "Synthese de Pyrimidines et de Pyrazoles a Partir d'Acyl-3 halogeno-5 Benzofurannes" Chem. Pharm. Bull 1975); vol. 23; No. 10; pp. 2427-2431.

* cited by examiner

*Primary Examiner* — D M Seaman
(74) *Attorney, Agent, or Firm* — AstraZeneca AB

(57) ABSTRACT

Compounds of formula (I) and their pharmaceutically acceptable salts are described. Processes for their preparation, pharmaceutical compositions containing them, their use as medicaments and their use in the treatment of bacterial infections are also described.

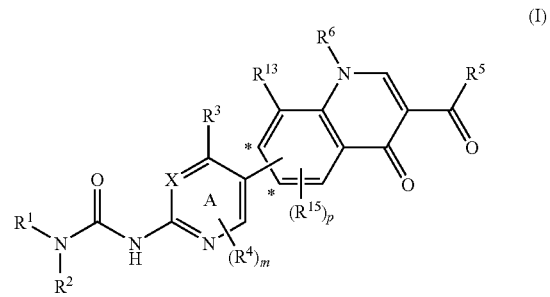

(I)

19 Claims, No Drawings

HETEROCYCLIC UREA DERIVATIVES AND METHODS OF USE THEREOF

RELATED APPLICATIONS

This application claims the benefit of U.S. Application No. 61/058,736 filed on Jun. 4, 2008, the entire teaching of which are incorporated herein by reference.

FIELD OF THE INVENTION

The present invention relates to compounds which demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular, this invention relates to compounds useful for the treatment of bacterial infections in warm-blooded animals such as humans, more particularly to the use of these compounds in the manufacture of medicaments for use in the treatment of bacterial infections in warm-blooded animals such as humans

BACKGROUND OF THE INVENTION

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. Antibiot. 47: 32-36). Despite potent activity against DNA gyrase, cyclothialidine is a poor antibacterial agent showing activity only against some eubacterial species (Nakada, N, 1993, Antimicrob. Agents Chemother. 37: 2656-2661).

Synthetic inhibitors that target the B subunit of DNA gyrase and topoisomerase IV are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087). AstraZeneca has also published certain applications describing anti-bacterial compounds: WO2005/026149, WO2006/087544, WO2006/087548, WO2006/087543, WO2006/092599, WO2006/092608, and WO2007/071965.

SUMMARY OF THE INVENTION

We have discovered a new class of compounds which are useful for inhibiting DNA gyrase and/or topoisomerase IV.

In one embodiment, according to the present invention there is provided a compound of formula (I):

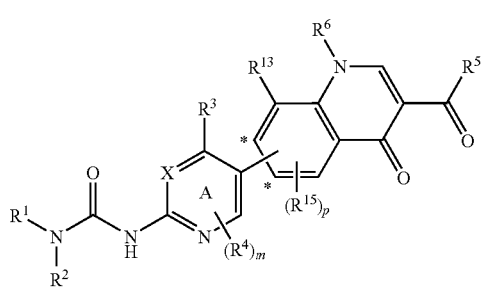

(I)

or a pharmaceutically acceptable salt thereof, wherein:

Ring A is attached to one of the carbon atoms indicated by "*";

X is N, CH or $CR^4$;

$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^7$;

$R^2$ is selected from hydrogen or $C_{1-6}$alkyl; wherein said $C_{1-6}$alkyl may be optionally substituted by one or more groups independently selected from halo, cyano, hydroxy, nitro and amino;

or $R^1$ and $R^2$ together with the nitrogen to which they are attached form a heterocyclyl; wherein said heterocyclyl may be optionally substituted on one or more carbon atoms with one or more $R^8$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^9$;

$R^3$ is a $C_{3-14}$carbocyclyl or a heterocyclyl; wherein the carbocyclyl or heterocyclyl may be optionally substituted on one or more carbon atoms by one or more $R^{10}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{11}$;

$R^4$ and $R^{15}$, for each occurrence, are independently selected from the group consisting of halo, nitro, cyano, hydroxy, amino, mercapto, $C_{1-6}$alkyl, $C_{2-6}$alkenyl, $C_{2-6}$alkynyl, $C_{1-6}$alkoxy, N—($C_{1-6}$alkyl)amino, N,N—($C_{1-6}$alkyl)$_2$amino, and $C_{1-6}$alkylsulfanyl; wherein $R^4$, $R^{13}$, and $R^{15}$ independently of each other may be optionally substituted on one or more carbon by one or more one or more $R^{12}$;

$R^5$ is —OH, —NH$_2$, a $C_{1-6}$alkoxy, an N—($C_{1-6}$alkyl)amino, or N,N—($C_{1-6}$alkyl)$_2$amino; wherein the $C_{1-6}$alkoxy, an N—($C_{1-6}$alkyl)amino, or N,N—($C_{1-6}$alkyl)$_2$amino may be optionally substituted on one or more carbon atoms with one or more, independently selected $R^{14}$;

$R^6$, for each occurrence, is independently selected from the group consisting of hydrogen, $C_{1-6}$alkyl, $C_{1-6}$alkylsulfanyl, carboxy, carbamoyl, N—($C_{1-6}$alkyl)carbamoyl, N,N—($C_{1-6}$alkyl)$_2$carbamoyl, $C_{3-14}$carbocyclyl, and heterocyclyl; wherein $R^6$ is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;

$R^{13}$ is selected from the group consisting of hydrogen, halo, nitro, cyano, hydroxy, amino, mercapto, $C_{1-6}$alkyl, $C_{2-6}$alkenyl, $C_{2-6}$alkynyl, $C_{1-6}$alkoxy, N—($C_{1-6}$alkyl)amino, N,N—($C_{1-6}$alkyl)$_2$amino, and $C_{1-6}$alkylsulfanyl; wherein $R^{13}$ may be optionally substituted on one or more carbon by one or more one or more $R^{16}$; or $R^6$ and $R^{13}$ together with the intervening ring atoms may form a fused heterocyclyl, wherein the fused heterocyclyl may be optionally substituted on one or more carbon atoms with one or more independently selected $R^{16}$; and wherein if said fused heterocyclyl contains an =N— or a —S— moiety that nitrogen may be optionally substituted by one oxo group and that sulfur may be optionally substituted by one or two oxo groups; and wherein if said fused heterocyclyl contains an —NH— moiety that nitrogen may be optionally substituted by a group selected from $R^{17}$;

m is 0 or 1;

p is 0, 1, or 2;

$R^7$, $R^8$, $R^{10}$, $R^{12}$, $R^{14}$ and $R^{16}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{3-6}$carbocyclyl or heterocyclyl; wherein $R^7$, $R^8$, R10, $R^{12}$, $R^{14}$ and $R^{16}$ independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups $R^9$, $R^{11}$, $R^{17}$ and $R^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^9$, $R^{11}$, $R^{17}$, and $R^{20}$ independently of each other may be optionally substituted on carbon by one or more $R^{23}$; and $R^{19}$ and $R^{23}$, for each occurrence, are independently selected from halo, nitro, cyano, hydroxy, trifluoromethoxy, trifluoromethyl, amino, carboxy, carbamoyl, mercapto, sulphamoyl, C1-6alkyl, C1-6alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl, provided that the compound is not one of the following compounds:

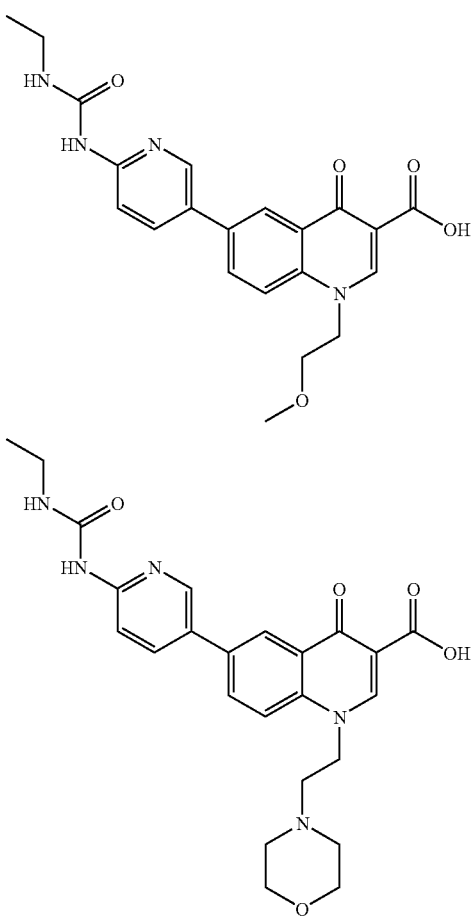

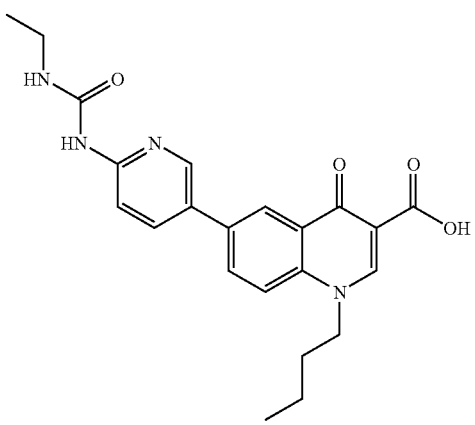

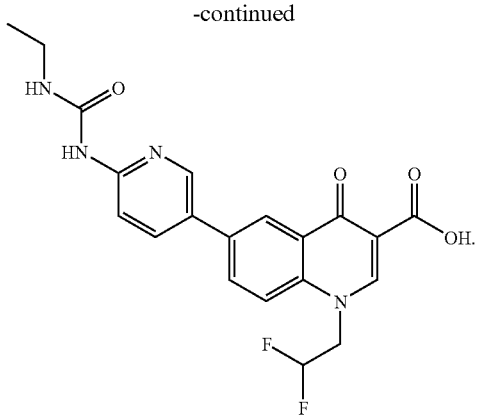

In another embodiment, the invention provides a compound of formula (I'):

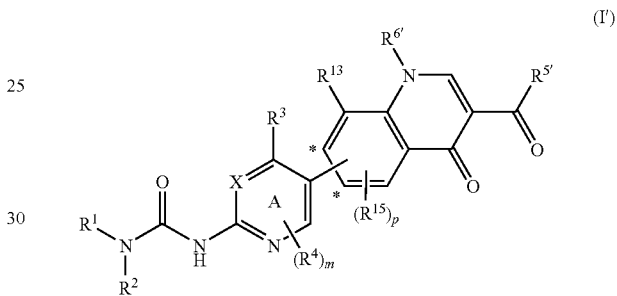

or a pharmaceutically acceptable salt thereof, wherein:

Ring A is attached to one of the carbon atoms indicated by "*";

X is N, CH or $CR^4$;

$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^7$;

$R^2$ is selected from hydrogen or $C_{1-6}$alkyl; wherein said $C_{1-6}$alkyl may be optionally substituted by one or more groups independently selected from halo, cyano, hydroxy, nitro and amino;

or $R^1$ and $R^2$ together with the nitrogen to which they are attached form a heterocyclyl; wherein said heterocyclyl may be optionally substituted on one or more carbon atoms with one or more $R^8$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^9$;

$R^3$ is a $C_{3-14}$carbocyclyl or a heterocyclyl; wherein the carbocyclyl or heterocyclyl may be optionally substituted on one or more carbon atoms by one or more $R^{10}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{11}$;

$R^4$ and $R^{15}$, for each occurrence, are independently selected from the group consisting of halo, nitro, cyano, hydroxy, amino, mercapto, $C_{1-6}$alkyl, $C_{2-6}$alkenyl, $C_{2-6}$alkynyl, $C_{1-6}$alkoxy, N—($C_{1-6}$alkyl)amino, N,N—($C_{1-6}$alkyl)$_2$ amino, and $C_{1-6}$alkylsulfanyl; wherein $R^4$, $R^{13}$, and $R^{15}$ independently of each other may be optionally substituted on one or more carbon by one or more one or more $R^{12}$;

$R^{5'}$ is —OH, a $C_{1-6}$alkoxy, $C_{3-14}$cycloalkoxy, or —$NR^aR^b$; wherein the $C_{1-6}$alkoxy group may be optionally substituted on one or more carbon atoms with one or more, independently selected $R^{14}$; and wherein $R^a$ and $R^b$ are each independently, hydrogen, a $C_{1-6}$alkyl, or a $C_{3-14}$carbocycle, or $R^a$ and $R^b$, together with the nitrogen to which they are attached form a heterocycle, wherein $R^a$ and $R^b$ may be optionally substituted on one or more carbon atoms with one or more, independently selected $R^{14}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{22}$;

$R^{6'}$, for each occurrence, is independently selected from the group consisting of hydrogen, $C_{1-6}$alkyl, $C_{1-6}$alkylsulfanyl, carboxy, carbamoyl, N—($C_{1-6}$alkyl)carbamoyl, N,N—($C_{1-6}$alkyl)$_2$carbamoyl, $C_{3-14}$carbocyclyl-L-, and heterocyclyl-L-; wherein $R^6$ is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;

$R^{13}$ is selected from the group consisting of hydrogen, halo, nitro, cyano, hydroxy, amino, mercapto, $C_{1-6}$alkyl, $C_{2-6}$alkenyl, $C_{2-6}$alkynyl, $C_{1-6}$alkoxy, N-($C_{1-6}$alkyl)amino, N,N—($C_{1-6}$alkyl)$_2$amino, and $C_{1-6}$alkylsulfanyl; wherein $R^{13}$ may be optionally substituted on one or more carbon by one or more one or more $R^{16}$; or $R^{6'}$ and $R^{13}$ together with the intervening ring atoms may form a fused heterocyclyl, wherein the fused heterocyclyl may be optionally substituted on one or more carbon atoms with one or more independently selected $R^{16}$; and wherein if said fused heterocyclyl contains an =N— or a —S— moiety that nitrogen may be optionally substituted by one oxo group and that sulfur may be optionally substituted by one or two oxo groups; and wherein if said fused heterocyclyl contains an —NH— moiety that nitrogen may be optionally substituted by a group selected from $R^{17}$;

m is 0 or 1;

p is 0, 1, or 2;

L, for each occurrence, is independently a direct bond or a $C_{1-6}$alkylene;

$R^7$, $R^8$, $R^{10}$, $R^{12}$, $R^{14}$ and $R^{16}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{3-6}$carbocyclyl or heterocyclyl; wherein $R^7$, $R^8$, $R^{10}$, $R^{12}$, $R^{14}$ and $R^{16}$ independently of each other may be optionally substituted on one or more carbon by one or more $R^{19}$; and wherein if said heterocyclyl contains an —NH— moiety that nitrogen may be optionally substituted by a group selected from $R^{20}$; and wherein if said heterocyclyl contains an =N— or a —S— moiety that nitrogen may be optionally substituted by one oxo group and that sulfur may be optionally substituted by one or two oxo groups;

$R^9$, $R^{11}$, and $R^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulphonyl; wherein $R^9$, $R^{11}$, and $R^{20}$ independently of each other may be optionally substituted on carbon by one or more $R^{23}$;

$R^{17'}$, for each occurrence, is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl, phenylsulphonyl, $C_{3-14}$carbocyclyl-L-, and heterocyclyl-L-; wherein each $R^{17'}$, independently, may be optionally substituted on carbon by one or more $R^{24}$; and wherein if said heterocyclyl contains an —NH-moiety that nitrogen may be optionally substituted by a group selected from $R^{25}$; and wherein if said heterocyclyl contains an =N— or a —S— moiety that nitrogen may be optionally substituted by one oxo group and that sulfur may be optionally substituted by one or two oxo groups;

$R^{22}$, for each occurrence is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N,N—($C_{1-6}$alkyl)$_2$sulfamoyl, N—($C_{1-6}$alkyl)carbamoyl, N,N—($C_{1-6}$alkyl)$_2$carbamoyl, benzyl, benzyloxycarbonyl, benzoyl and phenylsulphonyl; wherein $R^{22}$ for each occurrence may be independently optionally substituted on carbon by one or more $R^{23}$;

$R^{19}$ and $R^{23}$, for each occurrence, are independently selected from halo, nitro, cyano, hydroxy, trifluoromethoxy, trifluoromethyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

$R^{24}$, for each occurrence, are independently selected from halo, nitro, cyano, hydroxy, oxo, trifluoromethoxy, trifluoromethyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{25}$, for each occurrence is independently selected from a $C_{1-6}$alkyl, provided that the compound is not one of the following compounds:

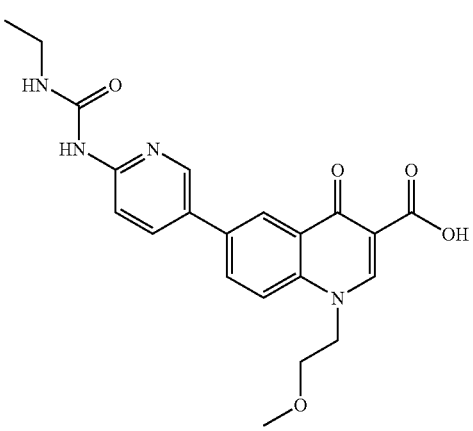

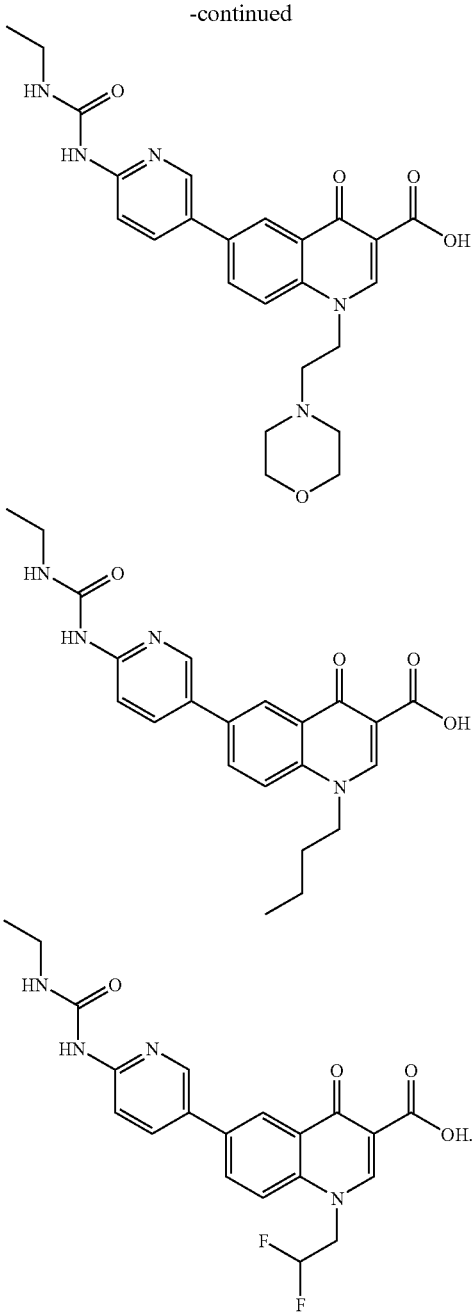

In another embodiment, the invention provides pharmaceutical compositions comprising a compound represented by formula (I) or (I'), or a pharmaceutically acceptable salt thereof, and a pharmaceutically acceptable excipient or carrier.

In another embodiment, the invention provides a method of inhibiting bacterial DNA gyrase and/or bacterial topoisomerase IV in a warm-blooded animal in need of such treatment, comprising administering to the animal an effective amount of a compound represented by formula (I) or (I'), or a pharmaceutically acceptable salt thereof. In a particular embodiment, the warm-blooded animal is a human.

In another embodiment, the invention provides a method of producing an antibacterial effect in a warm-blooded animal in need of such treatment, comprising administering to the animal an effective amount of a compound represented by formula (I) or (I'), or a pharmaceutically acceptable salt thereof. In a particular embodiment, the warm-blooded animal is a human.

In another embodiment, the invention provides a method of treating a bacterial infection in a warm-blooded animal in need thereof, comprising administering to the animal an effective amount of a compound represented by formula (I) or (I'), or a pharmaceutically acceptable salt thereof. In a particular embodiment, the warm-blooded animal is a human. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides the use of a compound represented by formula (I) or (I'), or a pharmaceutically acceptable salt thereof, for the manufacture of a medicament for use in the production of an antibacterial effect in a warm-blooded animal. In a particular embodiment, the warm-blooded animal is a human.

In another embodiment, the invention provides the use of a compound represented by formula (I) or (I'), or a pharmaceutically acceptable salt thereof, for the manufacture of a medicament for use in inhibition of bacterial DNA gyrase and/or topoisomerase IV in a warm-blooded animal. In a particular embodiment, the warm-blooded animal is a human.

In another embodiment, the invention provides the use of a compound represented by formula (I) or (I'), or a pharmaceutically acceptable salt thereof, for the manufacture of a medicament for use the treatment of a bacterial infection in a warm-blooded animal. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides a compound represented by formula (I) or (I'), or a pharmaceutically acceptable salt thereof, for use in production of an anti-bacterial effect in a warm-blooded animal.

In another embodiment, the invention provides a compound represented by formula (I) or (I'), or a pharmaceutically acceptable salt thereof, for use in inhibition of bacterial DNA gyrase and/or topoisomerase IV in a warm-blooded animal.

In another embodiment, the invention provides a compound represented by formula (I) or (I'), or a pharmaceutically acceptable salt thereof, for use in the treatment of a bacterial infection in a warm-blooded animal.

In another embodiment, the invention provides a compound represented by formula (I) or (I'), or a pharmaceutically acceptable salt thereof, for use in the treatment of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* or Vancomycin-Resistant Enterococci.

DETAILED DESCRIPTION OF THE INVENTION

In this specification the term alkyl includes both straight chained and branched saturated hydrocarbon groups. For example, "$C_{1-6}$alkyl" refers to an alkyl that has from 1 to 6 carbon atom and includes, for example, methyl, ethyl, propyl, isopropyl and t-butyl. However references to individual alkyl groups such as propyl are specific for the straight chain version only unless otherwise indicated (e.g., isopropyl). An analogous convention applies to other generic terms.

As used herein, the term "alkylene" refers to an alkyl group that has two points of attachment. Examples of alkylene groups include methylene, —$CH_2CH_2$—, —$CH_2CH_2CH_2$—, and —$CH_2C(CH_3)_2CH_2$—.

As used herein, the term "halo" refers to fluoro, chloro, bromo, and iodo.

A "heterocyclyl" is a saturated, partially saturated or unsaturated, mono or bicyclic ring containing 4-14 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring nitrogen may be optionally substituted with one oxo to form an N-oxide and a ring sulfur may be optionally substituted with one or two oxo groups to form S-oxide(s). In one embodiment of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked In a further aspect of the invention a "heterocyclyl" is an unsaturated, carbon-linked, monocyclic ring containing 5 or 6 atoms of which at least one atom is chosen from nitrogen, sulphur or oxygen. Examples and suitable values of the term "heterocyclyl" are morpholinyl, piperidyl, pyridinyl, pyranyl, pyrrolyl, pyrazolyl, isothiazolyl, indolyl, quinolinyl, thienyl, 1,3-benzodioxolyl, benzothiazolyl, thiadiazolyl, oxadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, 4,5-dihydro-oxazolyl, pyrimidinyl, pyrazinyl, pyridazinyl, isoxazolyl, thiazolyl, 1H-tetrazolyl, 1H-triazolyl, N-methylpyrrolyl, 4-pyridone, quinolin-4(1H)-one, pyridin-2(1H)-one, imidazo[1,2-a]pyridinyl, 1-isoquinolone, 2-pyrrolidone, 4-thiazolidone, quinoxalinyl, 5,6-dihydro[1,3]thiazolo[4,5-d]pyridazinyl, pyridine-N-oxide and quinoline-N-oxide. Suitable examples of "a nitrogen linked heterocyclyl" are morpholino, piperazin-1-yl, piperidin-1-yl and imidazol-1-yl. In a further aspect of the invention a "heterocyclyl" is a heteroaryl. The term "heteroaryl" refers to an unsaturated and aromatic heterocyclyl. Examples and suitable values for heteroaryl groups include pyridinyl, pyrrolyl, pyrazolyl, isothiazolyl, indolyl, quinolinyl, thienyl, benzothiazolyl, thiadiazolyl, oxadiazolyl, imidazolyl, pyrimidinyl, pyrazinyl, pyridazinyl, isoxazolyl, thiazolyl, 1H-tetrazolyl, 1H-triazolyl, N-methylpyrrolyl, quinolin-4(1H)-one, pyridin-2(1H)-one, imidazo[1,2-a]pyridinyl, 1-isoquinolone, quinoxalinyl, pyridine-N-oxide and quinoline-N-oxide. In a particular embodiment, the heteroaryl is a 5- or 6-membered heteroaryl, for example, pyridinyl, pyrrolyl, pyrazolyl, isothiazolyl, thienyl, thiadiazolyl, oxadiazolyl, imidazolyl, pyrimidinyl, pyrazinyl, pyridazinyl, isoxazolyl, thiazolyl, 1H-tetrazolyl, 1H-triazolyl, N-methylpyrrolyl, and pyridine-N-oxide.

A "carbocyclyl" is a saturated, partially saturated or unsaturated, mono-, bi- or tricyclic carbon ring that contains 3-14 atoms; wherein a —$CH_2$— group can optionally be replaced by a —C(O)—. In one embodiment, "carbocyclyl" is a monocyclic ring containing 5 or 6 atoms or a bicyclic ring containing 9 or 10 atoms. Examples of carbocyclyls include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. The term carbocyclyl encompasses both cycloalkyl and aryl groups. The term cycloalkyl refers to a carbocyclyl which is completely saturated, for example cyclopropyl, cyclobutyl, cyclopentyl, and cyclohexyl. The term "aryl" refers to a carbocyclyl which is completely unsaturated and is aromatic. A $C_{6-14}$aryl is an aromatic, mono-, bi- or tricyclic carbon ring that contains 6-14 atoms, for example phenyl or naphthenyl.

An example of "$C_{1-6}$alkanoyloxy" is acetoxy. Examples of "$C_{1-6}$alkoxycarbonyl" are methoxycarbonyl, ethoxycarbonyl, n- and t-butoxycarbonyl. Examples of "$C_{1-6}$alkoxycarbonylamino" are methoxycarbonylamino, ethoxycarbonylamino, n- and t-butoxycarbonylamino. Examples of "$C_{1-6}$ alkoxy" are methoxy, ethoxy and propoxy. Examples of "$C_{1-6}$ alkanoylamino" are formamido, acetamido and propionylamino. Examples of "$C_{1-6}$alkylS(O)$_a$ wherein a is 0, 1, or 2" are methylthio, ethylthio, methylsulphinyl, ethylsulphinyl, mesyl and ethylsulphonyl. Examples of "$C_{1-6}$alkanoyl" are propionyl and acetyl. Examples of "N—($C_{1-6}$alkyl)amino" are methylamino and ethylamino. Examples of "N,N—($C_{1-6}$alkyl)$_2$amino" are di-N-methylamino, di-(N-ethyl)amino and N-ethyl-N-methylamino. Examples of "$C_{2-4}$alkenyl" are vinyl, allyl and 1-propenyl. Examples of "$C_{2-4}$alkynyl" are ethynyl, 1-propynyl and 2-propynyl. Examples of "N—($C_{1-6}$ alkyl)sulphamoyl" are N-(methyl)sulphamoyl and N-(ethyl)sulphamoyl. Examples of "N,N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are methylaminocarbonyl and ethylaminocarbonyl. Examples of "N,N—($C_{1-6}$alkyl)$_2$carbamoyl" are dimethylaminocarbonyl and methylethylaminocarbonyl. Examples of "N—($C_{1-6}$ alkoxy)carbamoyl" are methoxyaminocarbonyl and isopropoxyaminocarbonyl. Examples of "N—($C_{1-6}$alkyl)-N—($C_{1-6}$ alkoxy)carbamoyl" are N-methyl-N-methoxyaminocarbonyl and N-methyl-N-ethoxyaminocarbonyl. Examples of "$C_{3-6}$cycloalkyl" are cyclopropyl, cyclobutyl, cyclopropyl and cyclohexyl. Examples of "$C_{1-6}$alkylsulphonylamino" are methylsulphonylamino, isopropylsulphonylamino and t-butylsulphonylamino. Examples of "$C_{1-6}$alkylsulphonylaminocarbonyl" are methylsulphonylaminocarbonyl, isopropylsulphonylaminocarbonyl and t-butylsulphonylaminocarbonyl. Examples of "$C_{1-6}$alkylsulphonyl" are methylsulphonyl, isopropylsulphonyl and t-butylsulphonyl.

The term "formula (I)", unless otherwise specified, refers to all embodiments of formula (I) including but not limited to formula (Ia), formula (Ib), and formula (Ic).

The term "formula (I')", unless otherwise specified, refers to all embodiments of formula (I') including but not limited to formula (Ia'), formula (Ib'), and formula (Ic').

A compound of formula (I) or (I') may form stable acid or basic salts, and in such cases administration of a compound as a salt may be appropriate, and pharmaceutically acceptable salts may be made by conventional methods such as those described below.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

Within the present invention it is to be understood that a compound of the formula (I) or (I'), or a salt thereof may exhibit the phenomenon of tautomerism and that the formulae drawings within this specification can represent only one of the possible tautomeric forms. It is to be understood that the invention encompasses any tautomeric form which inhibits DNA gyrase and/or topoisomerase IV and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein. The same applies to compound names.

It will be appreciated by those skilled in the art that certain compounds of formula (I) or (I') contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DNA gyrase and/or topoisomerase IV, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DNA gyrase and/or topoisomerase IV by the standard tests described hereinafter.

By way of clarity, compounds of the invention included all isotopes of the atoms present in formula (I) or (I') and any of the examples or embodiments disclosed herein. For example, H (or hydrogen) represents any isotopic form of hydrogen including $^1H$, $^2H$ (D), and $^3H$ (T); C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formula (I) or (I') comprises isomers of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formula (I) or (I'), when, for example, hydrogen is enriched in the deuterium isotope, the symbol "D" is used to represent the enrichment in deuterium. In one embodiment, when a compound of the invention is enriched in a radioactive isotope, for example $^3H$ and $^{14}C$, they may be useful in drug and/or substrate tissue distribution assays. It is to be understood that the invention encompasses all such isotopic forms which inhibit DNA gyrase and/or topoisomerase IV.

It is also to be understood that certain compounds of the formula (I) or (I'), and salts thereof can exist in solvated as well as unsolvated forms such as, for example, hydrated forms. It is to be understood that the invention encompasses all such solvated forms which inhibit DNA gyrase and/or topoisomerase IV.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

In one embodiment, compounds of the invention are represented by formula (Ia):

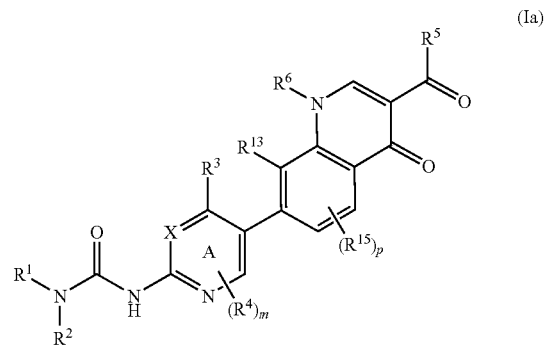

or a pharmaceutically acceptable salts thereof, wherein X, $R^1$, $R^2$, $R^3$, $R^4$, $R^5$, $R^6$, $R^{13}$, $R^{15}$, m and p are defined as for formula (I).

In another embodiment, compounds of the invention are represented by formula (Ia'):

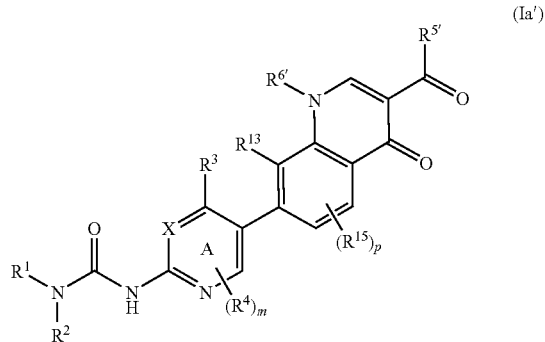

or a pharmaceutically acceptable salts thereof, wherein X, $R^1$, $R^2$, $R^3$, $R^4$, $R^{5'}$, $R^{6'}$, $R^{13}$, $R^{15}$, m and p are defined as for formula (I').

In another embodiment, the compound is represented by formula (Ib):

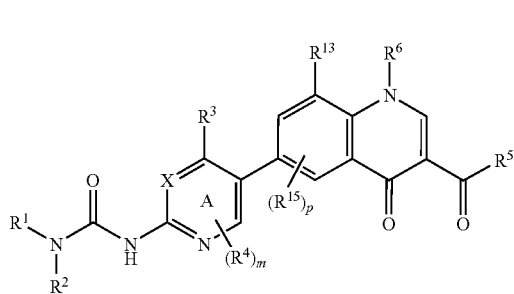

(Ib)

or a pharmaceutically acceptable salts thereof, wherein X, $R^1$, $R^2$, $R^3$, $R^4$, $R^5$, $R^6$, $R^{13}$, $R^{15}$, m and p are defined as for formula (I).

In another embodiment, the compound is represented by formula (Ib'):

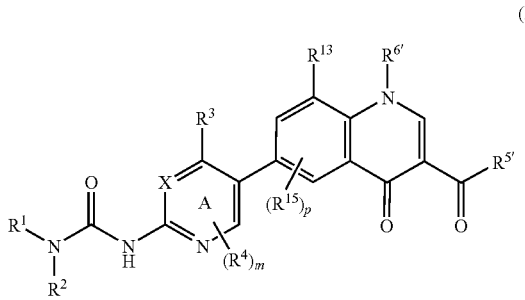

(Ib')

or a pharmaceutically acceptable salts thereof, wherein X, $R^1$, $R^2$, $R^3$, $R^4$, $R^{5'}$, $R^{6'}$, $R^{13}$, $R^{15}$, m and p are defined as for formula (I').

In another embodiment the invention provides compounds represented by formula (I) or (I') wherein X is CH.

In another embodiment the invention provides compounds represented by formula (I) or (I') wherein X is N.

In another embodiment the invention provides compounds represented by formula (I) or (I') wherein X is $CR^4$ and $R^4$ is fluoro, chloro, bromo, iodo, a $C_{1-4}$alkyl, or a $C_{1-4}$alkoxy.

In another embodiment the invention provides compounds represented by formula (I) or (I') wherein $R^1$ is a $C_{1-6}$alkyl. For example, $R^1$ is methyl, ethyl, propyl, isopropyl, butyl, isobutyl, sec-butyl, and tert-butyl. In a particular embodiment, $R^1$ is ethyl.

In another embodiment the invention provides compounds represented by formula (I) or (I') wherein $R^2$ is hydrogen.

In another embodiment the invention provides compounds represented by formula (I) or (I') wherein $R^2$ is a $C_{1-6}$alkyl. For example, $R^2$ is methyl, ethyl, propyl, isopropyl, butyl, isobutyl, sec-butyl, and tert-butyl.

In another embodiment the invention provides compounds represented by formula (I) or (I') wherein $R^3$ is a 5-membered heteroaryl; and wherein the heteroaryl may be optionally substituted on one or more carbon atoms by one or more $R^{10}$; and wherein if said heteroaryl contains an =N— or a —S— moiety that nitrogen may be optionally substituted by one oxo group and that sulfur may be optionally substituted by one or two oxo groups; and wherein if said heteroaryl contains an —NH— moiety that nitrogen may be optionally substituted by a group selected from $R^{11}$. In one aspect of this embodiment, $R^{10}$ is selected from the group consisting of methyl, ethyl, phenyl, trifluoromethyl, and pyridinyl. In another aspect of this embodiment, $R^{11}$ is methyl.

In another embodiment the invention provides compounds represented by formula (I) or (I') wherein $R^3$ is a thiazolyl; and wherein the thiazolyl may be optionally substituted on carbon by one or more $R^{10}$; and wherein the =N— of the thiazolyl may be optionally substituted by one oxo group; and wherein the —S— of the thiazolyl may be optionally substituted by one or two oxo groups. In one aspect of this embodiment, $R^{10}$ is selected from the group consisting of methyl, ethyl, phenyl, trifluoromethyl, and pyridinyl. In another aspect of this embodiment, $R^{11}$ is methyl.

In another embodiment the invention provides compounds represented by formula (I) or (I') wherein $R^3$ is a 1,3,4-oxadiazolyl; and wherein the 1,3,4-oxadiazolyl may be optionally substituted on one or more carbon by one or more $R^{10}$; and wherein each =N— of the 1,3,4-oxadiazolyl may be independently optionally substituted by one oxo group. In one aspect of this embodiment, $R^{10}$ is selected from the group consisting of methyl, phenyl, trifluoromethyl, and pyridinyl. In another aspect of this embodiment, $R^{11}$ is methyl.

In another embodiment the invention provides compounds represented by formula (I) or (I') wherein $R^3$ is a 1H-pyrazolyl; and wherein the 1H-pyrazolyl may be optionally substituted on one or more carbon by one or more $R^{10}$; and wherein the =N— of the 1H-pyrazolyl may be optionally substituted by one oxo group; and wherein the —NH— moiety of the 1H-pyrazolyl may be optionally substituted by a group selected from $R^{11}$. In one aspect of this embodiment, $R^{10}$ is selected from the group consisting of methyl, phenyl, trifluoromethyl, and pyridinyl. In another aspect of this embodiment, $R^{11}$ is methyl.

In another embodiment the invention provides compounds represented by formula (I) or (I') wherein $R^3$ is 1,3-benzothiazolyl; and wherein the 1,3-benzothiazolyl may be optionally substituted on one or more carbon by one or more $R^{10}$; and wherein the =N— of the 1,3-benzothiazolyl may be optionally substituted by one oxo group; and wherein the —S— of the 1,3-benzothiazolyl may be optionally substituted by one or two oxo groups. In one aspect of this embodiment, $R^{10}$ is selected from the group consisting of methyl, phenyl, trifluoromethyl, and pyridinyl. In another aspect of this embodiment, $R^{11}$ is methyl.

In another embodiment the invention provides compounds represented by formula (I) or (I') wherein $R^3$ is a $C_{6-14}$aryl which may be optionally substituted on one or more carbon atoms with one or more $R^{10}$.

In another embodiment the invention provides compounds represented by formula (I) or (I') wherein $R^3$ is 4-trifluouromethyl-thiazole-2-yl, 4-ethyl-thiazole-2-yl, or 4-phenyl-thiazole-2-yl.

In another embodiment the invention provides compounds represented by formula (I) wherein $R^5$ is —OH.

In another embodiment the invention provides compounds represented by formula (I') wherein $R^{5'}$ is —OH.

In another embodiment the invention provides compounds represented by formula (I) wherein $R^5$ is $C_{1-6}$alkoxy, wherein the $C_{1-6}$alkoxy group may be optionally substituted on one or more carbon atoms with one or more, independently selected $R^{14}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino.

In another embodiment the invention provides compounds represented by formula (I) wherein $R^5$ is $C_{1-6}$alkoxy.

In another embodiment, the invention provides compounds represented by formula (I) wherein $R^5$ is ethoxy.

In another embodiment the invention provides compounds represented by formula (I') wherein $R^{5'}$ is $C_{1-6}$alkoxy, wherein the $C_{1-6}$alkoxy group may be optionally substituted on one or more carbon atoms with one or more, independently selected $R^{14}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino.

In another embodiment the invention provides compounds represented by formula (I') wherein $R^{5'}$ is $C_{1-6}$alkoxy.

In another embodiment the invention provides compounds represented by formula (I') wherein $R^{5'}$ is ethoxy.

In another embodiment the invention provides compounds represented by formula (I) wherein $R^5$ is amino, N—($C_{1-6}$alkyl)amino or N,N—($C_{1-6}$alkyl)$_2$amino, wherein the each $C_{1-6}$alkyl group may be independently optionally substituted on one or more carbon atoms with one or more, independently selected $R^{14}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino.

In another embodiment the invention provides compounds represented by formula (I) wherein $R^5$ is amino, N—($C_{1-6}$alkyl)amino or N,N—($C_{1-6}$alkyl)$_2$amino.

In another embodiment the invention provides compounds represented by formula (I') wherein $R^{5'}$ is amino, N—($C_{1-6}$alkyl)amino or N,N—($C_{1-6}$alkyl)$_2$amino, wherein the each $C_{1-6}$alkyl group may be independently optionally substituted on one or more carbon atoms with one or more, independently selected $R^{14}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino.

In another embodiment the invention provides compounds represented by formula (I') wherein $R^{5'}$ is amino, N—($C_{1-6}$alkyl)amino or N,N—($C_{1-6}$alkyl)$_2$amino.

In another embodiment the invention provides compounds represented by formula (I) wherein $R^5$ is selected from the group consisting of —OH, ethoxy, N-methylamino, and N-ethylamino.

In another embodiment the invention provides compounds represented by formula (I') wherein $R^{5'}$ is selected from the group consisting of —OH, ethoxy, N-methylamino, and N-ethylamino.

In another embodiment the invention provides compounds represented by formula (I') wherein $R^{5'}$ is —NR$^a$R$^b$ and one of R$^a$ or R$^b$ is a $C_{1-6}$alkyl and the other is hydrogen, wherein the $C_{1-6}$alkyl may be optionally substituted on one or more carbon atoms with one or more, independently selected $R^{14}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino.

In another embodiment the invention provides compounds represented by formula (I') wherein $R^{5'}$ is —NR$^a$R$^b$ and one of R$^a$ or R$^b$ is a $C_{3-6}$cycloalkyl and the other is hydrogen, wherein the cycloalkyl may be optionally substituted on one or more carbon atoms with one or more, independently selected $R^{14}$.

In another, R5' is —NR$^a$R$^b$; wherein R$^a$ and R$^b$, together with the nitrogen to which they are attached form a heterocycle, wherein R$^a$ and R$^b$ may be optionally substituted on one or more carbon atoms with one or more, independently selected $R^{14}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{22}$. In one aspect of this embodiment, $R^{14}$, for each occurrence, is independently selected from hydroxy, N,N—($C_{1-6}$alkyl)$_2$-amino, morpholinyl, $C_{1-6}$alkoxy, piperazinyl, and N-alkyl-piperizinyl. In another aspect of this embodiment, $R^{14}$, for each occurrence, is independently selected from hydroxy, N,N-dimethylamino, morpholino, methoxy, piperazino, and N-methyl-piperizino. In another aspect of this embodiment, $R^{22}$, for each occurrence, is independently selected from a $C_{1-6}$alkyl, $C_{1-6}$alkylsulfonyl, N—($C_{1-6}$alkyl) sufamoyl, N,N—($C_{1-6}$alkyl)$_2$sufamoyl, and $C_{1-6}$alkanoyl. In another aspect of this embodiment, $R^{22}$, for each occurrence, is independently selected from methyl, methylsulfonyl, N,N-dimethylsufamoyl, and acetyl.

In another embodiment the invention provides compounds represented by formula (I') wherein $R^{5'}$ is selected from the group consisting of methylamino, N-cyclopropylamino, N-(2-hydroxyethyl)-amino, N-(3-hydroxypropyl)-amino, N-[2-(N,N-dimethylamino)-ethyl]-amino, N-(2-morpholinoethyl)-amino, N-[1-(methoxymethyl)-2-methoxy-ethyl]-amino, N-[1-(hydroxymethyl)-2-hydroxy-ethyl]-amino, N-[2-(4-methyl-piperazino)-ethyl]-amino, N-(2-piperazinoethyl)-amino, 4-acetyl-piperazino, 4-methylsulfonyl-piperazino, 4-(2-hydroxyethyl)-piperazino, and 4-(N,N-dimethylsulfamoyl)-piperazino.

In another embodiment the invention provides compounds represented by formula (I) wherein $R^5$ is selected from the group consisting of —OH, ethoxy, methylamino, N-(2-hydroxyethyl)-amino, N-(3-hydroxypropyl)-amino, N-[2-(N,N-dimethylamino)-ethyl]-amino, N-(2-morpholinoethyl)-amino, N-[1-(methoxymethyl)-2-methoxy-ethyl]-amino, N-[1-(hydroxymethyl)-2-hydroxy-ethyl]-amino, N-[2-(4-methyl-piperazino)-ethyl]-amino, and N-(2-piperazinoethyl)-amino.

In another embodiment the invention provides compounds represented by formula (I') wherein $R^{5'}$ is selected from the group consisting of methylamino, N-(2-hydroxyethyl)-amino, N-(3-hydroxypropyl)-amino, N-[2-(N,N-dimethylamino)-ethyl]-amino, N-(2-morpholinoethyl)-amino, N-[1-(methoxymethyl)-2-methoxy-ethyl]-amino, N-[1-(hydroxymethyl)-2-hydroxy-ethyl]-amino, N-[2-(4-methyl-piperazino)-ethyl]-amino, and N-(2-piperazino-ethyl)-amino.

In another embodiment the invention provides compounds represented by formula (I') wherein $R^{5'}$ is selected from the group consisting of 4-acetyl-piperazino, 4-methylsulfonyl-piperazino, 4-(2-hydroxyethyl)-piperazino, and 4-(N,N-dimethylsulfamoyl)-piperazino.

In another embodiment the invention provides compounds represented by formula (I) wherein $R^6$ is a $C_{1-6}$alkyl which is substituted on one or more carbon atoms with one or more independently selected $R^{16}$. In one aspect of this embodiment, $R^{16}$, for each occurrence, is independently selected from the group consisting of —OH, fluoro, N-methylamino, N,N-dimethylamino, methoxy, ethoxy, methylsulfanyl, methylsulfonyl, piperidinyl, piperazinyl, morpholinyl, pyrrolidinyl, 2-oxopyrrolidinyl, pyrrolyl, imidazolyl, triazolyl, and phenyl which may be optionally substituted with one or more halo, isoxazolyl, pyridinyl, and cyclopropyl. In another aspect of this embodiment, $R^{16}$, for each occurrence, is independently selected from N,N—$(C_{1-6}$alkyl$)_2$amino, hydroxy, $C_{1-6}$alkoxy, and carboxy. In another aspect of this embodiment, $R^{16}$, for each occurrence, is independently selected from N,N-dimethylamino, hydroxy, methoxy, and carboxy.

In another embodiment the invention provides compounds represented by formula (I') wherein $R^{6'}$ is a $C_{1-6}$alkyl which is substituted on one or more carbon atoms with one or more independently selected $R^{16}$. In one aspect of this embodiment, $R^{16}$, for each occurrence, is independently selected from the group consisting of —OH, carboxy, fluoro, N-methylamino, N,N-dimethylamino, methoxy, ethoxy, methylsulfanyl, methylsulfonyl, cyclohexyl, piperidinyl, piperazinyl, morpholinyl, pyrrolidinyl, 2-oxopyrrolidinyl, pyrrolyl, imidazolyl, triazolyl, and phenyl. In another aspect of this embodiment, $R^{16}$, for each occurrence, is independently selected from N,N—$(C_{1-6}$alkyl$)_2$amino, hydroxy, $C_{1-6}$alkoxy, and carboxy. In another aspect of this embodiment, $R^{16}$, for each occurrence, is independently selected from N,N-dimethylamino, hydroxy, methoxy, and carboxy.

In another embodiment the invention provides compounds represented by formula (I') wherein $R^{6'}$ is a $C_{3-6}$carbocycle-$C_{1-6}$alkylene which is optionally substituted on one or more carbon atoms with one or more $R^{16}$.

In another embodiment the invention provides compounds represented by formula (I') wherein $R^{6'}$ is an unsubstituted $C_{3-6}$carbocycle-$C_{1-6}$alkylene.

In another embodiment the invention provides compounds represented by formula (I') wherein $R^{6'}$ is a cyclopropylmethyl or benzyl.

In another embodiment the invention provides compounds represented by formula (I') wherein $R^{6'}$ is a heterocyclyl-$C_{1-6}$alkylene which is optionally substituted on one or more carbon atoms with one or more $R^{16}$; wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17'}$. In one aspect of this embodiment, $R^{16}$, for each occurrence, is independently selected from oxo, $C_{3-6}$cycloalkyl, N,N—$(C_{1-6}$alkyl$)_2$amino, hydroxy, $C_{1-6}$alkoxy, and carboxy. In another aspect of this embodiment, $R^{16}$, for each occurrence, is independently selected from oxo, cyclopropyl, N,N-dimethylamino, hydroxy, methoxy, and carboxy. In another aspect of this embodiment, $R^{16}$, for each occurrence, is independently selected from oxo and cyclopropyl. In another aspect of this embodiment, $R^{17'}$, for each occurrence, is independently selected from $C_{1-6}$alkylsulfonyl$(C_{1-6})$alkyl, hydroxy$C_{1-6}$alkyl, heterocyclyl-$(C_{1-6})$alkylene, $C_{1-6}$alkyl, amino$C_{1-6}$alkyl, N—$(C_{1-6}$alkyl)amino, and N,N—$(C_{1-6}$alkyl$)_2$amino. In another aspect of this embodiment, $R^{17'}$, for each occurrence, is independently selected from 2-(methylsulfonyl)-ethyl, 1-methyl-pyrrol-2-ylmethyl, 2,2-dimethyl-propyl, 2-morpholino-ethyl, 2-(N,N-diethylamino)-ethyl, 3-morpholino-2,2-dimethyl-propyl, 2-hydroxyethyl, methyl, ethyl, pyridin-4-ylmethyl, and tetrahydrofuran-2-ylmethyl. In another aspect of this embodiment, $R^{17'}$, for each occurrence, is independently selected from a $C_{1-6}$alkyl or heterocyclyl-$C_{1-6}$alkene. In another aspect of this embodiment, $R^{17'}$, for each occurrence, is independently selected from methyl, ethyl, tetrahydrofuran-methyl, 2-hydroxyethyl, and 2-morpholino-ethyl.

In another embodiment the invention provides compounds represented by formula (I) wherein $R^6$ is a carbocyclyl which is optionally substituted on one or more carbon atoms with one or more $R^{16}$. In one aspect of this embodiment, $R^{16}$, for each occurrence is independently selected from oxo, $C_{3-6}$cycloalkyl, amino, N—$(C_{1-6}$alkyl)amino, N,N—$(C_{1-6}$alkyl$)_2$amino, hydroxy, $C_{1-6}$alkoxy, and carboxy. In another aspect of this embodiment, $R^{16}$, for each occurrence, is independently selected from oxo, cyclopropyl, amino, N,N-dimethylamino, hydroxy, methoxy, and carboxy. In another aspect of this embodiment, $R^{16}$, for each occurrence, is independently selected from hydroxy or amino In another embodiment the invention provides compounds represented by formula (I') wherein $R^{6'}$ is a carbocyclyl which is optionally substituted on one or more carbon atoms with one or more $R^{16}$. In one aspect of this embodiment, $R^{16}$, for each occurrence is independently selected from oxo, $C_{3-6}$cycloalkyl, amino, N—$(C_{1-6}$alkyl)amino, N,N—$(C_{1-6}$alkyl$)_2$amino, hydroxy, $C_{1-6}$alkoxy, and carboxy. In another aspect of this embodiment, $R^{16}$, for each occurrence, is independently selected from oxo, cyclopropyl, amino, N,N-dimethylamino, hydroxy, methoxy, and carboxy. In another aspect of this embodiment, $R^{16}$, for each occurrence, is independently selected from hydroxy or amino.

In another embodiment the invention provides compounds represented by formula (I) wherein $R^6$ is a heterocyclyl which is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$. In one aspect of this embodiment, $R^{16}$, for each occurrence is independently selected from oxo, $C_{3-6}$cycloalkyl, amino, N—$(C_{1-6}$ alkyl)amino, N,N—$(C_{1-6}$alkyl$)_2$amino, hydroxy, $C_{1-6}$alkoxy, and carboxy. In another aspect of this embodiment, $R^{16}$, for each occurrence, is independently selected from oxo, cyclopropyl, amino, N,N-dimethylamino, hydroxy, methoxy, and carboxy. In another aspect of this embodiment, $R^{16}$, for each occurrence, is independently selected from hydroxy or amino. In another aspect of this embodiment, $R^{17}$, for each occurrence, is independently selected from 2-(methylsulfonyl)-ethyl, 2,2-dimethyl-propyl, 2-(N,N-diethylamino)-ethyl, 2-hydroxyethyl, methyl, and ethyl. In another aspect of this embodiment, $R^{17}$, for each occurrence, is independently selected from a $C_{1-6}$alkyl. In another aspect of this embodiment, $R^{17}$, for each occurrence, is independently selected from methyl, ethyl, and 2-hydroxyethyl.

In another embodiment the invention provides compounds represented by formula (I') wherein $R^{6'}$ is a heterocyclyl which is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17'}$. In one aspect of this embodiment, $R^{16}$, for each occurrence is independently selected from oxo, $C_{3-6}$cycloalkyl, amino, N—($C_{1-6}$alkyl)amino, N,N—($C_{1-6}$alkyl)$_2$amino, hydroxy, $C_{1-6}$alkoxy, and carboxy. In another aspect of this embodiment, $R^{16}$, for each occurrence, is independently selected from oxo, cyclopropyl, amino, N,N-dimethylamino, hydroxy, methoxy, and carboxy. In another aspect of this embodiment, $R^{16}$, for each occurrence, is independently selected from hydroxy or amino. In another aspect of this embodiment, $R^{17'}$, for each occurrence, is independently selected from $C_{1-6}$alkylsulfonyl($C_{1-6}$)alkyl, hydroxy$C_{1-6}$alkyl, heterocyclyl-($C_{1-6}$)alkylene, $C_{1-6}$alkyl, amino$C_{1-6}$alkyl, N—($C_{1-6}$alkyl)amino, and N,N—($C_{1-6}$alkyl)$_2$amino. In another aspect of this embodiment, $R^{17'}$, for each occurrence, is independently selected from 2-(methylsulfonyl)-ethyl, 1-methyl-pyrrol-2-ylmethyl, 2,2-dimethyl-propyl, 2-morpholino-ethyl, 2-(N,N-diethylamino)-ethyl, 3-morpholino-2,2-dimethyl-propyl, 2-hydroxyethyl, methyl, ethyl, pyridin-4-ylmethyl, and tetrahydrofuran-2-ylmethyl. In another aspect of this embodiment, $R^{17'}$, for each occurrence, is independently selected from a $C_{1-6}$alkyl or heterocyclyl-$C_{1-6}$alkene. In another aspect of this embodiment, $R^{17'}$, for each occurrence, is independently selected from methyl, ethyl, tetrahydrofuran-methyl, 2-hydroxyethyl, and 2-morpholino-ethyl.

In another embodiment the invention provides compounds represented by formula (I) wherein $R^6$ is hydrogen.

In another embodiment the invention provides compounds represented by formula (I) wherein $R^6$ is $C_{1-6}$alkyl or a $C_{3-6}$cycloalkyl.

In another embodiment the invention provides compounds represented by formula (I) wherein $R^6$ is a non-aromatic heterocyclyl having 3 to 6 ring atoms; wherein said heterocyclyl is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$.

In another embodiment the invention provides compounds represented by formula (I) wherein $R^{13}$ and $R^6$ together with the intervening ring atoms form a 5- or 6-membered fused heterocyclyl. In one aspect of this embodiment, the compounds of the invention are represented by formula (Ic):

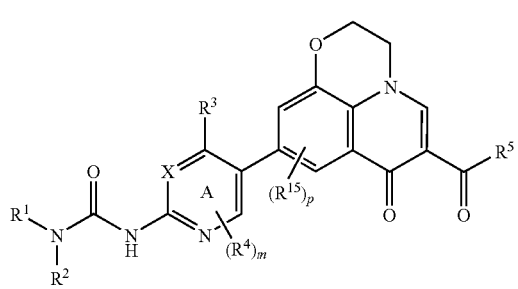

(Ic)

or a pharmaceutically acceptable salts thereof, wherein X, $R^1$, $R^2$, $R^3$, $R^4$, $R^5$, $R^{15}$, m and p are defined as for formula (I).

In another embodiment the invention provides compounds represented by formula (I') wherein $R^{13}$ and $R^{6'}$ together with the intervening ring atoms form a 5- or 6-membered fused heterocyclyl. In one aspect of this embodiment, the compounds of the invention are represented by formula (Ic'):

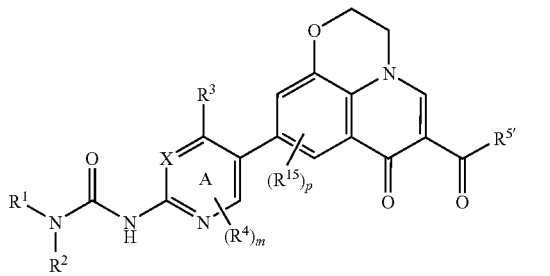

(Ic')

or a pharmaceutically acceptable salts thereof, wherein X, $R^1$, $R^2$, $R^3$, $R^4$, $R^{5'}$, $R^{15}$, m and p are defined as for formula (I').

In another embodiment the invention provides compounds represented by formula (I) wherein $R^6$ is selected from hydrogen, 2-(N,N-dimethylamino)-ethyl, 1-methyl-2-hydroxy-ethyl, morpholin-3-ylmethyl, 2-(N,N-dimethylamino)-propyl, 2-hydroxycyclohexyl, 1-(2-mesyl-ethyl)-piperidin-3-yl, 1-(2,2-dimethyl-propyl)-piperidin-3-yl, 1-[2-(N,N-dimethylamino)-ethyl]-piperidin-3-yl, 2-hydroxyethyl, ethyl, 3-methoxypropyl, methyl, cyclopropyl, isopropyl, 3-methyl-butyl, propyl, cyclopropylmethyl, 2-hydroxyethyl, 1-methoxymethyl-2-methoxy-ethyl, 1-methyl-azetidine-3-yl, benzyl, 3-hydroxy-propyl, cyclohexyl, tetrahydro-2H-pyran-4-yl, 1-methyl-piperidin-4-yl, isobutyl, 2-methoxyethyl, 1-methyl-piperidin-4-ylmethyl, 1-ethyl-2-hydroxy-ethyl, 1-hydroxymethyl-3-methyl-butyl, 1-carboxy-2-methyl-propyl, 1-methoxymethyl-2-methyl-propyl, pyrrolidin-1-ylethyl, 1-hydroxymethyl-2-methyl-butyl, pyridin-3-ylmethyl, 2-methoxy-ethyl, tetrahydro-2H-pyran-4-ylmethyl, tetrahydrofuran-2-ylmethyl, 1-hydroxymethyl-2,2-dimethyl-propyl, 5-cyclopropyl-1,2,4-oxadiazol-3-yl, 1-methyl-imidazol-4-ylmethyl, pyridin-4-ylmethyl, 1-hydroxmethy-propyl, 4-methyl-piperazin-1-ylethyl, 1-methyl-2-(N,N-dimethylamino)-ethyl, 1-methyl-piperidin-2-yl, piperidin-2-yl, 1-hydroxymethyl-2-methyl-propyl, 1-hydroxymethyl-2-hydroxy-ethyl, 1-hydroxmethyl-2-phenyl-ethyl, 1-hydroxmethyl2-hydroxy-propyl, 1-ethyl-pyrrolidin-3-yl, 4-hydroxy-pyrrolidin-3-yl, 1-methyl-pyrrolidin-3-yl, 1-hydroxmethyl-ethyl, 1-(2-hydroxy-ethyl)-pyrrolidin-3-ylmethyl, 2-amino-cyclohexyl, tetrahydro-2H-pyran-4-ylethyl, 1-cyclohexyl-2-hydroxy-ethyl, 1-hydroxymethyl-2-(4-hydroxyphenyl)-ethyl, 1-(2-hydroxyethyl)-piperidin-3-yl, pyrrolidin-3-ylmethyl, piperidin-3-ylmethyl, piperidin-3-yl, 1-ethyl-pyrrolidin-3-yl, 1-ethyl-piperidin-3-yl, 1-methyl-pyrrolidin-3-yl, and 1-ethyl-piperidin-3-ylmethyl.

In another embodiment the invention provides compounds represented by formula (I') wherein $R^{6'}$ is selected from hydrogen, 2-(N,N-dimethylamino)-ethyl, 1-methyl-2-hydroxy-ethyl, morpholin-3-ylmethyl, 2-(N,N-dimethylamino)-propyl, 2-hydroxycyclohexyl, 1-(2-mesyl-ethyl)-piperidin-3-yl, 1-(1-methyl-pyrrol-2-ylmethyl)-piperidin-3-yl, 1-(2,2-dimethyl-propyl)-piperidin-3-yl, 1-(2-morpholino-ethyl)-pyrrolidin-3-ylmethyl, 1-(2-morpholinoethyl)-piperidin-3-yl, 1-[2-(N,N-dimethylamino)-ethyl]-piperidin-3-yl, 1-(2,2-dimethyl-3-morpholino-propyl)-piperidin-3-yl, 2-hydroxyethyl, ethyl, 3-methoxypropyl, methyl, cyclopropyl, 3-(2-oxo-pyrrolidin-1-yl)-propyl, isopropyl, 3-methyl-butyl, propyl, cyclopropylmethyl, 2-hydroxyethyl, 1-methoxymethyl2-methoxy-ethyl, 1-methyl-azetidine-3-yl, benzyl, 3-hydroxy-propyl, cyclohexyl, tetrahydro-2H-pyran-4-yl, 1-methyl-piperidin-4-yl, isobutyl, 2-methoxyethyl, 1-methyl-piperidin-4-ylmethyl, 1-ethyl-2-hydroxy-ethyl, 1-hydroxymethyl3-methyl-butyl, 1-carboxy-2-methyl-propyl, 1-methoxymethyl2-methyl-propyl, pyrrolidin-1-ylethyl, 1-hydroxymethyl-2-methyl-butyl, pyridin-3-ylmethyl, 2-methoxy-ethyl, tetrahydro-2H-pyran-4-ylmethyl, tetrahydrofuran-2-ylmethyl, 1-hydroxymethyl2,2-dimethyl-propyl, 5-cyclopropyl-1,2,4-oxadiazol-3-yl, 1-methyl-imidazol-4-ylmethyl, pyridin-4-ylmethyl, 1-hydroxmethy-propyl, 4-methyl-piperazin-1-ylethyl, 1-methyl-2-(N,N-dimethylamino)-ethyl, 1-methyl-piperidin-2-yl, piperidin-2-yl, 1-hydroxymethyl2-methyl-propyl, 1-hydroxymethyl2-hydroxy-ethyl, 1-hydroxmethyl2-phenyl-ethyl, 1-hydroxmethyl2-hydroxy-propyl, 1-ethyl-pyrrolidin-3-yl, 4-hydroxy-pyrrolidin-3-yl, 1-methyl-pyrrolidin-3-yl, 1-hydroxmethyl-ethyl, 1-(pyridin-4-ylmethyl)-piperidin-3-yl, 1-(tetrahydrofuran-2-yl)-pyrrolidin-3-ylmethyl, 1-(2-hydroxy-ethyl)-pyrrolidin-3-ylmethyl, 2-amino-cyclohexyl, tetrahydro-2H-pyran-4-ylethyl, 1-cyclohexyl2-hydroxy-ethyl, 1-hydroxymethyl-2-(4-hydroxyphenyl)-ethyl, 1-(2-hydroxyethyl)-piperidin-3-yl, pyrrolidin-3-ylmethyl, piperidin-3-ylmethyl, piperidin-3-yl, 1-ethyl -pyrrolidin-3-yl, 1-ethyl-piperidin-3-yl, 1-methyl-pyrrolidin-3-yl, 1-ethyl-piperidin-3-ylmethyl.

In another embodiment the invention provides compounds represented by formula (I) wherein $R^6$ is selected from the group consisting of methyl, ethyl, propan-1-yl, propan-2-yl, 1-hydroxy-4-methyl-pentan-2-yl, 2-methyl-propan-1-yl, 3-methyl-butan-1-yl, 2-hydroxyethyl, 2-methoxyethyl, cyclopropyl, cyclopropylmethyl, benzyl, pyridin-3-ylmethyl, 3-methoxypropan-1-yl, 2-(N,N-dimethyl)-ethyl, 3-(2-oxopyrrolidin-1-yl)-propan-1-yl, 1,3-dimethoxy-propan-2-yl, and 1-methyl-azetidine-3-yl.

In another embodiment the invention provides compounds represented by formula (I) or (I') wherein $R^{13}$ is hydrogen.

In another embodiment the invention provides compounds represented by formula (I) or (I') wherein m is 0.

In another embodiment the invention provides compounds represented by formula (I) or (I') wherein m is 0 and X is CH.

In another embodiment the invention provides compounds represented by formula (I) or (I') wherein m is 0 and X is N.

In another embodiment the invention provides compounds represented by formula (I) or (I') wherein m is 1.

In another embodiment the invention provides compounds represented by formula (I) or (I') wherein p is 0.

In another embodiment the invention provides compounds represented by formula (I) or (I') wherein p is 1.

In a particular embodiment, the present invention provides compounds having a structural formula (I) as recited above wherein:
  X is CH;
  $R^1$ is $C_{1-4}$alkyl;
  $R^2$ is hydrogen;
  $R^3$ is a thiazolyl; wherein the thiazolyl may be optionally substituted on carbon by one or more $R^{10}$;
  $R^5$ is —OH, ethoxy, N-methylamino, or N-ethylamino;
  $R^6$ is a $C_{1-6}$alkyl which is optionally substituted on one or more carbon atom with one or more $R^{16}$;
  $R^{10}$ is trifluoromethyl, ethyl, or phenyl;
  $R^{13}$ is hydrogen;
  $R^{16}$, for each occurrence, is independently selected from the group consisting of —OH, fluoro, N-methylamino, N,N-dimethylamino, methoxy, ethoxy, methylsulfanyl, methylsulfonyl, piperidinyl, piperazinyl, morpholinyl, pyrrolidinyl, 2-oxopyrrolidinyl, pyrrolyl, imidazolyl, triazolyl, phenyl which may be optionally substituted with one or more halo, isoxazolyl, pyridinyl, and cyclopropyl.
  m is 0; and
  p is 0.

In a particular embodiment, the present invention provides compounds having a structural formula (I') as recited above wherein:
  X is CH;
  $R^1$ is $C_{1-4}$alkyl;
  $R^2$ is hydrogen;
  $R^3$ is a thiazolyl; wherein the thiazolyl may be optionally substituted on carbon by one or more $R^{10}$;
  $R^{5'}$ is —OH, ethoxy, N-methylamino, or N-ethylamino;
  $R^{6'}$ is a $C_{1-6}$alkyl which is optionally substituted on one or more carbon atom with one or more $R^{16}$;
  $R^{10}$ is trifluoromethyl, ethyl, or phenyl;
  $R^{13}$ is hydrogen;
  $R^{16}$, for each occurrence, is independently selected from the group consisting of —OH, fluoro, N-methylamino, N,N-dimethylamino, methoxy, ethoxy, methylsulfanyl, methylsulfonyl, piperidinyl, piperazinyl, morpholinyl, pyrrolidinyl, 2-oxopyrrolidinyl, pyrrolyl, imidazolyl, triazolyl, phenyl which may be optionally substituted with one or more halo, isoxazolyl, pyridinyl, and cyclopropyl;
  m is 0; and
  p is 0.

In a particular embodiment, the present invention provides compounds having a structural formula (I) as recited above wherein:
  X is CH;
  $R^1$ is ethyl;
  $R^2$ is hydrogen;
  $R^3$ is a thiazolyl; wherein the thiazolyl may be optionally substituted on carbon by one or more $R^{10}$;
  $R^5$ is —OH, ethoxy, N-methylamino, or N-ethylamino;
  $R^6$ is a $C^{1-6}$alkyl which is optionally substituted on one or more carbon atom with one or more $R^{16}$;
  $R^{10}$ is trifluoromethyl;
  $R^{13}$ is hydrogen;
  $R^{16}$, for each occurrence, is independently selected from —OH or $C_{1-6}$alkoxy;
  m is 0; and
  p is 0.

In a particular embodiment, the present invention provides compounds having a structural formula (I') as recited above wherein:
  X is CH;
  $R^1$ is ethyl;
  $R^2$ is hydrogen;
  $R^3$ is a thiazolyl; wherein the thiazolyl may be optionally substituted on carbon by one or more $R^{10}$;
  $R^{5'}$ is —OH, ethoxy, N-methylamino, or N-ethylamino;
  $R^{6'}$ is a $C^{1-6}$alkyl which is optionally substituted on one or more carbon atom with one or more $R^{16}$;
  $R^{10}$ is trifluoromethyl;
  $R^{13}$ is hydrogen;
  $R^{16}$, for each occurrence, is independently selected from —OH or $C_{1-6}$alkoxy;
  m is 0; and
  p is 0.

Particular compounds of the invention are the compounds of the Examples, and pharmaceutically acceptable salts thereof, each of which provides a further independent aspect of the invention.

In another embodiment, the invention provides pharmaceutical compositions comprising a pharmaceutically acceptable excipient or carrier and a compound represented by formula (I) or (I'), or a pharmaceutically acceptable salt thereof.

In a further aspect, the present invention provides a process for preparing a compound of formula (I) or (I'), or a pharmaceutically-acceptable salt thereof, wherein variable groups in the schemes below are as defined in formula (I) or (I') unless otherwise specified. In general, the compounds of formula (I) can be prepared by a palladium catalyzed Suzuki coupling reaction of a boronic ester or acid derivative (i) or (iv) and a halo derivative (ii) or (iii), as shown in Schemes I and II.

Likewise, the compounds of formula (I') can be prepared by a palladium catalyzed Suzuki coupling reaction of a boronic ester or acid derivative (i) or (iv') and a halo derivative (ii') or (iii), as shown in Schemes I' and II'. Typically, the coupling reaction is heated and is carried out in the presence of a base such as $Cs_2CO_3$.

Scheme I

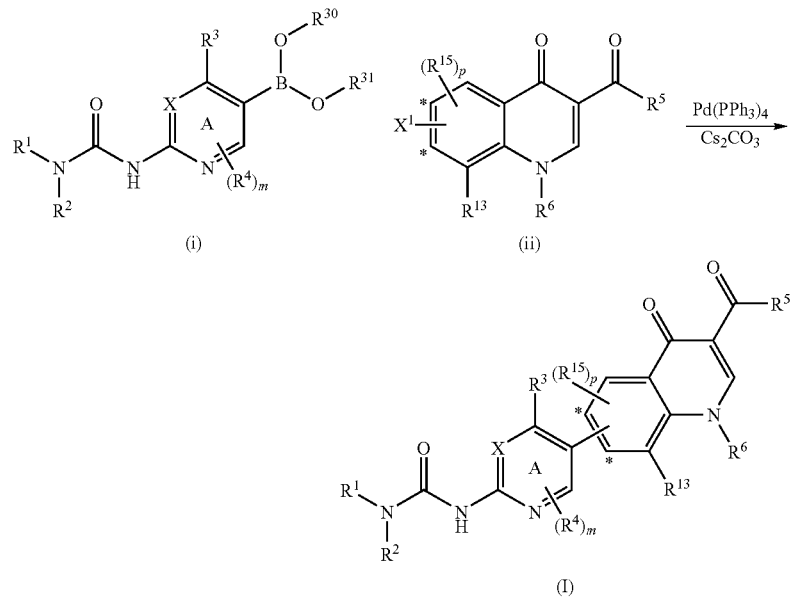

$X^1$ is a halo.
$R^{30}$ and $R^{31}$ are each independently hydrogen, an alkyl group or $R^{30}$ and $R^{31}$, together with
—O—B—O—, can form a cyclic boronic ester such as 4,4,5,5,-tetramethyl-1,3,2-dioxaborolan-2-yl.

Scheme I'

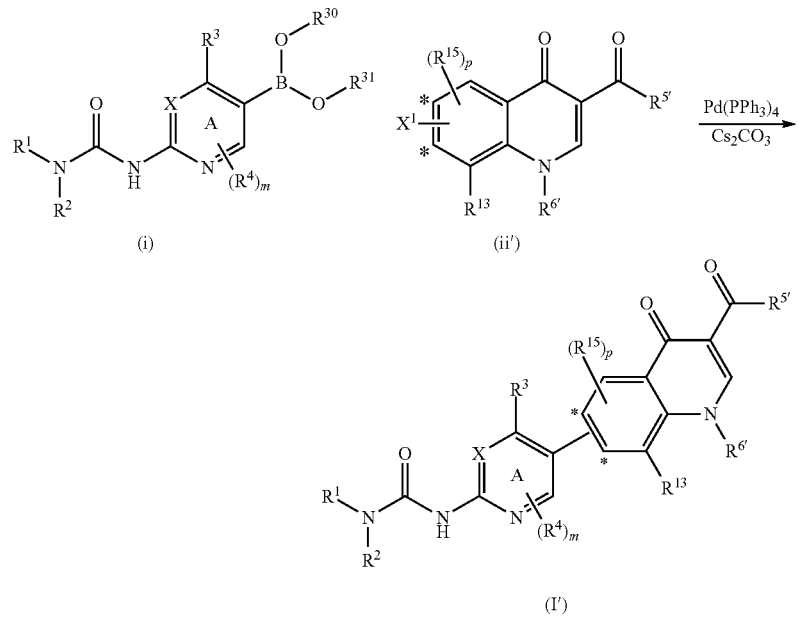

$X^1$ is a halo.
$R^{30}$ and $R^{31}$ are each independently hydrogen, an alkyl group or $R^{30}$ and $R^{31}$, together with
—O—B—O—, can form a cyclic boronic ester such as 4,4,5,5,-tetramethyl-1,3,2-dioxaborolan-2-yl.

Scheme II

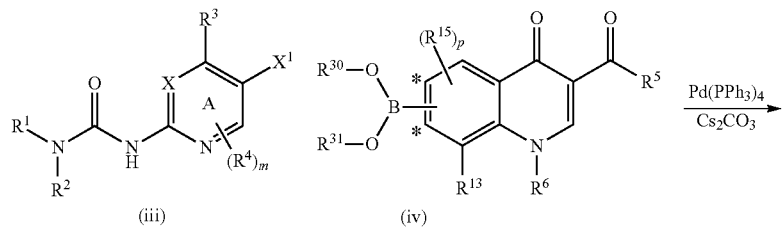

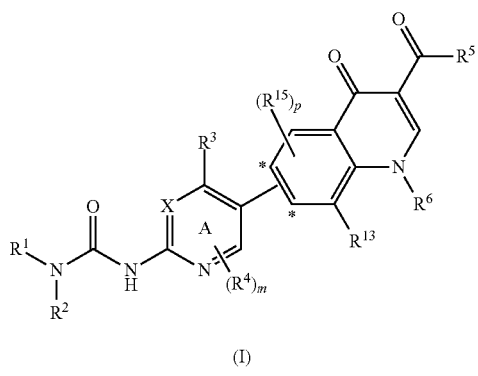

$X^1$ is a halo.

$R^{30}$ and $R^{31}$ are each independently hydrogen, an alkyl group or $R^{21}$ and $R^{22}$, together with —O—B—O—, can form a cyclic boronic ester such as 4,4,5,5,-tetramethyl-1,3,2-dioxaborolan-2-yl.

Scheme II'

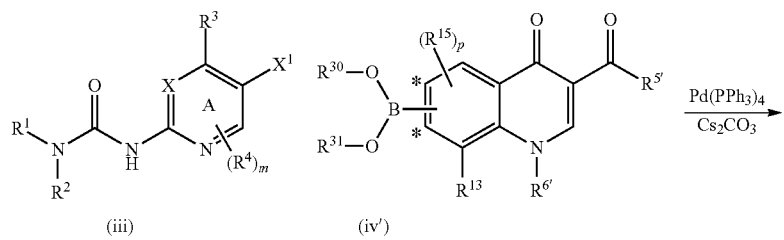

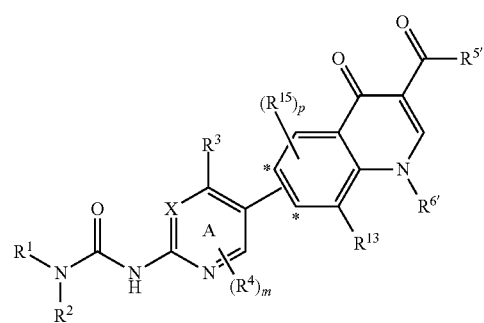

$X^1$ is a halo.

$R^{30}$ and $R^{31}$ are each independently hydrogen, an alkyl group or $R^{21}$ and $R^{22}$, together with —O—B—O—, can form a cyclic boronic ester such as 4,4,5,5,-tetramethyl-1,3,2-dioxaborolan-2-yl.

Boronic ester derivatives can be prepared by heating a halo derivative with a diboron compound such as 4,4,4',4',5,5,5',5'-octamethyl-2,2'-bi(1,3,2-dioxaborolane) in the presence of 1,1'-bis(diphenylphosphino)ferrocene-palladium dichloride in an organic solvent.

$R^5$ or $R^{5'}$ in Intermediate (ii), (ii'), (iv), and (iv') is typically an alkoxy group which is generally stable during the Suzuki coupling reaction. $R^5$ or $R^{5'}$ can be converted to an —OH group after the coupling reaction by treating the product with a strong base in a protic solvent such as water, an alcohol or a mixture of an alcohol and an organic solvent (e.g. THF/MeOH). $R^5$ or $R^{5'}$ can be converted to an amino, an N-alkylamino or an N,N-dialkylamino by heating the ester derivative with an amino, an N-alkylamino or an N,N-dialkylamino neat or in a solvent such as an alcohol.

The urea portion of the compounds of the invention can be prepared from an isocyanate derivative either before or after the Suzuki coupling reaction from an amine derivative. If the Suzuki coupling reaction is preformed before formation of the urea, the amine is protected with an amine protecting group. When forming the urea derivative, an isocyanate derivative (vi) is typically combined with the amine derivative (v) in an organic solvent and heated, as shown in Scheme III. The solvent can be aqueous, organic or a mixture of an aqueous miscible organic solvent and water.

Scheme III

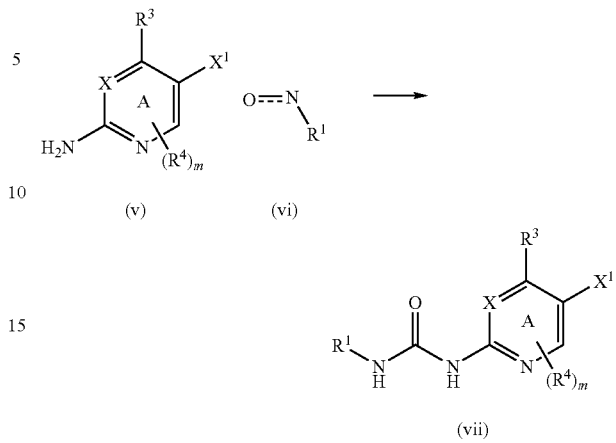

When $R^3$ is an aryl or a heteroaryl, a Suzuki coupling reaction can be used to attach it to ring A as shown in Scheme IV. Although Scheme IV shows the coupling reaction of $R^3$ occurring before the coupling reaction to link ring A to the 1,4-dihydroquinoline ring, the reactions could be preformed in the alternative order. When the $R^3$ group is attached before the coupling reaction to attach 1,4-dihydroquinoline ring, ring A can be brominated by heating it with 1-bromopyrrolidine-2,5-dione to form a substrate for the Suzuki coupling reaction shown in Scheme II.

Scheme IV

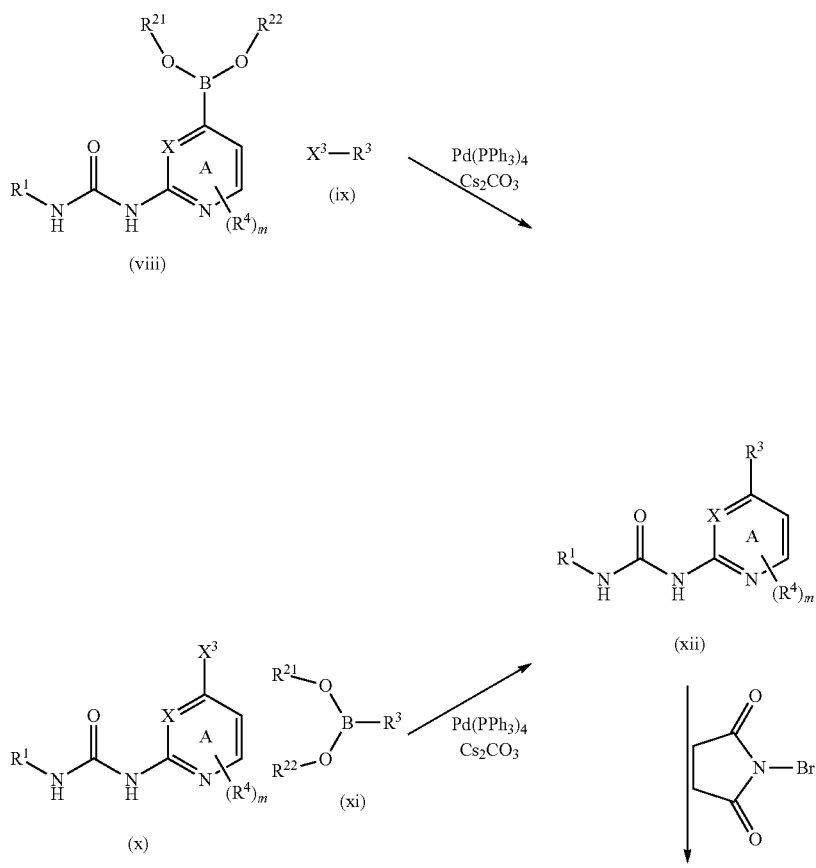

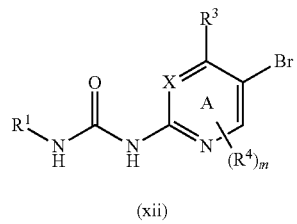

(xii)

$X^3$ is a halo.

Alternatively, when $R^3$ is a heterocyclyl, it can be prepared from an ester derivative either before or after coupling of the 1,4-dihydroquinoline ring to ring A. For example, when $R^3$ is a thiazolyl group, an ester derivative (xiii) can be converted to an amide (xiv) by treating it with a solution of ammonia in an alcohol. The amide derivative (xiv) can then be converted to a thioamide (xv) by treating the amide with Lawessons reagent. The thioamide (xv) is then heated with an α-halo-ketone or an α-halo-aldehyde (xvi) followed by treatment with an acid such as trifluoroacetic acid to form the thiazole (xvii) (see Scheme V). Although the thiazole ring is prepared before the Suzuki coupling reaction to attach 1,4-dihydroquinoline ring in Scheme V, it could also be prepared after the coupling reaction of the ester derivative to the 1,4-dihydroquinoline ring.

Scheme V

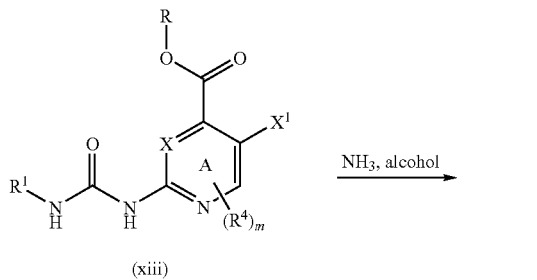

(xiii)

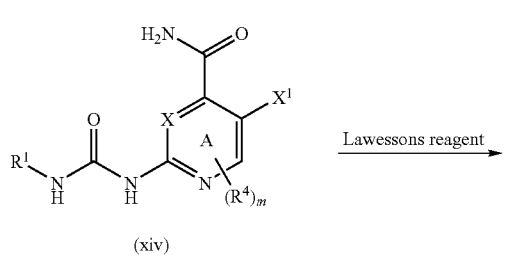

(xiv)

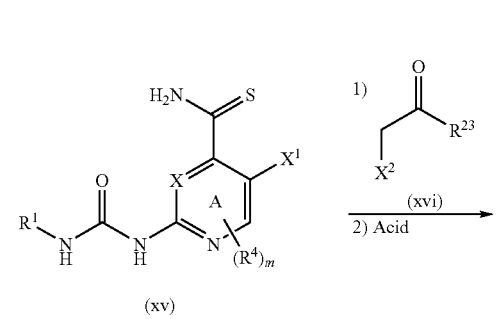

(xv)

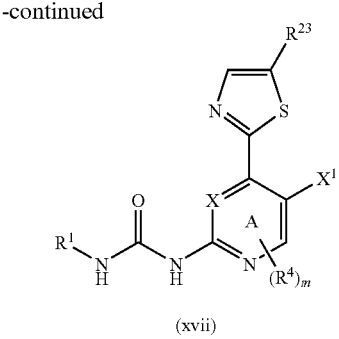

(xvii)

$X^2$ is a halo.
R is an alkyl.
$R^{23}$ is hydrogen, an optionally substituted alkyl, a carbocyclyl or a heterocyclyl.

When $R^3$ is tetrazolyl, it can be prepared by heating a cyano derivative with sodium azide and ammonium chloride in a solvent as shown in Scheme VI. An $R^3$ tetrazolyl group can be prepared by the reaction shown in Scheme VI either before or after coupling of the 1,4-dihydroquinoline ring to ring A.

Scheme VI

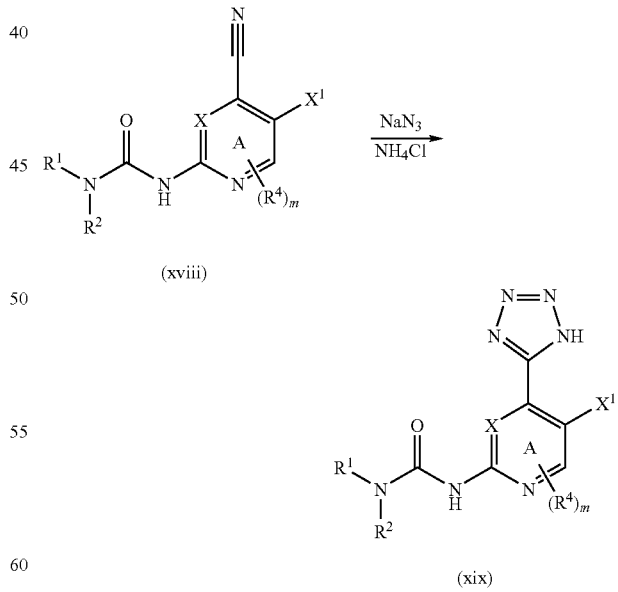

When $R^3$ is a 1,3,4-oxadiazolyl group, it can be prepared from an ester derivative (xx) by treating the ester with a base in to form a carboxylic acid (xxi). The carboxylic acid (xxi) is then coupled to a hydrazide derivative (xxii) in the presence of the amide coupling reagent HATU to form a dihydrazide derivative (xxiii). The dihydrazide (xxiii) is then treated with triphenyl phosphine in an aprotic organic solvent in the presence of an excess amount of an aprotic base to form a compound in which the $R^3$ group is 1,3,4-oxadiazolyl (xxiv) as shown in Scheme VII. An $R^3$ 1,3,4-oxadiazolyl group can be prepared by the reaction shown in Scheme VII either before or after coupling of the 1,4-dihydroquinoline ring to ring A.

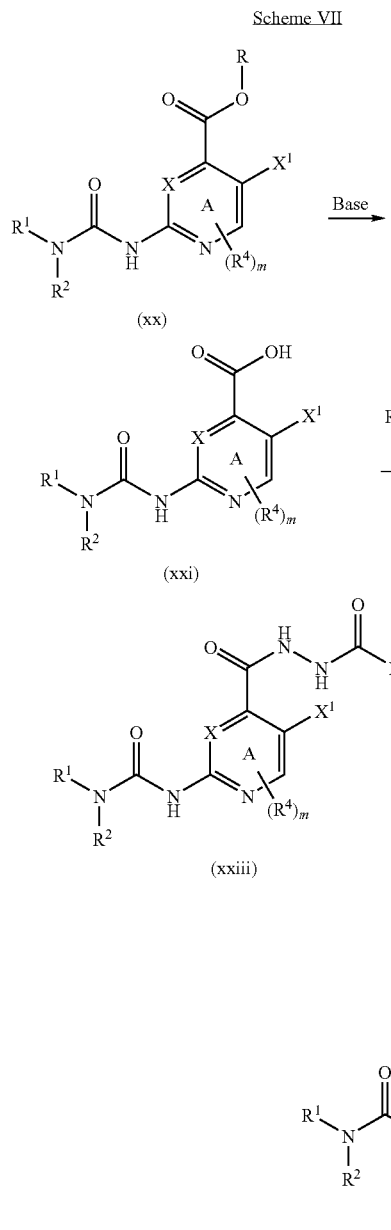

When $R^3$ is a 1,3,4-thiadiazolyl group, it can be prepared from a dihydrazide derivative (xxiii) (see Scheme VII for preparation of dihydrazide derivatives). The dihydrazide derivative (xxiii) is heated with phosphorous pentasulfide and hexamethyldisiloxane in an organic solvent to form a compound having an $R^3$ 1,3,4-thiadiazolyl group (xxv) as shown in Scheme VIII. An $R^3$ 1,3,4-thiadiazolyl group can be prepared by the reaction shown in Scheme VIII either before or after coupling of the 1,4-dihydroquinoline ring to ring A.

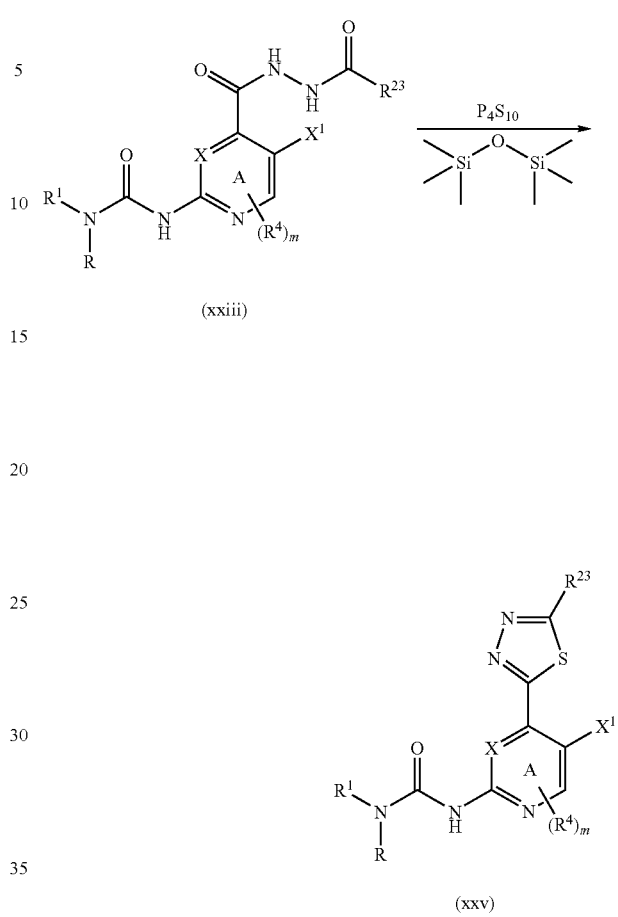

When $R^3$ is a 2-oxo-1,3,4-oxadiazolyl or a 2-thioxo-1,3,4-oxadiazolyl group, it can be prepared from a carboxylic acid (xxi) (see Scheme VII for preparation of the carboxylic acid derivative). The carboxylic acid derivative (xxi) is heated with hydrazine hydrate in an alcohol to form a hydrazide derivative (xxvi). The hydrazide derivative (xxvi) is then reacted with carbonyl diimidazole or di(1-H-imidazol-2-yl)methanethione (xxvii) in the presence of an aprotic base in an aprotic solvent to form a compound which has an $R^3$ 2-oxo-1,3,4-oxadiazolyl or a 2-thioxo-1,3,4-oxadiazolyl group (xxviii) as shown in Scheme IX. An $R^3$ 2-oxo-1,3,4-oxadiazolyl or a 2-thioxo-1,3,4-oxadiazolyl group can be prepared by the reaction shown in Scheme IX either before or after coupling of the 1,4-dihydroquinoline ring to ring A.

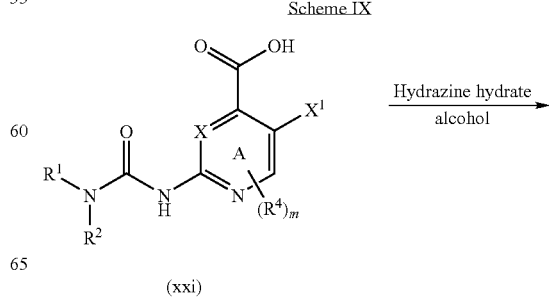

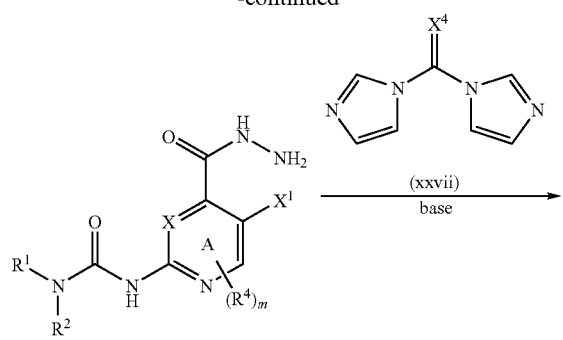

(xxvi)

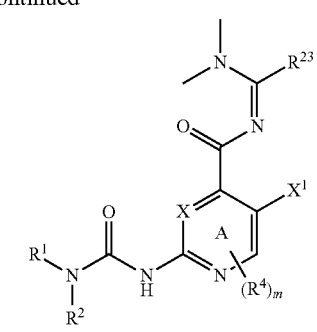

(xxxi)

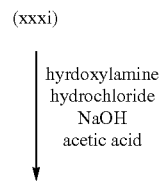

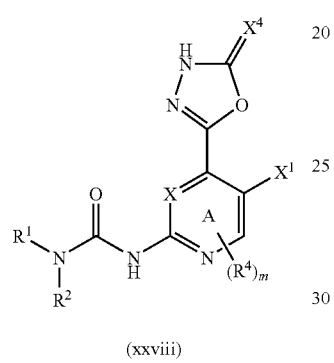

(xxviii)

$X^4$ is O or S.

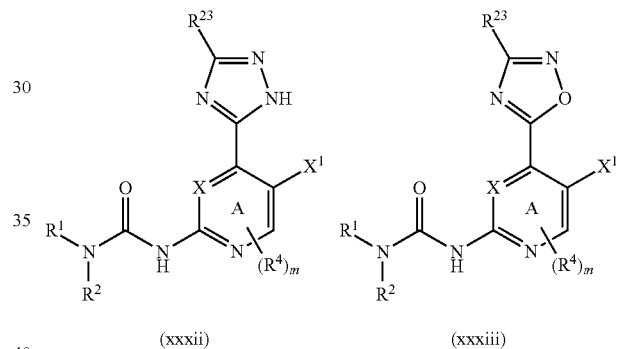

(xxxii)     (xxxiii)

When $R^3$ is a 1,2,4-triazolyl group, it can be prepared from an amide derivative (xxix) by heating it in 1-(N,N-dimethylamino)-1,1-dimethoxy-ethane (xxx) to form (xxxi) (xxxi) is then heated with acetohydrazide in acetic acid to form a compound that has an $R^3$ 1,2,4-triazolyl group (xxxii) as shown in Scheme X. An $R^3$ 1,2,4-triazolyl group can be prepared by the reaction shown in Scheme X either before or after coupling of the 1,4-dihydroquinoline ring to ring A.

When $R^3$ is a 1,2,4-oxadiazolyl group, it can be prepared from (xxxi) by heating (xxxi) with hydroxyl amine hydrochloride in a solution of sodium hydroxide in 70% acetic acid in dioxane to form a compound in which $R^3$ is a 1,2,4-oxadiazolyl group (xxxiii) as shown in Scheme X. An $R^3$ 1,2,4-oxadiazolyl group can be prepared by the reaction shown in Scheme X either before or after coupling of the 1,4-dihydroquinoline ring to ring A.

When $R^3$ is an imidazolyl group, it can be prepared from a cyano derivative (xvii) by stirring the cyano derivative (xvii) at room temperature in a solution of sodium methoxide in methanol for several hours. 1,1-Dimethoxy-2-aminoethane (xxxiv) is then added to the solution and it is heated to give a compound in which $R^3$ is an imidazolyl group (xxxv) as shown in Scheme XI. An $R^3$ imidazolyl group can be prepared by the reaction shown in Scheme XI either before or after coupling of the 1,4-dihydroquinoline ring to ring A.

Scheme X

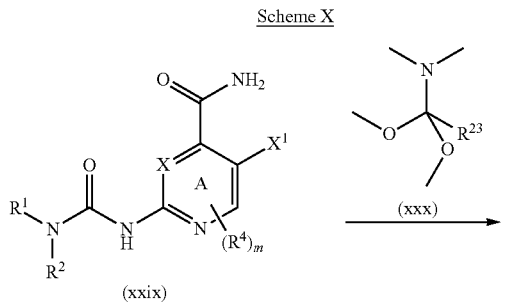

(xxix)

Scheme XI

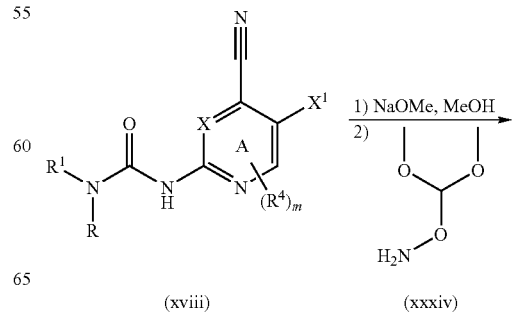

(xviii)     (xxxiv)

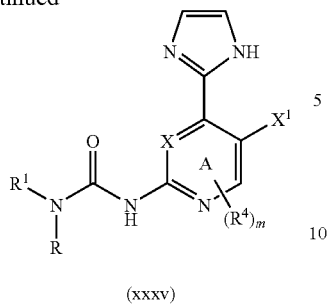

(xxxv)

The 1,4-dihydroquinoline derivative (xxxviii) can be prepared from an alkyl (Z)-3-(dimethylamino)-2-(2-fluoro-5-halobenzoyl)acrylate or an alkyl (Z)-3-(dimethylamino)-2-(2-fluoro-4-halobenzoyl)acrylate (xxxvi) by heating it with a primary amine (xxxvii) in the presence of a base as shown in Scheme XII.

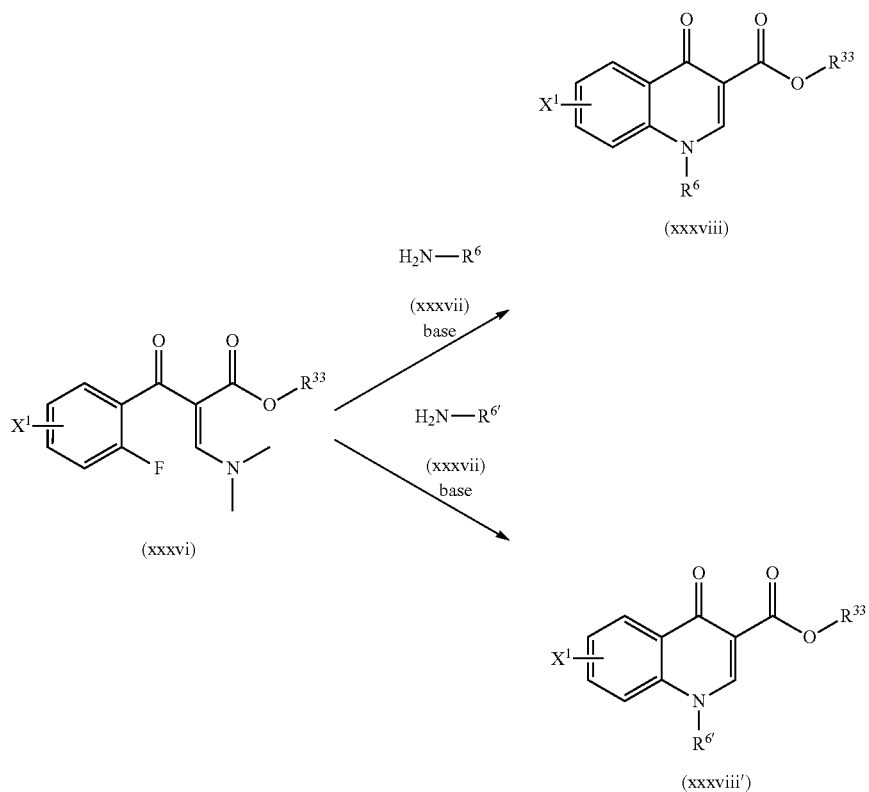

$R^{33}$ is an alkyl.

Alternatively, 1,4-dihydroquinoline derivative (xxxix) can be prepared by heating an analine (xl) in the presence of a dialkyl(alkoxymethylidene)propanedioate (xli) to form intermediate (xlii). Intermediate (lxii) can either be heated in a solvent to about 200° C. to 300° C. or it can be heated to at a lower temperature (e.g., about 80° C.-120° C.) in the presence of a dehydrating reagent such as Eaton's reagent to give 1,4-dihydroquinoline derivative (xxxix). 1,4-Dihydroquinoline derivative (xxxix) can be converted to 1,4-dihydroquinoline derivative (xxxviii) by heating it with an alkyl halide in the presence of a base such as potassium carbonate.

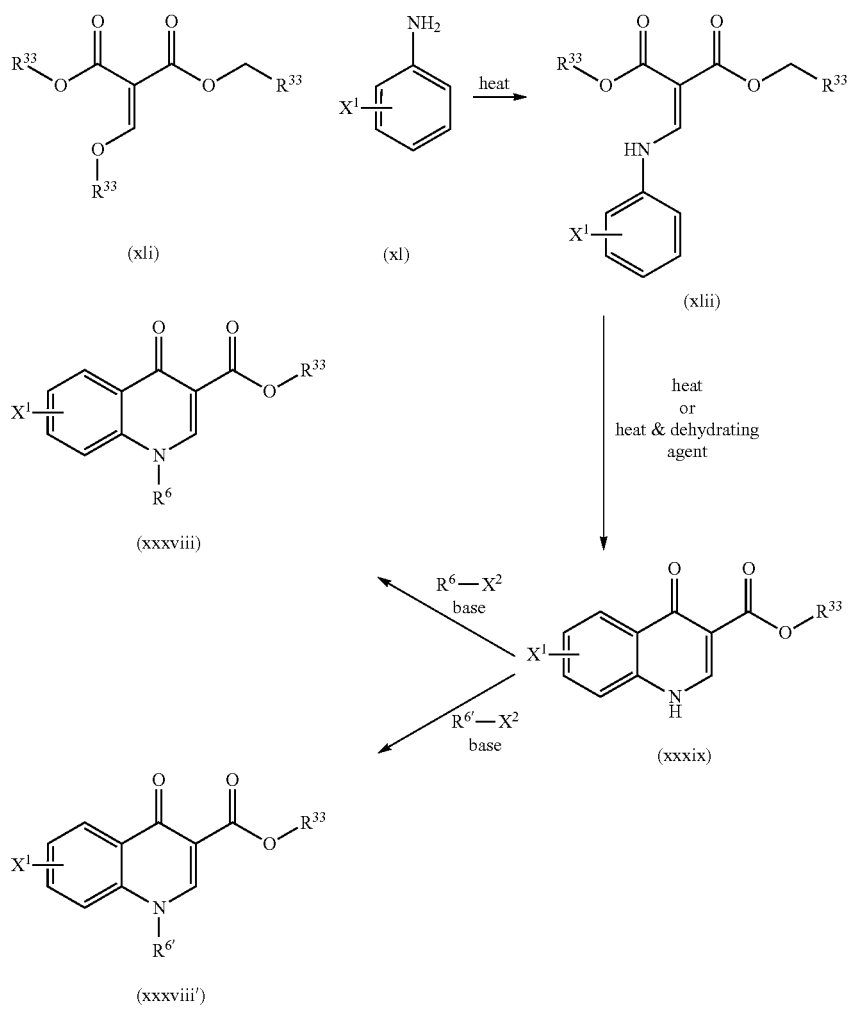

The formation of a pharmaceutically-acceptable salt is within the skill of an ordinary organic chemist using standard techniques.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art.

Introduction of substituents into a ring may convert one compound of the formula (I) into another compound of the formula (I). Likewise, introduction of substituents into a ring may convert one compound of the formula (I') into another compound of the formula (I'). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include oxidation of alkylthio to alkylsulphinyl or alkylsulphonyl.

The skilled organic chemist will be able to use and adapt the information contained and referenced within the above references, and accompanying Examples therein and also the Examples herein, to obtain necessary starting materials, and products. If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the Examples. It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon, or for example, an allyl group which may be removed, for example, by use of a palladium catalyst such as palladium acetate.

The protecting groups may be removed at any convenient stage in the synthesis using conventional techniques well known in the chemical art, or they may be removed during a later reaction step or work-up.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Enzyme Potency Testing Methods

*E. coli* GyrB ATPase Inhibition Activity: Compounds can be tested for inhibition of *E. coli* GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1 mM 1,4-Dithio-DL-threitol, 200 nM bovine serum albumin, 1.6 µg/ml sheared salmon sperm DNA, 400 pM *E. coli* GyrA, 400 pM *E. coli* GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid.

Plates can be read in an absorbance plate reader at 650 nm and percent inhibition values are calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

*E. coli* Topoisomerase IV ATPase Inhibition Activity: Compounds can be tested for inhibition of *E. coli* topoisomerase IV ATPase activity as described above for *E. coli* GyrB except the 30 µl reactions contained the following: 20 mM TRIS buffer pH 8, 50 mM ammonium acetate, 8 mM magnesium chloride, 5% glycerol, 5 mM 1,4-Dithio-DL-threitol, 0.005% Brij-35, 5 µg/ml sheared salmon sperm DNA, 500 pM *E. coli* ParC, 500 pM *E. coli* ParE, 160 µM ATP, and compound in dimethylsulfoxide. An $IC_{50}$ measurement of compound potency for each compound can be determined from reactions performed in the presence of 10 different compound concentrations.

Many of the compounds of the invention were tested in an assay substantially similar to the assays described above for measuring the inhibition of *E. coli* GyrB ATPase and *E. coli* Topoisomerase IV ATPase and had $IC_{50}$ values of <200 µM in one or both assays.

*S. aureus* GyrB ATPase Inhibition Activity: Compounds may be tested for inhibition of *S. aureus* GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1.0 mM 1,4-Dithio-DL-threitol, 200 nM bovine serum albumin, 1.0 µg/ml sheared salmon sperm DNA, 250 pM *E. coli* GyrA, 250 pM *S. aureus* GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid. Plates can be read in an absorbance plate reader at 650 nm and percent inhibition values can be calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

The compounds in the table below were tested in an assay substantially similar to the assay described above for measuring the inhibition of S. aureus GyrB ATPase and were found to have a percent inhibition of S. aureus GyrB ATPase a 1 μM as shown in the table. If a compound was tested more than once, a percent inhibition value for each test is shown in the table.

| Example | % Inhibition |
|---|---|
| 1 | 100 |
|  | 104 |
| 2 | 100 |
| 3 | No data |
| 4 | 98 |
| 5 | No data |
| 6 | No data |
| 7 | 100 |
| 8 | No data |
| 9 | 106 |
| 10 | 99 |
| 11 | 102 |
| 12 | 93 |
| 13 | 98 |
| 14 | No data |
| 15 | 101 |
| 16 | 101 |
| 17 | 103 |
| 18 | 98 |
| 19 | 98 |
| 20 | 96 |
| 21 | 98 |
| 22 | 99 |
| 23 | 101 |
| 24 | 99 |
| 25 | 99 |
| 26 |  |
| 27 | 99 |
| 28 | 97 |
| 29 | No data |
| 30 | 95 |
| 31 | No data |
| 32 | 98 |
| 33 | 97 |
|  | 109 |
| 34 | 100 |
| 35 | No data |
| 36 | 64 |
| 37 | 96 |
| 38 | 99 |
| 39 | 101 |
| 40 | No data |
| 41 | 105 |
| 42 | 113 |
| 43 | No data |
| 44 | 98 |
| 45 | No data |
| 46 | No data |
| 47 | No data |
| 48 | 106 |
| 49 | No data |
| 50 | No data |
| 51 | No data |
| 52 | No data |
| 53 | No data |
| 54 | No data |
| 55 | No data |
| 56 | No data |
| 57 | No data |
| 58 | No data |
| 59 | No data |
| 60 | No data |
| 61 | No data |
| 62 | No data |
| 63 | No data |
| 64 | No data |
| 65 | No data |
| 66 | No data |
| 67 | No data |
| 68 | No data |
| 69 | No data |
| 70 | No data |
| 71 | 107 |
| 72 | 103 |
| 73 | 105 |
| 74 | 103 |
| 75 | 102 |
| 76 | 110 |
| 77 | 110 |
| 78 | 102 |
| 79 | 97 |
| 80 | 96 |
| 81 | 96 |
| 82 | 111 |
| 83 | 96 |
| 84 | 95 |
| 85 | 96 |
| 86 | 98 |
| 87 | 96 |
| 88 | 90 |
| 89 | 91 |
| 90 | 97 |
| 91 | No data |
| 92 | No data |
| 93 | 95 |
| 94 | 95 |
| 95 | 109 |
| 96 | 95 |
| 97 | No data |
| 98 | No data |
| 99 | No data |
| 100 | No data |
| 101 | No data |
| 102 | No data |
| 103 | No data |
| 104 | No data |
| 105 | No data |
| 106 | No data |
| 107 | No data |
| 108 | No data |
| 109 | No data |
| 110 | No data |
| 111 | No data |
| 112 | No data |
| 113 | No data |
| 114 | No data |
| 115 | No data |
| 116 | No data |
| 117 | No data |
| 118 | No data |
| 119 | No data |
| 120 | No data |
| 121 | No data |
| 122 | 95 |
| 123 | 95 |
| 124 | 87 |
| 125 | 93 |
| 126 | 117 |
| 127 | 117 |
| 128 | 92 |
| 129 | 93 |
| 130 | 101 |
| 131 | No data |
| 132 | No data |
| 133 | No data |
| 134 | No data |
| 135 | No data |
| 136 | No data |
| 137 | No data |
| 138 | No data |
| 139 | No data |
| 140 | 95 |

| Example | % Inhibition |
|---|---|
| 141 | 97 |
| 142 | 97 |
| 143 | 95 |
| 144 | 94 |
| 145 | 92 |
| 146 | No data |
| 147 | 102 |
| 148 | 93 |
| 149 | 93 |
| 150 | No data |
| 151 | No data |
| 152 | 95 |
|  | 106 |
| 153 | 105 |
| 154 | 107 |
| 155 | 94 |
| 156 | 105 |
| 157 | 103 |
| 158 | 106 |
| 159 | 105 |
| 160 | 103 |
| 161 | 101 |
| 162 | 106 |
| 163 | 106 |
| 164 | 107 |
| 165 | 109 |
| 166 | 104 |
| 167 | 109 |
| 168 | 102 |
| 169 | 105 |
| 170 | 102 |
| 171 | 112 |
| 172 | 107 |
| 173 | No data |
| 174 | No data |
| 175 | No data |
| 176 | No data |
| 177 | No data |
| 178 | No data |
| 179 | No data |
| 180 | No data |
| 181 | No data |
| 182 | No data |
| 183 | No data |
| 184 | No data |
| 185 | No data |
| 186 | No data |
| 187 | No data |
| 188 | No data |
| 189 | 100 |
| 190 | No data |
| 191 | 94 |
| 192 | 92 |
| 193 | 93 |
| 194 | 93 |
| 195 | 98 |
| 196 | 97 |
| 197 | 116 |
| 198 | 108 |
| 199 | 103 |
| 200 | 111 |
| 201 | No data |
| 202 | 103 |
| 203 | 87 |
| 204 | No data |
| 205 | 94 |
| 206 | 92 |
| 207 | 93 |
| 208 | 97 |
| 209 | No data |
| 210 | 93 |
| 211 | 97 |
| 212 | 94 |
| 213 | 94 |
| 214 | 118 |
| 215 | 120 |
| 216 | 109 |
| 217 | 105 |
| 218 | 97 |
| 219 | 86 |
| 220 | 97 |
| 221 | 72 |
| 222 | 106 |
| 223 | 98 |
| 224 | 96 |
| 225 | 95 |
| 226 | 94 |
| 227 | 91 |
| 228 | 104 |
| 229 | 106 |
| 230 | 102 |
| 231 | No data |
| 232 | 98 |
| 233 | No data |
| 234 | No data |
| 235 | No data |
| 236 | No data |
| 237 | 103 |
| 238 | 97 |
| 239 | No data |
| 240 | No data |
| 241 | 105 |
|  | 100 |
|  | 102 |
| 242 | 104 |
| 243 | 116 |
| 244 | 111 |
| 245 | 105 |
| 246 | 104 |
| 247 | 115 |
| 248 | 103 |
| 249 | 113 |
| 250 | 112 |
| 251 | 113 |
| 252 | 105 |
| 253 | No data |
| 254 | No data |
| 255 | No data |
| 256 | No data |
| 257 | No data |
| 258 | No data |
| 259 | No data |
| 260 | No data |
| 261 | No data |
| 262 | No data |
| 263 | No data |
| 264 | No data |
| 265 | No data |
| 266 | No data |
| 267 | No data |
| 268 | No data |
| 269 | No data |
| 270 | No data |
| 271 | No data |
| 272 | No data |
| 273 | No data |
| 274 | No data |
| 275 | No data |
| 276 | 106 |
| 277 | 103 |
| 278 | 101 |
| 279 | 103 |
| 280 | 103 |
| 281 | 106 |
| 282 | 105 |
| 283 | 102 |
| 284 | 107 |
| 285 | 105 |
| 286 | 102 |
| 287 | 100 |
| 288 | 99 |
| 289 | 103 |
| 290 | 100 |
| 291 | 107 |
| 292 | 102 |
| 293 | 106 |

-continued

| Example | % Inhibition |
|---|---|
| 294 | 109 |
| 295 | No data |
| 296 | No data |
| 297 | No data |
| 298 | No data |
| 299 | No data |
| 300 | No data |
| 301 | No data |
| 302 | No data |
| 302 | No data |
| 304 | No data |
| 305 | 103 |
| 306 | 105 |
|  | 100 |
|  | 102 |
| 307 | 105 |
| 308 | 111 |
| 309 | 109 |
| 310 | 106 |
| 311 | 100 |
| 312 | 105 |
| 313 | 103 |
| 314 | 114 |
| 315 | No data |
| 316 | No data |
| 317 | No data |
| 318 | No data |
| 319 | No data |
| 320 | 98 |
| 321 | 100 |
| 322 | 96 |
| 323 | 106 |
| 324 | No data |
| 325 | 96 |
| 326 | 97 |
| 327 | 100 |
| 328 | 109 |
| 329 | 97 |
| 330 | 109 |
| 331 | 109 |
| 332 | 109 |
| 333 | 106 |
| 334 | 95 |
| 335 | 107 |
| 336 | 109 |
| 337 | 106 |
| 338 | 99 |
| 339 | 109 |
| 340 | 93 |
| 341 | 99 |
| 342 | 99 |
| 343 | 98 |
| 344 | 95 |
| 345 | 98 |
| 346 | 87 |
| 347 | 100 |
| 348 | 98 |
| 349 | 108 |
| 350 | 96 |
| 351 | 95 |
| 352 | 88 |
| 353 | 99 |
| 354 | 98 |
| 355 | 87 |
| 356 | 85 |
| 357 | 87 |
| 358 | 95 |
| 359 | 92 |
| 360 | No data |
| 361 | 97 |
| 362 | 94 |
| 363 | 95 |
| 364 | 97 |
| 365 | 99 |
| 366 | 99 |
| 367 | 100 |
| 368 | 87 |
| 369 | 97 |
| 370 | 98 |
| 371 | 98 |
| 372 | 98 |
| 373 | 94 |
| 374 | 86 |
| 375 | 99 |
| 376 | 108 |
| 377 | 106 |
| 378 | 107 |
| 379 | 97 |
| 380 | No data |

Bacterial Susceptibility Testing Methods

Compounds may be tested for antimicrobial activity by susceptibility testing in liquid media. Compounds may be dissolved in dimethylsulfoxide and tested in 10 doubling dilutions in the susceptibility assays. The organisms used in the assay may be grown overnight on suitable agar media and then suspended in a liquid medium appropriate for the growth of the organism. The suspension can be a 0.5 McFarland and a further 1 in 10 dilution can be made into the same liquid medium to prepare the final organism suspension in 100 µL. Plates can be incubated under appropriate conditions at 37° C. for 24 hrs prior to reading. The Minimum Inhibitory Concentration (MIC) may be determined as the lowest drug concentration able to reduce growth by 80% or more.

In an assay comparable to the above, Example 9 had an MIC of 0.02 µM against *Streptococcus pneumoniae*.

According to a further feature of the invention there is provided a compound of the formula (I) or (I'), or a pharmaceutically-acceptable salt thereof, for use in a method of treatment of the human or animal body by therapy.

In one embodiment, the invention provides a method of treating a bacterial infection in an animal, such as a human, comprising administering to the animal or human an effective amount of a compound of any one of formulas (I) or (I'), or a pharmaceutically acceptable salt thereof.

We have found that compounds of the present invention inhibit bacterial DNA gyrase and/or topoisomerase IV and are therefore of interest for their antibacterial effects. In one aspect of the invention the compounds of the invention inhibit bacterial DNA gyrase and are therefore of interest for their antibacterial effects. In one aspect of the invention, the compounds of the invention inhibit topoisomerase IV and are therefore of interest for their antibacterial effects. In one aspect of the invention, the compounds of the invention inhibit both DNA gyrase and topoisomerase IV and are therefore of interest for their antibacterial effects. Thus, the compounds of the invention are useful in treating or preventing bacterial infections.

In one aspect of the invention an "infection" or "bacterial infection" refers to an infection caused by *Acinetobacter baumanii*. In one aspect of the invention an "infection" or "bacterial infection" refers to an infection caused by *Acinetobacter haemolyticus*. In one aspect of the invention an "infection" or "bacterial infection" refers to an infection caused by *Acinetobacter junii*. In one aspect of the invention an "infection" or "bacterial infection" refers to an infection caused by *Acinetobacter johnsonii*. In one aspect of the invention an "infection" or "bacterial infection" refers to an infection caused by *Acinetobacter lwoffi*. In one aspect of the invention an "infection" or "bacterial infection" refers to an infection caused by *Bacteroides bivius*. In one aspect of the invention an "infection" or "bacterial infection" refers to an infection caused by *Bacteroides fragilis*. In one aspect of the invention an "infection" or "bacterial infection" refers to an infection caused by *Burkholderia cepacia*. In one aspect of the invention an "infection" or "bacterial infection" refers to an infection caused by *Campylobacter jejuni*. In one aspect of the invention an "infection" or "bacterial infection" refers to an infection caused by *Chlamydia pneumoniae*. In one aspect of the invention an "infection" or "bacterial infection" refers to an infection caused by *Chlamydia urealyticus*. In one aspect of the invention an "infection" or "bacterial infection" refers to an infection caused by *Chlamydophila pneumoniae*. In one aspect of the invention an "infection" or "bacterial infection" refers to an infection caused by *Clostridium difficile*. In one aspect of the invention an "infection" or "bacterial infection" refers to an infection caused by *Enterobacter aerogenes*. In one aspect of the invention an "infection" or "bacterial infection" refers to an infection caused by *Enterobacter cloacae*. In one aspect of the invention an "infection" or "bacterial infection" refers to an infection caused by *Enterococcus faecalis*. In one aspect of the invention an "infection" or "bacterial infection" refers to an infection caused by *Enterococcus faecium*. In one aspect of the invention an "infection" or "bacterial infection" refers to an infection caused by *Escherichia coli*. In one aspect of the invention an "infection" or "bacterial infection" refers to an infection caused by *Gardnerella vaginalis*. In one aspect of the invention an "infection" or "bacterial infection" refers to an infection caused by *Haemophilus parainfluenzae*. In one aspect of the invention an "infection" or "bacterial infection" refers to an infection caused by *Haemophilus influenzae*. In one aspect of the invention an "infection" or "bacterial infection" refers to an infection caused by *Helicobacter pylori*. In one aspect of the invention an "infection" or "bacterial infection" refers to an infection caused by *Klebsiella pneumoniae*. In one aspect of the invention an "infection" or "bacterial infection" refers to an infection caused by *Legionella pneumophila*. In one aspect of the invention an "infection" or "bacterial infection" refers to an infection caused by Methicillin-resistant *Staphylococcus aureus*. In one aspect of the invention an "infection" or "bacterial infection" refers to an infection caused by Methicillin-susceptible *Staphylococcus aureus*. In one aspect of the invention an "infection" or "bacterial infection" refers to an infection caused by *Moraxella catarrhalis*. In one aspect of the invention an "infection" or "bacterial infection" refers to an infection caused by *Morganella morganii*. In one aspect of the invention an "infection" or "bacterial infection" refers to an infection caused by *Mycoplasma pneumoniae*. In one aspect of the invention an "infection" or "bacterial infection" refers to an infection caused by *Neisseria gonorrhoeae*. In one aspect of the invention an "infection" or "bacterial infection" refers to an infection caused by Penicillin-resistant *Streptococcus pneumoniae*. In one aspect of the invention an "infection" or "bacterial infection" refers to an infection caused by Penicillin-susceptible *Streptococcus pneumoniae*. In one aspect of the invention an "infection" or "bacterial infection" refers to an infection caused by *Peptostreptococcus magnus*. In one aspect of the invention an "infection" or "bacterial infection" refers to an infection caused by *Peptostreptococcus micros*. In one aspect of the invention an "infection" or "bacterial infection" refers to an infection caused by *Peptostreptococcus anaerobius*. In one aspect of the invention an "infection" or "bacterial infection" refers to an infection caused by *Peptostreptococcus asaccharolyticus*. In one aspect of the invention an "infection" or "bacterial infection" refers to an infection caused by *Peptostreptococcus prevotii*. In one aspect of the invention an "infection" or "bacterial infection" refers to an infection caused by *Peptostreptococcus tetradius*. In one aspect of the invention an "infection" or "bacterial infection" refers to an infection caused by *Peptostreptococcus vaginalis*. In one aspect of the invention an "infection" or "bacterial infection" refers to an infection caused by *Proteus mirabilis*. In one aspect of the invention an "infection" or "bacterial infection" refers to an infection caused by *Pseudomonas aeruginosa*. In one aspect of the invention an "infection" or "bacterial infection" refers to an infection caused by Quinolone-Resistant *Staphylococcus aureus*. In one aspect of the invention an "infection" or "bacterial infection" refers to an infection caused by Quinolone-Resistant *Staphylococcus epidermis*. In one aspect of the invention an "infection" or "bacterial infection" refers to an infection caused by *Salmonella typhi*. In one aspect of the invention an "infection" or "bacterial infection" refers to an infection caused by *Salmonella paratyphi*. In one aspect of the invention an "infection" or "bacterial infection" refers to an infection caused by *Salmonella enteritidis*. In one aspect of the invention an "infection" or "bacterial infection" refers to an infection caused by *Salmonella typhimurium*. In one aspect of the invention an "infection" or "bacterial infection" refers to an infection caused by *Serratia marcescens*. In one aspect of the invention an "infection" or "bacterial infection" refers to an infection caused by *Staphylococcus aureus*. In one aspect of the invention an "infection" or "bacterial infection" refers to an infection caused by *Staphylococcus epidermidis*. In one aspect of the invention an "infection" or "bacterial infection" refers to an infection caused by *Staphylococcus saprophyticus*. In one aspect of the invention an "infection" or "bacterial infection" refers to an infection caused by *Streptoccocus agalactiae*. In one aspect of the invention an "infection" or "bacterial infection" refers to an infection caused by *Streptococcus pneumoniae*. In one aspect of the invention an "infection" or "bacterial infection" refers to an infection caused by *Streptococcus pyogenes*. In one aspect of the invention an "infection" or "bacterial infection" refers to an infection caused by *Stenotrophomonas maltophilia*. In one aspect of the invention an "infection" or "bacterial infection" refers to an infection caused by *Ureaplasma urealyticum*. In one aspect of the invention an "infection" or "bacterial infection" refers to an infection caused by Vancomycin-Resistant *Enterococcus faecium*. In one aspect of the invention an "infection" or "bacterial infection" refers to an infection caused by Vancomycin-Resistant *Enterococcus faecalis*. In one aspect of the invention an "infection" or "bacterial infection" refers to an infection caused by Vancomycin-Resistant *Staphylococcus aureus*. In one aspect of the invention an "infection" or "bacterial infection" refers to an infection caused by Vancomycin-Resistant *Staphylococcus epidermis*. In one aspect of the invention an "infection" or "bacterial infection" refers to an infection caused by *Mycobacterium tuberculosis*. In one aspect of the invention an "infection" or "bacterial infection" refers to an infection caused by *Clostridium perfringens*. In one aspect of the invention an "infection" or "bacterial infection" refers to an infection caused by *Klebsiella oxytoca*. In one aspect of the invention an "infection" or "bacterial infection" refers to an infection caused by Neisseria miningitidis. In one aspect of the invention an "infection" or "bacterial infection" refers to an infection caused by *Fusobacterium* spp. In one aspect of the invention an "infection" or "bacterial infection" refers to an infection caused by *Peptococcus* spp. In one aspect of the invention an "infection" or "bacterial infection" refers to an infection caused by *Proteus vulgaris*. In one aspect of the invention an "infection" or "bacterial infection" refers to an infection caused by Coagulase-negative *Staphylococcus* (including *Staphylococcus lugdunensis, Staphylococcus capitis, Staphylococcus hominis*, and *Staphylococcus saprophyticus*).

In one aspect of the invention an "infection" or "bacterial infection" refers to an infection caused by *Acinetobacter* spp. In one aspect of the invention an "infection" or "bacterial infection" refers to an infection caused by *Bacteroides* spp. In one aspect of the invention an "infection" or "bacterial infection" refers to an infection caused by *Burkholderia* spp. In one aspect of the invention an "infection" or "bacterial infection" refers to an infection caused by *Campylobacter* spp. In one aspect of the invention an "infection" or "bacterial infection" refers to an infection caused by *Chlamydia* spp. In one aspect of the invention an "infection" or "bacterial infection" refers to an infection caused by *Chlamydophila* spp. In one aspect of the invention an "infection" or "bacterial infection" refers to an infection caused by *Clostridium* spp. In one aspect of the invention an "infection" or "bacterial infection" refers to an infection caused by *Enterobacter* spp. In one aspect of the invention an "infection" or "bacterial infection" refers to an infection caused by *Enterococcus* spp. In one aspect of the invention an "infection" or "bacterial infection" refers to an infection caused by *Escherichia* spp. In one aspect of the invention an "infection" or "bacterial infection" refers to an infection caused by *Gardnerella* spp. In one aspect of the invention an "infection" or "bacterial infection" refers to an infection caused by *Haemophilus* spp. In one aspect of the invention an "infection" or "bacterial infection" refers to an infection caused by *Helicobacter* spp. In one aspect of the invention an "infection" or "bacterial infection" refers to an infection caused by *Klebsiella* spp. In one aspect of the invention an "infection" or "bacterial infection" refers to an infection caused by *Legionella* spp. In one aspect of the invention an "infection" or "bacterial infection" refers to an infection caused by *Moraxella* spp. In one aspect of the invention an "infection" or "bacterial infection" refers to an infection caused by *Morganella* spp. In one aspect of the invention an "infection" or "bacterial infection" refers to an infection caused by *Mycoplasma* spp. In one aspect of the invention an "infection" or "bacterial infection" refers to an infection caused by *Neisseria* spp. In one aspect of the invention an "infection" or "bacterial infection" refers to an infection caused by *Peptostreptococcus* spp. In one aspect of the invention an "infection" or "bacterial infection" refers to an infection caused by *Proteus* spp. In one aspect of the invention an "infection" or "bacterial infection" refers to an infection caused by *Pseudomonas* spp. In one aspect of the invention an "infection" or "bacterial infection" refers to an infection caused by *Salmonella* spp. In one aspect of the invention an "infection" or "bacterial infection" refers to an infection caused by *Serratia* spp. In one aspect of the invention an "infection" or "bacterial infection" refers to an infection caused by *Staphylococcus* spp. In one aspect of the invention an "infection" or "bacterial infection" refers to an infection caused by *Streptoccocus* spp. In one aspect of the invention an "infection" or "bacterial infection" refers to an infection caused by *Stenotrophomonas* spp. In one aspect of the invention an "infection" or "bacterial infection" refers to an infection caused by *Ureaplasma* spp. In one aspect of the invention an "infection" or "bacterial infection" refers to an infection caused by aerobes. In one aspect of the invention an "infection" or "bacterial infection" refers to an infection caused by obligate anaerobes. In one aspect of the invention an "infection" or "bacterial infection" refers to an infection caused by facultative anaerobes. In one aspect of the invention an "infection" or "bacterial infection" refers to an infection caused by gram-positive bacteria. In one aspect of the invention an "infection" or "bacterial infection" refers to an infection caused by gram-negative bacteria. In one aspect of the invention an "infection" or "bacterial infection" refers to an infection caused by gram-variable bacteria. In one aspect of the invention an "infection" or "bacterial infection" refers to an infection caused by atypical respiratory pathogens. In one aspect of the invention an "infection" or "bacterial infection" refers to an infection caused by Enterics. In one aspect of the invention an "infection" or "bacterial infection" refers to an infection caused by Shigella spp. In one aspect of the invention an "infection" or "bacterial infection" refers to an infection caused by Citrobacter.

In one aspect of the invention "infection" or "bacterial infection" refers to a gynecological infection. In one aspect of the invention "infection" or "bacterial infection" refers to a respiratory tract infection (RTI). In one aspect of the invention "infection" or "bacterial infection" refers to a sexually transmitted disease. In one aspect of the invention "infection" or "bacterial infection" refers to a urinary tract infection. In one aspect of the invention "infection" or "bacterial infection" refers to acute exacerbation of chronic bronchitis (ACEB). In one aspect of the invention "infection" or "bacterial infection" refers to acute otitis media. In one aspect of the invention "infection" or "bacterial infection" refers to acute sinusitis. In one aspect of the invention "infection" or "bacterial infection" refers to an infection caused by drug resistant bacteria. In one aspect of the invention "infection" or "bacterial infection" refers to catheter-related sepsis. In one aspect of the invention "infection" or "bacterial infection" refers to chancroid. In one aspect of the invention "infection" or "bacterial infection" refers to *chlamydia*. In one aspect of the invention "infection" or "bacterial infection" refers to community-acquired pneumonia (CAP). In one aspect of the invention "infection" or "bacterial infection" refers to complicated skin and skin structure infection. In one aspect of the invention "infection" or "bacterial infection" refers to uncomplicated skin and skin structure infection. In one aspect of the invention "infection" or "bacterial infection" refers to endocarditis. In one aspect of the invention "infection" or "bacterial infection" refers to febrile neutropenia. In one aspect of the invention "infection" or "bacterial infection" refers to gonococcal cervicitis. In one aspect of the invention "infection" or "bacterial infection" refers to gonococcal urethritis. In one aspect of the invention "infection" or "bacterial infection" refers to hospital-acquired pneumonia (HAP). In one aspect of the invention "infection" or "bacterial infection" refers to osteomyelitis. In one aspect of the invention "infection" or "bacterial infection" refers to sepsis. In one aspect of the invention "infection" or "bacterial infection" refers to syphilis. In one aspect of the invention "infection" or "bacterial infection" refers to ventilator-associated pneumonia. In one aspect of the invention "infection" or "bacterial infection" refers to intraabdominal infections. In one aspect of the invention "infection" or "bacterial infection" refers to gonorrhoeae. In one aspect of the invention "infection" or "bacterial infection" refers to meningitis. In one aspect of the invention "infection" or "bacterial infection" refers to tetanus. In one aspect of the invention "infection" or "bacterial infection" refers to tuberculosis.

In one embodiment, it is expected that the compounds of the present invention will be useful in treating bacterial infections including, but not limited to community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase and/or topoisomerase IV in a warm-blooded animal, such as a human being, in need of such treatment which comprises administering to said animal an effective amount of a compound of formula (I) or (I'), or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (I) or (I'), or a pharmaceutically acceptable salt thereof as defined hereinbefore.

According to a further feature of the invention there is provided a method of treating a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus,* methicillin-resistant *Staphylococcus epidermidis* and Vancomycin-Resistant Enterococciin a warm-blooded animal, such as a human being, in need of such treatment which comprises administering to said animal an effective amount of a compound of formula (I) or (I'), or a pharmaceutically acceptable salt thereof as defined hereinbefore.

A further feature of the present invention is a compound of formula (I) or (I'), and pharmaceutically acceptable salts thereof for use as a medicament. Suitably the medicament is an antibacterial agent.

According to a further aspect of the invention there is provided the use of a compound of formula (I) or (I'), or a pharmaceutically acceptable salt thereof in the manufacture of a medicament for use in the production of an anti-bacterial effect in a warm-blooded animal such as a human being.

According to a further aspect of the invention there is provided the use of a compound of formula (I) or (I'), or a pharmaceutically acceptable salt thereof, in the manufacture of a medicament for use in inhibition of bacterial DNA gyrase and/or topoisomerase IV in a warm-blooded animal such as a human being.

Thus according to a further aspect of the invention there is provided the use of a compound of formula (I) or (I'), or a pharmaceutically acceptable salt thereof, in the manufacture of a medicament for use in the treatment of a bacterial infection in a warm-blooded animal such as a human being.

Thus according to a further aspect of the invention there is provided the use of a compound of formula (I) or (I'), or a pharmaceutically acceptable salt thereof, in the manufacture of a medicament for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in a warm-blooded animal such as a human being.

According to a further aspect of the invention there is provided a compound of formula (I) or (I'), or a pharmaceutically acceptable salt thereof, for use in the production of an anti-bacterial effect in a warm-blooded animal such as a human being.

According to a further aspect of the invention there is provided a compound of formula (I) or (I'), or a pharmaceutically acceptable salt thereof, for use in inhibition of bacterial DNA gyrase and/or topoisomerase IV in a warm-blooded animal such as a human being.

Thus according to a further aspect of the invention there is provided a compound of formula (I) or (I'), or a pharmaceutically acceptable salt thereof, for use in the treatment of a bacterial infection in a warm-blooded animal such as a human being.

Thus according to a further aspect of the invention there is provided a compound of formula (I) or (I'), or a pharmaceutically acceptable salt thereof, for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus,* methicillin-resistant *Staphylococcus epidermidis* and Vancomycin-Resistant Enterococci in a warm-blooded animal such as a human being.

In order to use a compound of the formula (I) or (I'), or a pharmaceutically-acceptable salt thereof, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or (I'), or a pharmaceutically-acceptable salt thereof, and a pharmaceutically-acceptable diluent or carrier.

According to a further aspect of the invention there is provided a pharmaceutical composition which comprises a compound of formula (I) or (I'), as defined hereinbefore or a pharmaceutically acceptable salt thereof, in association with a pharmaceutically acceptable excipient or carrier for use in producing an anti-bacterial effect in a warm-blooded animal, such as a human being.

According to a further aspect of the invention there is provided a pharmaceutical composition which comprises a compound of formula (I) or (I'), as defined hereinbefore or a pharmaceutically acceptable salt thereof, in association with a pharmaceutically acceptable excipient or carrier for use in inhibition of bacterial DNA gyrase and/or topoisomerase IV in an warm-blooded animal, such as a human being.

According to a further aspect of the invention there is provided a pharmaceutical composition which comprises a compound of formula (I) or (I'), as defined hereinbefore or a pharmaceutically acceptable salt thereof, in association with a pharmaceutically acceptable excipient or carrier for use in the treatment of a bacterial infection in a warm-blooded animal, such as a human being.

According to a further aspect of the invention there is provided a pharmaceutical composition which comprises a compound of formula (I) or (I'), as defined hereinbefore or a pharmaceutically acceptable salt thereof, in association with a pharmaceutically acceptable excipient or carrier for use in the treatment of a bacterial infection selected from community-acquired pneumoniae, hospital-acquired pneumoniae, skin & skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci in an warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of the invention described herein may be applied as a sole therapy or may involve, in addition to a compound of the invention, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following:

i) other antibacterial agents for example macrolides e.g. erythromycin, azithromycin or clarithromycin; quinolones e.g. ciprofloxacin or levofloxacin; β-lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability-increasing protein (BPI) products; and/or iv) efflux pump inhibitors.

Therefore, in a further aspect of the invention there is provided a compound of the formula (I) or (I'), or a pharmaceutically acceptable salt thereof, and a chemotherapeutic agent selected from:

i) one or more additional antibacterial agents; and/or
ii) one or more anti-infective agents; and/or
iii) biological protein therapeutics for example antibodies, cytokines, bactericidal/permeability-increasing protein (BPI) products; and/or
iv) one or more efflux pump inhibitors.

In another embodiment, the invention relates to a method of treating a bacterial infection in an animal, such as a human, comprising administering to the animal an effective amount of a compound of formula (I) or (I'), or a pharmaceutically acceptable salt thereof, and a chemotherapeutic agent selected from:

i) one or more additional antibacterial agents; and/or
ii) one or more anti-infective agents; and/or
iii) biological protein therapeutics for example antibodies, cytokines, bactericidal/permeability-increasing protein (BPI) products; and/or
iv) one or more efflux pump inhibitors.

As stated above the size of the dose required for the therapeutic or prophylactic treatment of a particular disease state will necessarily be varied depending on the host treated, the route of administration, the severity of the illness being treated, and whether or not an additional chemotherapeutic agent is administered in combination with a compound of the invention. Preferably a daily dose in the range of 1-50 mg/kg is employed. However the daily dose will necessarily be varied depending upon the host treated, the particular route of administration, the severity of the illness being treated, and whether or not an additional chemotherapeutic agent is administered in combination with a compound of the invention. Accordingly the optimum dosage may be determined by the practitioner who is treating any particular patient.

As noted above, one embodiment of the present invention is directed to treating or preventing diseases caused by bacterial infections, wherein the bacteria comprise a GyrB ATPase or topoisomerase IV ATPase enzyme. "Treating a subject with a disease caused by a bacterial infection" includes achieving, partially or substantially, one or more of the following: the reducing or amelioration of the progression, severity and/or duration of the infection, arresting the spread of an infection, ameliorating or improving a clinical symptom or indicator associated with a the infection (such as tissue or serum components), and preventing the reoccurrence of the infection.

As used herein, the terms "preventing a bacterial infection" refer to the reduction in the risk of acquiring the infection, or the reduction or inhibition of the recurrence of the infection. In a preferred embodiment, a compound of the invention is administered as a preventative measure to a patient, preferably a human, before a surgical procedure is preformed on the patient to prevent infection.

As used herein, the term "effective amount" refers to an amount of a compound of this invention for treating or preventing a bacterial infection is an amount which is sufficient to prevent the onset of an infection, reduce or ameliorate the severity, duration, or progression, of an infection, prevent the advancement of an infection, cause the regression of an infection, prevent the recurrence, development, onset or progression of a symptom associated with an infection, or enhance or improve the prophylactic or therapeutic effect(s) of another therapy.

In addition to its use in therapeutic medicine, compounds of formula (I), and their pharmaceutically acceptable salts, are also useful as pharmacological tools in the development and standardization of in-vitro and in-vivo test systems for the evaluation of the effects of inhibitors of DNA gyrase and/or topoisomerase IV in laboratory animals such as cats, dogs, rabbits, monkeys, rats and mice, as part of the search for new therapeutic agents.

In the above other, pharmaceutical composition, process, method, use and medicament manufacture features, the alternative and particular embodiments of the compounds of the invention described herein also apply.

EXAMPLE

The invention is now illustrated but not limited by the following Example in which unless otherwise stated:

(i) evaporations were carried out by rotary evaporation in-vacuo and work-up procedures were carried out after removal of residual solids by filtration;

(ii) operations were generally carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable; the structure of the endproducts of the invention were generally confirmed by NMR and mass spectral techniques; proton magnetic resonance spectra is quoted and was generally determined in DMSO-$d_6$ unless otherwise stated using a Bruker DRX-300 spectrometer operating at a field strength of 300 MHz. Chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MSD equipped with Sedex 75ELSD, run in atmospheric pressure chemical ionization mode and, where appropriate, either positive ion data or negative ion data were collected; mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;

(vi) each intermediate was purified to the standard required for the subsequent stage and was characterized in sufficient detail to confirm that the assigned structure was correct; purity was assessed by high pressure liquid chromatography, thin layer chromatography, or NMR and identity was determined by infra-red spectroscopy (IR), mass spectroscopy or NMR spectroscopy as appropriate;

(vii) the following abbreviations may be used:
 ACN is acetonitrile;
 $CDCl_3$ is deuterated chloroform;
 DBU is 1,8-diazabicyclo[5.4.0]undec-7-ene;
 DCM is dichloromethane;
 DIEA is diisopropyl ethylamine;
 DMF is N,N-dimethylformamide;
 DMSO is dimethylsulfoxide;
 EDC is 1-ethyl-3-(3-dimethyllaminopropyl)carbodiimide;
 EtOAc is ethyl acetate;
 EtOH is ethanol;
 HATU is N-[(dimethylamino)-1H,2,3-triazolo[4,5-b-]pyridin-1-ylmethylene]-N-methylmethanaminium hexafluorophosphate N-oxide;
 HOBT is 1-hydroxybenzotriazole;
 MeOH is methanol;
 MS is mass spectroscopy;
 RT or rt is room temperature;
 SM is starting material;
 TFA is trifluoroacetic acid;
 TFAA is trifluoroacetic anhydride;
 THF is tetrahydrofuran; and
(viii) temperatures are quoted as ° C.

Example 1

6-(6-(3-Ethylureido)-4-(4-(trifluoromethyl)thiazol-2-yl)pyridin-3-yl)-1-(2-methoxyethyl)-4-oxo-1,4-dihydroquinoline-3-carboxylic acid

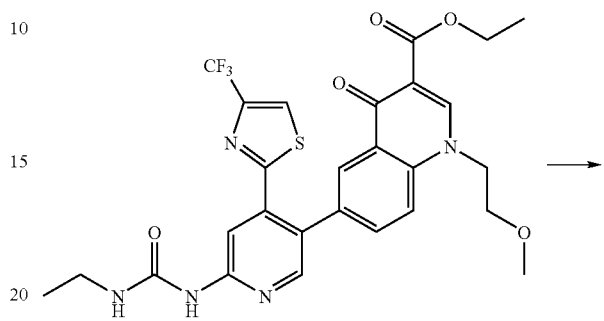

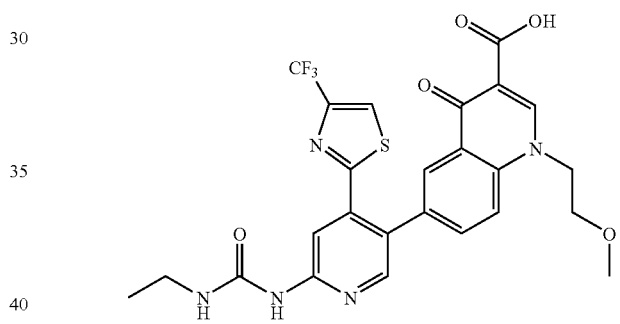

Ethyl 6-(6-(3-ethylureido)-4-(4-(trifluoromethyl)thiazol-2-yl)pyridin-3-yl)-1-(2-methoxyethyl)-4-oxo-1,4-dihydroquinoline-3-carboxylate (Example 51, 0.090 g, 0.15 mmol) and LiOH (0.092 mL, 0.18 mmol) were combined in MeOH (1 mL)/THF (1 mL) and heated to 100° C. in the microwave for 15 min The reaction mixture was cooled to room temperature, diluted with water (1.000 mL) and heated until the compound dissolved. The resulting solution was filtered and the filtrate was then concentrated under reduced pressure to remove methanol. HCl (1 N) was added and the resulting precipitate was collected by filtration, washed with water and dried overnight to yield a white solid (0.063 g).

MS (ES) (M+H)$^+$: 562 for $C_{25}H_{22}F_3N_5O_5S$;

NMR: 1.11 (t, 3H), 3.19-3.23 (m, 5H), 3.71 (d, 2H), 4.81 (q, 2H), 7.60 (dd, 1H), 7.86 (d, 1H), 8.12 (d, 1H), 8.22 (s, 1H), 8.31 (s, 1H), 8.38 (s, 1H), 8.52 (s, 1H), 8.96 (s, 1H), 8.49 (s, 1H).

Examples 2-4

The following Examples were prepared by the procedure described in Example 1 from the starting materials (SM) indicated.

| Ex | Compound | Data | SM |
|---|---|---|---|
| 2 | 6-(6-(3-ethylureido)-4-(4-phenylthiazol-2-yl)pyridin-3-yl)-1-(2-methoxyethyl)-4-oxo-1,4-dihydroquinoline-3-carboxylic acid | MS (ES) (M + H)$^+$: 570 for $C_{30}H_{27}N_5O_5S$<br>NMR: 1.12 (t, 3H), 3.18-3.21 (m, 5H), 3.69 (t, 2H), 4.63 (q, 2H), 7.31-7.39 (m, 3H), 7.75-7.83 (m, 4H), 7.88 (d, 1H), 8.14 (s, 1H), 8.29 (s, 3H), 8.81 (s, 1H), 9.47 (s, 1H). | Example 52 |
| 3 | 6-(6-(3-ethylureido)-4-(4-(trifluoromethyl)thiazol-2-yl)pyridin-3-yl)-4-oxo-1-(3-(2-oxopyrrolidin-1-yl)propyl)-1,4-dihydroquinoline-3-carboxylic acid | MS (ES) (M + H)$^+$: 629 for $C_{29}H_{27}F_3N_6O_5S$ | Example 53 |
| 4 | 1-(1,3-dimethoxypropan-2-yl)-6-(6-(3-ethylureido)-4-(4-(trifluoromethyl)thiazol-2-yl)pyridin-3-yl)-4-oxo-1,4-dihydroquinoline-3-carboxylic acid | MS (ES) (M + H)$^+$: 606 for $C_{27}H_{26}F_3N_5O_6S$ | Example 54 |

Example 5

Sodium 6-(6-(3-Ethylureido)-4-(4-(trifluoromethyl)thiazol-2-yl)pyridin-3-yl)-1-(2-methoxyethyl)-4-oxo-1,4-dihydroquinoline-3-carboxylate

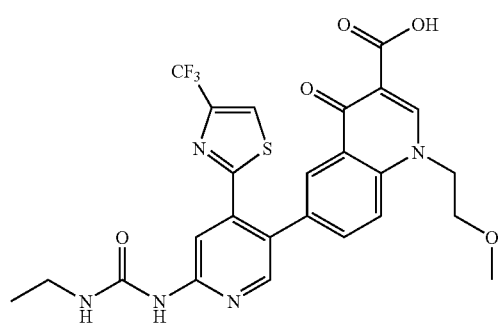

→

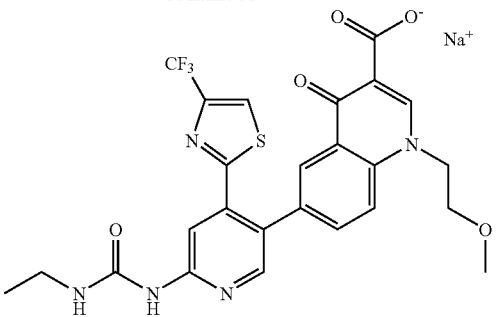

6-(6-(3-Ethylureido)-4-(4-(trifluoromethyl)thiazol-2-yl)pyridin-3-yl)-1-(2-methoxyethyl)-4-oxo-1,4-dihydroquinoline-3-carboxylic acid (0.032 g, 0.06 mmol, Example 1) was suspended in MeOH (1.0 mL)/THF (1.0 mL). 1N NaOH (0.057 mL, 0.06 mmol) was added. Once in solution, the reaction mixture was concentrated under reduced pressure and dried for several hours to yield a white solid (0.030 g).

Examples 6-8

The following Examples were prepared by the procedure described in Example 5 from the starting materials (SM) indicated.

| Ex | Compound | Data | SM |
|----|----------|------|-----|
| 6 | sodium 6-(6-(3-ethylureido)-4-(4-phenylthiazol-2-yl)pyridin-3-yl)-1-(2-methoxyethyl)-4-oxo-1,4-dihydroquinoline-3-carboxylate | MS (ES) (M + H)$^+$: 570 for $C_{30}H_{27}N_5O_5S[Na+]$ NMR: 1.12 (t, 3H), 3.18-3.21 (m, 5H), 3.69 (t, 2H), 4.60 (q, 2H), 7.31-7.39 (m, 3H), 7.75-7.83 (m, 4H), 7.88 (d, 1H), 8.14 (s, 1H), 8.29 (s, 3H), 8.81 (s, 1H), 9.49 (s, 1H). | Example 2 |
| 7 | 6-(6-(3-ethylureido)-4-(4-(trifluoromethyl)thiazol-2-yl)pyridin-3-yl)-4-oxo-1-(3-(2-oxopyrrolidin-1-yl)propyl)-1,4-dihydroquinoline-3-carboxylic acid sodium | MS (ES) (M + H)$^+$: 629 for $C_{29}H_{27}F_3N_6O_5S[Na+]$ NMR: 1.11 (t, 3H), 1.94 (m, 5H), 2.22 (t, 3H), 3.31-3.36 (m, 4H), 4.35 (q, 2H), 7.60 (d, 1H), 7.80 (d, 1H), 8.20 (m, 1H), 8.25 (s, 1H), 8.32 (s, 1H), 8.38 (s, 1H), 8.44 (s, 1H), 8.66 (s, 1H), 10.18 (s, 1H). | Example 3 |

-continued

| Ex | Compound | Data | SM |
|---|---|---|---|
| 8 | 1-(1,3-dimethoxypropan-2-yl)-6-(6-(3-ethylureido)-4-(4-(trifluoromethyl)thiazol-2-yl)pyridin-3-yl)-4-oxo-1,4-dihydroquinoline-3-carboxylic acid | MS (ES) (M + H)$^+$: 570 for $C_{27}H_{26}F_3N_5O_6S \cdot [Na+]$ | Example 4 |

Examples 9-32

The following Examples were prepared by the procedure described in Example 1 from the starting materials (SM) indicated.

| Ex | Compound | Data | SM |
|---|---|---|---|
| 9 | 1-ethyl-7-(6-(3-ethylureido)-4-(4-trifluoromethylthiazol-2-yl)pyridin-3-yl)-4-oxo-1,4-dihydroquinoline-3-carboxylic acid | MS (ESP): 532 (MH$^+$) for $C_{24}H_{20}F_3N_5O_4S$<br>$^1$H NMR (d$_6$-DMSO): δ 1.11 (t, 3H), 1.24 (t, 3H), 3.21 (m, 2H), 4.58 (q, 2H), 7.56-7.61 (m, 2H), 8.07 (d, 1H), 8.24 (s, 1H), 8.38-8.42 (m, 2H), 8.51 (d, 1H), 9.09 (s, 1H), 9.55 (s, 1H) | Example 42 |
| 10 | 1-ethyl-6-(6-(3-ethylureido)-4-(4-trifluoromethylthiazol-2-yl)pyridin-3-yl)-4-oxo-1,4-dihydroquinoline-3-carboxylic acid | MS (ESP): 532 (MH$^+$) for $C_{24}H_{20}F_3N_5O_4S$<br>$^1$H NMR (d$_6$-DMSO): δ 1.11 (t, 3H), 1.40 (t, 3H), 3.20 (m, 2H), 4.64 (q, 2H), 7.63 (bt, 1H), 7.85 (d, 1H), 8.11 (d, 1H), 8.23 (s, 1H), 8.32 (d, 1H), 8.37 (s, 1H), 8.51 (d, 1H), 9.11 (s, 1H), 9.51 (s, 1H) | Example 45 |

| Ex | Compound | Data | SM |
|---|---|---|---|
| 11 | 9-(6-(3-ethylureido)-4-(4-trifluoromethylthiazol-2-yl)pyridin-3-yl)-7-oxo-3,7-dihydro-2H-[1,4]oxazino[2,3,4-ij]quinoline-6-carboxylic acid | MS (ESP): 546 (MH$^+$) for $C_{24}H_{18}F_3N_5O_5S$<br>$^1$H NMR (d$_6$-DMSO): δ 1.11 (t, 3H), 3.17-3.24 (m, 2H), 4.51-4.69 (m, 4H), 7.45 (d, 1H), 7.62 (bt, 1H), 7.80 (d, 1H), 8.22 (s, 1H), 8.32 (s, 1H), 8.53 (d, 1H), 8.99 (s, 1H), 9.48 (s, 1H). | Example 48 |
| 12 | 6-(6-(3-ethylureido)-4-(4-(trifluoromethyl)thiazol-2-yl)pyridin-3-yl)-1-(3-methoxypropyl)-4-oxo-1,4-dihydroquinoline-3-carboxylic acid | MS (ESP): 576 (MH$^+$) for $C_{26}H_{24}F_3N_5O_5S$<br>$^1$H NMR (300 MHz, DMSO-d6) δ 1.11 t, J = 7 Hz, 3H), 2.05 (m, 2H), 3.18 (m, 4H), 3.20 (s, 3H), 4.65 (m, 2H), 7.61 (m, 1H), 7.88 (m, 1H), 8.05 (m, 1H), 8.22 (s, 1H), 8.34 (m, 1H), 8.37 (s, 1H), 8.52 (s, 1H), 9.02 (s, 1H), 9.49 (s, 1H), 15.06 (br s, 1H). | Example 55 |
| 13 | 1-ethyl-6-(6-(3-ethylureido)-4-(4-ethylthiazol-2-yl)pyridin-3-yl)-4-oxo-1,4-dihydroquinoline-3-carboxylic acid | MS (ESP): 492 (MH$^+$) for $C_{25}H_{25}N_5O_4S$<br>$^1$H NMR (d$_6$-DMSO): δ 1.02-1.14 (m, 6H), 1.43 (t, 3H), 2.64 (q, 2H), 3.23 (m, 2H), 4.63 (q, 2H), 7.35 (s, 1H), 7.72 (bt, 1H), 7.82 (d, 1H), 8.07 (d, 1H), 8.13 (s, 1H), 8.26-8.30 (m, 2H), 9.10 (s, 1H), 9.43 (s, 1H) | Example 46 |
| 14 | 9-(6-(3-ethylureido)-4-(4-ethylthiazol-2-yl)pyridin-3-yl)-7-oxo-3,7-dihydro-2H-[1,4]oxazino[2,3,4-ij]quinoline-6-carboxylic acid | MS (ESP): 506 (MH$^+$) for $C_{25}H_{23}N_5O_5S$<br>$^1$H NMR (d$_6$-DMSO): δ 1.11 (t, 6H), 2.67 (q, 2H), 3.21 (m, 2H), 4.58 (m, 4H), 7.37 (m, 2H), 7.73 (bt, 1H), 7.76 (d, 1H), 8.12 (s, 1H), 8.26 (s, 1H), 8.98 (s, 1H), 9.42 (s, 1H) | Example 49 |

-continued

| Ex | Compound | Data | SM |
|----|----------|------|-----|
| 15 | 1-ethyl-7-(6-(3-ethylureido)-4-(4-phenylthiazol-2-yl)pyridin-3-yl)-4-oxo-1,4-dihydroquinoline-3-carboxylic acid | MS (ESP): 540 (MH$^+$) for C$_{29}$H$_{25}$N$_5$O$_4$S<br>$^1$H NMR (d$_6$-DMSO): δ 1.08-1.27 (m, 6H), 3.15-3.24 (m, 2H), 4.58 (bq, 2H), 7.26-7.35 (m, 3H), 7.59 (d, 1H), 7.61-7.70 (m, 3H), 8.08 (s, 1H), 8.18 (s, 1H), 8.27 (s, 1H), 8.35-8.41 (m, 2H), 9.08 (s, 1H), 9.51 (s, 1H) | Example 44 |
| 16 | 1-ethyl-6-(6-(3-ethylureido)-4-(4-phenylthiazol-2-yl)pyridin-3-yl)-4-oxo-1,4-dihydroquinoline-3-carboxylic acid | MS (ESP): 540 (MH$^+$) for C$_{29}$H$_{25}$N$_5$O$_4$S<br>$^1$H NMR (d$_6$-DMSO): δ 1.12 (t, 3H), 1.41 (t, 3H), 3.16-3.28 (m, 2H), 4.60 (bq, 2H), 7.31-7.39 (m, 3H), 7.71-7.81 (m, 4H), 8.05 (d, 1H), 8.17 (s, 1H), 8.29-8.36 (m, 2H), 9.05 (s, 1H), 9.61 (br s, 1H) | Example 47 |
| 17 | 9-(6-(3-ethylureido)-4-(4-phenylthiazol-2-yl)pyridin-3-yl)-7-oxo-3,7-dihydro-2H-[1,4]oxazino[2,3,4-ij]quinoline-6-carboxylic acid | MS (ESP): 554 (MH$^+$) for C$_{29}$H$_{23}$N$_5$O$_5$S<br>$^1$H NMR (d$_6$-DMSO): δ 1.09 (t, 3H), 3.19-3.26 (m, 2H), 4.59 (m, 4H), 7.34-7.38 (m, 3H), 7.43 (d, 1H), 7.70 (bt, 1H), 7.80 (d, 1H), 7.83 (d, 1H), 7.87 (d, 1H), 8.18 (s, 1H), 8.26 (s, 1H), 8.29 (s, 1H), 8.99 (s, 1H), 9.45 (s, 1H) | Example 50 |

-continued

| Ex | Compound | Data | SM |
|---|---|---|---|
| 18 | 1-(2-(dimethylamino)ethyl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 575 (M + 1) for $C_{26}H_{25}F_3N_6O_4S$<br>$^1$H-NMR (DMSO-$d_6$): 1.11 (t, J = 7.20 Hz, 3H); 2.87 (br. s., 6H); 3.13-3.28 (m, 2H); 3.57 (br. s., 2H); 5.01 (br. s., 2H); 7.64 (br. s., 1H); 7.92 (dd, J = 8.72, 1.64 Hz, 1H); 8.14-8.28 (m, 2H); 8.28-8.41 (m, 2H); 8.54 (s, 1H); 9.17 (s, 1H); 9.51 (s, 1H); 10.74 (br. s., 1H); 14.91 (br. s., 1H) | Example 56 |
| 19 | 6-(6-(3-Ethylureido)-4-(4-(trifluoromethyl)thiazol-2-yl)pyridin-3-yl)-1-(2-hydroxyethyl)-4-oxo-1,4-dihydroquinoline-3-carboxylic acid | MS (ESP): 548 (M + 1) for $C_{24}H_{20}F_3N_5O_5S$<br>$^1$H-NMR (DMSO-$d_6$) δ: 1.11 (t, J = 7.20 Hz, 3H); 3.15-3.28 (m, 2H); 3.73-3.83 (m, 2H); 4.59-4.72 (m, 2H); 5.10 (t, J = 5.56 Hz, 1H); 7.62 (br. s., 1H); 7.86 (dd, J = 8.97, 2.15 Hz, 1H); 8.13 (d, J = 8.84 Hz, 1H); 8.23 (s, 1H); 8.33 (d, J = 2.27 Hz, 1H); 8.37 (s, 1H); 8.52 (s, 1H); 8.94 (s, 1H) | Example 57 |
| 20 | 1-Cyclopropyl-6-(6-(3-ethylureido)-4-(4-(trifluoromethyl)thiazol-2-yl)pyridin-3-yl)-4-oxo-1,4-dihydroquinoline-3-carboxylic acid | MS (ESP): 544 (M + 1) for $C_{25}H_{20}F_3N_5O_4S$<br>$^1$H-NMR (DMSO-$d_6$): 1.11 (t, J = 7.20 Hz, 3H); 1.16-1.25 (m, 2H); 1.29-1.38 (m, 2H); 3.15-3.28 (m, 2H); 3.83-3.93 (m, 2H); 7.56-7.66 (m, 1H); 7.92 (dd, J = 8.84, 2.02 Hz, 1H); 8.23 (s, 1H); 8.27-8.39 (m, 2H); 8.52 (s, 1H); 8.80 (s, 1H); 9.48 (s, 1H) | Example 58 |

| Ex | Compound | Data | SM |
|----|----------|------|-----|
| 21 | 6-(6-(3-Ethylureido)-4-(4-(trifluoromethyl)thiazol-2-yl)pyridin-3-yl)-1-isopropyl-4-oxo-1,4-dihydroquinoline-3-carboxylic acid | MS (ESP): 546 (M + 1) for $C_{25}H_{22}F_3N_5O_4S$<br>$^1$H-NMR (DMSO-$d_6$): 1.11 (t, J = 7.20 Hz, 3H); 1.54 (d, J = 5.81 Hz, 6H); 3.14-3.26 (m, 2H); 5.10-5.29 (m, 1H); 7.51-7.82 (m, 2H); 8.09 (br. s., 1H); 8.25 (s, 1H); 8.28-8.39 (m, 2H); 8.45 (br. s., 1H); 8.95 (s, 1H); 9.46 (s, 1H) | Example 59 |
| 22 | 7-(6-(3-Ethylureido)-4(4-(trifluoromethyl)thiazol-2-yl)pyridin-3-yl)-1-methyl-4-oxo-1,4-dihydroquinoline-3-carboxylic acid | MS (ESP): 518 (M + 1) $C_{23}H_{18}F_3N_5O_4S$<br>$^1$H-NMR (DMSO-$d_6$): 1.11 (t, J = 7.20 Hz, 3H); 3.15-3.26 (m, 2H); 4.08 (s, 3H); 7.51 (d, J = 7.83 Hz, 1H); 7.55-7.63 (m, 1H); 8.04 (s, 1H); 8.24 (s, 1H); 8.34 (d, J = 8.34 Hz, 1H); 8.45 (s, 1H); 8.53 (s, 1H); 9.08 (s, 1H); 9.53 (s, 1H); 15.18 (s, 1H) | Example 60 |
| 23 | 7-(6-(3-Ethylureido)-4-(4-(trifluoromethyl)thiazol-2-yl)pyridin-3-yl)-4-oxo-1,4-dihydroquinoline-3-carboxylic acid | MS (ESP): 504 (M + 1) $C_{22}H_{16}F_3N_5O_4S$<br>$^1$H-NMR (DMSO-$d_6$): 1.11 (t, J = 7.07 Hz, 3H); 3.09-3.28 (m, 2H); 7.50 (d, J = 8.34 Hz, 1H); 7.53-7.64 (m, 1H); 7.76 (s,1H); 8.24 (s, 1H); 8.30 (d, J = 8.34 Hz, 1H); 8.37 (s, 1H); 8.52 (s, 1H); 8.89-9.00 (m, 1H); 9.51 (s, 1H); 13.43 (br. s., 1H) | Example 61 |

| Ex | Compound | Data | SM |
|---|---|---|---|
| 24 | 6-(6-(3-ethylureido)-4-(4-(trifluoromethyl)thiazol-2-yl)pyridin-3-yl)-1-(1-methylazetidin-3-yl)-4-oxo-1,4-dihydroquinoline-3-carboxylic acid | MS (ESP): 573 (M + 1) for $C_{26}H_{23}F_3N_6O_4S$<br>$^1$H NMR (DMSO-$d_6$): 1.11 (t, J = 7.07 Hz, 3H); 2.33 (s, 3H); 3.14-3.27 (m, 2H); 3.35-3.46 (m, 2H); 3.90 (t, J = 6.69 Hz, 2H); 5.19-5.33 (m, 1H); 7.64-7.92 (m, 3H); 8.23-8.40 (m, 3H); 8.49 (s, 1H); 8.87 (s, 1H); 9.80 (br s, 1H) | Example 62 |
| 25 | 7-{6-[(ethylcarbamoyl)amino]-4-[4-(trifluoromethyl)-1,3-thiazol-2-yl]pyridin-3-yl}-1-(3-methylbutyl)-4-oxo-1,4-dihydroquinoline-3-carboxylic acid | $^1$H NMR (400 MHz, DMSO-$d_6$): 0.83 (d, 6H), 1.13 (t, 3H), 1.44 (q, 2H), 1.55 (m, 1H), 3.21 (q, 2H), 4.52 (t, 2H), 7.56 (m, 1H), 7.63 (d, 1H), 7.93 (s, 1H), 8.25 (s, 1H), 8.40 (s, 1H), 8.43 (d, 1H), 8.51 (s, 1H), 9.06 (s, 1H), 9.48 (s, 1H). | Example 63 |
| 26 | 7-{6-[(ethylcarbamoyl)amino]-4-[4-(trifluoromethyl)-1,3-thiazol-2-yl]pyridin-3-yl}-1-(2-methylpropyl)-4-oxo-1,4-dihydroquinoline-3-carboxylic acid | $^1$H NMR (400 MHz, DMSO-$d_6$): 0.75 (d, 6H), 1.13 (t, 3H), 1.64 (m, 1H), 3.21 (q, 2H), 4.33 (d, 2H), 7.59 (m, 4H), 7.94 (s, 1H), 8.19 (s, 1H), 8.40 (s, 1H), 8.43 (d, 1H), 8.53 (s, 1H), 9.00 (s, 1H), 9.49 (s, 1H). | Example 64 |

| Ex | Compound | Data | SM |
|---|---|---|---|
| 27 | 7-{6-[(ethylcarbamoyl)amino]-4-[4-(trifluoromethyl)-1,3-thiazol-2-yl]pyridin-3-yl}-4-oxo-1-propyl-1,4-dihydroquinoline-3-carboxylic acid | $^1$H NMR (400 MHz, DMSO-d$_6$): 0.79 (t, 3H), 1.11 (t, 3H), 1.55 (q, 2H), 3.21 (q, 2H), 4.48 (t, 2H), 7.60 (m, 2H), 8.00 (s, 1H), 8.21 (s, 1H), 8.41 (t, 2H), 8.51 (s, 1H), 9.06 (s, 1H), 9.49 (s, 1H). | Example 65 |
| 28 | 1-benzyl-7-{6-[(ethylcarbamoyl)amino]-4-[4-(trifluoromethyl)-1,3-thiazol-2-yl]pyridin-3-yl}-4-oxo-1,4-dihydroquinoline-3-carboxylic acid | $^1$H NMR (400 MHz, DMSO-d$_6$): 1.10 (t, 3H), 3.20 (q, 2H), 5.84 (s, 2H), 7.15 (t, 2H), 7.23 (m, 3H), 7.53 (d, 2H), 7.92 (s, 1H), 8.15 (s, 1H), 8.24 (s, 1H), 8.34 (s, 1H), 8.41 (d, 1H), 9.29 (s, 1H), 9.48 (s, 1H). | Example 66 |
| 29 | 7-{6-[(ethylcarbamoyl)amino]-4-[4-(trifluoromethyl)-1,3-thiazol-2-yl]pyridin-3-yl}-4-oxo-1-(pyridin-3-ylmethyl)-1,4-dihydroquinoline-3-carboxylic acid | $^1$H NMR (400 MHz, DMSO-d$_6$): 0.85 (m, 3H), 1.10 (t, 3H), 3.19 (q, 2H), 5.92 (s, 2H), 7.39 (m, 1H), 7.54 (m, 2H), 7.67 (d, 1H), 7.96 (s, 1H), 8.17 (s, 1H), 8.25 (s, 1H), 8.36 (s, 1H), 8.41 (d, 1H), 8.50 (d, 1H), 8.57 (br s, 1H), 9.34 (s, 1H), 9.50 (s, 1H). | Example 67 |

| Ex | Compound | Data | SM |
|---|---|---|---|
| 30 | 7-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydroquinoline-3-carboxylic acid | $^1$H NMR (400 MHz, DMSO-$d_6$): 1.11 (t, 3H), 3.22 (q, 2H), 3.61 (q, 2H), 4.62 (s, 2H), 5.02 (s, 1H), 7.51 (d, 1H), 7.63 (s, 1H), 8.14 (s, 1H), 8.26 (s, 1H), 8.41 (d, 2H), 8.51 (s, 1H), 8.91 (s, 1H), 9.56 (s, 1H). | Example 68 |
| 31 | 7-{6-[(ethylcarbamoyl)amino]-4-[4-(trifluoromethyl)-1,3-thiazol-2-yl]pyridin-3-yl}-1-(2-methoxyethyl)-4-oxo-1,4-dihydroquinoline-3-carboxylic acid | $^1$H NMR (400 MHz, DMSO-$d_6$): 1.11 (t, 3H), 3.21 (m, 5H), 3.50 (t, 2H), 4.75 (m, 2H), 7.58 (d, 2H), 8.12 (s, 1H), 8.24 (s, 1H), 8.40 (m, 2H), 8.52 (s, 1H), 8.92 (s, 1H), 9.49 (s, 1H). | Example 69 |
| 32 | 1-(cyclopropylmethyl)-7-{6-[(ethylcarbamoyl)amino]-4-[4-(trifluoromethyl)-1,3-thiazol-2-yl]pyridin-3-yl}-4-oxo-1,4-dihydroquinoline-3-carboxylic acid | $^1$H NMR (400 MHz, DMSO-$d_6$): 0.44 (m, 4H), 1.09 (m, 1H), 1.11 (t, 3H), 3.22 (m, 3H), 4.42 (d, 2H), 7.61 (m, 2H), 8.13 (s, 1H), 8.21 (s, 1H), 8.40 (s, 1H), 8.42 (s, 1H), 9.08 (s, 1H), 9.50 (s, 1H). | Example 70 |

Examples 33-41

The following compounds were synthesized by the general procedure described below.

The ethyl ester starting material (SM) (0.09 mmol) was suspended in 33% methylamine in ethanol (3.5 ml). The resulting suspension was heated at 90° C. in a microwave for 1.5 h. When the reaction was complete, the solution was cooled to room temperature, and methyl tert-butyl ether (4 ml) was added. The reaction mixture was allowed to stand for 1 h then filtered. The solid was washed with methyl tert-butyl ether (4 ml) and dried in a vacuum oven at 50° C. for 4 hours.

| Ex | Compound | Data | SM |
|---|---|---|---|
| 33 | 1-ethyl-7-(6-(3-ethylureido)-4-(4-(trifluoromethyl)thiazol-2-yl)pyridin-3-yl)-N-methyl-4-oxo-1,4-dihydroquinoline-3-carboxamide | MS (ESP): 545.1 (MH$^+$) for $C_{25}H_{23}F_3N_6O_3S$ $^1$H NMR ($d_6$-DMSO): 1.11 (t, 3H), 1.24 (t, 3H), 3.21 (m, 2H), 4.58 (q, 2H), 7.45 (dd, 1H), 7.62 (br t, 1H), 7.91 (d, 1H), 8.22 (d, 1H), 8.34-8.40 (m, 2H), 8.48 (d, 1H), 8.89 (s, 1H), 9.50 (s, 1H), 9.78 (m, 1H) | Example 42 |
| 34 | 1-ethyl-6-(6-(3-ethylureido)-4-(4-(trifluoromethyl)thiazol-2-yl)pyridin-3-yl)-N-methyl-4-oxo-1,4-dihydroquinoline-3-carboxamide | MS (ESP): 545.1 (MH$^+$) for $C_{25}H_{23}F_3N_6O_3S$ $^1$H NMR ($d_6$-DMSO): 1.11 (t, 3H), 1.40 (t, 3H), 2.85 (d, 3H), 3.20 (m, 2H), 4.54 (q, 2H), 7.64 (br t, 1H), 7.68 (dd, 1H), 7.98 (d, 1H), 8.23-8.26 (m, 2H), 8.34 (d, 1H), 8.48 (d, 1H), 8.92 (s, 1H), 9.46 (s, 1H), 9.73 (d, 1H) | Example 45 |
| 35 | N-methyl-9-(6-(3-ethylureido)-4-(4-trifluoromethylthiazol-2-yl)pyridin-3-yl)-7-oxo-3,7-dihydro-2H-[1,4]oxazino[2,3,4-ij]quinoline-6-carboxamide | MS (ESP): 559.2 (MH$^+$) for $C_{25}H_{21}F_3N_6O_4S$ $^1$H NMR ($d_6$-DMSO): 1.11 (t, 3H), 2.49 (d, 3H), 3.19-3.28 (m, 2H), 4.51-4.58 (br s, 4H), 7.32 (d, 1H), 7.63 (br t, 1H), 7.73 (d, 1H), 8.22 (s, 1H), 8.29 (s, 1H), 8.50 (d, 1H), 8.79 (s, 1H), 9.45 (s, 1H), 9.72 (d, 1H) | Example 48 |

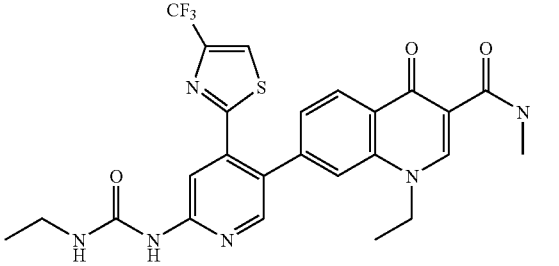

-continued

| Ex | Compound | Data | SM |
|---|---|---|---|
| 36 | 1-ethyl-7-(4-(4-ethylthiazol-2-yl)-6-(3-ethylureido)pyridin-3-yl)-N-methyl-4-oxo-1,4-dihydroquinoline-3-carboxamide | MS (ESP): 505.2 (MH$^+$) for C$_{26}$H$_{28}$N$_6$O$_3$S<br>$^1$H NMR (d$_6$-DMSO): 1.00-1.16 (m, 9H), 2.64 (q, 2H), 2.87 (d, 3H), 3.24 (q, 2H), 4.46 (q, 2H), 7.34 (s, 1H), 7.39 (d, 1H), 7.73 (m, 1H), 7.82 (s, 1H), 8.11 (s, 1H), 8.33-8.36 (m, 2H), 8.87 (s, 1H), 9.44 (s, 1H), 9.80 (d, 1H) | Example 43 |
| 37 | 1-ethyl-6-(4-(4-ethylthiazol-2-yl)-6-(3-ethylureido)pyridin-3-yl)-N-methyl-4-oxo-1,4-dihydroquinoline-3-carboxamide | MS (ESP): 505.2 (MH$^+$) C$_{26}$H$_{28}$N$_6$O$_3$S<br>$^1$H NMR (d$_6$-DMSO): 1.00-1.14 (m, 6H), 1.40 (t, 3H), 2.65 (q, 2H), 2.85 (d, 3H), 3.21 (m, 2H), 4.53 (q, 2H), 7.33 (s, 1H), 7.68-7.72 (m, 2H), 7.93 (d, 1H), 8.13 (s, 1H), 8.21 (d, 1H), 8.26 (s, 2H), 8.90 (s, 1H), 9.43 (s, 1H), 9.76 (m, 1H) | Example 46 |
| 38 | 9-(4-(4-ethylthiazol-2-yl)-6-(3-ethylureido)pyridin-3-yl)-N-methyl-7-oxo-3,7-dihydro-2H-[1,4]oxazino[2,3,4-ij]quinoline-6-carboxamide | MS (ESP): 518.3 (MH$^+$) for C$_{26}$H$_{26}$N$_6$O$_4$S<br>$^1$H NMR (d$_6$-DMSO): 1.06-1.16 (m, 6H), 2.50 (q, 2H), 2.85 (d, 3H), 3.16-3.22 (m, 2H), 4.52 (br s, 4H), 7.24 (d, 1H), 7.33 (s, 1H), 7.70 (d, 1H), 7.76 (br t, 1H), 8.12 (s, 1H), 8.23 (s, 1H), 8.78 (s, 1H), 9.40 (s, 1H), 9.74 (m, 1H) | Example 49 |
| 39 | 1-ethyl-7-(6-(3-ethylureido)-4-(4-phenylthiazol-2-yl)pyridin-3-yl)-N-methyl-4-oxo-1,4-dihydroquinoline-3-carboxamide | MS (ESP): 553.2 (MH$^+$) for C$_{30}$H$_{28}$N$_6$O$_3$S<br>$^1$H NMR (d$_6$-DMSO): 1.08-1.22 (m, 6H), 2.87 (d, 3H), 3.15-3.24 (m, 2H), 4.47 (br q, 2H), 7.26-7.42 (m, 3H), 7.47 (d, 1H), 7.72-7.76 (m, 3H), 7.93 (s, 1H), 8.16 (s, 1H), 8.26 (s, 1H), 8.33-8.37 (m, 2H), 8.88 (s, 1H), 9.48 (s, 1H), 9.81 (m, 1H) | Example 44 |

| Ex | Compound | Data | SM |
|---|---|---|---|
| 40 | 1-ethyl-6-(6-(3-ethylureido)-4-(4-phenylthiazol-2-yl)pyridin-3-yl)-N-methyl-4-oxo-1,4-dihydroquinoline-3-carboxamide | MS (ESP): 553.2 (MH$^+$) for $C_{30}H_{28}N_6O_3S$<br>$^1$H NMR ($d_6$-DMSO): 1.12 (t, 3H), 1.41 (t, 3H), 3.16-3.28 (m, 2H), 4.60 (br q, 2H), 7.31-7.39 (m, 3H), 7.71-7.81 (m, 4H), 8.05 (d, 1H), 8.17 (s, 1H), 8.29-8.36 (m, 2H), 9.05 (s, 1H), 9.61 (br s, 1H) | Example 47 |
| 41 | 9-(6-(3-ethylureido)-4-(4-phenylthiazol-2-yl)pyridin-3-yl)-N-methyl-7-oxo-3,7-dihydro-2H-[1,4]oxazino[2,3,4-ij]quinoline-6-carboxamide | MS (ESP): 567.3 (MH$^+$) for $C_{30}H_{26}N_6O_4S$<br>$^1$H NMR ($d_6$-DMSO): 1.12 (t, 3H), 2.84 (d, 3H), 3.16-3.28 (m, 2H), 4.53 (br s, 4H), 7.35-7.44 (m, 4H), 7.77-7.85 (m, 4H), 8.17 (s, 1H), 8.26 (m, 2H), 8.79 (s, 1H), 9.47 (s, 1H), 9.75 (m, 1H) | Example 50 |

Example 42

Ethyl 1-ethyl-7-(6-(3-ethylureido)-4-(4-trifluoromethylthiazol-2-yl)pyridin-3-yl)-4-oxo-1,4-dihydroquinoline-3-carboxylate

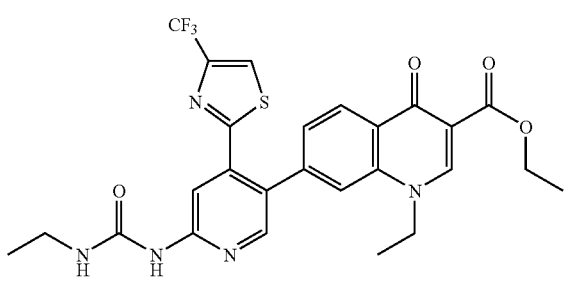

To a slurry of 6-(3-ethylureido)-4-(4-trifluoromethylthiazol-2-yl)pyridin-3-ylboronic acid (Intermediate 17, 330 mg, 0.91 mmol), ethyl 1-ethyl7-iodo-4-oxo-1,4-dihydroquinoline-3-carboxylate (Intermediate 9, 281 mg, 0.75 mmol) and trans-dichlorobis(triphenylphosphine)palladium (II) (53 mg, 0.075 mmol) in 1,4-dioxane (8 ml) was added a solution of potassium carbonate (210 mg, 1.52 mmol) in water (3 ml). The reaction was stirred for 1.5 hours at 70° C. The reaction was cooled to room temperature, and ethyl acetate (8 mL) was added to help separate the layers. The water was removed, and the organic phase was washed with water (3 mL). The reaction was then concentrated and ethanol (5 mL) was added. The suspension was filtered, and the solid washed with methyl tert-butyl ether (2×, 5 ml). The solid was dried in a vacuum oven at 50° C. for 4 hours to give 195 mg (60%) of ethyl 1-ethyl7-(6-(3-ethylureido)-4-(4-trifluoromethylthiazol-2-yl)pyridin-3-yl)-4-oxo-1,4-dihydroquinoline-3-carboxylate as an off white solid.

MS (ESP): 560 (MH$^+$) for $C_{26}H_{24}F_3N_5O_4S$
$^1$H NMR (CDCl$_3$): δ 1.24 (m, 3H), 1.28 9 (m, 6H), 3.50 (m, 2H), 4.20 (m, 2H), 4.42 (m,2H), 7.34 (m, 2H), 7.53 (s, 1H), 7.72 (s, 1H), 8.29 (s, 1H), 8.53 (s, 1H) 8.59 (m, 1H), 9.03 (m, 1H).

Examples 43-50

The following Examples were prepared by the procedure described in Example 42 from the starting materials (SM) indicated.

| Ex | Compound | Data | SM |
|---|---|---|---|
| 43 | ethyl 1-ethyl-7-(6-(3-ethylureido)-4-(4-ethylthiazol-2-yl)pyridin-3-yl)-4-oxo-1,4-dihydroquinoline-3-carboxylate | MS (ESP): 520.2 (MH$^+$) for $C_{27}H_{29}N_5O_4S$ | Intermediate 18 and Intermediate 9 |
| 44 | ethyl 1-ethyl-7-(6-(3-ethylureido)-4-(4-phenylthiazol-2-yl)pyridin-3-yl)-4-oxo-1,4-dihydroquinoline-3-carboxylate | MS (ESP): 568.2 (MH$^+$) for $C_{31}H_{29}N_5O_4S$<br>$^1$H NMR (CDCl$_3$): δ 1.22-1.35 (m, 6H), 1.42 (t, 3H), 3.40-3.52 (m, 2H), 4.09 (q, 2H), 4.41 (q, 2H), 7.27-7.41 (m, 5H), 7.61 (s, 1H), 7.72 (m, 2H), 8.29 (s, 1H), 8.46 (s, 1H), 8.52-8.61 (m, 2H), 9.04 (br s, 1H) | Intermediate 19 and Intermediate 9 |
| 45 | ethyl 1-ethyl-6-(6-(3-ethylureido)-4-(4-trifluoromethylthiazol-2-yl)pyridin-3-yl)-4-oxo-1,4-dihydroquinoline-3-carboxylate | MS (ESP): 560.1 (MH$^+$) for $C_{26}H_{24}F_3N_5O_4S$<br>$^1$H NMR (d$_6$-DMSO): δ 1.12 (t, 3H), 1.26 (t, 3H), 1.39 (t, 3H), 3.15-3.21 (m, 2H), 4.24 (q, 3H), 4.44 (q, 2H), 7.64 (bt, 1H), 7.71 (d, 1H), 7.91 (d, 1H), 8.18 (d, 1H), 8.23 (s, 1H), 8.33 (s, 1H), 8.42 (s, 1H), 8.72 (s, 1H), 9.42 (s, 1H) | Intermediate 17 and Intermediate 6 |
| 46 | ethyl 1-ethyl-6-(6-(3-ethylureido)-4-(4-ethylthiazol-2-yl)pyridin-3-yl)-4-oxo-1,4-dihydroquinoline-3-carboxylate | MS (ESP): 520.1 (MH$^+$) for $C_{27}H_{29}N_5O_4S$<br>$^1$H NMR (d$_6$-DMSO): δ 1.10 (m, 6H), 1.28 (t, 3H), 1.37 (t, 3H), 2.68 (q, 2H), 3.14-3.21 (m, 2H), 4.22 (q, 3H), 4.45 (q, 2H), 7.35 (s, 1H), 7.66 (d, 1H), 7.79 (bt, 1H), 7.84 (d, 1H), 8.15 (d, 1H), 8.23 (s, 1H), 8.74 (s, 1H), 9.41 (s, 1H) | Intermediate 18 and Intermediate 6 |

-continued

| Ex | Compound | Data | SM |
|----|----------|------|-----|
| 47 | ethyl 1-ethyl-6-(6-(3-ethylureido)-4-(4-phenylthiazol-2-yl)pyridin-3-yl)-4-oxo-1,4-dihydroquinoline-3-carboxylate | MS (ESP): 568.2 (MH$^+$) for $C_{31}H_{29}N_5O_4S$<br>$^1$H NMR (d$_6$-DMSO): δ 1.11 (t, 3H), 1.28 (t, 3H), 1.35 (t, 3H), 3.18-3.23 (m, 2H), 4.19 (q, 2H), 4.46 (q, 2H), 7.28-7.41 (m, 4H), 62-7.80 (m, 5H), 7.85 (d, 1H), 8.14 (d, 1H), 8.19 (d, 1H), 8.24 (m, 2H), 8.75 (s, 1H), 9.41 (bs, 1H) | Intermediate 19 and Intermediate 6 |
| 48 | ethyl 9-(6-(3-ethylureido)-4-(4-trifluoromethylthiazol-2-yl)pyridin-3-yl)-7-oxo-3,7-dihydro-2H-[1,4]oxazino[2,3,4-ij]quinoline-6-carboxylate | MS (ESP): 574.2 (MH$^+$) for $C_{26}H_{22}F_3N_5O_3S$<br>$^1$H NMR (d$_6$-DMSO): δ 1.11 (t, 3H), 1.28 (t, 3H), 3.18-3.22 (m, 2H), 4.23 (q, 2H), 4.45 (m, 2H), 4.51 (m, 2H), 7.28 (s, 1H), 7.63-7.70 (m, 2H), 8.22 (s, 1H), 8.28 (s, 1H), 8.51 (s, 1H), 8.62 (s, 1H), 9.44 (s, 1H) | Intermediate 17 and Intermediate 13 |
| 49 | ethyl 9-(6-(3-ethylureido)-4-(4-ethylthiazol-2-yl)pyridin-3-yl)-7-oxo-3,7-dihydro-2H-[1,4]oxazino[2,3,4-ij]quinoline-6-carboxylate | MS (ESP): 534.1 (MH$^+$) for $C_{27}H_{27}N_5O_5S$ | Intermediate 18 and Intermediate 13 |

| Ex | Compound | Data | SM |
|---|---|---|---|
| 50 | ethyl 9-(6-(3-ethylureido)-4-(4-phenylthiazol-2-yl)pyridin-3-yl)-7-oxo-3,7-dihydro-2H-[1,4]oxazino[2,3,4-ij]quinoline-6-carboxylate | MS (ESP): 581.9 (MH$^+$) for C$_{31}$H$_{27}$N$_5$O$_5$S<br>$^1$H NMR (d$_6$-DMSO): δ 1.08-1.18 (m, 6H), 1.27 (t, 3H), 3.17-3.24 (m, 2H), 4.22 (q, 2H), 4.44 (m, 4H), 7.23-7.55 (m, 5H), 7.71-7.82 (m, 2H), 8.00-8.29 (m, 2H), 8.61 (m, 1H), 9.51 (bs, 1H) | Intermediate 19 and Intermediate 13 |

Example 51

Ethyl 6-(6-(3-ethylureido)-4-(4-(trifluoromethyl)thiazol-2-yl)pyridin-3-yl)-1-(2-methoxyethyl)-4-oxo-1,4-dihydroquinoline-3-carboxylate

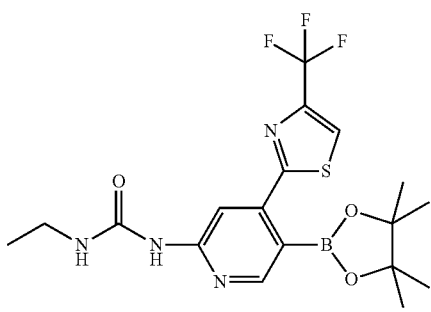

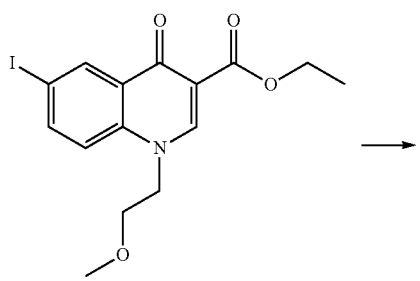

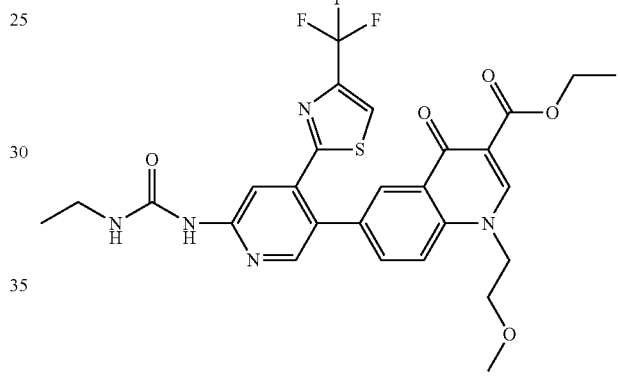

1-Ethyl-3-(5-(4,4,5,5-tetramethyl-1,3,2-dioxaborolan-2-yl)-4-(4-(trifluoromethyl)thiazol-2-yl)pyridin-2-yl)urea (0.171 g, 0.39 mmol, Intermediate 17), ethyl 6-iodo-1-(2-methoxyethyl)-4-oxo-1,4-dihydroquinoline-3-carboxylate (0.155 g, 0.39 mmol, Intermediate 20), cesium carbonate (0.214 g, 0.66 mmol, Aldrich) and tris(dibenzylideneacetone)palladium (0) (0.035 g, 0.04 mmol, Aldrich) or tetrakis(triphenylphosphine)palladium (0) (5 mol %, Strem) were combined in dioxane (2 mL)/water (0 mL) and heated to 100° C. The reaction mixture was stirred for 1 h. The reaction mixture was cooled to room temperature and then placed in an ice-bath. The resulting precipitate was collected by filtration and dried under vacuum to provide the desired product (0.090 g).

MS (ES) (M+H)$^+$: 590 for C$_{27}$H$_{26}$F$_3$N$_5$O$_5$S;

NMR: 1.11 (t, 3H), 1.28 (t, 3H), 3.24 (m, 5H), 3.66 (d, 2H), 4.24 (q, 2H), 4.61 (q, 2H), 7.70 (m, 2H), 7.91 (d, 1H), 8.14 (s, 1H), 8.22 (s, 1H), 8.33 (s, 1H), 8.49 (s, 1H), 8.62 (s, 1H), 9.46 (s, 1H).

Examples 52-54

The following Examples were prepared by the procedure described in Example 51 from the starting materials (SM) indicated.

| Ex | Compound | Data | SM |
|---|---|---|---|
| 52 | ethyl 6-(6-(3-ethylureido)-4-(4-phenylthiazol-2-yl)pyridin-3-yl)-1-(2-methoxyethyl)-4-oxo-1,4-dihydroquinoline-3-carboxylate | MS (ES) (M + H)$^+$: 598 for C$_{32}$H$_{31}$N$_5$O$_5$S NMR: 1.12 (t, 3H), 1.28 (t, 3H), 3.18-3.22 (m, 5H), 3.66 (d, 2H), 4.22 (q, 2H), 4.61 (q, 2H), 7.32-7.38 (m, 3H), 7.70-7.77 (m, 4H), 7.89 (d, 1H), 8.16 (s, 1H), 8.20 (s, 1H), 8.26 (d, 1H), 8.62 (s, 1H), 9.44 (s, 1H). | Intermediate 19 and Intermediate 20 |
| 53 | ethyl 6-(6-(3-ethylureido)-4-(4-(trifluoromethyl)thiazol-2-yl)pyridin-3-yl)-4-oxo-1-(3-(2-oxopyrrolidin-1-yl)propyl)-1,4-dihydroquinoline-3-carboxylate | MS (ES) (M + H)$^+$: 657 for C$_{31}$H$_{31}$F$_3$N$_6$O$_5$S NMR: 1.11 (t, 3H), 1.29 (t, 3H), 2.22 (m, 4H), 2.73 (d, 1H), 3.31 (s, 6H), 4.22 (q, 2H), 4.39 (q, 2H), 7.70 (s, 1H), 7.73 (d, 1H), 7.87 (d, 1H), 8.15 (s, 1H), 8.23 (s, 1H), 8.33 (s, 1H), 8.49 (s, 1H), 8.75 (s, 1H), 9.49 (s, 1H). | Intermediate 17 and Intermediate 21 |
| 54 | ethyl 1-(1,3-dimethoxypropan-2-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 634 for C$_{29}$H$_{30}$F$_3$N$_5$O$_6$S | Intermediate 17 and Intermediate 22 |

Examples 55-61

The following Examples were prepared by the procedure described in Example 51 from the starting materials (SM) indicated.

| Ex | Compound | Data | SM |
|---|---|---|---|
| 55 | ethyl 6-(6-(3-ethylureido)-4-(4-(trifluoromethyl)thiazol-2-yl)pyridin-3-yl)-1-(3-methoxypropyl)-4-oxo-1,4-dihydroquinoline-3-carboxylate | MS (ES) (M + H)$^+$: 604 for C$_{28}$H$_{28}$F$_3$N$_5$O$_5$S | Intermediate 17 and Intermediate 23 |
| 56 | Ethyl 1-(2-(dimethylamino)ethyl)-6-(6-(3-ethylureido)-4-(4-(trifluoromethyl)thiazol-2-yl)pyridin-3-yl)-4-oxo-1,4-dihydroquinoline-3-carboxylate | MS (ESP): 603 (M + 1) for C$_{28}$H$_{29}$F$_3$N$_6$O$_4$S<br>$^1$H-NMR (DMSO-d$_6$) 1.11 (t, J = 7.07 Hz, 3H); 1.29 (t, J = 7.07 Hz, 3H); 2.21 (br. s., 6H); 2.57-2.69 (m, 2H); 3.16-3.27 (m, 2H); 4.24 (q, J = 7.07 Hz, 2H); 4.51 (br. s., 2H); 7.59-7.66 (m, 1H); 7.69 (dd, J = 8.59, 2.02 Hz, 1H); 7.88 (d, J = 9.09 Hz, 1H); 8.15 (d, J = 2.02 Hz, 1H); 8.22 (s, 1H); 8.33 (s, 1H); 8.51 (s, 1H); 8.66 (s, 1H); 9.45 (s, 1H) | Intermediate 17 and Intermediate 29 |
| 57 | Ethyl 6-(6-(3-ethylureido)-4-(4-(trifluoromethyl)thiazol-2-yl)pyridin-3-yl)-1-(2-hydroxyethyl)-4-oxo-1,4-dihydroquinoline-3-carboxylate | MS (ESP): 576 (M + 1) for C$_{26}$H$_{24}$F$_3$N$_5$O$_5$S<br>$^1$H-NMR (DMSO-d$_6$): 1.11 (t, J = 7.20 Hz, 3H); 1.28 (t, J = 7.07 Hz, 3H); 3.16-3.26 (m, 2H); 3.71-3.78 (m, 2H); 4.24 (q, J = 7.07 Hz, 2H); 4.41-4.51 (m, 2H); 5.07 (t, J = 5.43 Hz, 1H); 7.60-7.67 (m, 1H); 7.69 (dd, J = 8.84, 2.27 Hz, 1H); 7.91 (d, J = 8.84 Hz, 1H); 8.16 (d, J = 2.27 Hz, 1H); 8.23 (s, 1H); 8.31 (s, 1H); 8.49 (s, 1H); 8.61 (s, 1H); 9.45 (s, 1H) | Intermediate 17 and Intermediate 30 |

| Ex | Compound | Data | SM |
|---|---|---|---|
| 58 | Ethyl 1-cyclopropyl-6-(6-(3-ethylureido)-4-(4-(trifluoromethyl)thiazol-2-yl)pyridin-3-yl)-4-oxo-1,4-dihydroquinoline-3-carboxylate | MS (ESP): 572 (M + 1) for $C_{27}H_{24}F_3N_5O_4S$ | Intermediate 17 and Intermediate 27 |
| 59 | Ethyl 6-(6-(3-ethylureido)-4-(4-(trifluoromethyl)thiazol-2-yl)pyridin-3-yl)-1-isopropyl-4-oxo-1,4-dihydroquinoline-3-carboxylate | MS (ESP): 574 (M + 1) for $C_{27}H_{26}F_3N_5O_4S$ | Intermediate 17 and Intermediate 28 |
| 60 | Ethyl 7-(6-(3-ethylureido)-4-(4-(trifluoromethyl)thiazol-2-yl)pyridin-3-yl)-1-methyl-4-oxo-1,4-dihydroquinoline-3-carboxylate | MS (ESP): 546 (M + 1) for $C_{25}H_{22}F_3N_5O_4S$ | Intermediate 17 and Intermediate 25 |
| 61 | Ethyl 7-(6-(3-ethylureido)-4-(4-(trifluoromethyl)thiazol-2-yl)pyridin-3-yl)-1-isopropyl-4-oxo-1,4-dihydroquinoline-3-carboxylate | MS (ESP): 574 (M + 1) for $C_{27}H_{26}F_3N_5O_4S$ | Intermediate 17 and Intermediate 26 |

Example 62

The following Intermediate was prepared by the procedure described in Example 51 from the starting materials (SM) indicated.

| Ex | Compound | Data | SM |
|---|---|---|---|
| 62 | Ethyl 6-(6-(3-ethylureido)-4-(4-(trifluoromethyl)thiazol-2-yl)pyridin-3-yl)-1-(1-methylazetidin-3-yl)-4-oxo-1,4-dihydroquinoline-3-carboxylate | MS (ESP): 601 (M + 1) for $C_{28}H_{27}F_3N_6O_4S$ | Intermediate 17 and Intermediate 31 |

Examples 63-70

The following Intermediates were prepared by the procedure described in Example 42 from the starting materials (SM) indicated.

| Ex | Compound | Data | SM |
|---|---|---|---|
| 63 | Ethyl 7-{6-[(ethylcarbamoyl)amino]-4-[4-(trifluoromethyl)-1,3-thiazol-2-yl]pyridin-3-yl}-1-(3-methylbutyl)-4-oxo-1,4-dihydroquinoline-3-carboxylate | $^1$H NMR (400 MHz, DMSO-d$_6$): 0.91 (d, 6H), 1.12 (t, 3H), 1.31 (t, 3H), 1.39 (d, 2H), 1.56 (m, 1H), 3.21 (q, 2H), 4.21 (q, 2H), 4.31 (t, 2H), 7.48 (d, 1H), 7.58 (t, 2H), 7.68 (s, 1H), 8.24 (s, 1H), 8.30 (d, 1H), 8.38 (s, 1H), 8.51 (s, 1H), 8.68 (s, 1H). | Intermediate 17 and Intermediate 34 |

| Ex | Compound | Data | SM |
|---|---|---|---|
| 64 | Ethyl 7-{6-[(ethylcarbamoyl)amino]-4-[4-(trifluoromethyl)-1,3-thiazol-2-yl]pyridin-3-yl}-1-(2-methylpropyl)-4-oxo-1,4-dihydroquinoline-3-carboxylate | $^1$H NMR (400 MHz, DMSO-$d_6$): 0.78 (d, 6H), 1.15 (t, 3H), 1.32 (t, 3H), 1.61 (m, 1H), 3.38 (q, 2H), 4.12 (d, 2H), 4.36 (q, 2H), 7.48 (d, 1H), 7.61 (d, 2H), 7.71 (s, 1H), 8.18 (s, 1H), 8.31 (d, 1H), 8.39 (s, 1H), 8.52 (s, 1H), 8.64 (s, 1H), 9.52 (s, 1H). | Intermediate 17 and Intermediate 35 |
| 65 | Ethyl 7-{6-[(ethylcarbamoyl)amino]-4-[4-(trifluoromethyl)-1,3-thiazol-2-yl]pyridin-3-yl}-4-oxo-1-propyl-1,4-dihydroquinoline-3-carboxylate | $^1$H NMR (400 MHz, DMSO-$d_6$): 0.91 (t, 3H), 1.16 (t, 3H), 1.56 (m, 2H), 3.21 (q, 2H), 3.34 (s, 2H), 4.26 (q, 2H), 7.41 (d, 1H), 7.60 (s, 1H), 7.78 (s, 1H), 8.21 (s, 1H), 8.28 (d, 1H), 8.52 (s, 1H), 8.68 (s, 1H), 9.42 (s, 1H). | Intermediate 17 and Intermediate 36 |
| 66 | Ethyl 1-benzyl-7-{6-[(ethylcarbamoyl)amino]-4-[4-(trifluoromethyl)-1,3-thiazol-2-yl]pyridin-3-yl}-4-oxo-1,4-dihydroquinoline-3-carboxylate | $^1$H NMR (400 MHz, DMSO-$d_6$): 1.10 (t, 3H), 1.31 (t, 3H), 3.21 (q, 2H), 4.24 (q, 2H), 5.63 (s, 1H), 7.14 (d, 2H), 7.22 (d, 3H), 7.36 (d, 1H), 7.56 (s, 1H), 7.77 (s, 1H), 8.14 (s, 1H), 8.24 (s, 1H), 8.31 (s, 2H), 8.89 (s, 1H), 9.41 (s, 1H). | Intermediate 17 and Intermediate 37 |

| Ex | Compound | Data | SM |
|---|---|---|---|
| 67 | Ethyl 7-{6-[(ethylcarbamoyl)amino]-4-[4-(trifluoromethyl)-1,3-thiazol-2-yl]pyridin-3-yl}-4-oxo-1-(pyridin-3-ylmethyl)-1,4-dihydroquinoline-3-carboxylate | $^1$H NMR (400 MHz, DMSO-$d_6$): 1.08 (t, 3H), 1.36 (t, 3H), 3.21 (q, 2H), 4.21 (q, 2H), 5.68 (s, 2H), 7.38 (d, 2H), 7.61 (d, 2H), 7.71 (s, 1H), 8.18 (s, 1H), 8.22 (s, 1H), 8.31 (d, 1H), 8.34 (s, 1H), 8.51 (s, 2H). | Intermediate 17 and Intermediate 38 |
| 68 | Ethyl 7-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydroquinoline-3-carboxylate | $^1$H NMR (400 MHz, DMSO-$d_6$): δ 1.16 (t, 3H), 1.29 (t, 3H), 3.21 (t, 2H), 3.61 (t, 2H), 4.21 (q, 2H), 4.41 (s, 2H), 5.01 (s, 2H), 7.26 (s, 1H), 7.38 (d, 2H), 7.65 (s, 1H), 7.89 (s, 1H), 8.26 (d, 2H), 8.36 (s, 1H), 8.48 (s, 1H), 8.58 (s, 1H), 9.52 (s, 1H). | Intermediate 17 and Intermediate 39 |

| Ex | Compound | Data | SM |
|---|---|---|---|
| 69 | Ethyl 7-{6-[(ethylcarbamoyl)amino]-4-[4-(trifluoromethyl)-1,3-thiazol-2-yl]pyridin-3-yl}-1-(2-methoxyethyl)-4-oxo-1,4-dihydroquinoline-3-carboxylate | $^1$H NMR (400 MHz, DMSO-$d_6$): 1.14 (t, 3H), 1.32 (t, 3H), 3.11 (s, 3H), 3.30 (s, 2H), 3.46 (s, 1H), 4.21 (q, 2H), 4.58 (s, 2H), 7.41 (d, 1H), 7.64 (s, 1H), 7.86 (s, 1H), 8.24 (d, 2H), 8.38 (s, 1H), 8.50 (s, 1H), 8.58 (s, 1H). | Intermediate 17 and Intermediate 40 |
| 70 | Ethyl 1-(cyclopropylmethyl)-7-{6-[(ethylcarbamoyl)amino]-4-[4-(trifluoromethyl)-1,3-thiazol-2-yl]pyridin-3-yl}-4-oxo-1,4-dihydroquinoline-3-carboxylate | $^1$H NMR (400 MHz, DMSO-$d_6$): 0.38 (m, 4H), 0.98 (m, 1H), 1.10 (t, 3H), 1.29 (t, 3H), 3.19 (q, 2H), 4.29 (q, 2H), 7.40 (d, 1H), 7.61 (s, 1H), 7.91 (s, 1H), 8.21 (s, 1H), 8.23 (d, 1H), 8.38 (s, 1H), 8.48 (s, 1H), 8.71 (s, 1H), 9.42 (s, 1H). | Intermediate 17 and Intermediate 41 |

Example 71

(S)-6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylic acid

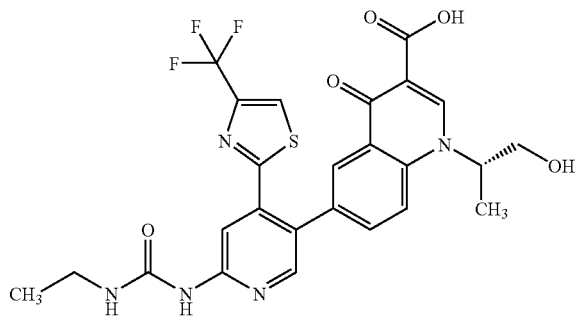

To a solution of (S)-ethyl 6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylate (Example 97, 200 mg, 0.34 mmol, 1 equiv.) in tetrahydrofuran (1 mL) and methanol (1 mL) was added 2 M lithium hydroxide (0.339 mL). The mixture was stirred in the microwave at 100° C. for 15 min The reaction mixture was cooled to room temperature and diluted with water. 1 N HCl was added until pH 3-4 was reached. The reaction mixture was partitioned between ethyl acetate (5 mL) and water (5 mL). The aqueous layer was extracted with ethyl acetate (2×5 mL), and the organics were washed with brine (10 mL), dried over sodium sulfate, and concentrated under reduced pressure. Purification via reverse phase HPLC (C18 column, acetonitrile/water 0-95% gradient) and concentrated under reduced pressure to provide (S)-6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylic acid as a light yellow solid (92 mg, 48%).

MS (ESP) [M+H]$^+$: 562 for $C_{25}H_{22}F_3N_5O_5S$.

H$^1$NMR ($d_6$-DMSO) δ 14.98 (s, 1H), 9.53 (s, 1H), 8.93 (s, 1H), 8.51 (s, 1H), 8.36 (s, 1H), 8.34 (d, 1H), 8.25 (d, 1H), 8.23 (s, 1H), 7.87-7.83 (dd, 1H), 7.65 (t, 1H), 5.28 (s, 2H), 3.81 (s, 2H), 3.25-3.16 (m, 3H), 1.56 (d, 3H), 1.11 (t, 3H).

Examples 72-79

The following examples were prepared by the procedure described in Example 71 from the indicated starting material

| Ex | Compound | Data | SM |
|---|---|---|---|
| 72 | (R)-6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylic acid | MS (ESP): 562 (M + 1) for $C_{25}H_{22}F_3N_5O_5S$<br>NMR ($d_6$-DMSO) δ 15.09 (s, 1H), 9.51 (s, 1H), 8.94 (s, 1H), 8.51 (s, 1H), 8.36 (d, 2H), 8.24 (s, 2H), 7.87 (d, 1H), 7.65 (s, 1H), 5.3 (s, 2H), 3.82 (s, 2H), 3.21 (m, 3H), 1.56 (d, 3H), 1.11 (t, 3H) | Example 98 |
| 73 | 1-((2R,3R)-1,3-dihydroxybutan-2-yl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 592 (M + 1) for $C_{26}H_{24}F_3N_5O_6S$<br>NMR ($d_6$-DMSO) δ 15.1 (s, 1H), 9.48 (s, 1H), 9.12 (s, 1H), 8.53 (s, 1H), 8.38, (s, 1H), 8.33 (d, 1H), 8.29 (d, 1H), 8.22 (s, 1H), 7.84 (dd, 1H), 7.61 (t, 1H), 5.3-5.1 (m, 2H), 4.26 (t, 1H), 4.04-3.97 (m, 1H), 3.87 (d, 1H), 3.23-3.17 (m, 2), 1.14 (d, 3H), 1.11 (t, 3H) | Example 99 |
| 74 | (S)-6-(6-(3-ethylureido)-4-(4-(trifluoromethyl)thiazol-2-yl)pyridin-3-yl)-1-(1-hydroxy-3-phenylpropan-2-yl)-4-oxo-1,4-dihydroquinoline-3-carboxylic acid | MS (ESP): 638 (M + 1) for $C_{31}H_{26}F_3N_5O_5S$<br>NMR ($d_6$-DMSO) δ 14.47 (s, 1H), 9.47 (s, 1H), 9.05 (s, 1H), 8.58 (s, 1H), 8.32 (s, 1H), 8.24 (d, 1H), 8.22 (s, 1H), 8.19 (d, 1H), 7.77 (dd, 1H), 7.6 (t, 1H), 7.2-7.15 (m, 5H), 5.55 (s, 1H), 5.36 (t, 1H), 3.99-3.82 (m, 2H), 3.22-3.16 (m, 2H), 1.11 (t, 3H) | Example 109 |

| Ex | Compound | Data | SM |
|---|---|---|---|
| 75 | 1-(1,3-dihydroxypropan-2-yl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 578 (M + 1) for $C_{25}H_{22}F_3N_5O_6S$<br>NMR ($d_6$-DMSO) δ 9.5 (s, 1H), 8.96 (s, 1H), 8.51 (d, 1H), 8.36 (s, 1H), 8.35 (d, 1H), 8.26 (d, 1H), 8.23 (s, 1H), 7.87 (dd, 1H), 7.63 (t, 1H), 5.28-5.19 (m, 2H), 3.99-3.84 (m, 4H), 3.25-3.16 (2H), 1.11 (t, 3H) | Example 100 |
| 76 | (R)-6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylic acid | MS (ESP): 604 (M + 1) for $C_{28}H_{28}F_3N_5O_5S$<br>NMR ($d_6$-DMSO) δ 9.59 (s, 1H), 8.87 (s, 1H), 8.55 (s, 1H), 8.47 (d, 1H), 8.39 (s, 1H), 8.33 (d, 1H), 8.23 (s, 1H), 7.8 (dd, 1H), 7.67 (t, 1H), 5.21-5.17 (m, 1H), 4.16-4.03 (m, 2H), 3.25-3.16 (m, 2H), 1.11 (t, 3H), 0.97 (s, 9H) | Example 108 |
| 77 | (R)-6-(6-(3-ethylureido)-4-(4-(trifluoromethyl)thiazol-2-yl)pyridin-3-yl)-1-(1-hydroxy-3-(4-hydroxyphenyl)propan-2-yl)-4-oxo-1,4-dihydroquinoline-3-carboxylic acid | MS (ESP): 604 (M + 1) for $C_{31}H_{26}F_3N_5O_6S$<br>NMR ($d_6$-DMSO) δ 14.99 (s, 1H), 9.46 (s, 1H), 89.25 (s, 1H), 9.01 (s, 1H), 8.51 (s, 1H), 8.32 (s, 1H), 8.24 (s, 1H), 8.19 (d, 1H), 7.79 (d, 1H), 7.6 (t, 1H), 6.98 (d, 2H), 6.56 (d, 2H), 5.51-5.44 (m 1H), 5.33 (t, 1H), 3.99-3.79 (m, 2H), 3.26-3.09 (m, 3H), 1.11 (t, 3H), 0.07 (s, 1H) | Example 117 |

| Ex | Compound | Data | SM |
|---|---|---|---|
| 78 | (S)-1-(1-cyclohexyl-2-hydroxyethyl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 630 (M + 1) for $C_{30}H_{30}F_3N_5O_5S$<br>NMR ($d_6$-DMSO) δ 15.03 (s, 1H), 9.48 (s, 1H), 9.01 (s, 1H), 8.54 (s, 1H), 8.39 (s, 1H), 8.34 (d, 1H), 8.32 (d, 1H), 8.2 (s, 1H), 7.82 (dd, 1H), 7.59 (t, 1H), 5.27 (t, 1H), 5.02-4.95 (m, 1H), 4.07-3.97 (m, 1H), 3.81-3.75 (m, 1H), 3.26-3.18 (m, 2H), 2.15-2.01 (m, 1H), 1.97-1.9 (m 1H), 1.81-1.73 (m, 1H), 1.61-1.55 (m, 2H), 1.3-1.17 (m, 2H), 1.11 (t, 3H) | Example 118 |
| 79 | (R)-6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylic acid | MS (ESP): 576 (M + 1) for $C_{26}H_{24}F_3N_5O_5S$<br>NMR ($d_6$-DMSO) δ 15.1 (s, 1H), 9.48 (s, 1H), 8.93 (s, 1H), 8.53 (s, 1H), 8.38 (s, 1H), 8.34 (d, 1H), 8.3 (d, 1H), 8.22 (s, 1H), 7.86 (dd, 1H), 7.6 (t, 1H), 5.13 (m, 2H), 3.92-3.84 (m, 2H), 3.26-3.17 (m, 2H), 2.06-1.92 (m, 2H), 1.11 (t, 3H), 0.89 (t, 3H) | Example 102 |

Example 80

6-(6-(3-ethylureido)-4-(4-(trifluoromethyl)thiazol-2-yl)pyridin-3-yl)-1-(-hydroxy-1-(tetrahydro-H-pyran-4-yl)ethyl)-4-oxo-1,4-dihydroquinoline-3-carboxylic acid

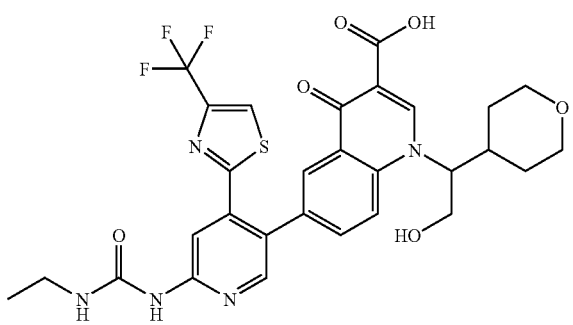

To a solution of ethyl 6-(6-(3-ethylureido)-4-(4-(trifluoromethyl)thiazol-2-yl)pyridin-3-yl)-1-(2-hydroxy-1-(tetrahydro-2H-pyran-4-yl)ethyl)-4-oxo-1,4-dihydroquinoline-3-carboxylate (Example 103, 107 mg, 0.16 mmol, 1 equiv.) in tetrahydrofuran (1 mL) and methanol (1 mL) was added 2 M lithium hydroxide (0.162 mL, 0.32 mmol). The reaction mixture was heated to 100° C. for 15 min in a microwave. The reaction mixture was cooled to room temperature and diluted with water. The reaction mixture was filtered, and the filtrate was dried. Purification via reverse phase HPLC (C18, acetonitrile/water 0-95% gradient) and concentrated under reduced pressure to provide 6-(6-(3-ethylureido)-4-(4-(trifluoromethyl)thiazol--yl)pyridin-3-yl)-1-(2-hydroxy-1-(tetrahydro-2H-pyran-4-yl)ethyl)-4-oxo-1,4-dihydroquinoline-3-carboxylic acid as a light yellow solid (26.5 mg, 26%).

MS (ESP): 632 (M+1) for $C_{29}H_{28}F_3N_5O_6S$.

NMR ($d_6$-DMSO) δ 15.03 (s, 1H), 9.39 (s, 1H), 8.98 (s, 1H), 8.46 (s, 1H), 8.32 (s, 1H), 8.29 (d, 1H), 8.25 (d, 1H), 8.13 (s, 1H), 7.76 (dd, 1H), 7.51 (t, 1H), 4.97 (m, 1H), 3.98 (dd, 1H), 3.83 (dd, 1H), 3.73-3.63 (3H), 3.19-3.10 (m, 2H), 2.31-

2.2 (m, 1H), 1.73-1.68 (m, 1H), 1.59-1.5 (m, 1H), 1.16-1.09 (m, 1H), 1.04 (t, 3H), 1.0-0.94 (m, 1H).

Example 81

6-{6-[(ethylcarbamoyl)amino]-4-[4-(trifluoromethyl)-1,3-thiazol-2-yl]pyridin-3-yl}-1-[(1S)-1-(hydroxymethyl)-2,2-dimethylpropyl]-4-oxo-1,4-dihydroquinoline-3-carboxylic acid

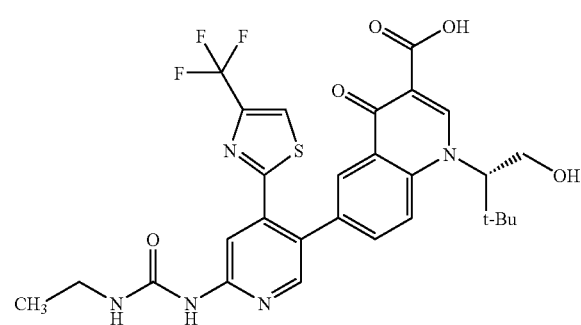

To a solution of (S)-ethyl 6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylate (Example 104, 212.7 mg, 0.34 mmol) in tetrahydrofuran (1 mL) and methanol (1 mL) was added 2 M lithium hydroxide (0.253 mL, 0.51 mmol). The reaction mixture was heated at 100° C. for 15 min in a microwave reactor. The reaction mixture was cooled to room temperature and diluted with water. 1 N HCl was added until pH 3-4 was reached. The precipitate that formed was collected by filtration, washed with water and hexanes. Purification via column chromatography (silica, 95:5 methylene chloride/methanol) provided (S)-6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylic acid as a light yellow solid (72.3 mg, 35%).

MS (ESP): 604 (M+1) for $C_{28}H_{28}F_3N_5O_5S$.

NMR (d$_6$-DMSO) δ 15.01 (s, 1H), 9.4 (s, 1H), 8.78 (s, 1H), 8.46 (s, 1H), 8.37 (d, 1H), 8.31 (s, 1H), 8.25 (d, 1H), 8.11 (s, 1H), 7.72 (dd, 1H), 7.5 (t, 1H), 5.12-5.08 (m, 1H), 4.09-3.96 (m, 2H), 3.17-3.08 (m, 2H), 1.02 (t, 3H), 0.89 (s, 9H).

Example 82

6-{6-[(ethylcarbamoyl)amino]-4-[4-(trifluoromethyl)-1,3-thiazol-2-yl]pyridin-3-yl}-1-[(1S)-1-(hydroxymethyl)-2-methylpropyl]-4-oxo-1,4-dihydroquinoline-3-carboxylic acid

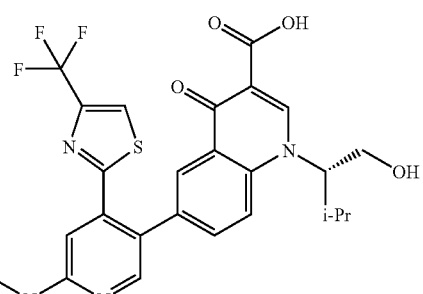

To a solution of (S)-ethyl 6-(6-(3-ethylureido)-4-(4-(trifluoromethyl)thiazol-2-yl)pyridin-3-yl)-1-(1-hydroxy-3-methylbutan-2-yl)-4-oxo-1,4-dihydroquinoline-3-carboxylate (Example 110, 213 mg, 0.35 mmol) in tetrahydrofuran (1 mL) and methanol (1 mL) was added 2 M lithium hydroxide (0.259 mL, 0.52 mmol). The reaction mixture was heated at 100° C. for 15 min in a microwave reactor. The reaction mixture was cooled to room temperature, diluted with water, and treated with 1 N HCl until pH 3-4. The precipitate that formed was collected by filtration, washed with water and hexanes. Purification via reverse phase HPLC (C18, acetonitrile/water 0-95% gradient) provided (S)-6-(6-(3-ethylureido)-4-(4-(trifluoromethyl)thiazol-2-yl)pyridin-3-yl)-1-(1-hydroxy-3-methylbutan-2-yl)-4-oxo-1,4-dihydroquinoline-3-carboxylic acid as a light yellow solid (146.4 mg, 72%).

MS (ESP): 590 for $C_{27}H_{26}F_3N_5O_5S$.

NMR (d$_6$-DMSO) δ 14.98 (s, 1H), 9.5 (s, 1H), 9.0 (s, 1H), 8.53 (s, 1H), 8.39 (s, 1H), 8.33 (d, 1H), 8.21 (s, 1H), 7.83 (dd, 1H), 7.62 (t, 1H), 5.26 (s, 1H), 4.92 (s, 1H), 4.0 (d, 1H), 3.81 (d, 1H), 3.22-3.19 (m, 2H), 2.38 (m, 1H), 1.11 (t, 3H), 1.09 (d, 3H), 0.74 (d, 3H).

Examples 83-95

The following examples were prepared by the procedure described in Example 83 from the indicated starting material.

| Ex | Compound | Data | SM |
|---|---|---|---|
| 83 | (S)-6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylic acid | MS (ESP): 604 for $C_{28}H_{28}F_3N_5O_5S$ NMR (d$_6$-DMSO) δ 14.88 (s, 1H), 9.53 (s, 1H), 8.9 (s, 1H), 8.54 (s, 1H), 8.39 (s, 1H), 8.34 (d, 1H), 8.32 (d, 1H), 8.22 (s, 1H), 7.85 (dd, 1H), 7.63 (t, 1H), 5.24 (s, 2H), 3.83-3.73 (m, 2H), 3.22-3.17 (m, 3H), 1.97-1.81 (m, 2H), 1.48-1.4 (m, 1H), 1.11 (t, 3H), 0.92 (d, 3H), 0.86 (d, 3H) | Example 111 |
| 84 | (S)-1-(1-hydroxy-3,3-dimethylbutan-2-yl)-4-oxo-6-(6-(3-propylureido)-4-(4-(trifluoromethyl)thiazol-2-yl)pyridin-3-yl)-1,4-dihydroquinoline-3-carboxylic acid | MS (ESP): 618 for $C_{29}H_{30}F_3N_5O_5S$ NMR (d$_6$-DMSO) δ 15.09 (s, 1H), 9.48 (s, 1H0, 8.91 (s, 1H), 8.54 (s, 1H), 8.39 (s, 1H), 8.34 (d, 1H), 8.3 (s, 1H), 8.22 (s, 1H), 7.87 (dd, 1H), 7.65 (t, 1H), 5.26-5.23 (m, 2H), 3.85-3.73 (m, 2H), 3.19-3.12 (m, 2H), 1.55-1.42 (m, 2H), 0.92 (t, 3H), 0.91 (s, 9H) | Example 101 |
| 85 | (R)-6-(6-(3-ethylureido)-4-(4-(trifluoromethyl)thiazol-2-yl)pyridin-3-yl)-1-(1-hydroxy-3-methylbutan-2-yl)-4-oxo-1,4-dihydroquinoline-3-carboxylic acid | MS (ESP): 590 for $C_{27}H_{26}F_3N_5O_5S$ H$^1$NMR (d$_6$-DMSO) δ 9.56 (s, 1H), 8.99 (s, 1H), 8.53 (s, 1H), 8.39 (s, 1H) 8.33 (d, 1H), 8.3 (s, 1H), 8.22 (s, 1H), 7.82 (dd, 1H), 7.67 (t, 1H), 4.91 (s, 1H), 4.04-3.98 (m, 1H), 3.8 (d, 1H), 3.25-3.16 (m, 2H), 2.42-2.35 (m, 1H), 1.11 (t, 3H), 1.09 (d, 3H), 0.73 (d, 3H) | Example 112 |

-continued

| Ex | Compound | Data | SM |
|---|---|---|---|
| 86 | (S)-6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylic acid | MS (ESP): 576 for $C_{30}H_{24}F_3N_5O_5S$ NMR ($d_6$-DMSO) δ 15.08 (s, 1H), 9.48 (s, 1H), 8.93 (s, 1H), 8.53 (s, 1H), 8.38 (s, 1H) 8.34 (d, 1H), 8.3 (d, 1H), 8.22 (s, 1H), 7.86 (dd, 1H), 7.6 (t, 1H), 5.13 (m, 2H), 3.89-3.75 (m, 2H), 3.26-3.17 (m, 2H), 2.09-1.92 (m, 2H), 1.11 (t, 3H), 0.89 (t, 3H) | Example 113 |
| 87 | (S)-1-(1-hydroxy-4-methylpentan-2-yl)-4-oxo-6-(6-(3-propylureido)-4-(4-(trifluoromethyl)thiazol-2-yl)pyridin-3-yl)-1,4-dihydroquinoline-3-carboxylic acid | MS (ESP): 618 for $C_{29}H_{30}F_3N_5O_5S$ $H^1$NMR ($d_6$-DMSO) δ 14.61 (s, 1H), 9.04 (s, 1H), 8.47 (s, 1H), 8.1 (s, 1H), 7.96 (s, 1H), 7.9 (s, 1H), 7.89 (d, 1H), 7.78 (s, 1H), 7.42 (dd, 1H), 7.2 (t, 1H), 4.79 (m, 1H), 3.3 (m, 2H), 2.74-2.69 (m, 2H), 1.54-1.47 (m, 1H), 1.44-1.39 (m, 1H), 1.1-.79 (m, 3H), 0.48 (t, 3H), 0.47 (d, 3H), 0.43 (d, 3H) | Example 114 |
| 88 | (S)-6-(6-(3-ethylureido)-4-(4-(trifluoromethyl)thiazol-2-yl)pyridin-3-yl)-4-oxo-1-((tetrahydrofuran-2-yl)methyl)-1,4-dihydroquinoline-3-carboxylic acid | MS (ESP): 588 for $C_{27}H_{24}F_3N_5O_5S$ $H^1$NMR ($d_6$-DMSO) δ 15.06 (s, 1H), 9.48 (s, 1H), 8.98 (s, 1H), 8.51 (s, 1H), 8.37 (s, 1H), 8.32 (s, 1H), 8.23 (s, 1H), 8.19 (d, 1H), 7.86 (dd, 1H), 7.61 (t, 1H), 4.88 (d, 1h), 4.55-4.46 (m, 1H), 4.21-4.16 (m, 1H), 3.86-3.78 (m, 1H), 3.78-3.62 (m, 1H), 3.24-3.18 (m, 2H), 2.11-2.07 (m, 1H), 1.94-1.87 (m, 1H), 1.87-1.81 (m, 1H), 1.67-1.61 (m 1H), 1.11 (t, 3H) | Example 105 |

| Ex | Compound | Data | SM |
|---|---|---|---|
| 89 | 6-(6-(3-ethylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxylic acid | MS (ESP): 629 for $C_{30}H_{31}F_3N_6O_4S$ NMR (d$_6$-DMSO) δ 15.02 (s, 1H), 9.44 (s, 1H), 9.1 (s, 1H), 8.49 (s, 1H), 8.33 (s, 1H), 8.28 (d, 1H), 8.18 (s, 1H), 8.02 (s, 1H), 7.83 (dd, 1H), 7.54 (t, 1H), 4.62-4.55 (m, 2H), 3.21-3.12 (m, 2H), 2.93-2.81 (m, 2H), 2.72(d, 3H), 1.95 (d, 2H), 1.77-1.69 (m, 3H), 1.37-1.25 (m, 2H), 1.07 (t, 3H) | Example 106 |
| 90 | 6-(6-(3-ethylureido)-4-(4-(trifluoromethyl)thiazol-2-yl)pyridin-3-yl)-4-oxo-1-((tetrahydro-2H-pyran-4-yl)methyl)-1,4-dihydroquinoline-3-carboxylic acid | MS (ESP): 602 for $C_{28}H_{26}F_3N_5O_5S$ NMR (d$_6$-DMSO) δ 15.08 (s, 1H), 9.48 (s, 1H), 9.06 (s, 1H), 8.54 (s, 1H), 8.39 (s, 1H), 8.31 (d, 1H), 8.21 (s, 1H), 8.17 (d, 1H), 7.84 (dd, 1H), 7.59 (t, 1H), 4.54 (dd, 2H), 3.86 (dd, 2H), 3.26-3.14 (m, 4H), 2.15-2.04 (m, 1H), 1.47-1.3 (m, 4H), 1.11 (t, 3H) | Example 107 |
| 91 | 1-((2S,3S)-1,3-dihydroxypentan-2-yl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 604 for $C_{28}H_{28}F_3N_5O_5S$ NMR (d$_6$-DMSO) δ 15.03 (s, 1H), 9.52 (s, 1H), 8.97 (s, 1H), 8.59 (s, 1H), 8.38 (s, 1H), 8.32 (d, 1H), 8.26 (d, 1H), 8.21 (s, 1H), 7.8 (m, 1H), 7.64 (t, 1H), 5.3-5.2 (m, 1H), 5.0-4.86 (m, 1H), 4.14-3.95 (m, 1H), 3.85-3.72 (m, 1H), 3.24-3.16 (m, 2H), 2.23-2.11 (m, 1H), 1.11 (t, 3H), 0.76-0.7 (m, 2H), 0.06 (t, 3H) | Example 115 |

| Ex | Compound | Data | SM |
|---|---|---|---|
| 92 | 6-(6-(3-ethylureido)-4-(4-(trifluoromethyl)thiazol-2-yl)pyridin-3-yl)-1-(1-methoxy-3-methylbutan-2-yl)-4-oxo-1,4-dihydroquinoline-3-carboxylic acid | MS (ESP): 604 for $C_{28}H_{28}F_3N_5O_5S$ H$^1$NMR (d$_6$-DMSO) δ 15.06 (s, 1H), 9.48 (s, 1H), 8.98 (s, 1H), 8.55 (s, 1H), 8.4 (s, 1H), 8.37 (d, 1H), 8.32 (s, 1H), 8.2 (s, 1H), 7.83 (dd, 1H), 7.59 (t, 1H), 5.19-5.05 (m, 1H), 4.06-3.93 (m, 1H), 3.8-3.73 (m, 1H), 3.63-3.59 (m, 1H), 3.3-3.23 (m, 2H), 3.24 (s, 3H), 1.81-1.73 (m, 1H), 1.11 (t, 3H), 1.09 (d, 3H), 0.72 (d, 3H) | Example 116 |
| 93 | 6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylic acid | MS (ESP): 576 for $C_{26}H_{24}F_3N_5O_5S$ NMR (d$_6$-DMSO) δ 15.13 (s, 1H), 9.48 (s, 1H), 8.93 (s, 1H), 8.53 (s, 1H), 8.38 (s, 1H), 8.34 (s, 1H), 8.3 (d, 1H), 8.21 (d, 1H), 8.21 (d, 1H), 7.86 (dd, 1H), 7.61 (t, 1H), 5.28-2.21 (m, 1H), 5.17-5.06 (m, 1H), 3.95-3.88 (m, 1H), 3.8-3.75 (m, 1H), 3.26-3.19 (m, 2H), 2.09-1.88 (m, 2H), 1.11 (t, 3H), 0.89 (t, 3H) | Example 120 |
| 94 | 6-(6-(3-ethylureido)-4-(4-(trifluoromethyl)thiazol-2-yl)pyridin-3-yl)-1-((1-methylpiperidin-4-yl)methyl)-4-oxo-1,4-dihydroquinoline-3-carboxylic acid | MS (ESP): 615 for $C_{29}H_{29}F_3N_6O_4S$ NMR (d$_6$-DMSO) δ 9.53 (s, 1H), 8.82 (s, 1H), 8.46 (s, 1H), 8.34 (s, 1H), 8.26 (s, 1H), 8.25 (s, 1H), 7.95 (dd, 1H), 7.72 (t, 1H), 7.65 (d, 1H), 4.35-4.3 (m, 2H), 3.26-3.18 (m, 2H), 2.76-2.71 (m, 2H), 2.1 (s, 3H), 1.75-1.67 (m, 2H), 1.48-1.4 (m, 2H), 1.37-1.31 (m, 2H), 1.25-1.22 (m, 1H), 1.1 (t, 3H) | Example 121 |

| Ex | Compound | Data | SM |
|---|---|---|---|
| 95 | (S)-6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylic acid | MS (ESP): 604 for $C_{28}H_{28}F_3N_5O_5S$ NMR ($d_6$-DMSO) δ 15.08 (s, 1H), 9.47 (s, 1H), 8.89 (s, 1H), 8.53 (s, 1H), 8.37 (s, 1H), 8.32 (d, 1H), 8.2 (s, 1H), 7.85 (dd, 1H), 7.58 (t, 1H), 5.23 (s, 2H), 3.84-3.75 (m, 2H), 3.24-3.17 (m, 2H), 1.92-1.82 (m, 2H), 1.48-1.42 (m, 1H), 1.09 (t, 3H), 0.91 (d, 3H), 0.85 (d, 3H) | Example 119 |

Example 96

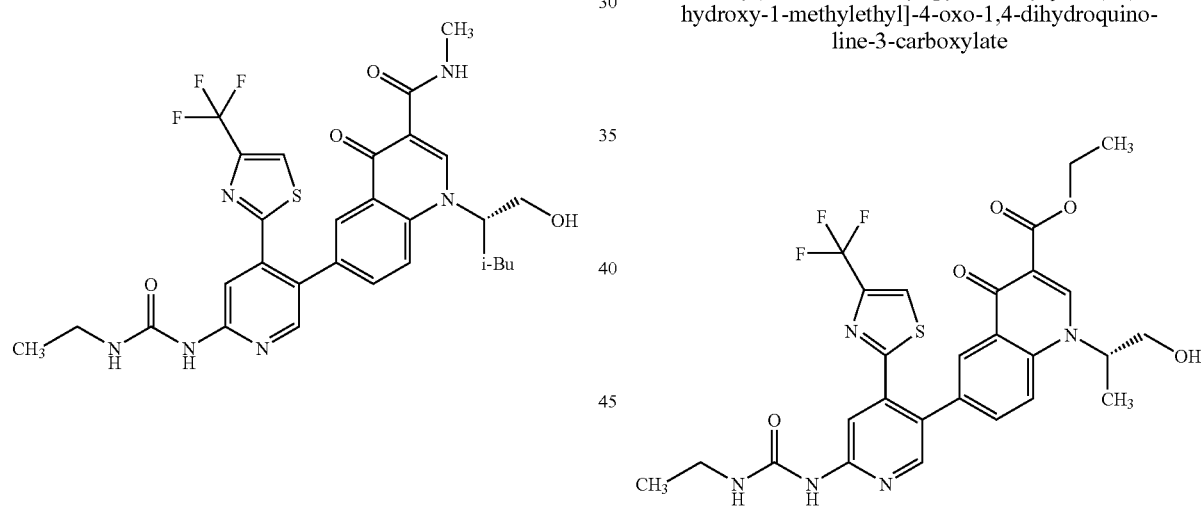

A solution of (S)-ethyl 6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylate (Example 119, 280 mg, 0.44 mmol) in 33 wt. % methylamine solution in absolute ethanol (4 mL, 32.13 mmol) was heated in the microwave at 80° C. for 30 min The reaction mixture was concentrated under reduced pressure. Purification via column chromatography to provide (silica, 95:5 methylene chloride/methanol) gave (S)-6-(6-(3-ethylureido)-4-(4-(trifluoromethyl)thiazol-2-yl)pyridin-3-yl)-1-(1-hydroxy-4-methylpentan-2-yl)-N-methyl-4-oxo-1,4-dihydroquinoline-3-carboxamide as a light yellow solid (219.2 mg, 80%).

MS (ESP): 617 for $C_{29}H_{31}F_3N_6O_4S$.

NMR ($d_6$-DMSO) δ 9.75-9.7 (m, 1H), 9.46 (s, 1H), 8.86 (s, 1H), 8.52 (s, 1H), 8.36 (s, 1H), 8.27 (d, 1H), 8.21 (s, 1H), 8.19 (d, 1H), 7.75 (dd, 1H), 7.62 (t, 1H), 5.19 (t, 1H), 5.12 (s, 1H), 3.79-3.7 (m, 2H), 3.25-3.17 (m, 2H), 2.86 (d, 3H), 1.96-1.85 (m, 1H), 1.85-1.74 (m, 1H), 1.48-1.34 (m, 1H), 1.11 (t, 3H), 0.91 (d, 3H), 0.85 (d, 3H).

Example 97 ethyl 6-{6-[(ethylcarbamoyl)amino]-4-[4-(trifluoromethyl)-1,3-thiazol-2-yl]pyridin-3-yl}-1-[(1S)-2-hydroxy-1-methylethyl]-4-oxo-1,4-dihydroquinoline-3-carboxylate To a solution of palladium (II) acetate (28.0 mg, 0.12 mmol, 0.1 equiv.) and 1,1'-bis(di-t-butylphosphino)ferrocene (59.1 mg, 0.12 mmol, 0.1 equiv.) in acetonitrile (3 mL) was added (S)-ethyl 1-(1-hydroxypropan-2-yl)-6-iodo-4-oxo-1,4-dihydroquinoline-3-carboxylate (Intermediate 49, 500 mg, 1.25 mmol), followed by 6-(3-ethylureido)-4-(4-(trifluoromethyl)thiazole-2-yl)pyridine-3-ylboronic acid (Intermediate 17, 453 mg, 1.26 mmol) and a solution of potassium carbonate (258 mg, 1.87 mmol, 1.5 equiv.) in water (1 mL). The reaction mixture was stirred at 60° C. for 2 h, cooled to room temperature, and diluted with water (2 mL). The precipitate that formed was collected by filtration, washed with water and hexanes and dried to provide (S)-ethyl 6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylate as a grey solid (583 mg, 79%).

MS (ESP): 590 for $C_{27}H_{26}F_3N_5O_5S$.

NMR (d$_6$-DMSO) δ 9.47 (s, 1H), 8.68 (s, 1H), 8.49 (s, 1H), 8.31 (s, 1H), 8.24 (s, 1H), 8.19 (d, 1h), 8.106 (d, 1H), 7.72 (dd, 1H), 7.66 (t, 1H), 5.26 (s, 1H), 5.11-5.06 (m, 1H), 4.28 (m, 2H), 3.79 (d, 2H), 3.25-3.17 (m, 2H), 1.51 (d, 3H), 1.29 (t, 3H), 1.11 (t, 3H).

Examples 98-108

The following examples were prepared by the procedure described in Example 97 from the indicated starting material.

| Ex | Compound | Data | SM |
|---|---|---|---|
| 98 | (R)-ethyl 6-(6-(3-ethylureido)-4-(4-(trifluoromethyl)thiazol-2-yl)pyridin-3-yl)-1-(1-hydroxypropan-2-yl)-4-oxo-1,4-dihydroquinoline-3-carboxylate | MS (ESP): 590 for C$_{27}$H$_{26}$F$_3$N$_5$O$_5$S NMR (d$_6$-DMSO) δ 9.48 (s, 1H), 8.68 (s, 1H), 8.49 (s, 1H), 8.31 (s, 1H),1 8.24 (s, 1h), 8.19 (d, 1H), 8.06 (d, 1H), 7.71 (dd, 2H), 5.35-5.25 (m, 1H), 5.11-5.06 (m, 1H), 4.28-4.21 (m, 2H), 3.79 (d, 2H), 3.25-3.19 (m, 2H), 1.51 (d, 3H), 1.29 (t, 3H), 1.11 (t, 3H) | Intermediate 48 and Intermediate 17 |
| 99 | Ethyl 1-((2R,3R)-1,3-dihydroxybutan-2-yl)-6-(6-(3-ethylureido)-4-(4-(trifluoromethyl)thiazol-2-yl)pyridin-3-yl)-4-oxo-1,4-dihydroquinoline-3-carboxylate | MS (ESP): 620 for C$_{28}$H$_{28}$F$_3$N$_5$O$_6$S NMR (d$_6$-DMSO) δ 9.47 (s, 1H), 8.89 (s, 1H), 8.51 (s, 1H), 8.32 (s, 1H), 8.23 (s, 1H), 8.17 (s, 1H), 8.07 (d, 1H), 7.7-7.65 (m, 2H), 5.22 (s, 1H), 4.87 (s, 1H), 4.25-4.22 (m, 3H), 3.97-3.82 (m, 2H), 3.25-3.18 (m, 2H), 1.28 (t, 3H), 1.13 (d, 3H), 1.11 (t, 3H) | Intermediate 50 and Intermediate 17 |
| 100 | Ethyl 1-(1,3-dihydroxypropan-2-yl)-6-(6-(3-ethylureido)-4-(4-(trifluoromethyl)thiazol-2-yl)pyridin-3-yl)-4-oxo-1,4-dihydroquinoline-3-carboxylate | MS (ESP): 606 for C$_{27}$H$_{26}$F$_3$N$_5$O$_6$S NMR (d$_6$-DMSO) δ 9.47 (s, 1H), 8.72 (s, 1H), 8.49 (s, 1H), 8.31 (s, 1H), 8.24 (s, 1H), 8.19 (d, 1H0, 8.13 (s, 1H), 7.71 (dd, 1H), 5.3 (s, 1H), 4.54-4.36 (m, 2H), 4.25-4.14 (m, 2H), 4.04-3.86 (m, 2H), 3.24-3.14 (m, 4H), 1.27 (t, 3H), 1.11 (t, 3H) | Intermediate 52 and Intermediate 17 |

| Ex | Compound | Data | SM |
|---|---|---|---|
| 101 | (S)-ethyl 6-(6-(3-propylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylate | MS (ESP): 646 for $C_{31}H_{34}F_3N_5O_5S$ | Intermediate 55 and Intermediate 47 |
| 102 | (R)-ethyl 6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylate | MS (ESP): 604 for $C_{28}H_{28}F_3N_5O_5S$ NMR (d$_6$-DMSO) δ 9.45 (s, 1H), 8.66 (s, 1H), 8.51 (s, 1H), 8.33 (s, 1H), 8.22 (s, 1H), 8.19 (d, 1H), 8.06 (d, 1H), 7.7-7.65 (m, 2H), 5.23-5.18 (m, 1H), 4.91 (s, 1H), 4.28-4.21 (m, 2H), 3.85-3.73 (m, 2H), 3.25-3.17 (m, 2H), 2.0-1.9 (m, 2H), 1.28 (t, 3H), 1.11 (t, 3H), 0.89 (t, 3H) | Intermediate 57 and Intermediate 17 |
| 103 | Ethyl 6-(6-(3-ethylureido)-4-(4-(trifluoromethyl)thiazol-2-yl)pyridin-3-yl)-1-(2-hydroxy-1-(tetrahydro-2H-pyran-4-yl)ethyl)-4-oxo-1,4-dihydroquinoline-3-carboxylate | MS (ESP): 660 for $C_{31}H_{32}F_3N_5O_6S$ NMR (d$_6$-DMSO) δ 9.44 (s, 1H), 8.79 (s, 1H), 8.53 (s, 1H), 8.35 (s, 1H), 8.22 (s, 1H), 8.19 (d, 1H), 8.15 (d, 1H), 7.68-7.6 (m, 2H), 5.27-5.23 (m, 1H), 4.83 (s, 1H), 4.29-4.22 (m, 2H), 4.0-3.92 (m, 2H), 3.81-3.75 (m, 2H), 3.25-3.2 (m, 2H), 2.3-2.25 (m, 1H), 1.83-1.76 (m, 2H), 1.3 (t, 3H), 1.23-1.17 (m, 2H), 1.13 (t, 3H) | Intermediate 59 and Intermediate 17 |

-continued

| Ex | Compound | Data | SM |
|---|---|---|---|
| 104 | (S)-ethyl 6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylate | MS (ESP): 632 for $C_{30}H_{32}F_3N_5O_5S$ NMR ($d_6$-DMSO) δ 9.45 (s, 1H), 8.65 (s, 1H), 8.53 (s, 1H), 8.34 (s, 1H), 8.21-8.17 (m, 3H), 7.63 (d, 2H), 5.12-5.09 (m, 1H), 4.97-4.92 (m, 1H), 4.29-4.2 (m, 2H), 4.05-4.0 (m, 2H), 3.26-3.18 (m, 2H), 1.28 (t, 3H), 1.11 (t, 3H), 0.97 (s, 9H) | Intermediate 55 and Intermediate 17 |
| 105 | (S)-ethyl 6-(6-(3-ethylureido)-4-(4-(trifluoromethyl)thiazol-2-yl)pyridin-3-yl)-4-oxo-1-((tetrahydrofuran-2-yl)methyl)-1,4-dihydroquinoline-3-carboxylate | MS (ESP): 616 for $C_{29}H_{28}F_3N_5O_5S$ NMR ($d_6$-DMSO) δ 9.45 (s, 1H), 8.63 (s, 1H), 8.49 (s, 1H), 8.32 (s, 1H), 8.23 (s, 1H), 8.15 (d, 1H), 7.98 (d, 1H), 7.7 (dd, 1H), 7.67 (t, 1H), 4.67 (d, 1H), 4.35-4.3 (m, 1H), 4.27-4.21 (m, 2H), 4.2-4.18 (m, 1H), 3.83-3.79 (m, 1H), 3.67-3.62 (m, 1H), 3.25-3.19 (m, 2H), 2.1-2.04 (m, 1H), 1.92-1.8 (m, 2H), 1.64-1.55 (m, 2H), 1.28 (t, 3H), 1.11 (t, 3H) | Intermediate 61 and Intermediate 17 |
| 106 | Ethyl 6-(6-(3-ethylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxylate | MS (ESP): 657 for $C_{32}H_{35}F_3N_6O_4S$ NMR ($d_6$-DMSO) δ 9.45 (s, 1H), 8.72 (s, 1H), 8.49 (s, 1H), 8.32 (s, 1H), 8.22 (s, 1H), 8.14 (s, 1H), 7.84 (d, 1H), 7.7 (dd, 1H), 7.62 (t, 1H), 4.48-4.4 (m, 1H), 4.27-4.19 (m, 2H), 3.25-3.19 (m, 2H), 2.82-2.72 (m, 2H), 2.15 (s, 3H), 1.86-1.82 (m, 2H), 1.75-1.68 (m, 2H), 1.28 (t, 3H), 1.11 (t, 3H) | Intermediate 69 and Intermediate 17 |

| Ex | Compound | Data | SM |
|---|---|---|---|
| 107 | Ethyl 6-(6-(3-ethylureido)-4-(4-(trifluoromethyl)thiazol-2-yl)pyridin-3-yl)-4-oxo-1-((tetrahydro-2H-pyran-4-yl)methyl)-1,4-dihydroquinoline-3-carboxylate | MS (ESP): 630 for $C_{30}H_{30}F_3N_5O_5S$ NMR ($d_6$-DMSO) δ 9.45 (s, 1H), 8.68 (s, 1H), 8.51 (s, 1H), 8.33 (s, 1H), 8.21 (s, 1H), 8.14 (s, 1H), 7.96 (d, 1H), 7.68 (dd, 1H), 7.62 (t, 1H), 4.34 (d, 1H), 4.24-4.2 (m, 2H), 3.86 (d, 2H), 3.24-3.17 (m, 4H), 2.1-2.06 (m, 1H), 1.46-1.42 (m, 4H), 1.28 (t, 3H), 1.11 (t, 3H) | Intermediate 62 and Intermediate 17 |
| 108 | (R)-ethyl 6-(6-(3-ethylureido)-4-(4-(trifluoromethyl)thiazol-2-yl)pyridin-3-yl)-1-(1-hydroxy-3,3-dimethylbutan-2-yl)-4-oxo-1,4-dihydroquinoline-3-carboxylate | MS (ESP): 632 for $C_{30}H_{32}F_3N_5O_5S$ | Intermediate 66 and Intermediate 17 |

Example 109 ethyl 1-[(1S)-1-benzyl-2-hydroxyethyl]-6-{6-[(ethyl-carbamoyl)amino]-4-[4-(trifluoromethyl)-1,3-thiazol-2-yl]pyridin-3-yl}-4-oxo-1,4-dihydroquinoline-3-carboxylate

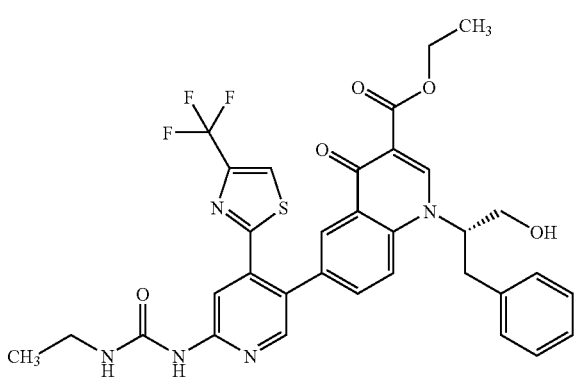

To a solution of palladium (II) acetate (23.52 mg, 0.10 mmol, 0.1 equiv.) and 1,1'-bis(di-t-butylphosphino)ferrocene (49.7 mg, 0.10 mmol, 0.1 equiv.) in acetonitrile (3 mL) was added (S)-ethyl 1-(1-hydroxy-3-phenylpropan-2-yl)-6-iodo-4-oxo-1,4-dihydroquinoline-3-carboxylate (Intermediate 51, 500 mg, 1.05 mmol), followed by 6-(3-ethylureido)-4-(4-(trifluoromethyl)thiazole-2-yl)pyridine-3-ylboronic acid (Intermediate 17, 381 mg, 1.06 mmol) and a solution of potassium carbonate (217 mg, 1.57 mmol) in water (1 mL). The reaction mixture was stirred at 60° C. for 2 h, cooled to room temperature, and diluted with water (2 mL). The reaction mixture was partitioned between water (10 mL) and ethyl acetate (10 mL). The aqueous layer was extracted with ethyl acetate (2×10 mL), and the organics were dried over sodium sulfate and concentrated to provide (S)-ethyl 6-(6-(3-ethylureido)-4-(4-(trifluoromethyl)thiazol-2-yl)pyridin-3-yl)-1-(1-hydroxy-3-phenylpropan-2-yl)-4-oxo-1,4-dihydroquinoline-3-carboxylate as a grey solid (619 mg, 89%).

MS (ESP): 620 for $C_{28}H_{28}F_3N_5O_6S$.

NMR ($d_6$-DMSO) δ 9.43 (s, 1H), 8.75 (s, 1H), 8.56 (s, 1H), 8.26 (s, 1H), 8.22 (s, 1H), 8.08 (d, 1H), 7.97 (d, 1H), 7.64-7.56 (m, 2H), 5.35-5.29 (m, 2H), 4.29-4.19 (m, 2H), 3.85 (s, 2H), 3.25-3.16 (m, 3H), 1.3 (t, 3H), 1.1 (t, 3H).

Examples 110-119

The following examples were prepared by the procedure described in Example 109 from the indicated starting material.

| Ex | Compound | Data | SM |
|---|---|---|---|
| 110 | (S)-ethyl 6-(6-(3-ethylureido)-4-(4-(trifluoromethyl)thiazol-2-yl)pyridin-3-yl)-1-(1-hydroxy-3-methylbutan-2-yl)-4-oxo-1,4-dihydroquinoline-3-carboxylate | MS (ESP): 618 for $C_{29}H_{30}F_3N_5O_5S$ NMR ($d_6$-DMSO) δ 9.44 (s, 1H), 8.72 (s, 1H), 8.51 (s, 1H), 8.33 (s, 1H), 8.2 (s, 1H), 8.17 (d, 1H), 8.11 (d, 1H), 7.62 (t, 2H), 5.22-5.17 (m, 1H), 4.68 (s, 1H), 4.27-4.2 (m, 2H), 3.95-3.91 (m, 1H), 3.8-3.74 (m, 1H), 3.24-3.15 (m 4H), 2.4-2.3 (m, 1H), 1.27 (t, 3H), 1.1 (t, 3H), 1.08 (d, 3H), 0.75 (d, 3H) | Intermediate 53 and Intermediate 17 |

| Ex | Compound | Data | SM |
|---|---|---|---|
| 111 | (R)-ethyl 6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylate | MS (ESP): 632 for $C_{30}H_{32}F_3N_5O_5S$ NMR ($d_6$-DMSO) δ 9.45 (s, 1H), 8.64 (s, 1H), 8.52 (s, 1H), 8.33 (s, 1H), 8.21 (s, 1H), 8.17 (d, 1H), 8.14 (d, 1H), 7.64 (t, 1H), 7.47 (dd, 1H), 5.19 (t, 1H), 5.02 (s, 1H), 4.27-4.2 (m, 3H), 3.76-3.72 (m, 2H), 3.25-3.15 (m, 4H), 1.9-1.78 (m, 1H), 1.76-1.72 (m, 1H), 1.56-1.45 (m, 2H), 1.28 (t, 3H), 1.11 (t, 3H), 0.92 (d, 3H), 0.86 (d, 3H) | Intermediate 54 and Intermediate 17 |
| 112 | (R)-ethyl 6-(6-(3-ethylureido)-4-(4-(trifluoromethyl)thiazol-2-yl)pyridin-3-yl)-1-(1-hydroxy-3-methylbutan-2-yl)-4-oxo-1,4-dihydroquinoline-3-carboxylate | MS (ESP): 618 for $C_{29}H_{30}F_3N_5O_5S$ NMR ($d_6$-DMSO) δ 9.45 (s, 1H), 8.73 (s, 1H), 8.51 (s, 1H), 8.34 (s, 1H), 8.21 (s, 1H), 8.17 (d, 1H), 8.12 (d, 1H), 7.63 (t, 2H), 5.22-5.17 (m, 1H), 4.7 (s, 1H), 4.27-4.2 (m, 2H), 3.98-3.91 (m, 1H), 3.81-3.76 (m, 1H) 3.25-3.15 (m, 2H), 2.34-3.27, (m, 1H), 1.28 (t, 3H), 1.11 (t, 3H), 1.08 (d, 3H), 0.75 (d, 3H) | Intermediate 56 and Intermediate 17 |
| 113 | (S)-ethyl 6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylate | MS (ESP): 604 for $C_{28}H_{28}F_3N_5O_5S$ NMR ($d_6$-DMSO) δ 9.45 (s, 1H), 8.66 (s, 1H), 8.51 (s, 1H), 8.33 (s, 1H), 8.22 (s, 1H), 8.18 (d, 1H), 8.08 (d, 1H), 7.69 (dd, 1H), 7.66 (t, 1H), 5.23-5.18 (m, 1H), 4.91 (s, 1H), 4.27-4.2 (m, 2H), 3.83-3.75 (m, 2H), 3.25-3.17 (m, 2H), 2.07-1.9 (m, 2H), 1.28 (t, 3H), 1.11 (t, 3H), 0.88 (t, 3H) | Intermediate 58 and Intermediate 17 |

| Ex | Compound | Data | SM |
|---|---|---|---|
| 114 | (S)-ethyl 1-(1-hydroxy-3,3-dimethylbutan-2-yl)-4-oxo-6-(6-(3-propylureido)-4-(4-(trifluoromethyl)thiazol-2-yl)pyridin-3-yl)-1,4-dihydroquinoline-3-carboxylate | MS (ESP): 646 for $C_{31}H_{34}F_3N_5O_5S$ NMR ($d_6$-DMSO) δ 9.44 (s, 1H), 8.64 (s, 1H), 8.52 (s, 1H), 8.33 (s, 1H), 8.22 (s, 1H), 8.17 (d, 1H), 8.1 (d, 1H), 7.7-7.66 (m, 2H), 5.22-5.18 (m, 1H), 5.02 (s, 1H), 4.27-4.2 (m, 2H), 3.76-3.73 (m, 2H), 3.18-3.12 (m, 2H), 1.99-94 (m, 1H), 1.93-1.88 (s, 1H), 1.54-1.44 (m, 2H), 1.28 (t, 3H), 0.92 (d, 3H), 0.9 (s, 9H), 0.88 (d, 3H) | Intermediate 60 and Intermediate 47 |
| 115 | Ethyl 1-((2S,3S)-1,3-dihydroxypentan-2-yl)-6-(6-(3-ethylureido)-4-(4-(trifluoromethyl)thiazol-2-yl)pyridin-3-yl)-4-oxo-1,4-dihydroquinoline-3-carboxylate | MS (ESP): 632 for $C_{30}H_{32}F_3N_5O_5S$ NMR ($d_6$-DMSO) δ 9.45 (s, 1H), 8.72 (s, 1H), 8.52 (s, 1H), 8.34 (s, 1H), 8.2 (d, 1H), 8.09 (d, 1H), 7.68-7.60 (m, 2H), 5.2-5.17 (m, 1H), 4.76 (s, 1H), 4.27-4.2 (m, 2H), 4.01-3.94 (m, 1H), 3.8-3.75 (m, 1H), 3.24-3.16 (m, 2H), 2.13 (s, 1H), 1.27 (t, 3H), 1.11 (t, 3H), 0.77-0.73 (m, 4H) | Intermediate 63 and Intermediate 17 |
| 116 | Ethyl 6-(6-(3-ethylureido)-4-(4-(trifluoromethyl)thiazol-2-yl)pyridin-3-yl)-1-(1-methoxy-3-methylbutan-2-yl)-4-oxo-1,4-dihydroquinoline-3-carboxylate | MS (ESP): 632 for $C_{30}H_{32}F_3N_5O_5S$ NMR ($d_6$-DMSO) δ 9.45 (s, 1H), 8.71 (s, 1H), 8.52 (s, 1H), 8.35 (s, 1H), 8.2-8.12 (m, 3H), 7.65-7.62 (m, 2H), 4.89 (s, 1H), 4.27-4.2 (m, 2H), 3.91 (s, 1H0, 3.74-3.71 (m, 1H), 3.26-3.21 (m, 2H), 3.25 (s, 3H), 2.3-2.27 (m, 2H), 1.28 (t, 3H), 1.11 (t, 3H), 0.75 (d, 3H) | Intermediate 70 and Intermediate 17 |

| Ex | Compound | Data | SM |
|---|---|---|---|
| 117 | (R)-ethyl 6-(6-(3-ethylureido)-4-(4-(trifluoromethyl)thiazol-2-yl)pyridin-3-yl)-1-(1-hydroxy-3-(4-hydroxyphenyl)propan-2-yl)-4-oxo-1,4-dihydroquinoline-3-carboxylate | MS (ESP): 682 for $C_{33}H_{30}F_3N_5O_6S$ | Intermediate 67 and Intermediate 17 |
| 118 | (S)-ethyl 1-(1-cyclohexyl-2-hydroxyethyl)-6-(6-(3-ethylureido)-4-(4-(trifluoromethyl)thiazol-2-yl)pyridin-3-yl)-4-oxo-1,4-dihydroquinoline-3-carboxylate | MS (ESP): 658 for $C_{32}H_{34}F_3N_5O_5S$ | Intermediate 68 and Intermediate 17 |
| 119 | (S)-ethyl 6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylate | MS (ESP): 632 for $C_{30}H_{32}F_3N_5O_5S$ NMR ($d_6$-DMSO) δ 9.45 (s, 1H), 8.64 (s, 1H), 8.52 (s, 1H), 8.33 (s, 1H), 8.21 (s, 1H), 8.18 (d, 1H), 8.1 (d, 1H), 7.69-7.61 (m, 2H), 5.21-5.18 (m, 1H), 5.02 (s, 1H), 4.27-4.21 (m, 2H), 3.78-3.71 (m, 2H), 3.25-3.17 (m, 2H), 1.92-1.84 (m, 1H), 1.78-1.74 (m, 1H), 1.49-1.42 (m, 2H), 1.28 (t, 3H), 1.11 (t, 3H), 0.92 (d, 3H), 0.86 (d, 3H) | Intermediate 60 and Intermediate 17 |

Example 120 ethyl 6-{6-[(ethylcarbamoyl)amino]-4-[4-(trifluoromethyl)-1,3-thiazol-2-yl]pyridin-3-yl}-[1-(hydroxymethyl)propyl]-4-oxo-1,4-dihydroquinoline-3-carboxylate

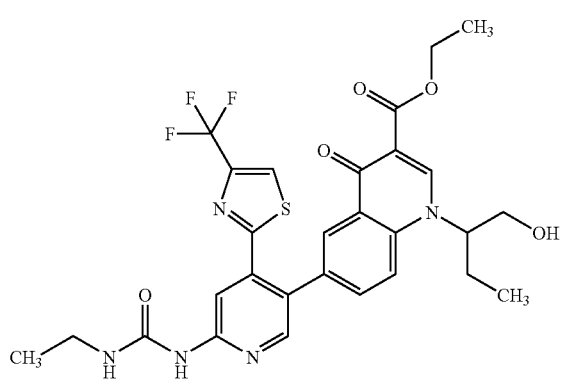

To a suspension of ethyl 1-(1-hydroxybutan-2-yl)-6-iodo-4-oxo-1,4-dihydroquinoline-3-carboxylate (Intermediate 64, 282 mg, 0.78 mmol) and 6-(3-ethylureido)-4-(4-(trifluoromethyl)thiazole-2-yl)pyridine-3-ylboronic acid (Intermediate 17, 350 mg, 0.84 mmol) in 1,4-dioxane (3 mL) was added a solution of cesium carbonate (467 mg, 1.43 mmol) in water (1 mL) followed by tetrakis(triphenylphosphino)palladium(0) (48.7 mg, 0.04 mmol). The reaction mixture was stirred at 100° C. for 2 h, cooled to room temperature, and diluted with water (2 mL). The precipitate that formed was collected by filtration, washed with water and hexanes. Purification via column chromatography (silica, 95:5 methylene chloride/methanol) provided ethyl 6-(6-(3-ethylureido)-4-(4-(trifluoromethyl)thiazol-2-yl)pyridin-3-yl)-1-(1-hydroxybutan-2-yl)-4-oxo-1,4-dihydroquinoline-3-carboxylate as a yellow/orange solid (136 mg, 27%).

MS (ESP): 604 for $C_{28}H_{28}F_3N_5O_5S$.
NMR ($d_6$-DMSO) δ 9.44 (s, 1H), 8.66 (s, 1H), 8.5 (s, 1H), 8.32 (s, 1H), 8.22 (s, 1H), 8.18 (d, 1H), 8.08 (d, 1H), 7.69-7.65 (m, 2H), 5.23-5.18 (m, 1H), 4.9 (s, 1H), 4.27-4.2 (m, 2H), 3.82-3.76 (m, 2H), 3.26-3.16 (m, 2H), 2.0-1.93 (m, 2H), 1.28 (t, 3H), 1.11 (t, 3H), 0.88 (t, 3H).

Example 121

The following example was prepared by the procedure described in Example 120 with the indicated starting material.

| Ex | Compound | Data | SM |
|---|---|---|---|
| 121 | Ethyl 6-(6-(3-ethylureido)-4-(4-(trifluoromethyl)thiazol-2-yl)pyridin-3-yl)-1-((1-methylpiperidin-4-yl)methyl)-4-oxo-1,4-dihydroquinoline-3-carboxylate | MS (ESP): 643 for $C_{31}H_{33}F_3N_6O_4S$ NMR ($d_6$-DMSO) δ 9.47 (s, 1H), 8.72 (s, 1H), 8.5 (s, 1H), 8.23 (s, 1H), 8.31 (s, 1H), 8.15 (d, 1H), 7.97 (d, 1H), 7.72 (dd, 1H), 7.66 (t, 1H), 4.4-4.36 (m, 1H), 4.26-4.21 (m, 2H), 3.39-3.35 (m, 2H), 3.25-3.19 (m, 2H), 2.85-2.8 (m, 2H), 2.69 (d, 3H), 1.8-1.76 (m, 2H), 1.63-1.5 (m, 2H), 1.28 (t, 3H), 1.11 (t, 3H) | Intermediate 65 and Intermediate 17 |

Example 122

6-(6-(3-ethylureido)-4-(4-(trifluoromethyl)thiazol-2-yl)pyridin-3-yl)-1-(4-(hydroxymethyl)tetrahydro-2H-pyran-4-yl)-4-oxo-1,4-dihydroquinoline-3-carboxylic acid

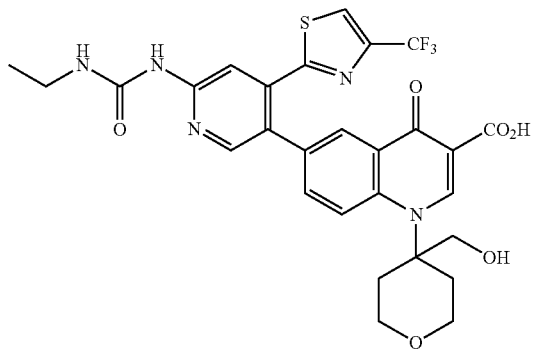

Ethyl 6-(6-(3-ethylureido)-4-(4-(trifluoromethyl)thiazol-2-yl)pyridin-3-yl)-1-(4-(hydroxymethyl)tetrahydro-2H-pyran-4-yl)-4-oxo-1,4-dihydroquinoline-3-carboxylate (Example 132, 0.225 g, 0.35 mmol) was diluted with 2:1 MeOH:THF (3 mL). A 2 M aq solution of LiOH (0.35 mL, 0.7 mmol) was added and the reaction mixture was heated in the microwave to 100° C. for 15 min. The mixture was conc in vacuo and acidified to approx. pH 3 with 1 N aq HCl. The resultant solid was collected and purified by column chromatography (silica 95:5 methylene chloride/methanol) followed by purification by reverse phase HPLC (C18, 0-95% acetonitrile/water gradient).

LC/MS (ES$^+$)[(M+H)$^+$]: 618 for $C_{28}H_{26}F_3N_5O_6S$ $^1$H NMR (DMSO-d$_6$): δ14.93 (br s, 1H); 9.52 (s, 1H); 8.96 (s, 1H); 8.55 (s, 1H); 8.49 (m, 1H); 8.37 (m, 2H); 8.22 (s, 1H); 7.73 (m, 1H); 7.63 (m, 1H); 5.48 (t, 1H); 4.29 (m, 2H); 3.75 (m, 4H); 3.21 (m, 2H); 2.54-2.32 (br m, 4H); 1.11 (t, 3H).

Example 123

6-(6-(3-ethylureido)-4-(4-(trifluoromethyl)thiazol-2-yl)pyridin-3-yl)-4-oxo-1-(piperidin-2-ylmethyl)-1,4-dihydroquinoline-3-carboxylic acid

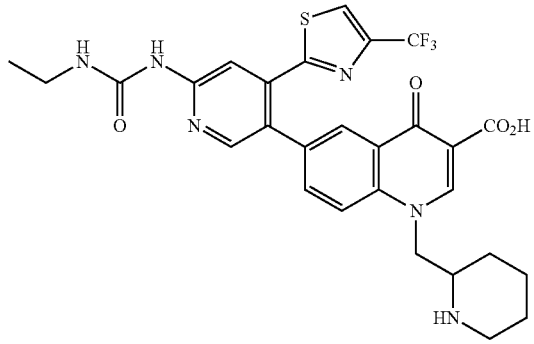

A solution of 1-((1-(tert-butoxycarbonyepiperidin-2-yl)methyl)-6-(6-(3-ethylureido)-4-(4-(trifluoromethyl)thiazol-2-yl)pyridin-3-yl)-4-oxo-1,4-dihydroquinoline -3-carboxylic acid (Example 138, 0.888 g, 1.27 mmol) in THF (10 mL) and anisole (0.208 mL, 1.90 mmol) was cooled to 0° C. A 4 M solution of HCl in dioxane (9.5 mL, 38 mmol) was added dropwise. After the addition was complete, the ice bath was removed and the reaction was stirred at room temperature for 1.5 h. An additional 40 mL of 4 M HCl in dioxane was added and the reaction mixture was stirred for 5 days. The volume of the reaction mixture was then reduced by two-thirds in vacuo. Diethyl ether (15 mL) was added to the reaction mixture under N$_2$ and it was stirred for 1 h. The resultant solid was collected and rinsed with ether. Purification was performed by reverse phase HPLC (C18, 0-95% acetonotrile/water gradient) to provide the desired product.

LC/MS (ES$^+$)[(M+H)$^+$]: 601 for $C_{28}H_{27}F_3N_6O_4S$ $^1$H NMR (DMSO-d$_6$): δ9.48 (s, 1H); 8.94 (s, 1H); 8.53 (s, 1H); 8.37 (s, 1H); 8.31 (d, 1H); 8.21 (s, 1H); 8.13 (d, 1H); 7.82 (dd, 1H); 7.60 (m, 1H); 4.60 (dd, 1H); 4.34 (m, 1H); 3.21 (m, 2H); 2.86 (m, 2H); 2.30 (m, 1H); 1.73 (m, 2H); 1.47 (m, 1H); 1.27 (m, 2H); 1.11 (m, 1H); 1.11 (t, 3H).

Examples 124-127

General Procedures

The following compounds were prepared by either of the procedures described below from the starting materials indicated in the table.

Procedure A: The appropriate ethyl ester (1 eq) was diluted with 2:1 MeOH:THF. A 2 M aq solution of LiOH (2 eq) was added and the reaction mixture was heated in the microwave to 100° C. for 15 min. The mixture was conc in vacuo and then diluted with CH$_2$Cl$_2$ and cooled to 0° C. The mixture was acidified to approximately pH 4 with 1 N aq HCl. The layers were separated and the organic layer was con concentrated in vacuo. Purification was performed by column chromatography (silica, 95:5 methylene chloride/methanol) to provide the desired product.

Procedure B: The appropriate ethyl ester (1 eq) was diluted with 2:1 MeOH:THF. A 2 M aq solution of LiOH (2 eq) was added and the reaction mixture was heated in the microwave to 100° C. for 15 min. The mixture was cooled to 0° C., acidified with 1 N aq HCl and conconcentrated in vacuo. Purification was performed by reverse phase HPLC (C18, 0-95% acetonitrile/water gradient) to provide the desired product.

| Ex | Compound | Data | SM |
|---|---|---|---|
| 124 | 6-(6-(3-ethylureido)-4-(4-(trifluoromethyl)thiazol-2-yl)pyridin-3-yl)-4-oxo-1-(pyridin-4-ylmethyl)-1,4-dihydroquinoline-3-carboxylic acid | LC/MS (ES$^+$)[(M + H)$^+$]: 595 for $C_{28}H_{21}F_3N_6O_4S$<br>$^1$H NMR (DMSO-d$_6$): δ 14.96 (s, 1H); 9.46 (s, 1H); 9.33 (s, 1H); 8.53 (m, 3H); 8.33 (m, 2H); 8.19 (s, 1H); 7.74 (s, 2H); 7.57 (m, 1H); 7.22 (m, 2H); 5.97 (s, 2H); 3.20 (m, 2H); 1.10 (t, 3H). | Example 133 |
| 125 | 6-(6-(3-ethylureido)-4-(4-(trifluoromethyl)thiazol-2-yl)pyridin-3-yl)-1-((1-methyl-1H-imidazol-4-yl)methyl)-4-oxo-1,4-dihydroquinoline-3-carboxylic acid | LC/MS (ES$^+$)[(M + H)$^+$]: 598 for $C_{27}H_{22}F_3N_7O_4S$<br>$^1$H NMR (DMSO-d$_6$): δ 15.04 (br s, 1H); 9.48 (s, 1H); 9.19 (s, 1H); 8.49 (s, 1H); 8.33 (s, 1H); 8.27 (m, 2H); 8.21 (s, 1H); 7.82 (m, 1H); 7.61 (m, 1H); 7.54 (s, 1H); 7.31 (s, 1H); 5.66 (s, 2H); 3.59 (s, 3H); 3.20 (m, 2H); 1.10 (t, 3H). | Example 136 |
| 126 | 1-(1-(dimethylamino)propan-2-yl)-6-(6-(3-ethylureido)-4-(4-(trifluoromethyl)thiazol-2-yl)pyridin-3-yl)-4-oxo-1,4-dihydroquinoline-3-carboxylic acid | LC/MS (ES$^+$)[(M + H)$^+$]: 589 for $C_{27}H_{27}F_3N_6O_4S$<br>$^1$H NMR (DMSO-d$_6$): δ 15.07 (s, 1H); 9.47 (s, 1H); 8.88 (s, 1H); 8.53 (s, 1H); 8.39 (s, 1H); 8.34 (d, 1H); 8.29 (d, 1H); 8.22 (s, 1H); 7.84 (m, 1H); 7.59 (m, 1H); 5.35 (br s, 1H); 3.22 (m, 2H); 3.10 (m, 1H); 2.62 (m, 1H); 2.14 (br s, 6H); 1.54 (m, 3H); 1.11 (t, 3H). | Example 134 |

| Ex | Compound | Data | SM |
|---|---|---|---|
| 127 | 6-(6-(3-ethylureido)-4-(4-(trifluoromethyl)thiazol-2-yl)pyridin-3-yl)-1-((1-methylpiperidin-2-yl)methyl)-4-oxo-1,4-dihydroquinoline-3-carboxylic acid, formic acid salt | LC/MS (ES⁺)[(M + H)⁺]: 615 for $C_{29}H_{29}F_3N_6O_4S$<br>¹H NMR (DMSO-d₆): δ 15.00 (br s, 1H); 9.46 (s, 1H); 9.01 (s, 1H); 8.53 (s, 1H); 8.39 (s, 1H); 8.30 (d, 1H); 8.21 (s, 1H); 8.14 (s, 1H); 8.05 (d, 1H); 7.84 (dd, 1H); 7.57 (m, 1H); 5.02 (m, 1H); 4.47 (m, 1H): 3.22 (m, 2H): 2.95 (m, 1H); 2.57 (m, 2H); 2.42 (s, 3H); 2.18 (m, 1H); 1.62 (m, 1H); 1.47 (m, 2H); 1.21 (m, 2H); 1.11 (t, 3H). | Example 135 |

Example 128

1-(1,3-dimethoxypropan-2-yl)-6-(6-(3-ethylureido)-4-(4-(trifluoromethyl)thiazol-2-yl)pyridin-3-yl)-4-oxo-N-(tetrahydro-2H-pyran-4-yl)-1,4-dihydroquinoline-3-carboxamide

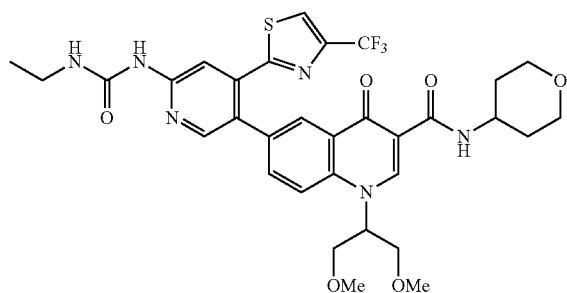

1-(1,3-Dimethoxypropan-2-yl)-6-(6-(3-ethylureido)-4-(4-(trifluoromethyl)thiazol-2-yl)pyridin-3-yl)-4-oxo-1,4-dihydroquinoline-3-carboxylic acid (Example 4, 0.112 g, 0.18 mmol) was suspended in DMF (1 mL). O-(7-Azabenzotriazol-1-yl)-N,N,N',N'-tetramethyluronium hexafluorophosphate (HATU) (0.105 g, 0.28 mmol) was added, followed by diisopropylethylamine (0.193 mL, 1.11 mmol). The reaction mixture was stirred for 15 min at RT. The 4-aminotetrahydropyran hydrochloride (0.038 g, 0.28 mmol) was added in one portion and the mixture was stirred at RT for 2 days. Water was added and the resultant solid was purified by column chromatography (silica, 95:5 methylene chloride/methanol) to provide the product as a solid. The solid was further purified by trituration with CH₂Cl₂ and hexanes.

LC/MS (ES⁺)[(M+H)⁺]: 689 for $C_{32}H_{35}F_3N_6O_6S$

¹H NMR (DMSO-d₆): δ9.99 (m, 1H); 9.46 (s, 1H); 8.93 (s, 1H); 8.50 (s, 1H); 8.32 (d, 2H); 8.24 (s, 1H); 8.15 (d, 1H); 7.73 (m, 1H); 7.61 (m, 1H); 5.45 (br s, 1H); 3.92 (m, 7H); 3.45 (m, 2H); 3.25 (m, 8H); 1.87 (m, 2H); 1.50 (m, 2H); 1.11 (t, 3H).

Example 129

1-(1,3-dimethoxypropan-2-yl)-6-(6-(3-ethylureido)-4-(4-(trifluoromethyl)thiazol-2-yl)pyridin-3-yl)-N-methyl-4-oxo-1,4-dihydroquinoline-3-carboxamide

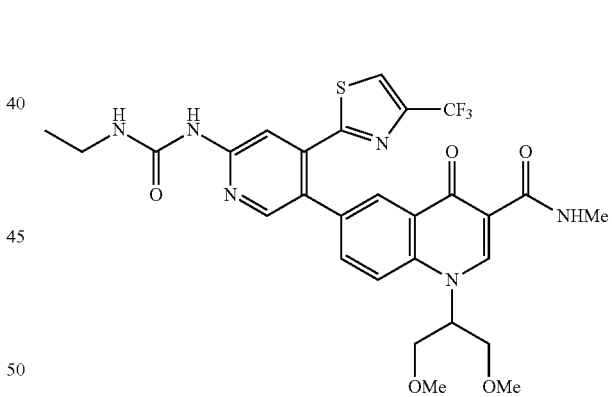

1-(1,3-Dimethoxypropan-2-yl)-6-(6-(3-ethylureido)-4-(4-(trifluoromethyl)thiazol-2-yl)pyridin-3-yl)-4-oxo-1,4-dihydroquinoline-3-carboxylic acid (Example 4, 0.112 g, 0.18 mmol) was suspended in DMF (1 mL). O-(7-Azabenzotriazol-1-yl)-N,N,N',N'-tetramethyluronium hexafluorophosphate (HATU) (0.105 g, 0.28 mmol) was added, followed by diisopropylethylamine (0.097 mL, 0.55 mmol). The reaction mixture was stirred for 15 min at RT. A 2.0 M solution of methylamine in THF (0.2 mL, 0.40 mmol) was added and the mixture was stirred at RT for 2 d. Water was added and the solid precipitate was purified by column chromatography (silica, 95:5 methylene chloride/methanol). The solid was further purified by trituration with CH₂Cl₂ and hexanes.

LC/MS (ES⁺)[(M+H)⁺]: 619 for $C_{28}H_{29}F_3N_6O_5S$ $^1$H NMR (DMSO-d$_6$): δ9.69 (m, 1H); 9.46 (s, 1H); 8.92 (s, 1H); 8.50 (s, 1H); 8.29 (m, 3H); 8.14 (d, 1H); 7.74 (m, 1H); 7.63 (m, 1H); 5.44 (br s, 1H); 3.84 (m, 4H); 3.25 (m, 8H); 2.86 (m, 3H); 1.11 (t, 3H).

Example 130

(S)-2-(6-(6-(3-ethylureido)-4-(4-(trifluoromethyl)thiazol-2-yl)pyridin-3-yl)-3-(methylcarbamoyl)-4-oxoquinolin-1(4H)-yl)-3-methylbutanoic acid

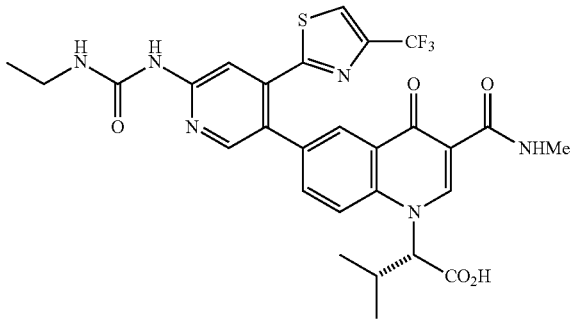

(S)-Tert-butyl 2-(6-(6-(3-ethylureido)-4-(4-(trifluoromethyl)thiazol-2-yl)pyridin-3-yl)pyridin-3-yl)-3-(methylcarbamoyl)-4-oxoquinolin-1(4H)-yl)-3-methylbutanoate (Example 131, 0.079 g, 0.12 mmol) was diluted with CH$_2$Cl$_2$ (4 mL). Triethylsilane (0.047 mL, 0.29 mmol) was added, followed immediately by the addition of trifluoroacetic acid (0.118 mL, 1.53 mmol). The solution was stirred at RT overnight. An additional 26 eq of TFA (0.24 mL) and 5 eq of triethylsilane (0.1 mL) were added and the mixture was stirred for 2 d. The mixture was conconcentrated in vacuo, then diluted with ether and conconcentrated in vacuo again. Ether was added to the residue and the resultant solid was collected and washed with ether. The solid was purified by trituration with EtOAc.

LC/MS (ES$^+$)[(M+H)$^+$]: 617 for C$_{28}$H$_{27}$F$_3$N$_6$O$_5$S $^1$H NMR (DMSO-d$_6$): δ9.64 (s, 1H); 9.46 (s, 1H); 8.91 (s, 1H); 8.50 (s, 1H); 8.36 (s, 1H); 8.23 (m, 2H); 7.76 (m, 1H); 7.62 (s, 1H); 5.43 (s, 1H); 3.21 (m, 3H); 2.86 (m, 3H); 1.13 (m, 6H); 0.81 (br s, 3H).

Example 131

(S)-tert-butyl 2-(6-(6-(3-ethylureido)-4-(4-(trifluoromethyl)thiazol-2-yl)pyridin-3-yl)-3-(methylcarbamoyl)-4-oxoquinolin-1(4H)-yl)-3-methylbutanoate

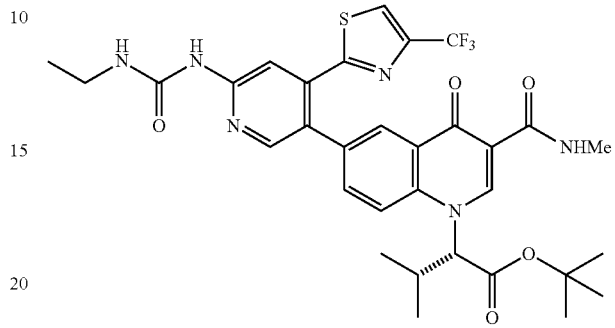

A solution of (S)-ethyl 1-(1-tert-butoxy-3-methyl-1-oxobutan-2-yl)-6-(6-(3-ethylureido)-4-(4-(trifluoromethyl)thiazol-2-yl)pyridin-3-yl)-4-oxo-1,4-dihydroquinoline-3-carboxylate (Example 137, 0.100 g, 0.15 mmol) in 33 wt. % methylamine solution in absolute ethanol (3 mL, 24.1 mmol) was heated in the microwave to 80° C. for 15 min. The mixture was conconcentrated in vacuo and purified by column chromatography (silica, 95:5 methylene chloride/methanol) to provide the desired product.

LC/MS (ES$^+$)[(M+H)$^+$]: 673 for C$_{32}$H$_{35}$F$_3$N$_6$O$_5$S $^1$H NMR (DMSO-d$_6$): δ9.62 (m, 1H); 9.46 (s, 1H); 8.90 (br s, 1H); 8.53 (s, 1H); 8.37 (s1H); 8.25 (d, 1H); 8.18 (s, 1H); 7.75 (m, 1H); 7.60 (m, 2H); 5.43 (m, 1H); 3.21 (m, 2H); 2.86 (d, 3H); 2.59 (m, 1H); 1.36 (br s, 9H); 1.17 (br s, 3H); 1.11 (t, 3H); 0.82 (br s, 3H).

Examples 132-137

The following compounds were synthesized by either of the procedures described below from the starting material in the table.

Procedure A: 6-(3-Ethylureido)-4-(4-(trifluoromethyl)thiazol-2-yl)pyridin-3-ylboronic acid (Intermediate 17) (1 eq) and the appropriate aryl iodide (1 eq) were combined and diluted with dioxane. A solution of Cs$_2$CO$_3$ (1.7 eq) in water was added (used a 4:1 ratio of dioxane to water in the reaction). Tetrakis(triphenylphosphine)palladium(0) (0.1 eq) was added and the reaction mixture was heated at 100° C. After cooling to RT, water was added and the resultant solid was collected. In some cases, purification was performed by column chromatography.

Procedure B: 6-(3-Ethylureido)-4-(4-(trifluoromethyl)thiazol-2-yl)pyridin-3-ylboronic acid (Intermediate 17) (1 eq) and the appropriate aryl iodide (1 eq) were combined and diluted with dioxane. A solution of Cs$_2$CO$_3$ (3 eq) in water was added (used a 4:1 ratio of dioxane to water in the reaction). Tetrakis(triphenylphosphine)palladium(0) (0.1 eq) was added and the reaction mixture was heated at 100° C. After cooling to RT, water was added and the resultant solid was collected. The solid was purified by column chromatography.

| Ex | Compound | Data | SM |
|---|---|---|---|
| 132 | ethyl 6-(6-(3-ethylureido)-4-(4-(trifluoromethyl)thiazol-2-yl)pyridin-3-yl)-1-(4-(hydroxymethyl)tetrahydro-2H-pyran-4-yl)-4-oxo-1,4-dihydroquinoline-3-carboxylate | LC/MS (ES+)[(M + H)+]: 646 for $C_{30}H_{30}F_3N_5O_6S$ | Intermediate 71 |
| 133 | ethyl 6-(6-(3-ethylureido)-4-(4-(trifluoromethyl)thiazol-2-yl)pyridin-3-yl)-4-oxo-1-(pyridin-4-ylmethyl)-1,4-dihydroquinoline-3-carboxylate | LC/MS (ES+)[(M + H)+]: 623 for $C_{30}H_{25}F_3N_6O_4S$ | Intermediate 73 |
| 134 | ethyl 1-(1-(dimethylamino)propan-2-yl)-6-(6-(3-ethylureido)-4-(4-(trifluoromethyl)thiazol-2-yl)pyridin-3-yl)-4-oxo-1,4-dihydroquinoline-3-carboxylate | LC/MS (ES+)[(M + H)+]: 617 for $C_{29}H_{31}F_3N_6O_4S$<br>$^1$H NMR (DMSO-d$_6$): δ 9.45 (s, 1H); 8.58 (s, 1H); 8.51 (d, 1H); 8.33 (s, 1H); 8.22 (s, 1H); 8.18 (d, 1H); 8.09 (d, 1H); 7.67 (dd, 1H); 7.63 (m, 1H); 5.12 (m, 1H); 4.22 (m, 2H); 3.21 (m, 2H); 2.99 (m, 1H); 2.57 (m, 1H); 2.15 (br s, 6H); 1.44 (d, 3H); 1.28 (t, 3H); 1.11 (t, 3H). | Intermediate 74 |

| Ex | Compound | Data | SM |
|---|---|---|---|
| 135 | ethyl 6-(6-(3-ethylureido)-4-(4-(trifluoromethyl)thiazol-2-yl)pyridin-3-yl)-1-((1-methylpiperidin-2-yl)methyl)-4-oxo-1,4-dihydroquinoline-3-carboxylate | LC/MS (ES+)[(M + H)+]: 643 for $C_{31}H_{33}F_3N_6O_4S$<br>$^1$H NMR (DMSO-d$_6$): δ 9.45 (s, 1H); 8.68 (s, 1H); 8.51 (d, 1H); 8.34 (s, 1H); 8.21 (s, 1H); 8.14 (d, 1H); 7.84 (d, 1H); 7.68 (dd, 1H); 7.61 (m, 1H); 4.86 (m, 1H); 4.23 (q, 2H); 4.22 (m, 1H); 3.21 (m, 2H); 2.85 (m, 1H); 2.45 (m, 1H); 2.38 (s, 3H); 2.10 (m, 1H); 1.63 (m, 1H); 1.46 (m, 2H); 1.28 (t, 3H); 1.26 (m, 2H); 1.11 (t, 3H); 1.11 (m, 1H). | Intermediate 75 |
| 136 | ethyl 6-(6-(3-ethylureido)-4-(4-(trifluoromethyl)thiazol-2-yl)pyridin-3-yl)-1-((1-methyl-1H-imidazol-4-yl)methyl)-4-oxo-1,4-dihydroquinoline-3-carboxylate | LC/MS (ES+)[(M + H)+]: 626 for $C_{29}H_{26}F_3N_7O_4S$ | Intermediate 76 |
| 137 | (S)-ethyl 1-(1-tert-butoxy-3-methyl-1-oxobutan-2-yl)-6-(6-(3-ethylureido)-4-(4-(trifluoromethyl)thiazol-2-yl)pyridin-3-yl)-4-oxo-1,4-dihydroquinoline-3-carboxylate | LC/MS (ES+)[(M + H)+]: 688 for $C_{33}H_{36}F_3N_5O_6S$<br>$^1$H NMR (DMSO-d$_6$): δ 9.46 (s, 1H); 8.70 (br m, 1H); 8.53 (s, 1H); 8.35 (m, 1H); 8.17 (m, 2H); 7.64 (m, 3H); 5.32 (m, 1H); 4.25 (q, 2H); 3.21 (m, 2H); 2.59 (m, 1H); 1.37 (br s, 9H); 1.28 (t, 3H); 1.17 (br s, 3H); 1.11 (t, 3H); 0.83 (br s, 3H). | Intermediate 77 |

Example 138

1-((1-(tert-butoxycarbonyl)piperidin-2-yl)methyl)-6-(6-(3-ethylureido)-4-(4-(trifluoromethyl)thiazol-2-yl)pyridin-3-yl)-4-oxo-1,4-dihydroquinoline-3-carboxylic acid

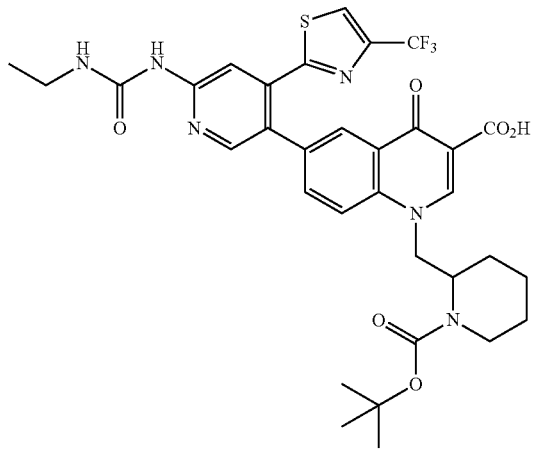

6-(3-Ethylureido)-4-(4-(trifluoromethyl)thiazol-2-yl)pyridin-3-ylboronic acid (Intermediate 17, 0.448 g, 1.24 mmol) and ethyl 1-((1-(tert-butoxycarbonyl)piperidin-2-yl)methyl)-6-iodo-4-oxo-1,4-dihydroquinoline-3-carboxylate (Intermediate 72, 0.672 g, 1.24 mmol) were combined and diluted with dioxane (6 mL). A solution of $Cs_2CO_3$ (0.689 g, 2.11 mmol) in water (1.5 mL) was added. Tetrakis(triphenylphosphine)palladium(0) (0.144 g, 0.12 mmol) was added. The mixture was heated at 100° C. overnight. After cooling to RT, water and MeOH were added and the mixture was conconcentrated in vacuo. The residue was acidified with 1 N aq HCl and then dried on a lyophilizer. The resultant solid with diluted with EtOAc and water and the layers were separated. The organic layer was washed with water, brine, dried over $Na_2SO_4$ and conconcentrated in vacuo to give the title compound which was used without further purification.

LC/MS (ES$^+$)[(M+H)$^+$]: 701 for $C_{33}H_{35}F_3N_6O_6S$

Example 139

Tert-butyl 4-{[1-(1,3-dimethoxypropan-2-yl)-6-{6-[(ethylcarbamoyl)amino]-4-[4-(trifluoromethyl)-1,3-thiazol-2-yl]pyridin-3-yl}-4-oxo-1,4-dihydroquinolin-3-yl]carbonyl}piperazine-1-carboxylate

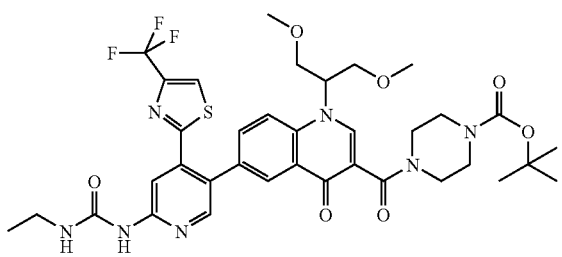

A solution of tert-butyl 4-{[1-(1,3-dimethoxypropan-2-yl)-6-iodo-4-oxo-1,4-dihydroquinolin-3-yl]carbonyl}piperazine-1-carboxylate (Intermediate 79, 400 mg, 0.68 mmol) in dimethylformamide (15 mL) was purged argon gas, then tetrakis(triphenylphosphine)palladium (69.25 mg, 0.06 mmol) followed by 1-ethyl-3-{5-(4,4,5,5-tetramethyl-1,3,2-dioxaborolan-2-yl)-4-[4-(trifluoromethyl)-1,3-thiazol-2-yl]pyridin-2-yl}urea (Intermediate 17, 360 mg, 0.82 mmol) was added. The mixture was stirred at room temperature and sodium carbonate (217 mg, 2.05 mmol) which was dissolved in minimum amount of water was added and the reaction mixture was heated to 95° C. for 3 h. After completion of the reaction, the reaction mixture was cooled to room temperature, filtered through celite, and the filtrate was poured into water (200 mL) and stirred for 30 min. The obtained solid was filtered and dried to give the crude compound. The crude was purified by column chromatography eluting with a gradient of 30% ethyl acetate/petroleum ether to 60% ethyl acetate/petroleum ether to afford 260 mg (49%) of tert-butyl 4-{[1-(1,3-dimethoxypropan-2-yl)-6-{6-[(ethylcarbamoyl)amino]-4-[4-(trifluoromethyl)-1,3-thiazol-2-yl]pyridin-3-yl}-4-oxo-1,4-dihydroquinolin-3-yl]carbonyl}piperazine-1-carboxylate.

$^1$H NMR (400 MHz, DMSO-d$_6$): δ 1.13 (t, 3H), 1.41 (s, 9H), 3.02 (s, 3H), 3.18-3.29 (m, 8H), 3.31-3.72 (m, 8H), 3.79 (m, 1H), 4.48 (m, 1H), 7.63 (d, 1H), 7.74 (d, 1H), 8.06 (d, 1H), 8.37 (2s, 2H), 8.39 (s, 1H), 8.47 (s, 1H), 8.75 (s, 1H), 9.47 (s, 1H).

MASS (APCI+ve Scan): m/z 774 (M+H).

Example 140

1-{5-[1-(1,3-dimethoxypropan-2-yl)-4-oxo-3-(piperazin-1-ylcarbonyl)-1,4-dihydroquinolin-6-yl]-4-[4-(trifluoromethyl)-1,3-thiazol-2-yl]pyridin-2-yl}-3-ethylurea

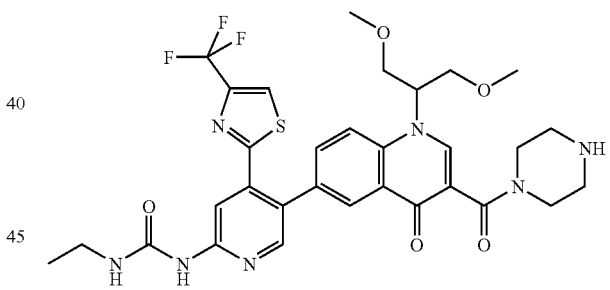

Tert-butyl 4-{[1-(1,3-dimethoxypropan-2-yl)-6-{6-[(ethylcarbamoyl)amino]-4-[4-(trifluoromethyl)-1,3-thiazol-2-yl]pyridin-3-yl}-4-oxo-1,4-dihydroquinolin-3-yl]carbonyl}piperazine-1-carboxylate (Example 139, 260 mg, 0.33 mmol) was dissolved in dichloromethane (15 mL). Trifluoroacetic acid (195 mg, 1.68 mmol) was added to the mixture and it was stirred for 30 h at room temperature. The reaction mixture was concentrated, and the pH was adjusted to 8 with saturated sodium bicarbonate solution to give solid compound which was filtered and dried to afford 160 mg (72%) of 1-{5-[1-(1,3-dimethoxypropan-2-yl)-4-oxo-3-(piperazin-1-ylcarbonyl)-1,4-dihydroquinolin-6-yl]-4-[4-(trifluoromethyl)-1,3-thiazol-2-yl]pyridin-2-yl}-3-ethylurea.

$^1$H NMR (400 MHz, DMSO-d$_6$): δ 1.13 (t, 3H), 2.4-2.82 (m, 3H), 3.02 (s, 3H), 3.18-3.29 (m, 7H), 3.31-3.72 (m, 8H), 3.79 (m, 1H), 4.48 (m, 1H), 7.63 (d, 1H), 7.74 (d, 1H), 8.06 (d, 1H), 8.37 (2s, 2H), 8.39 (s, 1H), 8.47 (s, 1H), 8.75 (s, 1H), 9.47 (s, 1H).

LC-MS: m/z 674 (M+H).

Example 141

1-{5-[1-(1,3-dimethoxypropan-2-yl)-3-{[4-(2-hydroxyethyl)piperazin-1-yl]carbonyl}-4-oxo-1,4-dihydroquinolin-6-yl]-4-[4-(trifluoromethyl)-1,3-thiazol-2-yl]pyridin-2-yl}-3-ethylurea

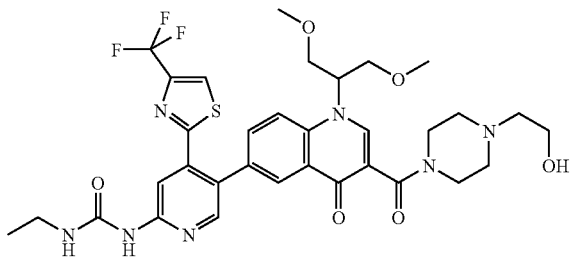

1-{5-[1-(1,3-Dimethoxypropan-2-yl)-4-oxo-3-(piperazin-1-ylcarbonyl)-1,4-dihydroquinolin-6-yl]-4-[4-(trifluoromethyl)-1,3-thiazol-2-yl]pyridin-2-yl}-3-ethylurea (Example 140, 180 mg, 0.267 mmol) was dissolved in acetonitrile (15 mL). Potassium carbonate (73.7 mg, 0.53 mmol) was added, followed by the addition of 2-bromoethanol (40 mg, 0.32 mmol) and the mixture was heated to 55° C. for 16 h. The reaction mixture was filtered, and the filtrate was concentrated and dried to give the crude compound. The crude was dissolved in water (10 mL) and the pH was adjusted to 2. The aqueous solution was washed with ethyl acetate, then basified to pH~8 with saturated sodium bicarbonate solution, then extracted with ethyl acetate. The organic layer was dried over anhydrous sodium sulphate, filtered and concentrated under reduced pressure to afford 65 mg (34%) of 1-{5-[1-(1,3-dimethoxypropan-2-yl)-3-{[4-(2-hydroxyethyl)piperazin-1-yl]carbonyl}-4-oxo-1,4-dihydroquinolin-6-yl]-4-[4-(trifluoromethyl)-1,3-thiazol-2-yl]pyridin-2-yl}-3-ethylurea as an off-white solid.

$^1$H NMR (400 MHz, DMSO-$d_6$): δ 1.09 (t, 3H), 2.41-2.44 (m, 5H), 2.66 (m, 1H), 3.04 (s, 3H), 3.21-3.24 (m, 7H), 3.49-3.60 (m, 7H), 3.77 (br s, 1H), 4.39 (t, 1H), 4.53 (t, 1H), 7.60 (s, 1H), 7.70 (d, 1H), 8.03 (d, 1H), 8.26 (s, 2H), 8.43 (d, 2H), 8.70 (s, 1H), 9.44 (s, 1H).

LC-MS: m/z 718.5 (M+H).

Example 142

4-{[1-(1,3-dimethoxypropan-2-yl)-6-{6-[(ethylcarbamoyl)amino]-4-[4-(trifluoromethyl)-1,3-thiazol-2-yl]pyridin-3-yl}-4-oxo-1,4-dihydroquinolin-3-yl]carbonyl}-N,N-dimethylpiperazine-1-sulfonamide

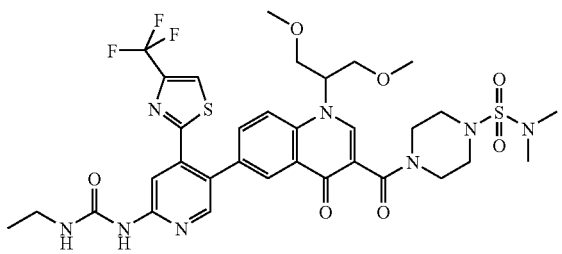

1-{5-[1-(1,3-Dimethoxypropan-2-yl)-4-oxo-3-(piperazin-1-ylcarbonyl)-1,4-dihydroquinolin-6-yl]-4-[4-(trifluoromethyl)-1,3-thiazol-2-yl]pyridin-2-yl}-3-ethylurea (Example 140, 250 mg, 0.37 mmol) was dissolved in acetonitrile (25 mL) and potassium carbonate 204.7 mg, 1.48 mmol) was added, followed by addition of dimethylsulfamyl chloride (133 mg, 0.92 mmol). The reaction mixture was stirred for 16 h at 70° C., then filtered. The filtrate was concentrated to give the crude compound. The crude compound was dissolved in ethyl acetate (60 mL) and washed with water (2×60 mL). The organic layer was dried over anhydrous sodium sulphate, filtered and concentrated under reduced pressure to afford 118 mg, of 4-{[1-(1,3-dimethoxypropan-2-yl)-6-{6-[(ethylcarbamoyl)amino]-4-[4-(trifluoromethyl)-1,3-thiazol-2-yl]pyridin-3-yl}-4-oxo-1,4-dihydroquinolin-3-yl]carbonyl}-N,N-dimethylpiperazine-1-sulfonamide $^1$H NMR (400 MHz, DMSO-$d_6$): δ 1.07-1.13 (m, 4H), 2.74-2.78 (m, 6H), 3.04 (s, 3H), 3.13-3.20 (m, 1H), 3.25-3.37 (m, 6H), 3.42 (m, 3H), 3.51 (d, 3H), 3.68-3.69 (br d, 1H), 3.85 (br d, 1H), 4.47-4.50 (t, 1H), 7.59 (s, 1H), 7.69-7.72 (d, 1H), 8.04-8.08 (m, 1H), LC-MS: m/z 781 (M+H).

Example 143

1-(5-{1-(1,3-dimethoxypropan-2-yl)-3-[(4-methylpiperazin-1-yl)carbonyl]-4-oxo-1,4-dihydroquinolin-6-yl}-4-[4-(trifluoromethyl)-1,3-thiazol-2-yl]pyridin-2-yl)-3-ethylurea

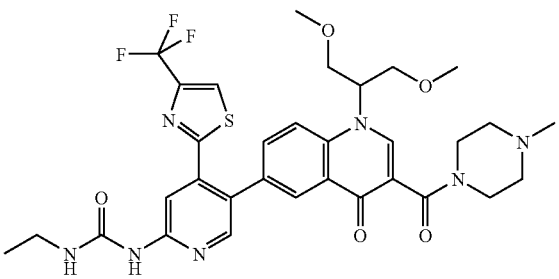

A solution of 1-(1,3-dimethoxypropan-2-yl)-6-iodo-3-[(4-methylpiperazin-1-yl)carbonyl]quinolin-4(1H)-one (Intermediate 80, 300 mg, 0.6012 mmol) in dimethylformamide (10 mL) was prepared. The solution was purged with argon gas and tetrakis(triphenylphosphine)palladium (69.25 mg, 0.060 mmol) followed by 1-ethyl-3-{5-(4,4,5,5-tetramethyl-1,3,2-dioxaborolan-2-yl)-4-[4-(trifluoromethyl)-1,3-thiazol-2-yl]pyridin-2-yl}urea (Intermediate 17, 398 mg, 0.90 mmol) were added and the mixture was stirred at room temperature. Sodium carbonate (125 mg, 1.18 mmol) was dissolved in minimum amount of water and the solution was added to the reaction mixture. The reaction mixture was heated to 95° C. for 3 h. After completion of the reaction, the reaction mixture was cooled to room temperature, filtered through celite, and the filtrate was poured into water (200 mL) and stirred for ½ h. The obtained solid was filtered and dried to get crude product which was purified by column chromatography eluting with a gradient of 100% ethyl acetate to 55 Methanol/ethyl acetate to afford 150 mg (48%) of 1-(5-{1-(1,3-dimethoxypropan-2-yl)-3-[(4-methylpiperazin-1-yl)carbonyl]-4-oxo-1,4-dihydroquinolin-6-yl}-4-[4-(trifluoromethyl)-1,3-thiazol-2-yl]pyridin-2-yl)-3-ethylurea.

¹H NMR (400 MHz, DMSO-d₆): δ 1.14 (t, 3H), 2.22 (s, 4H), 2.34 (d, 2H), 2.37 (d, 2H), 3.04 (s, 3H), 3.18-3.33 (m, 7H), 3.42 (m, 1H), 3.44-3.56(m, 4H), 4.83 (s, 1H), 4.51 (m, 1H), 7.64 (d, 1H), 7.72 (d, 1H), 8.06 (d, 1H), 8.28 (d, 2H), 8.37 (s, 1H), 8.46 (s, 1H), 8.72 (s, 1H), 9.48 (s, 1H).
LC-MS: m/z 688.5 (M+H) at 98.23%

Examples 144-145

The following compounds were prepared according to the procedure described for Example 143 from the starting materials indicated in the table.

| Ex | Compound | Data | SM |
|---|---|---|---|
| 144 | 1-(5-{3-[(4-acetylpiperazin-1-yl)carbonyl]-1-(1,3-dimethoxypropan-2-yl)-4-oxo-1,4-dihydroquinolin-6-yl}-4-[4-(trifluoromethyl)-1,3-thiazol-2-yl]pyridin-2-yl)-3-ethylurea | ¹H NMR (400 MHz, DMSO-d₆): δ 1.14 (t, 3H), 2.19 (d, 3H), 3.05 (s, 3H), 3.11-3.33 (m, 6H), 3.38 (m, 2H), 3.32-3.84 (m, 8H), 4.52 (m, 1H), 7.63 (d, 1H), 7.74 (d, 1H), 8.06 (d, 1H), 8.21 (s, 1H), 8.24 (d, 1H), 8.37 (s, 1H), 8.46 (s, 1H), 8.77 (d, 1H), 9.48 (s, 1H). LC-MS: m/z 716.5 (M + H). | Intermediate 81 and Intermediate 17 |
| 145 | 1-{5-[1-(1,3-dimethoxypropan-2-yl)-3-{[4-(methylsulfonyl)piperazin-1-yl]carbonyl}-4-oxo-1,4-dihydroquinolin-6-yl]-4-[4-(trifluoromethyl)-1,3-thiazol-2-yl]pyridin-2-yl}-3-ethylurea | ¹H NMR (400 MHz, DMSO-d₆): δ 1.14 (t, 3H), 2.92 (s, 3H), 3.06 (s, 3H), 3.11-3.24 (m, 6H), 3.33-3.46 (m, 4H), 3.52 (m, 3H), 3.64 (m, 1H), 4.04 (m, 1H), 4.48 (m, 1H), 7.62 (d, 1H), 7.74 (d, 1H), 8.06 (d, 1H), 8.26 (s, 1H), 8.32 (s, 1H), 8.38 (s, 3H), 8.46 (s, 1H), 8.76 (s, 1H), 9.46 (s, 1H). LC-MS: m/z 752 (M + H). | Intermediate 82 and Intermediate 17 |

Example 146

1-cyclopropyl-6-(6-(3-ethylureido)-4-(4-(trifluoromethyl)thiazol-2-yl)pyridin-3-yl)-N-(2-hydroxyethyl)-4-oxo-1,4-dihydroquinoline-3-carboxamide

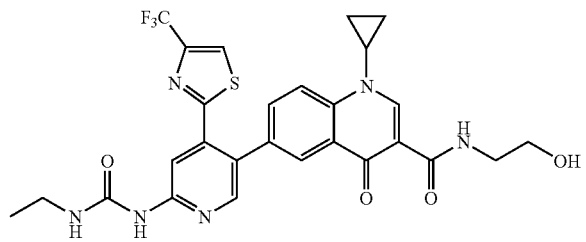

A suspension of ethyl 1-cyclopropyl-6-(6-(3-ethylureido)-4-(4-(trifluoromethyl)thiazol-2-yl)pyridin-3-yl)-N-(2-hydroxyethyl)-4-oxo-1,4-dihydroquinoline-3-carboxylate (Example 58, 50 mg, 0.09 mmol) in ethanolamine (0.5 mL) was heated to 100° C. in a microwave for 30 min The reaction mixture was cooled to room temperature. The precipitate that formed was isolated by filtration and washed with methyl tert-butyl ether and water then dried to give 20 mg of white solid.

MS (ESP): 587 (MH$^+$) for $C_{27}H_{25}F_3N_6O_4S$ $^1$H NMR (300 MHz, DMSO-d$_6$): δ 1.11 (m, 4H), 1.32 (m, 3H), 3.21 (q, 2H), 3.42 (q, 2H), 3.50 (q, 2H), 3.79 (brs, 1H), 4.82 (t, 1H), 7.65 (t, 1H), 7.79 (d, 1H), 8.20 (s, 1H), 8.25 (m, 2H), 8.32 (s, 1H), 8.48 (s, 1H), 8.75 (s, 1H), 9.47 (s, 1H), 9.91 (s, 1H).

Examples 147-149

The following compounds were prepared according to the procedure described for Example 146 from the indicated starting materials.

| Ex | Compound | Data | SM |
|---|---|---|---|
| 147 | 1-cyclopropyl-6-(6-(3-ethylureido)-4-(4-(trifluoromethyl)thiazol-2-yl)pyridin-3-yl)-N-(3-hydroxypropyl)-4-oxo-1,4-dihydroquinoline-3-carboxamide | MS (ESP): 601 (MH$^+$) for $C_{28}H_{27}F_3N_6O_4S$<br>$^1$H NMR (300 MHz, CD$_3$OD): δ 1.23 (m, 4H), 1.38 (m, 3H), 1.83 (m, 2H), 3.34 (q, 2H), 3.53 (q, 2H), 3.65 (q, 2H), 3.76 (brs, 1H), 7.77 (d, 1H), 7.89 (s, 1H), 8.14 (s, 1H), 8.25 (d, 1H), 8.35 (s, 1H), 8.36 (s, 1H), 8.9 (s, 1H). | Example 59 and propanolamine |
| 148 | 1-(1,3-dimethoxypropan-2-yl)-6-(6-(3-ethylureido)-4-(4-(trifluoromethyl)thiazol-2-yl)pyridin-3-yl)-N-(2-hydroxyethyl)-4-oxo-1,4-dihydroquinoline-3-carboxamide | MS (ESP): 649 (MH$^+$) for $C_{30}H_{31}F_3N_6O_5S$<br>$^1$H NMR (300 MHz, CD$_3$OD): δ 1.19 (t, 3H), 3.55 (brs, 2H), 3.71 (brs, 2H), 3.86 (brs 2H), 3.95 (brs, 2H), 5.34 (brs, 1H), 7.67 (d, 1H), 7.85 (s, 1H), 7.99 (d, 1H), 8.12 (s, 1H), 8.32 (s, 1H), 8.39 (s, 1H), 9.06 (s, 1H) | Example 54 and ethanolamine |

| Ex | Compound | Data | SM |
|---|---|---|---|
| 149 | 1-(1,3-dimethoxypropan-2-yl)-6-(6-(3-ethylureido)-4-(4-(trifluoromethyl)thiazol-2-yl)pyridin-3-yl)-N-(3-hydroxypropyl)-4-oxo-1,4-dihydroquinoline-3-carboxamide | MS (ESP): 663.3 (MH+) for $C_{31}H_{35}F_3N_6O_8S$ <br> $^1$H NMR (300 MHz, DMSO-$d_6$): δ 1.11 (t, 3H), 1.62-1.71 (m, 2H), 3.16-3.33 (m, 2H), 3.26 (s, 6H), 3.40-3.51 (m, 2H), 3.77-3.82 (m, 2H), 3.84-3.93 (m, 2H), 4.56, (t, 1H), 5.46 (m, 1H), 7.64 (bt, 1H), 7.73 (dd, 1H), 8.14 (d, 1H), 8.23 (s, 1H), 8.29 (d, 1H), 8.35 (s, 1H), 8.51 (d, 1H), 8.92 (s, 1H), 9.49 (s, 1H), 9.89 (bt, 1H) | Example 54 and propanol-amine |

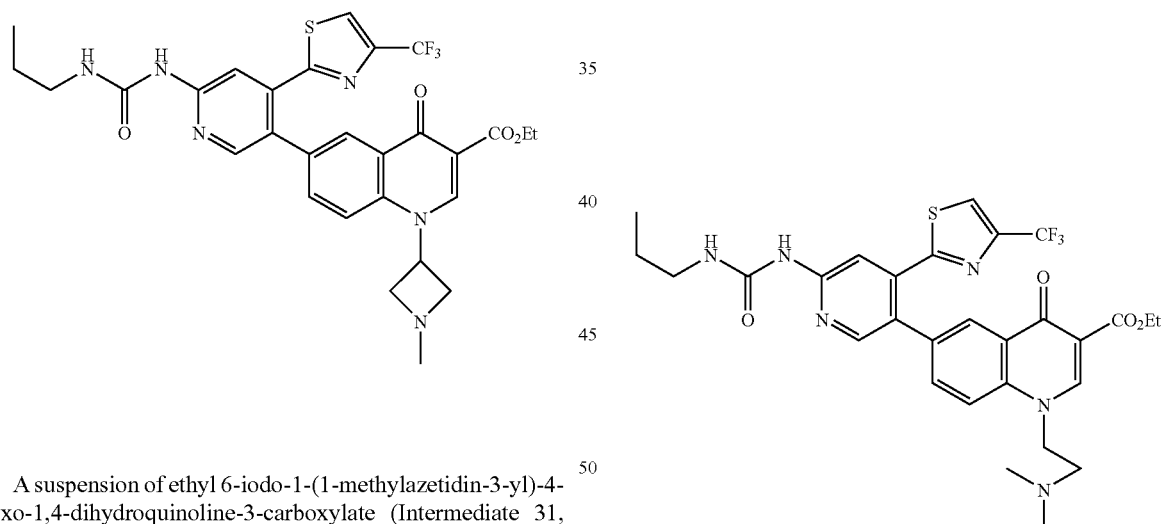

Example 150

Ethyl 1-(1-methylazetidin-3-yl)-4-oxo-6-(6-(3-propylureido)-4-(4-(trifluoromethyl)thiazol-2-yl)pyridin-3-yl)-1,4-dihydroquinoline-3-carboxylate Example 151

Ethyl 1-(1-methylazetidin-3-yl)-4-oxo-6-(6-(3-ethylureido)-4-(4-(trifluoromethyl)thiazol-2-yl)pyridin-3-yl)-1,4-dihydroquinoline-3-carboxylate A suspension of ethyl 6-iodo-1-(1-methylazetidin-3-yl)-4-oxo-1,4-dihydroquinoline-3-carboxylate (Intermediate 31, 500 mg, 1.21 mmol) in dimethoxyethane (9.7 mL) in a vial was stirred with heating to obtain solution. The solution was cooled to 30° C. and trans dichlorobis(triphenylphosphine) palladium (II) (111 mg, 0.16 mmol) was added. The mixture was stirred for ~10 min at room temperature, then 6-(3-propylureido)-4-(4-trifluoromethylthiazol-2-yl)pyridin-3-ylboronic acid (Intermediate 47, 1.3 eq) was added to the mixture followed by an aqueous solution of sodium bicarbonate (252 mg in 2.4 mL of water) and the vial was sealed. The mixture was stirred at 75° C. for 1 h and then cooled to 0° C. The solid that formed was isolated by filtration, washed with a small amount of dimethoxyethane, then methyl tert-butyl ether to give 735 mg of yellow solid, which was used without further purification.

MS (ESP): 615 (MH+) for $C_{29}H_{29}F_3N_6O_4S$

The following compound was prepared according to the procedure described for Example 150 from Intermediate 29 and Intermediate 47.

MS (ESP): 617 (MH+) for $C_{29}H_{31}F_3N_6O_4S$.

Example 152

1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxylic acid

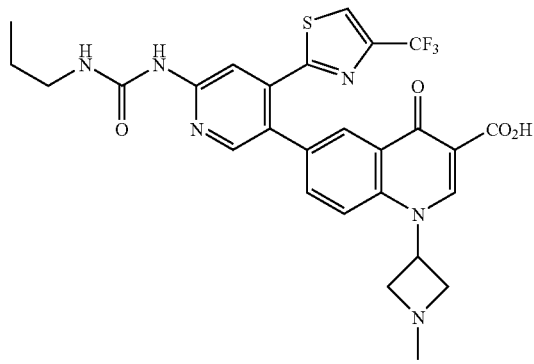

To a solution of ethyl 1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxylate (Example 150, 100 mg, 0.16 mmol) in tetrahydrofuran (2 mL) was added lithium hydroxide (1 M, 650 μL) and the mixture was stirred for 1 h at room temperature. The organics were removed under a stream of nitrogen and the precipitate that formed was isolated by filtration, washed with water (1 mL), and dried in a vacuum oven overnight at 40° C. to give 70 mg of yellowish solid.

MS (ESP): 589 (MH$^+$) for $C_{27}H_{27}F_3N_6O_4S$.

$^1$H NMR (300 MHz, CD$_3$OD): δ 1.11 (t, 3H), 1.63 (m, 3H), 2.32 (s, 6H), 2.87 (q, 2H), 4.50 (q, 2H), 4.39 (t, 2H), 7.65 (d, 1H), 7.82 (d, 1H), 7.87(s, 1H), 8.33 (s, 1H), 8.44 (s, 1H), 8.78 (s, 1H)

Example 153

1-(1-methylazetidin-3-yl)-4-oxo-6-(6-(3-propylureido)-4-(4-(trifluoromethyl)thiazol-2-yl)pyridin-3-yl)-1,4-dihydroquinoline-3-carboxylic acid

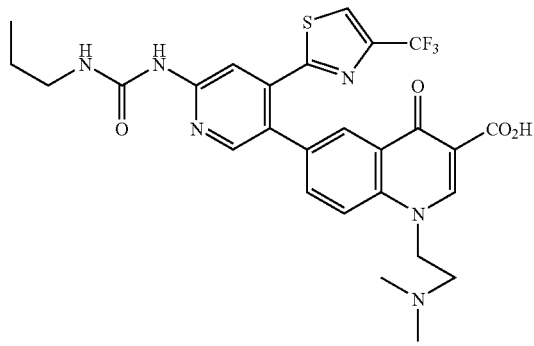

The following compound was prepared according to the procedure described for Example 152 using Example 151 as the starting material.

MS (ESP): 587 (MH$^+$) for $C_{27}H_{24}F_3N_6NaO_4S$.

$^1$H NMR (300 MHz, CD$_3$OD): δ 1.00 (t, 3H), 1.63 (m, 2H), 2.46 (s, 3H), 3.51 (m, 2H), 4.09 (t, 2H), 5.17 (m, 1H), 7.60 (s, 3H), 7.89 (s, 1H), 8.31 (s, 1H), 8.43(s, 1H), 8.66 (s, 1H).

Example 154

4-(1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carbonyl)-N,N-dimethylpiperazine-1-sulfonamide To a solution of 1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxylic acid (Example 153, 80 mg, 0.14 mmol) in dimethylformamide (0.5 mL) was added HATU (78.4 mg, 0.20 mmol) then diisopropylethylamine (95.2 uL, 0.55 mmol). This was followed by N,N-dimethylpiperazine-1-sulfonamide (52.7 mg, 0.27 mmol) and the reaction was stirred at room temperature for 1 h. The solvent was removed under reduced pressure and the residue purified by prep HPLC (Water-methanol-0.1% Formic acid).

MS (ESP): 764.4 (MH$^+$) for $C_{34}H_{42}F_3N_9O_7S_2$ $^1$H NMR (300 MHz, CD$_3$OD): δ 0.99 (t, 3H), 1.63 (m, 2H), 2.43 (s, 6H), 2.85 (s, 6H), 2.92 (t, 2H), 3.32 (brs, 6H), 3.47 (brs, 2H), 3.81 (brs, 2H), 4.55 (t, 2H), 7.67 (d, 1H), 7.84 (s, 1H), 7.87 (d, 1H), 8.18 (s, 1H), 8.29 (s, 1H), 8.32 (s, 2H).

Examples 155-172

The following compounds were prepared according to the procedure described for Example 154 from the starting materials indicated in the table.

| Ex | Compound | Data | SM |
|---|---|---|---|
| 155 | 1-(5-(1-(2-(dimethylamino)ethyl)-3-(4-methylpiperazine-1-carbonyl)-4-oxo-1,4-dihydroquinolin-6-yl)-4-(4-(trifluoromethyl)thiazol-2-yl)pyridin-2-yl)-3-ethylurea | MS (ESP): 657 (MH$^+$) for C$_{32}$H$_{37}$F$_3$N$_8$O$_5$S<br>$^1$H NMR (300 MHz, CD$_3$OD): δ 1.22 (t, 3H), 2.44 (s, 6H), 2.62 (s, 3H), 2.93 (brs, 6H), 3.34 (q, 2H), 3.54 (brs, 2H), 3.89 (brs, 2H), 4.55 (t, 2H), 7.70 (d, 1H), 7.85 (s, 1H), 7.88 (d, 1H), 8.19 (s, 1H), 8.28 (s, 1H), 8.32 (s, 1H), 8.35 (s, 1H) | Example 18 and 4-methyl-piperazine |
| 156 | 1-(5-(1-(2-(dimethylamino)ethyl)-3-(4-methylpiperazine-1-carbonyl)-4-oxo-1,4-dihydroquinolin-6-yl)-4-(4-(trifluoromethyl)thiazol-2-yl)pyridin-2-yl)-3-propylurea | MS (ESP): 671 (MH$^+$) for C$_{32}$H$_{37}$F$_3$N$_8$O$_3$S<br>$^1$H NMR (300 MHz, CD$_3$OD): δ 0.99 (t, 3H), 1.64 (m, 2H), 2.32 (s, 6H), 2.54 (brs, 4H), 2.77 (t, 2H), 3.45 (brs, 2H), 3.79 (brs, 2H), 4.49 (brs, 2H), 7.70 (d, 1H), 7.85 (m, 2H), 8.18 (s, 1H), 8.25 (s, 1H), 8.32 (s, 1H), 8.35 (s, 1H) | Example 153 and 4-methyl-piperzine |
| 157 | 1-(5-(1-(2-(dimethylamino)ethyl)-3-(4-(methylsulfonyl)piperazine-1-carbonyl)-4-oxo-1,4-dihydroquinolin-6-yl)-4-(4-(trifluoromethyl)thiazol-2-yl)pyridin-2-yl)-3-propylurea | MS (ESP): 735 (MH$^+$) for C$_{33}$H$_{39}$F$_3$N$_8$O$_7$S$_2$<br>$^1$H NMR (300 MHz, CD$_3$OD): δ 1.02 (t, 3H), 1.63 (m, 2H), 2.49 (s, 6H), 2.87 (s, 3H), 3.01 (t, 2H), 3.52 (brs, 2H), 3.86 (brs, 2H), 4.59 (t, 2H), 7.70 (d, 1H), 7.85 (m, 2H), 8.19 (s, 1H), 8.28 (s, 1H), 8.32 (d, 1H), 8.35 (s, 1H) | Example 153 and 4-methyl-sulfonyl piperazine |

| Ex | Compound | Data | SM |
|---|---|---|---|
| 158 | 1-(5-(1-(2-(dimethylamino)ethyl)-4-oxo-3-(piperazine-1-carbonyl)-1,4-dihydroquinolin-6-yl)-4-(4-(trifluoromethyl)thiazol-2-yl)pyridin-2-yl)-3-ethylurea | MS (ESP): 643 (MH⁺) for $C_{31}H_{35}F_3N_8O_5S$<br>¹H NMR (300 MHz, CD₃OD): δ 1.22 (t, 3H), 3.04 (s, 6H), 3.31 (m, 8), 3.68 (m, 4H), 4.0 (brs, 2H), 7.80 (d, 1H), 7.90 (s, 1H), 7.96 (d, 1H), 8.22 (s, 1H), 8.34 (s, 1H), 8.35 (s, 1H), 8.46 (s, 1H) | Example 18 and piperazine |
| 159 | 4-(1-(2-(dimethylamino)ethyl)-6-(6-(3-ethylureido)-4-(4-(trifluoromethyl)thiazol-2-yl)pyridin-3-yl)-4-oxo-1,4-dihydroquinoline-3-carbonyl)-N,N-dimethylpiperazine-1-sulfonamide | MS (ESP): 750 (MH⁺) for $C_{33}H_{40}F_3N_9O_7S_2$<br>¹H NMR (300 MHz, CD₃OD): δ 1.22 (t, 3H), 2.40 (s, 6H), 2.84 (s, 6H), 2.86 (t, 2H), 3.36 (m, 6H), 3.47 (brs, 2H), 3.82 (brs, 2H), 4.53 (t, 2H), 7.72 (d, 1H), 7.85 (s, 2H), 7.87 (d, 1H), 8.19 (s, 1H), 8.29 (s, 1H), 8.32 (s, 1H), 8.35 (s, 1H) | Example 18 and N,N-dimethyl-piperazine-1-sulfonamide |
| 160 | 1-(5-(3-(4-acetylpiperazine-1-carbonyl)-1-(2-(dimethylamino)ethyl)-4-oxo-1,4-dihydroquinolin-6-yl)-4-(4-(trifluoromethyl)thiazol-2-yl)pyridin-2-yl)-3-propylurea | MS (ESP): 699 (MH⁺) for $C_{34}H_{39}F_3N_8O_6S$<br>¹H NMR (300 MHz, CD₃OD): δ 0.99 (t, 3H), 1.61 (m, 2H), 2.15 (br s, 3H), 2.34 (s, 6H), 2.80 (t, 2H), 3.66 (brm, 8H), 4.51 (t, 2H), 7.68 (d, 1H), 7.85 (s, 2H), 7.88 (d, 1H), 8.19 (s, 1H), 8.28 (s, 1H), 8.32 (s, 1H), 8.36 (s, 1H) | Example 153 and 4-acetyl-piperazine |

| Ex | Compound | Data | SM |
|---|---|---|---|
| 161 | 1-(5-(1-(2-(dimethylamino)ethyl)-4-oxo-3-(piperazine-1-carbonyl)-1,4-dihydroquinolin-6-yl)-4-(4-(trifluoromethyl)thiazol-2-yl)pyridin-2-yl)-3-propylurea | MS (ESP): 657 (MH+) for $C_{31}H_{36}ClF_3N_8O_3S$<br>$^1$H NMR (300 MHz, CD$_3$OD): δ 0.99 (t, 3H), 1.62 (m, 2H), 3.05 (s, 6H), 3.31 (m, 4H), 3.72 (m, 6H), 3.99 (brs, 2H), 7.86 (d, 1H), 8.08 (s, 1H), 8.11 (d, 1H), 8.32 (s, 1H), 8.34 (s, 1H), 8.45 (s, 1H), 8.51 (1H). | Example 153 and piperazine |
| 162 | 1-(5-(3-(4-acetylpiperazine-1-carbonyl)-1-(2-(dimethylamino)ethyl)-4-oxo-1,4-dihydroquinolin-6-yl)-4-(4-(trifluoromethyl)thiazol-2-yl)pyridin-2-yl)-3-ethylurea | MS (ESP): 685 (MH+) for $C_{32}H_{35}F_3N_8O_4S$<br>$^1$H NMR (300 MHz, CD$_3$OD): δ 1.20 (t, 3H), 2.11 & 2.15 (s, 3H), 2.36 (s, 6H), 2.83 (t, 2H), 3.39 (q, 2H), 3.65 (m, 8H), 4.54 (t, 2H), 7.69 (d, 1H), 7.85 (s, 1H), 7.88 (d, 1H), 8.19 (s, 1H), 8.29 (s, 1H), 8.32 (s, 1H), 8.36 (s, 1H) | Example 18 and 4-acetyl-piperazine |
| 163 | 1-ethyl-3-(5-(1-(1-methylazetidin-3-yl)-3-(4-(methylsulfonyl)piperazine-1-carbonyl)-4-oxo-1,4-dihydroquinolin-6-yl)-4-(4-(trifluoromethyl)thiazol-2-yl)pyridin-2-yl)urea | MS (ESP): 719 (MH+) for $C_{32}H_{35}F_3N_8O_7S_2$<br>$^1$H NMR (300 MHz, CD$_3$OD): δ 1.22 (t, 3H), 2.57 (s, 3H), 2.87 (s, 3H), 3.32 (m, 6H), 3.52 (brs, 2H), 3.73 (t, 2H), 3.88 (brs, 2H), 4.18 (t, 2H), 5.31 (m, 1H), 7.65 (d, 1H), 7.68 (d, 1H), 7.85 (s, 1H), 8.19 (s, 1H), 8.22 (brs, 1H), 8.32 (s, 1H), 8.34 (s, 2H) | Example 24 and 4-(methyl-sulfonyl)-piperazine |

| Ex | Compound | Data | SM |
|----|----------|------|-----|
| 164 | N,N-dimethyl-4-(1-(1-methylazetidin-3-yl)-4-oxo-6-(6-(3-propylureido)-4-(4-(trifluoromethyl)thiazol-2-yl)pyridin-3-yl)-1,4-dihydroquinoline-3-carbonyl)piperazine-1-sulfonamide | MS (ESP): 762 (MH$^+$) for C$_{34}$H$_{40}$F$_3$N$_9$O$_7$S$_2$<br>$^1$H NMR (300 MHz, CD$_3$OD): δ 0.99 (t, 3H), 1.61 (m, 2H), 2.54 (s, 3H), 2.84 (s, 6H), 3.35 (brs, 6H), 3.47 (brs, 2H), 3.67 (brs, 2H), 3.84 (brs, 2H), 4.16 (t, 2H), 5.29 (brs, 1H), 7.66 (d, 1H), 7.69 (d, 1H), 7.84 (s, 1H), 8.18 (s, 1H), 8.33 (m, 3H). | Example 152 and N,N-dimethylpiperazine-1-sulfonamide |
| 165 | 4-(6-(6-(3-ethylureido)-4-(4-(trifluoromethyl)thiazol-2-yl)pyridin-3-yl)-1-(1-methylazetidin-3-yl)-4-oxo-1,4-dihydroquinoline-3-carbonyl)-N,N-dimethylpiperazine-1-sulfonamide | MS (ESP): 748 (MH$^+$)) for C$_{33}$H$_{38}$F$_3$N$_9$O$_7$S$_2$<br>$^1$H NMR (300 MHz, CD$_3$OD): δ 1.22 (t, 3H), 2.59 (s, 3H), 2.84 (s, 6H), 3.31 (m, 6H), 3.47 (brs, 2H), 3.84 (m, 4H), 4.22 (t, 2H), 5.33 (m, 1H), 7.62 (d, 1H), 7.68 (d, 1H), 7.84 (s, 1H), 8.19 (s, 2H), 8.35 (m, 3H). | Example 24 and N,N-dimethyl-piperazine-1-sulfonamide |
| 166 | 1-(5-(1-(1-methylazetidin-3-yl)-4-oxo-3-(piperazine-1-carbonyl)-1,4-dihydroquinolin-6-yl)-4-(4-(trifluoromethyl)thiazol-2-yl)pyridin-2-yl)-3-propylurea | MS (ESP): 655 (MH$^+$) for C$_{31}$H$_{34}$ClF$_3$N$_8$O$_3$S<br>$^1$H NMR (300 MHz, CD$_3$OD): δ 0.99 (t, 3H), 1.62 (m, 2H), 3.12 & 3.18 (s, 3H), 3.36 (brs, 4H), 3.72 (m, 4H), 4.01 (br, 2H), 4.89 (m, 2H), 5.01 (m, 2H), 5.86 & 6.0 (brs, 1H), 7.68 (d, 1H), 7.81 (d, 1H), 8.02 (s, 1H), 8.31 (s, 1H), 8.33 (s, 1H), 8.40 & 8.61 (s, 1H), 8.43 (s, 1H). | Example 152 and piperazine |

-continued

| Ex | Compound | Data | SM |
|---|---|---|---|
| 167 | 1-ethyl-3-(5-(1-(1-methylazetidin-3-yl)-3-(4-methylpiperazine-1-carbonyl)-4-oxo-1,4-dihydroquinolin-6-yl)-4-(4-(trifluoromethyl)thiazol-2-yl)pyridin-2-yl)urea | MS (ESP): 655 (MH$^+$) for C$_{32}$H$_{35}$F$_3$N$_8$O$_5$S<br>$^1$H NMR (300 MHz, CD$_3$OD): δ 1.22 (t, 3H), 2.33 (s, 3H), 2.46 (s, 3H), 2.50 (brs, 4H), 3.31 (q, 2H), 3.44 (brs, 2H), 3.51 (t, 2H), 3.80 (brs, 2H), 4.05 (t, 2H), 5.21 (m, 1H), 7.66 (d, 1H), 7.67 (d, 1H), 7.85 (s, 2H), 8.17 (s, 1H), 8.32 (m, 2H), 8.34 (s, 1H). | Example 24 and 4-methyl-piperazine |
| 168 | 1-(5-(3-(4-acetylpiperazine-1-carbonyl)-1-(1-methylazetidin-3-yl)-4-oxo-1,4-dihydroquinolin-6-yl)-4-(4-(trifluoromethyl)thiazol-2-yl)pyridin-2-yl)-3-propylurea | MS (ESP): 697 (MH$^+$) for C$_{33}$H$_{35}$F$_3$N$_8$O$_4$S<br>$^1$H NMR (300 MHz, CD$_3$OD): δ 0.99 (t, 3H), 1.61 (m, 2H), 2.11 & 2.16 (s, 3H), 2.47 (s, 3H), 3.52 (m, 7H), 4.07 (t, 2H), 5.23 (m, 1H), 7.67 (d, 1H), 7.69 (d, 1H), 7.85 (s, 2H), 8.19 (s, 1H), 8.35 (m, 3H). | Example 152 and 4-acetyl-piperazine |
| 169 | 1-(5-(3-(4-acetylpiperazine-1-carbonyl)-1-(1-methylazetidin-3-yl)-4-oxo-1,4-dihydroquinolin-6-yl)-4-(4-(trifluoromethyl)thiazol-2-yl)pyridin-2-yl)-3-ethylurea | MS (ESP): 683 (MH$^+$) for C$_{33}$H$_{35}$F$_3$N$_8$O$_6$S<br>$^1$H NMR (300 MHz, CD$_3$OD): δ 1.22 (t, 3H), 2.11 & 2.16 (s, 3H), 2.63 (s, 3H), 3.31 (m, 2H), 3.67 (brm, 8H), 3.81 (m, 2H), 4.25 (t, 2H), 5.36 (m, 1H), 7.64 (d, 1H), 7.69 (d, 1H), 7.85 (s, 2H), 8.18 (s, 1H), 8.34 (m, 3H). | Example 24 and 4-acetyl-piperazine |

| Ex | Compound | Data | SM |
|---|---|---|---|
| 170 | 1-(5-(1-(1-methylazetidin-3-yl)-3-(4-(methylsulfonyl)piperazine-1-carbonyl)-4-oxo-1,4-dihydroquinolin-6-yl)-4-(4-(trifluoromethyl)thiazol-2-yl)pyridin-2-yl)-3-propylurea | MS (ESP): 733 (MH$^+$) for C$_{33}$H$_{37}$F$_3$N$_8$O$_7$S$_2$<br>$^1$H NMR (300 MHz, CD$_3$OD): δ 0.99 (t, 3H), 1.61 (m, 2H), 2.57 (s, 3H), 2.88 (s, 3H), 3.52 (brs, 2H), 3.74 (t, 2H), 3.88 (brs, 2H), 4.19 (t, 2H), 5.31 (m, 1H), 7.65 (d, 1H), 7.69 (d, 1H), 7.85 (s, 2H), 8.19 (s, 1H), 8.35 (m, 3H). | Example 152 and 4-(methyl-sulfonyl)-piperazine |
| 171 | 1-ethyl-3-(5-(1-(1-methylazetidin-3-yl)-4-oxo-3-(piperazine-1-carbonyl)-1,4-dihydroquinolin-6-yl)-4-(4-(trifluoromethyl)thiazol-2-yl)pyridin-2-yl)urea | MS (ESP): 641.1 (MH$^+$) for C$_{30}$H$_{32}$ClF$_3$N$_8$O$_3$S<br>$^1$H NMR (300 MHz, CD$_3$OD): δ 1.22 (t, 3H), 3.12 & 3.18 (s, 3H), 3.39 (m, 4H), 3.67 (m, 4H), 4.02 (brs, 2H), 4.80 (m, 2H), 4.99 (m, 2H), 5.75 & 6.0 (brs, 1H), 7.71 (d, 1H), 7.86 (d, 1H), 8.07 (s, 1H), 8.33 (s, 2H), 8.41 & 8.64 (s, 1H), 8.45 (s, 1H). | Example 24 and piperazine |
| 172 | 1-(5-(1-(1-methylazetidin-3-yl)-3-(4-methylpiperazine-1-carbonyl)-4-oxo-1,4-dihydroquinolin-6-yl)-4-(4-(trifluoromethyl)thiazol-2-yl)pyridin-2-yl)-3-propylurea | MS (ESP): 669.3 (MH$^+$) for C$_{33}$H$_{37}$F$_3$N$_8$O$_5$S$_2$<br>$^1$H NMR (300 MHz, CD$_3$OD): δ 1.02 (t, 3H), 1.64 (m, 2H), 2.52 (s, 3H), 2.54 (s, 3H), 2.81 (brs, 4H), 3.53 (brs, 2H), 3.66 (t, 2H), 3.87 (brs, 2H), 4.12 (t, 2H), 5.27 (m, 1H), 7.65 (d, 1H), 7.68 (d, 1H), 7.85 (s, 1H), 8.17 (s, 1H), 8.29 (brs, 1H), 8.32 (s, 1H), 8.34 (s, 1H) | Example 152 and 4-methyl-piperazine |

Example 173 ethyl 1-(2-(dimethylamino)ethyl)-6-(6-(3-isopropylureido)-4-(4-(trifluoromethyl)thiazol-2-yl)pyridin-3-yl)-4-oxo-1,4-dihydroquinoline-3-carboxylate

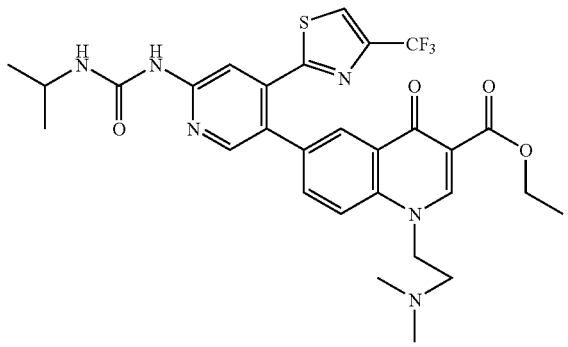

A suspension of ethyl 1-(2-(dimethylamino)ethyl)-6-iodo-4-oxo-1,4-dihydroquinoline-3-carboxylate (Intermediate 29, 250 mg, 0.60 mmol) in dimethoxyethane (4.8 mL) in a microwave vial was stirred with heating to obtain a solution. The solution was then cooled to 30° C., trans-dichlorobis(triphenylphosphine)palladium (II) (55 mg, 0.08 mmol) was added and the mixture was stirred for 10 min at room temperature. 6-(3-isopropylureido)-4-(4-(trifluoromethyl)thiazol-2-yl)pyridin-3-ylboronic acid (Intermediate 89, 294 mg, 0.79 mmol) was added to the mixture followed by an aqueous solution of sodium bicarbonate (163 mg in 1.2 mL of water) and the vial was sealed. The mixture was stirred at 65° C. for 30 min in a heating block then cooled to room temperature. The crude reaction mixture was placed into fridge for a 2 h. The solid precipitate that formed was collected by filtration, washed with a small amount of dimethoxyethane, methyl tert-butyl ether and dried to give ~270 mg yellowish solid.

MS (ESP): 634 (M+H$^+$) for $C_{29}H_{30}F_3N_5O_6S$.

Examples 174-188

The following compounds were prepared according to the procedure described for Example 171 from the indicated starting material.

| Ex | Compound | Data | SM |
|---|---|---|---|
| 174 | ethyl 1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxylate | MS (ESP): 634 (M + H$^+$) for $C_{29}H_{30}F_3N_5O_6S$ | Intermediate 29 and Intermediate 47 |
| 175 | ethyl 6-(6-(3-isopropylureido)-4-(4-(trifluoromethyl)thiazol-2-yl)pyridin-3-yl)-4-oxo-1-(2-(pyrrolidin-1-yl)ethyl)-1,4-dihydroquinoline-3-carboxylate | MS (ESP): 643.2 (M + H$^+$) for $C_{31}H_{33}F_3N_6O_4S$ | Intermediate 89 and Intermediate 93 |

| Ex | Compound | Data | SM |
|---|---|---|---|
| 176 | ethyl 4-oxo-6-(6-(3-propylureido)-4-(4-(trifluoromethyl)thiazol-2-yl)pyridin-3-yl)-1-(2-(pyrrolidin-1-yl)ethyl)-1,4-dihydroquinoline-3-carboxylate 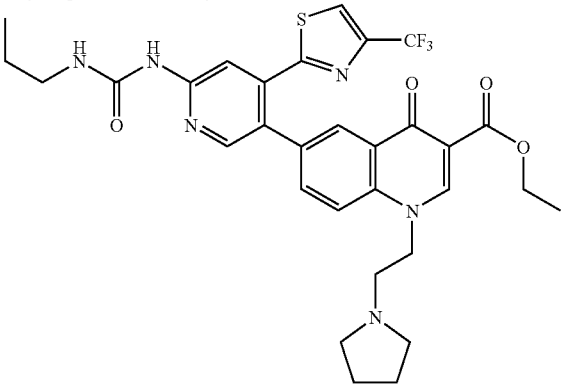 | MS (ESP): 643.2 (M + H+) for $C_{31}H_{33}F_3N_6O_4S$ | Intermediate 47 and Intermediate 93 |
| 177 | ethyl 1-(2-(1-methylpiperidin-4-yl)ethyl)-4-oxo-6-(6-(3-propylureido)-4-(4-(trifluoromethyl)thiazol-2-yl)pyridin-3-yl)-1,4-dihydroquinoline-3-carboxylate 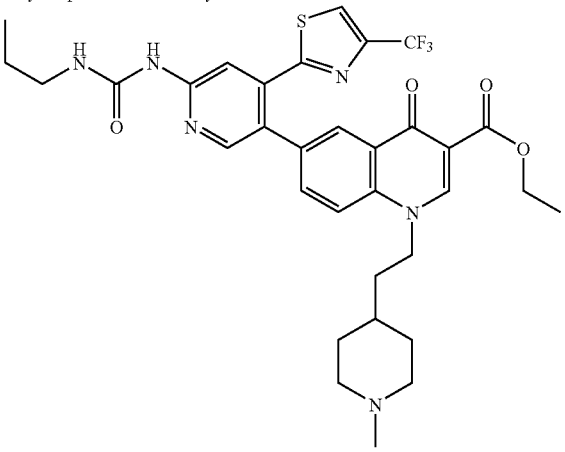 | MS (ESP): 671.1 (M + H+) for $C_{33}H_{37}F_3N_6O_4S$ | Intermediate 47 and Intermediate 69 |

| Ex | Compound | Data | SM |
|---|---|---|---|
| 178 | ethyl 6-(6-(3-isopropylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxylate 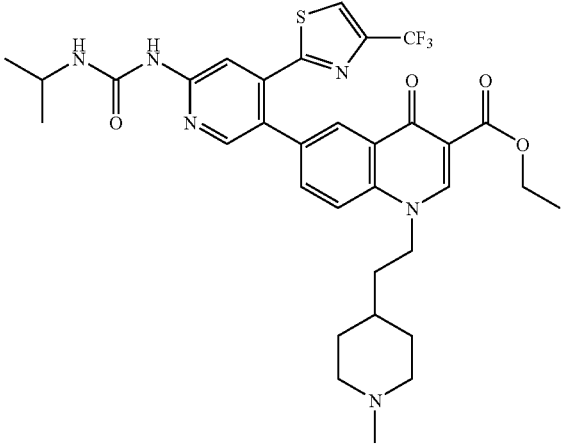 | MS (ESP): 671.1 (M + H$^+$) for C$_{33}$H$_{37}$F$_3$N$_6$O$_4$S | Intermediate 89 and Intermediate 69 |
| 179 | ethyl 6-(6-(3-isopropylureido)-4-(4-(trifluoromethyl)thiazol-2-yl)pyridin-3-yl)-1-(2-(4-methylpiperazin-1-yl)ethyl)-4-oxo-1,4-dihydroquinoline-3-carboxylate 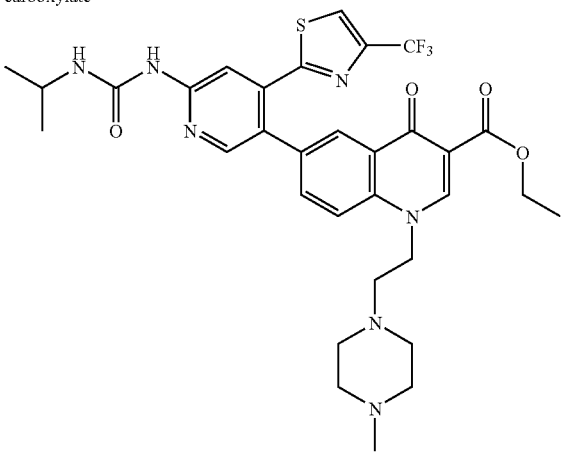 | MS (ESP): 673 (M + H$^+$) for C$_{32}$H$_{36}$F$_3$N$_7$O$_4$S | Intermediate 89 and Intermediate 92 |

| Ex | Compound | Data | SM |
|---|---|---|---|
| 180 | ethyl 1-(2-(4-methylpiperazin-1-yl)ethyl)-4-oxo-6-(6-(3-propylureido)-4-(4-(trifluoromethyl)thiazol-2-yl)pyridin-3-yl)-1,4-dihydroquinoline-3-carboxylate 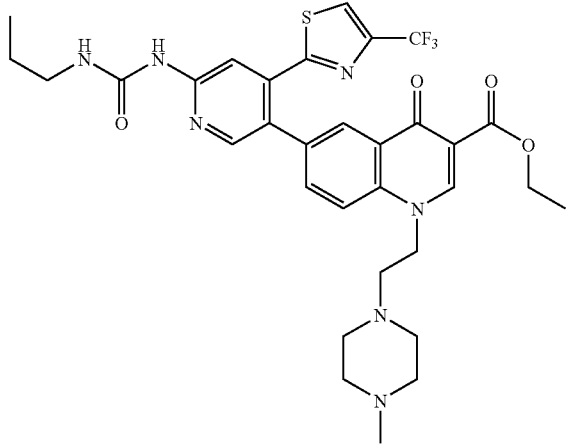 | MS (ESP): 673 (M + H$^+$) for C$_{32}$H$_{36}$F$_3$N$_7$O$_4$S | Intermediate 47 and Intermediate 92 |
| 181 | ethyl 1-(2-morpholinoethyl)-4-oxo-6-(6-(3-propylureido)-4-(4-(trifluoromethyl)thiazol-2-yl)pyridin-3-yl)-1,4-dihydroquinoline-3-carboxylate 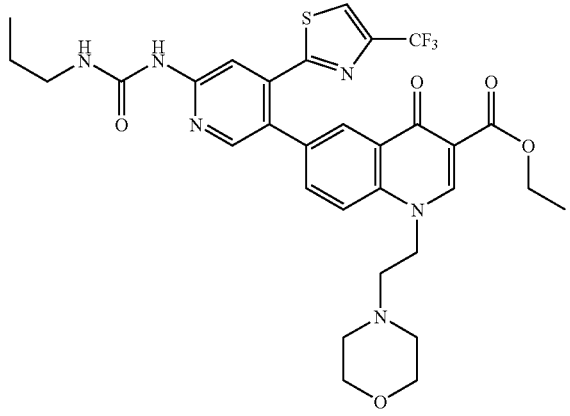 | MS (ESP): 660.1 (M + H$^+$) for C$_{31}$H$_{33}$F$_3$N$_6$O$_5$S | Intermediate 47 and Intermediate 90 |
| 182 | ethyl 6-(6-(3-isopropylureido)-4-(4-(trifluoromethyl)thiazol-2-yl)pyridin-3-yl)-1-(2-morpholinoethyl)-4-oxo-1,4-dihydroquinoline-3-carboxylate 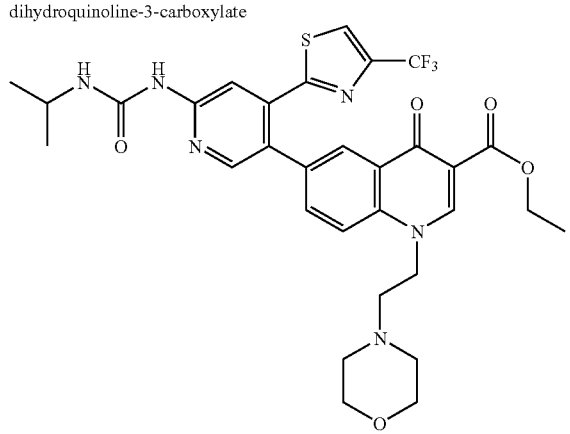 | MS (ESP): 660.1 (M + H$^+$) for C$_{31}$H$_{33}$F$_3$N$_6$O$_5$S | Intermediate 89 and Intermediate 90 |

| Ex | Compound | Data | SM |
|---|---|---|---|
| 183 | ethyl 6-(6-(3-isopropylureido)-4-(4-(trifluoromethyl)thiazol-2-yl)pyridin-3-yl)-4-oxo-1-(2-(tetrahydro-2H-pyran-4-yl)ethyl)-1,4-dihydroquinoline-3-carboxylate | MS (ESP): 659 (M + H$^+$) for C$_{32}$H$_{34}$F$_3$N$_5$O$_5$S | Intermediate 89 and Intermediate 94 |
| 184 | ethyl 4-oxo-6-(6-(3-propylureido)-4-(4-(trifluoromethyl)thiazol-2-yl)pyridin-3-yl)-1-(2-(tetrahydro-2H-pyran-4-yl)ethyl)-1,4-dihydroquinoline-3-carboxylate | MS (ESP): 659 (M + H$^+$) for C$_{32}$H$_{34}$F$_3$N$_5$O$_5$S | Intermediate 47 and Intermediate 94 |
| 185 | ethyl 1-(2-methoxyethyl)-4-oxo-6-(6-(3-propylureido)-4-(4-(trifluoromethyl)thiazol-2-yl)pyridin-3-yl)-1,4-dihydroquinoline-3-carboxylate | MS (ESP): 604.6 (M + H$^+$) for C$_{28}$H$_{28}$F$_3$N$_5$O$_5$S | Intermediate 47 and Intermediate 20 |

| Ex | Compound | Data | SM |
|---|---|---|---|
| 186 | ethyl 6-(6-(3-isopropylureido)-4-(4-(trifluoromethyl)thiazol-2-yl)pyridin-3-yl)-1-(2-methoxyethyl)-4-oxo-1,4-dihydroquinoline-3-carboxylate | MS (ESP): 604.6 (M + H$^+$) for C$_{28}$H$_{28}$F$_3$N$_5$O$_5$S | Intermediate 89 and Intermediate 20 |
| 187 | ethyl 6-(6-(3-isopropylureido)-4-(4-(trifluoromethyl)thiazol-2-yl)pyridin-3-yl)-4-oxo-1-(tetrahydro-2H-pyran-4-yl)-1,4-dihydroquinoline-3-carboxylate | MS (ESP): 631 (M + H$^+$) for C$_{30}$H$_{30}$F$_3$N$_5$O$_5$S | Intermediate 89 and Intermediate 91 |
| 188 | ethyl 4-oxo-6-(6-(3-propylureido)-4-(4-(trifluoromethyl)thiazol-2-yl)pyridin-3-yl)-1-(tetrahydro-2H-pyran-4-yl)-1,4-dihydroquinoline-3-carboxylate | MS (ESP): 631 (M + H$^+$) for C$_{30}$H$_{30}$F$_3$N$_5$O$_5$S | Intermediate 47 and Intermediate 91 |

Example 189

1-(2-(dimethylamino)ethyl)-7-(6-(3-isopropylureido)-4-(4-(trifluoromethyl)thiazol-2-yl)pyridin-3-yl)-4-oxo-1,4-dihydroquinoline-3-carboxylate

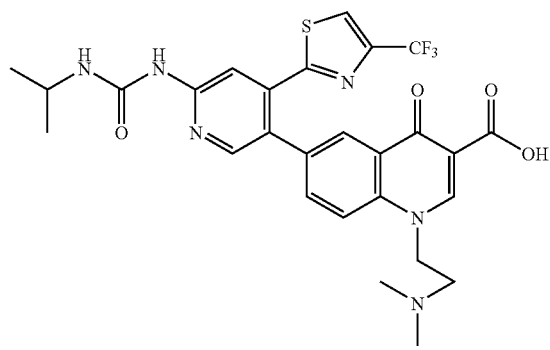

A solution of ethyl 1-(2-(dimethylamino)ethyl)-6-(6-(3-isopropylureido)-4-(4-(trifluoromethyl)thiazol-2-yl)pyridin-3-yl)-4-oxo-1,4-dihydroquinoline-3-carboxylate (Example 173, 100 mg, 0.16 mmol) was dissolved in tetrahydrofuran (4 mL) and treated with 1M lithium hydroxide (1 mL) and the mixture stirred at room temperature for 24 h. The reaction mixture was concentrated under reduced pressure, diluted with water, and acidified to pH 4 with 1 N HCl. The solid that formed was collected by filtration and washed with ethyl acetate to give 60 mg of product after drying.

MS (ESP): 589.2 (M+H$^+$) for $C_{27}H_{26}F_3N_6NaO_4S$.

$^1$H NMR (300 MHz, DMSO-d$_6$): δ 1.07 (d, 6H), 2.19 (s, 6H), 2.58 (t, 2H), 3.35-3.80 (m, 1H), 4.38 (t, 2H), 7.41 (d, 1H), 7.67 (d, 1H), 8.02-8.05 (m, 2H), 8.14 (d, 1H), 8.39 (s, 1H), 8.54 (d, 1H)

Examples 190-202

The following compounds were according to the procedure described for Example 189 from the starting materials indicated in the table.

| Ex | Compound | Data | SM |
|---|---|---|---|
| 190 | 4-oxo-6-(6-(3-propylureido)-4-(4-(trifluoromethyl)thiazol-2-yl)pyridin-3-yl)-1-(2-(pyrrolidin-1-yl)ethyl)-1,4-dihydroquinoline-3-carboxylic acid | MS (ESP): 614 (M + H$^+$) for $C_{29}H_{29}F_3N_6O_4S$<br>$^1$H NMR (300 MHz, CD$_3$OD): δ 0.99 (t, 3H), 1.63 (m, 2H), 1.81 (m, 4H), 2.63 (m, 4H), 2.97 (m, 2H), 4.51 (m, 2H), 7.68 (d, 1H), 7.85 (d, 1H), 7.87 (s, 1H), 8.15 (s, 1H), 8.33 (s, 1H), 8.43 (s, 1H), 8.77 (s, 1H) | Example 176 |
| 191 | 1-(2-methoxyethyl)-4-oxo-6-(6-(3-propylureido)-4-(4-(trifluoromethyl)thiazol-2-yl)pyridin-3-yl)-1,4-dihydroquinoline-3-carboxylic acid | MS (ESP): 576 (M + H$^+$) for $C_{26}H_{23}F_3N_5NaO_5S$<br>$^1$H NMR (300 MHz, DMSO-d$_6$): δ 0.90 (t, 3H), 1.50 (m, 2H), 3.15 (s, 2H), 3.23 (s, 3H), 3.69 (brs, 2H), 4.61 (brs, 2H), 7.66 (d, 1H), 7.82 (s, 1H), 7.92 (d, 1H), 8.25 (s, 1H), 8.28 (s, 1H), 8.32 (s, 1H), 8.45 (s, 1H), 8.78 (s, 1H), 9.61 (s, 1H). | Example 185 |

| Ex | Compound | Data | SM |
|---|---|---|---|
| 192 | 4-oxo-6-(6-(3-propylureido)-4-(4-(trifluoromethyl)thiazol-2-yl)pyridin-3-yl)-1-(tetrahydro-2H-pyran-4-yl)-1,4-dihydroquinoline-3-carboxylic acid | MS (ESP): 603 (M + H$^+$) for $C_{28}H_{25}F_3N_5NaO_5S$<br>$^1$H NMR (300 MHz, DMSO-d$_6$): δ 0.90 (t, 3H), 1.50 (m, 2H), 2.02 (m, 4H), 3.13 (m, 2H), 3.64 (m, 2H), 4.02 (m, 2H), 5.05 (brs, 1H), 7.62 (d, 1H), 7.80 (brs, 1H), 8.19 (d, 1H), 8.28 (s, 1H), 8.31 (s, 1H), 8.44 (s, 2H), 8.94 (s, 1H), 9.5 (s, 1H) | Example 184 |
| 193 | 1-(2-morpholinoethyl)-4-oxo-6-(6-(3-propylureido)-4-(4-(trifluoromethyl)thiazol-2-yl)pyridin-3-yl)-1,4-dihydroquinoline-3-carboxylic acid | MS (ESP): 631 (M + H$^+$) for $C_{29}H_{28}F_3LiN_6O_5S$<br>$^1$H NMR (300 MHz, DMSO-d$_6$): δ 0.90 (t, 3H), 1.49 (m, 2H), 2.49 (brs, 4H), 2.73 (m, 2H), 3.16 (m, 2H), 3.46 (m, 2H), 4.52 (brs, 2H), 7.61 (d, 1H), 7.75 (brs, 1H), 7.90 (d, 1H), 8.25 (s, 2H), 8.31 (s, 1H), 8.44 (s, 1H), 8.78 (s, 1H), 9.53 (s, 1H), 9.46 (s, 1H) | Example 181 |
| 194 | 6-(6-(3-isopropylureido)-4-(4-(trifluoromethyl)thiazol-2-yl)pyridin-3-yl)-1-(2-methoxyethyl)-4-oxo-1,4-dihydroquinoline-3-carboxylic acid | MS (ESP): 576 (M + H$^+$) for $C_{26}H_{24}F_3N_5O_5S$<br>$^1$H NMR (300 MHz, CD$_3$OD): δ 1.24 (d, 6H), 3.81 (t, 2H), 3.99 (m, 1H), 4.71 (t, 2H), 7.78 (d, 1H), 7.90 (s, 1H), 8.00 (d, 1H), 8.18 (s, 1H), 8.37 (s, 1H), 8.42 (s, 1H), 8.89 (s, 1H) | Example 186 |

| Ex | Compound | Data | SM |
|---|---|---|---|
| 195 | 6-(6-(3-isopropylureido)-4-(4-(trifluoromethyl)thiazol-2-yl)pyridin-3-yl)-1-(2-morpholinoethyl)-4-oxo-1,4-dihydroquinoline-3-carboxylic acid | MS (ESP): 631 (M + H$^+$) for C$_{29}$H$_{29}$F$_3$N$_6$O$_5$S<br>$^1$H NMR (300 MHz, CD$_3$OD): δ 1.24 (d, 6H), 3.4 (brs, 2H), 3.63 (brs, 2H), 3.99 (brs, 5H), 4.97 (brs, 2H), 7.86 (d, 1H), 7.90 (s, 1H), 8.03 (d, 1H), 8.21 (s, 2H), 8.34 (s, 1H), 8.41 (s, 1H), 9.04 (s, 1H). | Example 182 |
| 196 | 1-(2-(4-methylpiperazin-1-yl)ethyl)-4-oxo-7-(6-(3-propylureido)-4-(4-(trifluoromethyl)thiazol-2-yl)pyridin-3-yl)-1,4-dihydroquinoline-3-carboxylic acid | MS (ESP): 644.1 (M + H$^+$) for C$_{30}$H$_{32}$F$_3$N$_7$O$_4$S<br>$^1$H NMR (300 MHz, DMSO-d$_6$): δ 0.91 (t, 3H), 1.50 (m, 2H), 2.10 (s, 3H), 2.22-2.73 (m, 10H), 3.16 (q, 2H), 4.69 (t, 2H), 7.65 (s, 1H), 7.85 (dd, 1H), 8.11 (d, 1H), 8.22 (s, 1H), 8.28 (s, 1H), 8.30 (d, 1H), 8.39 (s, 1H), 8.52 (d, 1H), 8.92 (d, 1H), 9.48 (s, 1H) | Example 180 |

| Ex | Compound | Data | SM |
|---|---|---|---|
| 197 | 7-(6-(3-isopropylureido)-4-(4-(trifluoromethyl)thiazol-2-yl)pyridin-3-yl)-4-oxo-1-(2-(tetrahydro-2H-pyran-4-yl)ethyl)-1,4-dihydroquinoline-3-carboxylate | MS (ESP): 630.3 (M + H$^+$) for C$_{30}$H$_{29}$F$_3$N$_5$NaO$_5$S<br>$^1$H NMR (300 MHz, CD$_3$OD): δ 1.25 (d, 6H), 1.35-1.40 (m, 2H), 1.71-1.87 (m, 4H), 3.43 (t, 2H), 3.72 (m, 1H), 3.90-4.05 (m, 3H), 4.40 (t, 2H), 7.55-7.65 (m, 3H), 7.77 (d, 1H), 7.92 (s, 1H), 8.14 (d, 1H), 8.33 (s, 1H), 8.41 (d, 1H), 8.51 (s, 1H) | Example 183 |
| 198 | 1-(2-(1-methylpiperidin-4-yl)ethyl)-4-oxo-6-(6-(3-propylureido)-4-(4-(trifluoromethyl)thiazol-2-yl)pyridin-3-yl)-1,4-dihydroquinoline-3-carboxylic acid | MS (ESP): 643 (M + H$^+$) for C$_{31}$H$_{33}$F$_3$N$_6$O$_4$S<br>$^1$H NMR (300 MHz, CD$_3$OD): δ 0.99 (t, 3H), 1.37 (m, 2H), 1.63 (m, 2H), 1.84 (m, 3H), 2.03 (t, 2H), 2.25 (s, 3H), 2.99 (m, 2H), 4.40 (t, 2H), 7.61 (d, 1H), 7.76 (d, 1H), 7.90 (s, 1H), 8.32 (s, 1H), 8.44 (s, 1H), 8.61 (s, 1H) | Example 177 |
| 199 | 6-(6-(3-isopropylureido)-4-(4-(trifluoromethyl)thiazol-2-yl)pyridin-3-yl)-4-oxo-1-(tetrahydro-2H-pyran-4-yl)-1,4-dihydroquinoline-3-carboxylic acid | MS (ESP): 602 (M + H$^+$) for C$_{28}$H$_{26}$F$_3$N$_5$O$_5$S<br>$^1$H NMR (300 MHz, CD$_3$OD): δ 1.26 (d, 6H), 2.16 (m, 4H), 3.75 (m, 2H), 3.99 (m, 1H), 4.15 (m, 2H), 5.15 (brs, 1H), 7.82 (d, 1H), 7.90 (s, 1H), 8.18 (s, 1H), 8.22 (d, 1H), 8.38 (s, 1H), 8.47 (s, 1H), 9.01 (s, 1H). | Example 187 |

-continued

| Ex | Compound | Data | SM |
|---|---|---|---|
| 200 | 4-oxo-6-(6-(3-propylureido)-4-(4-(trifluoromethyl)thiazol-2-yl)pyridin-3-yl)-1-(2-(tetrahydro-2H-pyran-4-yl)ethyl)-1,4-dihydroquinoline-3-carboxylic acid | MS (ESP): 630 (M + H+) for $C_{30}H_{30}F_3N_5O_5S$<br>$^1$H NMR (300 MHz, CD$_3$OD): δ 0.99 (t, 3H), 1.38 (m, 2H), 1.71 (m, 7H), 3.43 (m, 2H), 3.92 (m, 1H), 4.40 (m, 2H), 7.60 (d, 1H), 7.75 (d, 1H), 7.90 (s, 1H), 8.30 (s, 1H), 8.43 (s, 1H), 8.54 (s, 1H), 8.59 (s, 1H). | Example 188 |
| 201 | 6-(6-(3-isopropylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxylic acid | MS (ESP): 589.2 (M + H+) for $C_{27}H_{27}F_3N_6O_4S$<br>$^1$H NMR (300 MHz, CD$_3$OD): δ 1.00 (t, 3H), 1.88 (m, 2H), 2.34 (s, 6H), 2.79 (t, 2H), 4.46 (t, 2H), 7.62 (d, 1H), 7.79 (d, 1H), 7.89 (s, 1H), 8.14 (s, 1H), 8.34 (s, 1H), 8.43 (s, 1H), 8.55 (s, 1H). | Example 174 |
| 202 | 6-(6-(3-isopropylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxylic acid | MS (ESP): 643.2 (M + H+) for $C_{31}H_{33}F_3N_6O_4S$<br>$^1$H NMR (300 MHz, CD$_3$OD): δ 1.25 (d, 6H), 1.52 (m, 2H), 1.93 (m, 3H), 2.13 (brd, 2H), 2.87 (s, 3H), 3.02 (m, 2H), 3.53 (m, 2H), 4.02 (m, 1H), 4.60 (t, 2H), 7.81 (d, 1H), 7.92 (s, 1H), 7.96 (d, 1H), 8.21 (s, 1H), 8.38 (s, 1H), 8.43 (s, 1H), 9.00 (s, 1H). | Example 179 |

Example 203

1-(2-(dimethylamino)ethyl)-N-(2-hydroxyethyl)-4-oxo-6-(6-(3-propylureido)-4-(4-(trifluoromethyl)thiazol-2-yl)pyridin-3-yl)-1,4-dihydroquinoline-3-carboxamide

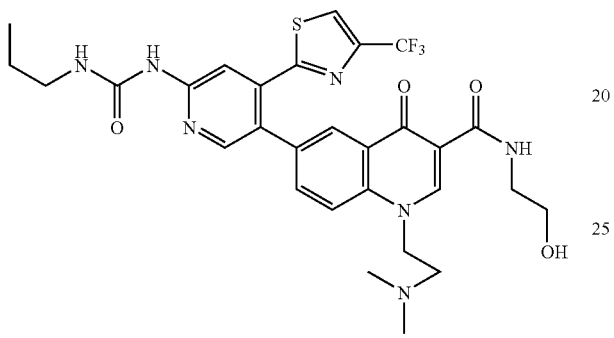

A suspension of ethyl 1-(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxylate (Example 174, 50 mg, 0.09 mmol) in ethanolamine (0.5 mL) was heated to 85-90° C. for 3 h. The reaction mixture was cooled to room temperature and the precipitate that formed was isolated by filtration and washed with acetonitrile and water then dried overnight under high vacuum.

MS (ESP): 589 (M+H$^+$) for $C_{29}H_{32}F_3N_7O_4S$ $^1$H NMR (300 MHz, CD$_3$OD): δ 1.00 (t, 3H), 1.64 (m, 2H), 2.33 (s, 6H), 2.78 (t, 2H), 3.37 (q, 2H), 3.66 (m, 2H), 3.83 (brs, 2H), 4.37 (t, 2H), 7.60 (m, 4H), 8.01 (s, 1H), 8.24 (s, 1H), 8.59 (s, 1H), 8.84 (s, 1H), 9.1 (brs, 1H), 10.25 (brs, 1H).

Examples 204-232

The following compounds were prepared according to the procedure described for Example 203 from the starting materials indicated in the table.

| Ex | Compound | Data | SM |
|---|---|---|---|
| 204 | N-(2-hydroxyethyl)-4-oxo-6-(6-(3-propylureido)-4-(4-(trifluoromethyl)thiazol-2-yl)pyridin-3-yl)-1-(2-(pyrrolidin-1-yl)ethyl)-1,4-dihydroquinoline-3-carboxamide | MS (ESP): 658 (M + H$^+$) for $C_{31}H_{34}F_3N_7O_4S$<br>$^1$H NMR (300 MHz, CD$_3$OD): δ 1.00 (t, 3H), 1.62 (m, 2H), 1.80 (m, 4H), 2.62 (m, 4H), 2.98 (m, 2H), 3.56 (m, 2H), 3.72 (m, 2H), 4.59 (m, 2H) 7.73 (d, 1H), 7.86 (s, 1H), 7.89 (d, 1H), 8.15 (s, 1H), 8.35 (s, 1H), 8.39 (s, 1H), 8.88 (s, 1H) | Example 176 and ethanolamine |

-continued

| Ex | Compound | Data | SM |
|---|---|---|---|
| 205 | N-(2-hydroxyethyl)-1-(2-morpholinoethyl)-4-oxo-6-(6-(3-propylureido)-4-(4-(trifluoromethyl)thiazol-2-yl)pyridin-3-yl)-1,4-dihydroquinoline-3-carboxamide | MS (ESP): 675 (M + H$^+$) for C$_{31}$H$_{34}$F$_3$N$_7$O$_5$S<br>$^1$H NMR (300 MHz, CD$_3$OD): δ 0.90 (t, 3H), 1.49 (m, 2H), 2.4 (brs, 4H), 2.67 (m, 2H), 3.16 (m, 2H), 3.41 (m, 2H), 3.50 (brs, 6H), 4.60 (brs, 2H), 7.70 (s, 1H), 7.73 (d, 1H), 7.96 (d, 1H), 8.23 (s, 1H), 8.25 (s, 1H), 8.34 (s, 1H), 8.48 (s, 1H), 8.84 (s, 1H), 9.46 (s, 1H), 9.97 (s, 1H) | Example 181 and ethanolamine |
| 206 | N-(2-hydroxyethyl)-4-oxo-6-(6-(3-propylureido)-4-(4-(trifluoromethyl)thiazol-2-yl)pyridin-3-yl)-1-(tetrahydro-2H-pyran-4-yl)-1,4-dihydroquinoline-3-carboxamide | MS (ESP): 645 (M + H$^+$) for C$_{30}$H$_{31}$F$_3$N$_6$O$_5$S<br>$^1$H NMR (300 MHz, CD$_3$OD): δ 0.99 (t, 3H), 2.18 (m, 4H), 3.55 (m, 2H), 3.74 (m, 4H), 4.17 (m, 2H), 5.10 (m, 1H), 7.72 (d, 1H), 7.86 (s, 1H), 8.09 (d, 1H), 8.14 (s, 1H), 8.34 (s, 1H), 8.42 (s, 1H), 8.99 (s, 1H) | Example 188 and ethanolamine |
| 207 | N-(2-hydroxyethyl)-1-(2-methoxyethyl)-4-oxo-6-(6-(3-propylureido)-4-(4-(trifluoromethyl)thiazol-2-yl)pyridin-3-yl)-1,4-dihydroquinoline-3-carboxamide | MS (ESP): 619 (M + H$^+$) for C$_{29}$H$_{31}$F$_3$N$_6$O$_7$S<br>$^1$H NMR (300 MHz, dmso-d$_6$): δ 0.91 (t, 3H), 1.49 (m, 2H), 3.16 (q, 2H), 3.23 (s, 3H), 3.40 (m, 2H), 3.50 (m, 2H), 3.69 (m, 2H), 4.70 (brs, 2H), 4.82 (t, 1H), 7.67 (t, 1H), 7.72 (d, 1H), 7.99 (d, 1H), 8.26 (s, 1H), 8.24 (s, 1H), 8.34 (s, 1H), 8.79 (s, 1H), 9.47 (s, 1H), 9.98 (t, 1H) | Example 185 and ethanolamine |

| Ex | Compound | Data | SM |
|---|---|---|---|
| 208 | N-(2-hydroxyethyl)-6-(6-(3-isopropylureido)-4-(4-(trifluoromethyl)thiazol-2-yl)pyridin-3-yl)-1-(2-methoxyethyl)-4-oxo-1,4-dihydroquinoline-3-carboxamide | MS (ESP): 619 (M + H$^+$) for C$_{28}$H$_{29}$F$_3$N$_6$O$_5$S<br>$^1$H NMR (300 MHz, DMSO-d$_6$): δ 1.15 (d, 6H), 3.34 (s, 3H), 3.41 (m, 2H), 3.51 (m, 2H), 3.69 (m, 3H), 3.83 (m, 1H), 4.70 (brs, 2H), 4.82 (t, 1H), 7.71 (d, 1H), 7.74 (d, 1H), 8.02 (d, 1H), 8.26 (s, 1H), 8.28 (s, 1H), 8.35 (s, 1H), 8.49 (s, 1H), 8.80 (s, 1H), 9.34 (s, 1H), 9.98 (t, 1H) | Example 186 and ethanolamine |
| 209 | N-(2-hydroxyethyl)-6-(6-(3-isopropylureido)-4-(4-(trifluoromethyl)thiazol-2-yl)pyridin-3-yl)-1-(2-morpholinoethyl)-4-oxo-1,4-dihydroquinoline-3-carboxamide | MS (ESP): 674 (M + H$^+$) for C$_{31}$H$_{34}$F$_3$N$_7$O$_5$S<br>$^1$H NMR (300 MHz, dmso-d$_6$): δ 1.15 (d, 6H), 2.44 (brs, 4H), 2.67 (brs, 2H), 3.42 (m, 2H), 3.53 (brs, 6H), 3.82 (m, 1H), 4.61 (brs, 2H), 4.82 (t, 1H), 7.48 (d, 1H), 7.73 (d, 1H), 7.98 (d, 1H), 8.25 (s, 1H), 8.27 (s, 1H), 8.35 (s, 1H), 8.49 (s, 1H), 8.84 (s, 1H), 9.46 (s, 1H), 9.97 (s, 1H) | Example 182 and ethanolamine |
| 210 | N-(2-hydroxyethyl)-6-(6-(3-isopropylureido)-4-(4-(trifluoromethyl)thiazol-2-yl)pyridin-3-yl)-4-oxo-1-(tetrahydro-2H-pyran-4-yl)-1,4-dihydroquinoline-3-carboxamide | MS (ESP): 645 (M + H$^+$) for C$_{30}$H$_{31}$F$_3$N$_6$O$_5$S<br>$^1$H NMR (300 MHz, CD$_3$OD): δ 1.22 (d, 6H), 2.18 (m, 4H), 2.72 (m, 1H), 3.57 (t, 2H), 3.72 (m, 4H), 3.99 (m, 1H), 4.14 (m, 2H), 5.10 (m, 1H), 7.73 (d, 1H), 7.91 (s, 1H), 8.10 (d, 1H), 8.14 (s, 1H), 8.35 (s, 1H), 8.43 (s, 1H), 9.00 (s, 1H) | Example 187 and ethanolamine |

| Ex | Compound | Data | SM |
|---|---|---|---|
| 211 | N-(2-hydroxyethyl)-1-(2-(4-methylpiperazin-1-yl)ethyl)-4-oxo-7-(6-(3-propylureido)-4-(4-(trifluoromethyl)thiazol-2-yl)pyridin-3-yl)-1,4-dihydroquinoline-3-carboxamide | MS (ESP): 687.3 (M + H$^+$) for $C_{32}H_{37}F_3N_8O_4S$<br>$^1$H NMR (300 MHz, dmso-d$_6$): δ 0.91 (t, 3H), 1.46-1.53 (m, 2H), 2.09 (s, br, 3H), 2.14-2.45 (m, 5H), 2.66 (t, 2H), 3.16 (q, 2H), 3.37-3.40 (m, 4H), 3.51 (q, 3H), 4.60 (t, br, 2H), 4.83 (t, 1H), 7.68-7.74 (m, 2H), 7.97 (d, 1H), 8.23 (s, 1H), 8.25 (d, 1H), 8.35 (s, 1H), 8.50 (t, 1H), 8.82 (d, 1H), 9.47 (s, 1H), 9.99 (t, 1H) | Example 180 and ethanolamine |
| 212 | N-(2-hydroxyethyl)-6-(4-(3-isopropylureido)-2-(4-(trifluoromethyl)thiazol-2-yl)phenyl)-1-(2-(4-methylpiperazin-1-yl)ethyl)-4-oxo-1,4-dihydroquinoline-3-carboxamide | MS (ESP): 687 (M + H$^+$) for $C_{33}H_{37}F_3N_8O_4S$<br>$^1$H NMR (300 MHz, dmso-d$_6$): δ 1.17 (d, 6H), 2.10 (s, 3H), 2.43 (brs, 2H), 2.49 (brs, 2H), 2.66 (brs, 2H), 3.31 (m, 2H), 3.52 (m, 2H), 3.85 (m, 1H), 4.58 (m, 2H), 4.58 (t, 1H), 7.43 (d, 1H), 7.69 (d, 1H), 7.69 (d, 1H), 7.94 (d, 1H), 8.24 (s, 1H), 8.26 (s, 1H), 8.34 (s, 1H), 8.48 (s, 1H), 9.91 (s, 1H), 9.99 (t, 1H) | Example 179 and ethanolamine |

| Ex | Compound | Data | SM |
|---|---|---|---|
| 213 | N-(2-hydroxyethyl)-1-(2-(1-methylpiperidin-4-yl)ethyl)-4-oxo-6-(4-(3-propylureido)-2-(4-(trifluoromethyl)thiazol-2-yl)phenyl)-1,4-dihydroquinoline-3-carboxamide | MS (ESP): 686 (M + H+) for $C_{33}H_{38}F_3N_7O_4S$<br>$^1$H NMR (300 MHz, dmso-d$_6$): δ 0.91 (t, 3H), 1.23 (m, 3H), 1.59 (m, 2H), 1.76 (m, 4H), 2.12 (s, 3H), 2.75 (m, 2H), 3.18 (m, 2H), 3.37 (m, 1H), 3.50 (m, 2H), 4.49 (brs, 2H), 4.80 (brs, 1H), 7.72 (d, 1H), 7.89 (d, 1H), 7.69 (d, 1H), 7.82 (s, 2H), 8.31 (s, 1H), 8.48 (s, 1H), 8.89 (s, 1H), 9.53 (s, 1H), 9.95 (t, 1H) | Example 177 and ethanolamine |
| 214 | N-(2-hydroxyethyl)-4-oxo-6-(6-(3-propylureido)-4-(4-(trifluoromethyl)thiazol-2-yl)pyridin-3-yl)-1-(2-(tetrahydro-2H-pyran-4-yl)ethyl)-1,4-dihydroquinoline-3-carboxamide | MS (ESP): 673 (M + H+) for $C_{32}H_{35}F_3N_6O_5S$<br>$^1$H NMR (300 MHz, dmso-d$_6$): δ 0.90 (t, 3H), 1.27 (m, 2H), 1.48 (m, 2H), 1.64 (m, 4H), 2.92 (m, 1H), 3.24 (m, 2H), 3.28 (m, 2H), 3.39 (m, 2H), 3.86 (m, 2H), 4.51 (t, 2H), 4.81 (s, 1H), 7.75 (d, 1H), 7.93 (d, 1H), 8.25 (s, 2H), 8.34 (s, 1H), 8.49 (s, 2H), 8.91 (s, 1H), 9.57 (s, 1H), 9.98 (t, 1H) | Example 184 and ethanolamine |

-continued

| Ex | Compound | Data | SM |
|---|---|---|---|
| 215 | N-(2-hydroxyethyl)-7-(6-(3-isopropylureido)-4-(4-(trifluoromethyl)thiazol-2-yl)pyridin-3-yl)-4-oxo-1-(2-(tetrahydro-2H-pyran-4-yl)ethyl)-1,4-dihydroquinoline-3-carboxamide | MS (ESP): 673.2 (M + H$^+$) for C$_{32}$H$_{35}$F$_3$N$_6$O$_5$S<br>$^1$H NMR (300 MHz, dmso-d$_6$): δ 1.15 (d, 6H), 1.23-1.35 (m, 3H), 1.64-1.79 (m, 6H), 3.05-3.12 (m, 2H), 3.49-3.53 (m, 2H), 3.83-3.87 (m, 3H), 4.54 (br, 2H), 4.64 (t, 1H), 4.80 (t, 1H), 7.45 (dd, 1H), 7.74 (dd, 1H), 7.92 (d, 1H), 8.25 (d, 1H), 8.27 (d, 1H), 8.34 (d, 1H), 8.49 (d, 1H), 8.91 (s, 1H), 9.32 (s, 1H), 9.98 (t, 1H) | Example 183 and ethanolamine |
| 216 | N-(2-hydroxyethyl)-6-(6-(3-isopropylureido)-4-(4-(trifluoromethyl)thiazol-2-yl)pyridin-3-yl)-1-(2-(1-methylpiperidin-4-yl)ethyl)-4-oxo-1,4-dihydroquinoline-3-carboxamide | MS (ESP): 686 (M + H$^+$) for C$_{33}$H$_{38}$F$_3$N$_7$O$_4$S<br>$^1$H NMR (300 MHz, dmso-d$_6$): δ 1.20 (d, 3H), 1.24 (m, 2H), 1.68 (m, 3H), 1.83 (m, 2H), 2.08 (s, 3H), 2.75 (brs, 2H), 3.41 (m, 2H), 3.50 (m, 2H), 3.83 (m, 1H), 4.53 (t, 2H), 4.81 (t, 1H), 7.46 (d, 1H), 7.76 (d, 1H), 7.89 (d, 1H), 8.25 (s, 1H), 8.27 (s, 1H), 8.34 (s, 1H), 8.49 (s, 1H), 8.89 (s, 1H), 9.32 (s, 1H), 9.98 (t, 1H) | Example 178 and ethanolamine |

| Ex | Compound | Data | SM |
|---|---|---|---|
| 217 | 1-(2-(dimethylamino)ethyl)-N-(2-hydroxyethyl)-7-(6-(3-isopropylureido)-4-(4-(trifluoromethyl)thiazol-2-yl)pyridin-3-yl)-4-oxo-1,4-dihydroquinoline-3-carboxamide 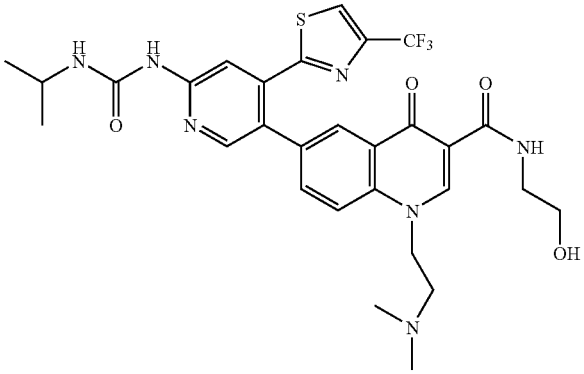 | MS (ESP): 632.1 (M + H$^+$) for C$_{29}$H$_{32}$F$_3$N$_7$O$_4$S<br>$^1$H NMR (300 MHz, dmso-d$_6$): δ 1.15 (d, 6H), 2.19 (s, 6H), 2.62 (t, 2H), 3.40 (q, 2H), 3.43-3.51 (m, 2H), 3.81-3.88 (m, 1H), 4.59 (t, br, 2H), 4.81 (br, 1H), 7.46 (d, 1H), 7.72 (dd, 1H), 7.95 (d, 1H), 8.25 (d, 1H), 8.27 (s, 1H), 8.34 (d, 1H), 8.49 (d, 1H), 8.82 (s, 1H), 9.33 (s, 1H), 9.99 (t, 1H) | Example 173 and ethanolamine |
| 218 | N-(2-(dimethylamino)ethyl)-1-(2-(4-methylpiperazin-1-yl)ethyl)-4-oxo-7-(6-(3-propylureido)-4-(4-(trifluoromethyl)thiazol-2-yl)pyridin-3-yl)-1,4-dihydroquinoline-3-carboxamide 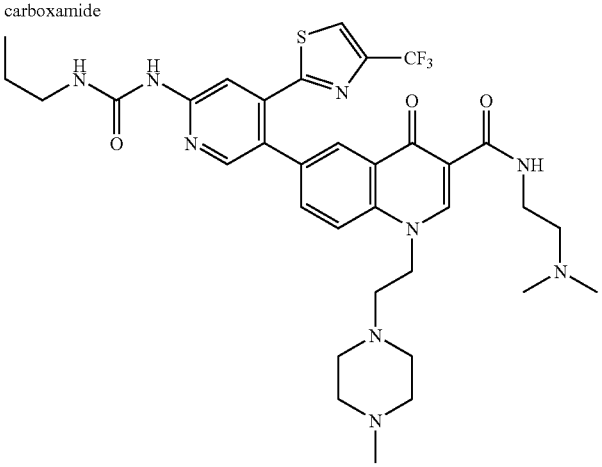 | MS (ESP): 714.3 (M + H$^+$) for C$_{34}$H$_{42}$F$_3$N$_9$O$_3$S<br>$^1$H NMR (300 MHz, dmso-d$_6$): δ 0.91 (t, 3H), 1.47-1.54 (m, 2H), 2.11 (s, 3H), 2.18 (s, 6H), 2.19-2.38 (m, 2H), 2.40-2.50 (m, 4H), 2.66 (t, 2H), 3.15 (q, 2H), 3.42 (q, 2H), 4.58 (t, 2H), 7.66-7.72 (m, 2H), 7.96 (d, 1H), 8.24 (s, 1H), 8.27 (d, 1H), 8.34 (d, 1H), 8.49 (d, 1H), 8.80 (s, 1H), 9.44 (s, 1H), 9.92 (t, 1H) | Example 180 and N$^1$,N$^1$-dimethyl-ethane-1,2-diamine |

| Ex | Compound | Data | SM |
|---|---|---|---|
| 219 | N,1-bis(2-(dimethylamino)ethyl)-4-oxo-6-(6-(3-propylureido)-4-(4-(trifluoromethyl)thiazol-2-yl)pyridin-3-yl)-1,4-dihydroquinoline-3-carboxamide | MS (ESP): 659 (M + H$^+$) for C$_{31}$H$_{37}$F$_3$N$_8$O$_3$S<br>$^1$H NMR (300 MHz, dmso-d$_6$): δ 0.91 (t, 3H), 1.51 (m, 2H), 2.17 (s, 6H), 2.39 (t, 2H), 2.61 (brs, 2H), 3.16 (m, 2H), 3.42 (m, 2H), 4.57 (t, 2H), 7.69 (s, 1H), 7.71 (d, 1H), 7.96 (d, 1H), 8.24 (s, 1H), 8.27 (s, 1H), 8.33 (s, 1H), 8.48 (s, 1H), 8.80 (s, 1H), 9.4 (s, 1H), 9.93 (brs, 1H) | Example 174 and N$^1$,N$^1$-dimethyl-ethane-1,2-diamine |
| 220 | N-(2-(dimethylamino)ethyl)-7-(6-(3-isopropylureido)-4-(4-(trifluoromethyl)thiazol-2-yl)pyridin-3-yl)-1-(2-morpholinoethyl)-4-oxo-1,4-dihydroquinoline-3-carboxamide | MS (ESP): 701.4 (M + H$^+$) for C$_{33}$H$_{39}$F$_3$N$_8$O$_4$S<br>$^1$H NMR (300 MHz, dmso-d$_6$): δ 1.15 (d, 6H), 2.12 (d, 1H), 2.18 (s, 6H), 2.27 (t, 1H), 2.37-2.51 (m, 8H), 2.65 (t, 1H), 2.73 (t, 1H), 3.42 (q, 1H), 3.50 (t, 2H), 3.8 (q, 1H), 4.60 (t, 1H), 7.45 (d, 1H), 7.70 (dd, 1H), 7.96 (d, 1H), 8.27 (m, 2H), 8.34 (s, 1H), 8.48 (d, 1H), 8.83 (s, 1H), 9.34 (s, 1H), 9.91 (m, 1H) | Example 182 and N$^1$,N$^1$-dimethyl-ethane-1,2-diamine |
| 221 | N-(2-(dimethylamino)ethyl)-7-(6-(3-isopropylureido)-4-(4-(trifluoromethyl)thiazol-2-yl)pyridin-3-yl)-4-oxo-1-(tetrahydro-2H-pyran-4-yl)-1,4-dihydroquinoline-3-carboxamide | MS (ESP): 672.3 (M + H$^+$) for C$_{32}$H$_{36}$F$_3$N$_7$O$_4$S<br>$^1$H NMR (300 MHz, dmso-d$_6$): δ 1.15 (d, 6H), 2.03-2.16 (m, 4H), 2.16 (s, 6H), 3.60-3.70 (m, 1H), 3.80-3.90 (m, 1H), 4.0-4.1 (m, 1H), 5.05-5.10 (m, 1H), 7.50 (d, 1H), 7.72 (dd, 1H), 8.20-8.32 (m, 3H), 8.46 (s, 1H), 8.84 (s, 1H), 9.32 (d, 1H), 9.88 (m, 1H) | Example 187 and N$^1$,N$^1$-dimethyl-ethane-1,2-diamine |

| Ex | Compound | Data | SM |
|---|---|---|---|
| 222 | N-(2-(dimethylamino)ethyl)-7-(6-(3-isopropylureido)-4-(4-(trifluoromethyl)thiazol-2-yl)pyridin-3-yl)-1-(2-methoxyethyl)-4-oxo-1,4-dihydroquinoline-3-carboxamide | MS (ESP): 646.2 (M + H$^+$) for C$_{30}$H$_{34}$F$_3$N$_7$O$_4$S<br>$^1$H NMR (300 MHz, CDCl$_3$): δ 1.29 (d, 6H), 2.32 (s, 6H), 2.56 (t, 2H), 3.34 (s, 3H), 3.60 (q, 2H), 3.80 (t, 2H), 4.11 (q, 1H), 4.46 (t, 2H), 7.22 (d, 1H), 7.42 (s, 1H), 7.51-7.61 (m, 2H), 7.68 (s, 1H), 8.28 (s, 1H), 8.57 (d, 1H), 8.84 (s, 1H), 8.91 (d, 1H), 10.02 (br, 1H) | Example 186 and N$^1$,N$^1$-dimethyl-ethane-1,2-diamine |
| 223 | N-(2-(dimethylamino)ethyl)-1-(2-methoxyethyl)-4-oxo-7-(6-(3-propylureido)-4-(4-(trifluoromethyl)thiazol-2-yl)pyridin-3-yl)-1,4-dihydroquinoline-3-carboxamide | MS (ESP): 646.2 (M + H$^+$) for C$_{30}$H$_{34}$F$_3$N$_7$O$_4$S<br>$^1$H NMR (300 MHz, CDCl$_3$): δ 1.01 (t, 3H), 1.67 (q, 2H), 2.18 (s, 6H), 2.32 (t, 2H), 3.34 (s, 3H), 3.39 (q, 2H), 3.60 (q, 2H), 3.80 (t, 2H), 4.46 (t, 2H), 7.44 (s, 1H), 7.48 (s, 1H), 7.52-7.61 (m, 2H), 7.68 (d, 1H), 8.27 (s, 1H), 8.57 (d, 1H), 8.85 (s, 1H), 9.11 (br, 1H), 10.02 (br, 1H) | Example 185 and N$^1$,N$^1$-dimethyl-ethane-1,2-diamine |
| 224 | N-(2-(dimethylamino)ethyl)-4-oxo-7-(6-(3-propylureido)-4-(4-(trifluoromethyl)thiazol-2-yl)pyridin-3-yl)-1-(tetrahydro-2H-pyran-4-yl)-1,4-dihydroquinoline-3-carboxamide | MS (ESP): 672.3 (M + H$^+$) for C$_{32}$H$_{36}$F$_3$N$_7$O$_4$S<br>$^1$H NMR (300 MHz, CDCl$_3$): δ 1.01 (t, 3H), 1.67 (q, 2H), 2.10-2.30 (m, 4H), 2.31 (s, 6H), 2.56 (t, 2H), 3.41 (q, 2H), 3.57-3.70 (m, 4H), 4.25 (dd, 2H), 4.73 (m, 1H), 7.44 (s, 1H), 7.50 (s, 1H), 7.54-7.66 (m, 2H), 7.68 (d, 1H), 8.27 (d, 1H), 8.62 (d, 1H), 9.03 (s, 1H), 9.09 (br, 1H), 10.01 (t, br, 1H) | Example 188 and N$^1$,N$^1$-dimethyl-ethane-1,2-diamine |

-continued

| Ex | Compound | Data | SM |
|---|---|---|---|
| 225 | N-(2-(dimethylamino)ethyl)-1-(2-morpholinoethyl)-4-oxo-7-(6-(3-propylureido)-4-(4-(trifluoromethyl)thiazol-2-yl)pyridin-3-yl)-1,4-dihydroquinoline-3-carboxamide | MS (ESP): 701.4 (M + H+) for $C_{33}H_{39}F_3N_8O_4S$<br>$^1$H NMR (300 MHz, CDCl$_3$): δ 1.01 (t, 3H), 1.64 (q, 2H), 2.32 (s, 6H), 2.52-2.56 (m, 6H), 2.81 (t, 2H), 3.38 (q, 2H), 3.59-3.70 (m, 6H), 4.37 (t, 2H), 7.40 (s, 1H), 7.55 (d, 2H), 7.69 (s, 1H), 8.27 (s, 1H), 8.58 (s, 1H), 8.82 (s, 1H), 9.05 (br, 1H), 10.01 (br, 1H) | Example 181 and N$^1$,N$^1$-dimethyl-ethane-1,2-diamine |
| 226 | N-(2-(dimethylamino)ethyl)-6-(4-(3-isopropylureido)-2-(4-(trifluoromethyl)thiazol-2-yl)phenyl)-1-(2-(1-methylpiperidin-4-yl)ethyl)-4-oxo-1,4-dihydroquinoline-3-carboxamide | MS (ESP): 686 (M + H+) for $C_{35}H_{43}F_3N_8O_3S$<br>$^1$H NMR (300 MHz, dmso-d$_6$): δ 1.17 (d, 6H), 1.23 (m, 3H), 1.72 (m, 4H), 1.80 (m, 2H), 2.12 (s, 3H), 2.17 (s, 6H), 2.39 (t, 2H), 2.71 (m, 2H), 3.41 (m, 2H), 3.85 (m, 1H), 4.52 (brs, 1H), 7.45 (d, 1H), 7.73 (d, 1H), 7.89 (d, 1H), 8.27 (s, 2H), 8.34 (s, 1H), 8.48 (s, 1H), 8.89 (s, 1H), 9.33 (s, 1H), 9.92 (t, 1H) | Example 178 and N$^1$,N$^1$-dimethyl-ethane-1,2-diamine |

| Ex | Compound | Data | SM |
|---|---|---|---|
| 227 | N-(2-(dimethylamino)ethyl)-6-(6-(3-isopropylureido)-4-(4-(trifluoromethyl)thiazol-2-yl)pyridin-3-yl)-1-(2-(4-methylpiperazin-1-yl)ethyl)-4-oxo-1,4-dihydroquinoline-3-carboxamide | MS (ESP): 714 (M + H$^+$) for C$_{34}$H$_{42}$F$_3$N$_9$O$_3$S<br>$^1$H NMR (300 MHz, dmso-d$_6$): δ 1.14 (d, 6H), 2.12 (s, 3H), 2.18 (s, 6H), 2.27 (brs, 2H), 2.36 (m, 6H), 2.66 (t, 2H), 3.41 (m, 2H), 3.87 (m, 1H), 4.58 (t, 2H), 7.48 (d, 1H), 7.71 (d, 1H), 7.97 (d, 1H), 8.26 (s, 2H), 8.34 (s, 1H), 8.48 (s, 1H), 8.80 (s, 1H), 9.34 (s, 1H), 9.92 (t, 1H) | Example 179 and N$^1$,N$^1$-dimethyl-ethane-1,2-diamine |
| 228 | N-(2-(dimethylamino)ethyl)-7-(6-(3-isopropylureido)-4-(4-(trifluoromethyl)thiazol-2-yl)pyridin-3-yl)-4-oxo-1-(2-(tetrahydro-2H-pyran-4-yl)ethyl)-1,4-dihydroquinoline-3-carboxamide | MS (ESP): 700.2 (M + H$^+$) for C$_{34}$H$_{40}$F$_3$N$_7$O$_4$S<br>$^1$H NMR (300 MHz, dmso-d$_6$): δ 1.15 (d, 6H), 1.23-1.35 (m, 3H), 1.64-1.79 (m, 6H), 2.22 (s, 6H), 3.20-3.40 (m, 2H), 3.43-3.53 (m, 2H), 3.83-3.87 (m, 3H), 4.54 (br, 2H), 7.45 (d, 1H), 7.73 (dd, 1H), 7.91 (d, 1H), 8.27 (d, 2H), 8.34 (d, 1H), 8.49 (d, 1H), 8.91 (s, 1H), 9.32 (s, 1H), 9.94 (t, 1H) | Example 183 and N$^1$,N$^1$-dimethyl-ethane-1,2-diamine |

| Ex | Compound | Data | SM |
|---|---|---|---|
| 229 | N-(2-(dimethylamino)ethyl)-4-oxo-7-(6-(3-propylureido)-4-(4-(trifluoromethyl)thiazol-2-yl)pyridin-3-yl)-1-(2-(pyrrolidin-1-yl)ethyl)-1,4-dihydroquinoline-3-carboxamide | MS (ESP): 685.2 (M + H$^+$) for C$_{34}$H$_{41}$F$_3$N$_8$O$_5$S<br>$^1$H NMR (300 MHz, dmso-d$_6$): δ 0.83-0.88 (m, 2H), 0.91 (t, 3H), 1.47-1.54 (m, 2H), 1.65 (br, 4H), 2.18 (s, 6H), 2.39 (t, 2H), 2.82 (t, 2H), 3.15 (q, 2H), 3.34-3.50 (m, 4H), 4.60 (t, 2H), 7.67-7.73 (m, 2H), 7.95 (d, 1H), 8.24 (s, 1H), 8.27 (d, 1H), 8.35 (s, 1H), 8.48 (d, 1H), 8.82 (s, 1H), 9.46 (s, 1H), 9.92 (t, 1H) | Example 176 and N$^1$,N$^1$-dimethyl-ethane-1,2-diamine |
| 230 | N,1-bis(2-(dimethylamino)ethyl)-7-(6-(3-isopropylureido)-4-(4-(trifluoromethyl)thiazol-2-yl)pyridin-3-yl)-4-oxo-1,4-dihydroquinoline-3-carboxamide | MS (ESP): 659.4 (M + H$^+$) for C$_{31}$H$_{37}$F$_3$N$_8$O$_3$S<br>$^1$H NMR (300 MHz, dmso-d$_6$): δ 1.16 (d, 6H), 2.19 (s, 6H), 2.21 (s, 6H), 2.44 (t, 2H), 2.62 (t, 2H), 3.43 (q, 2H), 3.80-3.86 (m, 1H), 4.58 (t, br, 2H), 7.44 (d, 1H), 7.71 (dd, 1H), 7.95 (d, 1H), 8.27 (d, 2H), 8.35 (d, 1H), 8.49 (d, 1H), 8.81 (s, 1H), 9.32 (s, 1H), 9.95 (t, 1H) | Example 173 and N$^1$,N$^1$-dimethyl-ethane-1,2-diamine |

-continued

| Ex | Compound | Data | SM |
|---|---|---|---|
| 231 | N-(2-(dimethylamino)ethyl)-1-(2-(1-methylpiperidin-4-yl)ethyl)-4-oxo-6-(6-(3-propylureido)-4-(4-(trifluoromethyl)thiazol-2-yl)pyridin-3-yl)-1,4-dihydroquinoline-3-carboxamide | MS (ESP): 713 (M + H$^+$) for C$_{36}$H$_{45}$F$_3$N$_8$O$_5$S<br>$^1$H NMR (300 MHz, dmso-d$_6$): δ 0.91 (t, 3H), 1.25 (brs, 4H), 1.51 (m, 2H), 1.72 (m, 3H), 1.89 (t, 2H), 2.40 (t, 2H), 2.80 (m, 2H), 2.50 (s, 9H), 3.16 (q, 2H), 3.43 (m, 2H), 4.52 (t, 2H), 7.67 (t, 1H), 7.74 (d, 1H), 7.89 (d, 1H), 8.24 (s, 1H), 8.27 (s, 1H), 8.34 (s, 1H), 8.48 (s, 1H), 8.89 (s, 1H), 9.45 (s, 1H), 9.92 (s, 1H) | Example 177 and N$^1$,N$^1$-dimethyl-ethane-1,2-diamine |
| 232 | N-(2-(dimethylamino)ethyl)-4-oxo-6-(6-(3-propylureido)-4-(4-(trifluoromethyl)thiazol-2-yl)pyridin-3-yl)-1-(2-(tetrahydro-2H-pyran-4-yl)ethyl)-1,4-dihydroquinoline-3-carboxamide | MS (ESP): 700 (M + H$^+$) for C$_{35}$H$_{42}$F$_3$N$_7$O$_6$S<br>$^1$H NMR (300 MHz, CD$_3$OD): δ 1.00 (t, 3H), 1.36 (m, 2H), 1.59 (m, 2H), 1.64 (m, 3H), 1.84 (m, 2H), 2.60 (s, 6H), 2.93 (t, 2H), 3.43 (t, 2H), 3.68 (t, 2H), 3.97 (m, 2H), 4.53 (t, 2H), 7.75 (d, 1H), 7.87 (s, 1H), 7.90 (d, 1H), 8.17 (s, 1H), 8.35 (s, 1H), 8.39 (s, 1H), 8.51 (brs, 1H), 8.89 (s, 1H) | Example 184 and N$^1$,N$^1$-dimethyl-ethane-1,2-diamine |

Example 233

(R)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate

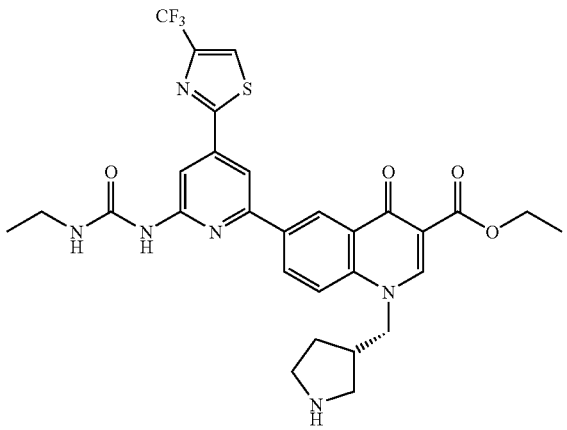

A vial was charged with (R)-ethyl 6-iodo-4-oxo-1-(pyrrolidin-3-ylmethyl)-1,4-dihydroquinoline-3-carboxylate hydrochloride (Intermediate 97, 1.0 g, 2.16 mmol), 6-(3-ethylureido)-4-(4-trifluoromethylthiazol-2-yl)pyridin-3-yl-boronic acid (Intermediate 17, 940 mg, 2.61 mmol), and sodium bicarbonate (730 mg, 8.65 mmol) in dimethoxyethane (10 mL) and water (2 mL). The reaction mixture was purged with $N_2$ for about 5 min, then trans-dichlorobis(triphenylphosphine)palladium (II) (160 mg, 0.228 mmol) was added. The reaction mixture was heated for 3 h at 80-85° C., then cooled to room temperature and water (10 mL) was added. The precipitated solid was collected by filtration to give (R)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (1.1 g, 82.7%) as a light brown solid after drying under vacuum at 40° C. overnight.

MS (ESP): 615.3 (M+H$^+$) for $C_{29}H_{29}F_3N_6O_4S$.

Example 234

(S)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate

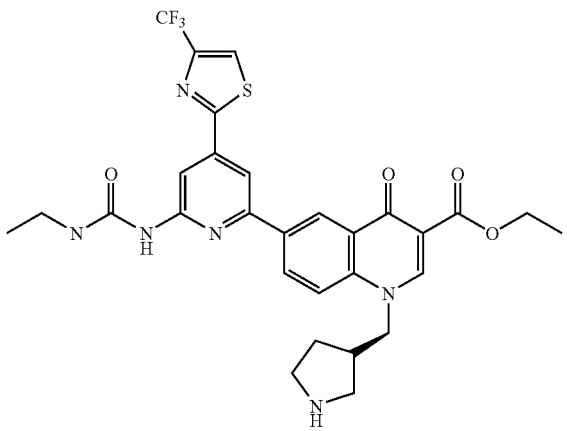

A vial was charged with (S)-ethyl 6-iodo-4-oxo-1-(pyrrolidin-3-ylmethyl)-1,4-dihydroquinoline-3-carboxylate hydrochloride (Intermediate 98, 1.0 g, 2.16 mmol), 6-(3-ethylureido)-4-(4-trifluoromethylthiazol-2-yl)pyridin-3-yl-boronic acid (Intermediate 17, 940 mg, 2.61 mmol), and sodium bicarbonate (730 mg, 8.65 mmol) in dimethoxyethane (10 mL) and water (2 mL). The reaction mixture was purged by $N_2$ for about 5 min, then trans-dichlorobis(triphenylphosphine)palladium (II) (160 mg, 0.228 mmol) was added. The reaction was heated for 1 hour at 80-85° C., then cooled to room temperature, and water (10 mL) was added. The precipitate that formed was collected by filtration to give (S)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (1.16 g, 87.2%) as a light brown solid after drying under vacuum at 40° C. overnight.

MS (ESP): 615.3 (M+H$^+$) for $C_{29}H_{29}F_3N_6O_4S$.

Example 235

(R)-ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate

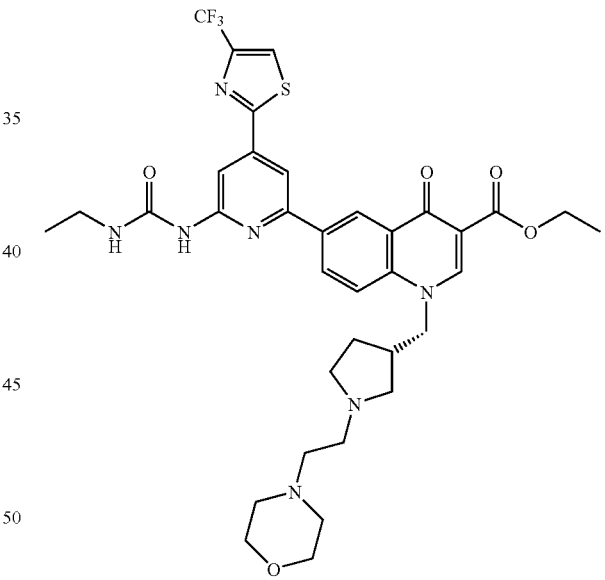

A vial was charged with (R)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (Example 233, 700 mg, 1.14 mmol) and morpholin-4-yl-acetaldehyde monohydrate hydrochloride (250 mg, 1.37 mmol) in methanol (10 mL). MP-cyanoborohydride (730 mg, 1.71 mmol) beads were added and the resulting mixture was allowed to stir at room temperature overnight. The reaction mixture was filtered and the beads were washed with more methanol. The filtrate was concentrated under reduced pressure and purified by Analogix SF15-24 g in dichloromethane/methanol system to give a light yellow solid (320 mg, 38.6%).

MS (ESP): 728.1 (MH$^+$) for $C_{35}H_{40}F_3N_7O_5S$.

Example 236

(S)-ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate

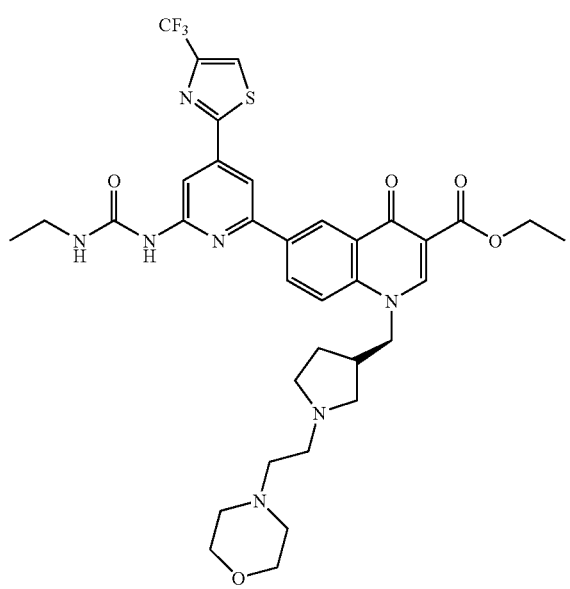

A vial was charged with (S)-ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (Example 234, 800 mg, 1.3 mmol) and morpholin-4-yl-acetaldehyde monohydrate hydrochloride (270 mg, 1.47 mmol) in methanol (10 mL). MP-cyanoborohydride (850 mg, 2.0 mmol) beads were added and the resulting mixture was allowed to stir at room temperature overnight. The mixture was filtered and the beads were washed with more methanol. The filtrate was concentrated and purified by Analogix SF15-24 g in DCM/methanol system to give a light yellow solid (380 mg, 45.8%).

MS (ESP): 728.1 (MH$^+$) for $C_{35}H_{40}F_3N_7O_5S$

Example 237

(R)-6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylic acid

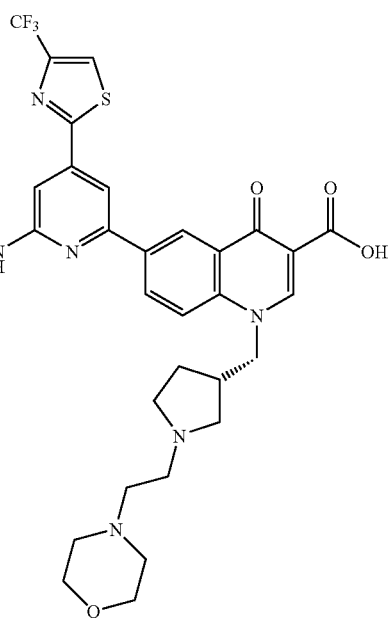

(R)-ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate (Example 235, 320 mg) was dissolved in methanol (3 mL) and tetrahydrofuran (3 mL). To this solution was added 24 wt % sodium hydroxide (1 mL) and the reaction mixture was stirred at room temperature overnight. The reaction mixture was then concentrated to remove the organic solvents. Water (10 mL) was added and the aqueous layer was acidified to pH 6~7 with 1N hydrochloric acid. The solution was centrifuged to help isolate the solid that precipitated, and the precipitate was washed with cold water once to give a light yellow solid (260 mg, 86.9%) after drying.

MS (ESP): 700.2 (MH$^+$) for $C_{33}H_{36}F_3N_7O_5S$ $^1$H NMR (300 MHz, DMSO-d$_6$):1.11 (t, 3H), 2.38-2.50 (bm, 4H), 3.18-3.25 (bm, 8H), 3.50-3.62 (bm, 6H), 4.13 (br, 1H), 4.75 (br, 2H), 7.67 (bt, 1H), 7.86 (dd, 1H), 8.23-8.25 (b, 1H), 8.25 (s, 1H), 8.31 (d, 1H), 8.37 (s, 1H), 8.54 (s, 1H), 9.11 (s, 1H), 9.55 (s, 1H)

$^{19}$F NMR Spectrum (DMSO-d$_6$)-62.79

Example 238

(S)-6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylic acid

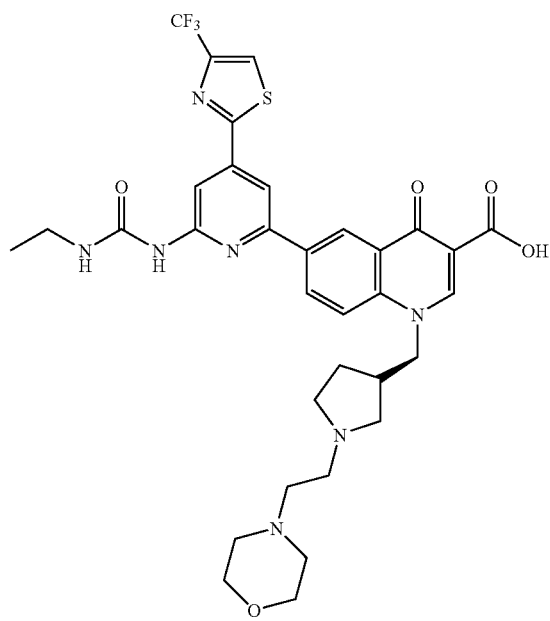

(S)-ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate (Example 236, 380 mg) was dissolved in methanol (3 mL) and tetrahydrofuran (3 mL). To this solution was added 24 wt % sodium hydroxide (1 mL) and the reaction was stirred at room temperature overnight. The solution was then concentrated to remove the organic solvents. Water (10 mL) was added and the aqueous layer was carefully acidified to pH 6~7 with 1N hydrochloric acid. The solution was centrifuged to help isolate the solid that precipitated which was washed with cold water once to give a light yellow solid (300 mg, 82.1%) after drying.

MS (ESP): 700.2 (MH$^+$) for $C_{33}H_{36}F_3N_7O_5S$ $^1$H NMR (300 MHz, CD$_3$OD): 1.23 (m, 3H), 1.99-2.1 (br, 1H), 2.25-2.4 (br, 2H), 3.2-3.3 (m, 4H), 3.30-3.5 (m, 6H), 3.6-3.7 (m, 4H), 3.9-4.0 (m, 4H), 4.70-4.8 (br, 2H), 7.85 (d, 1H), 7.88 (s, 1H), 8.11 (d, 1H), 8.22 (s, 1H), 8.37 (s, 1H), 8.46 (d, 1H), 9.09 (s, 1H)

$^{19}$F NMR Spectrum (CD$_3$OD)-65.78.

Example 239 ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate

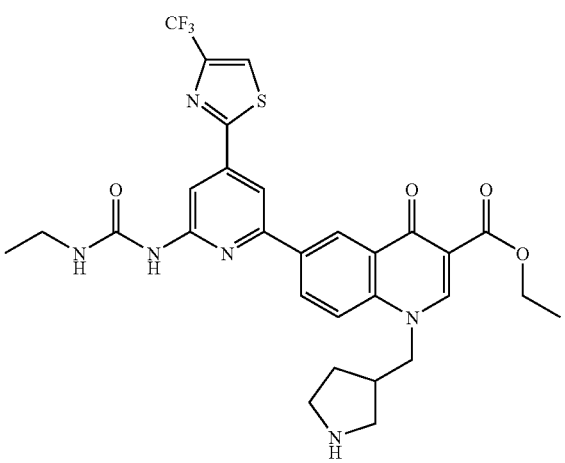

A tall vial was charged with ethyl 6-iodo-4-oxo-1-(pyrrolidin-3-ylmethyl)-1,4-dihydroquinoline-3-carboxylate hydrochloride (Intermediate 126, 1.5 g, 3.24 mmol), 6-(3-ethylureido)-4-(4-trifluoromethylthiazol-2-yl)pyridin-3-ylboronic acid (Intermediate 17, 1.41 g, 3.9 mmol) and sodium bicarbonate (1.1 g, 12.9 mmol) in dimethoxyethane (10 mL) and water (2 mL). The reaction mixture was purged by N$_2$ for about 5 minutes, then trans-dichlorobis(triphenylphosphine)palladium (II) (228 mg, 0.324 mmol) was added. The reaction was stirred for 1 h at 75° C. The reaction mixture was cooled to room temperature, and water (10 mL) was added. A solid precipitated and was collected to give ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (1.6 g, 80.4%) as a light brown solid after drying in a vacuum oven at 40° C. overnight.

MS (ESP): 615.0 (M+H$^+$) for $C_{29}H_{29}F_3N_6O_4S$.

Example 240 ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate

Example 241

6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylic acid

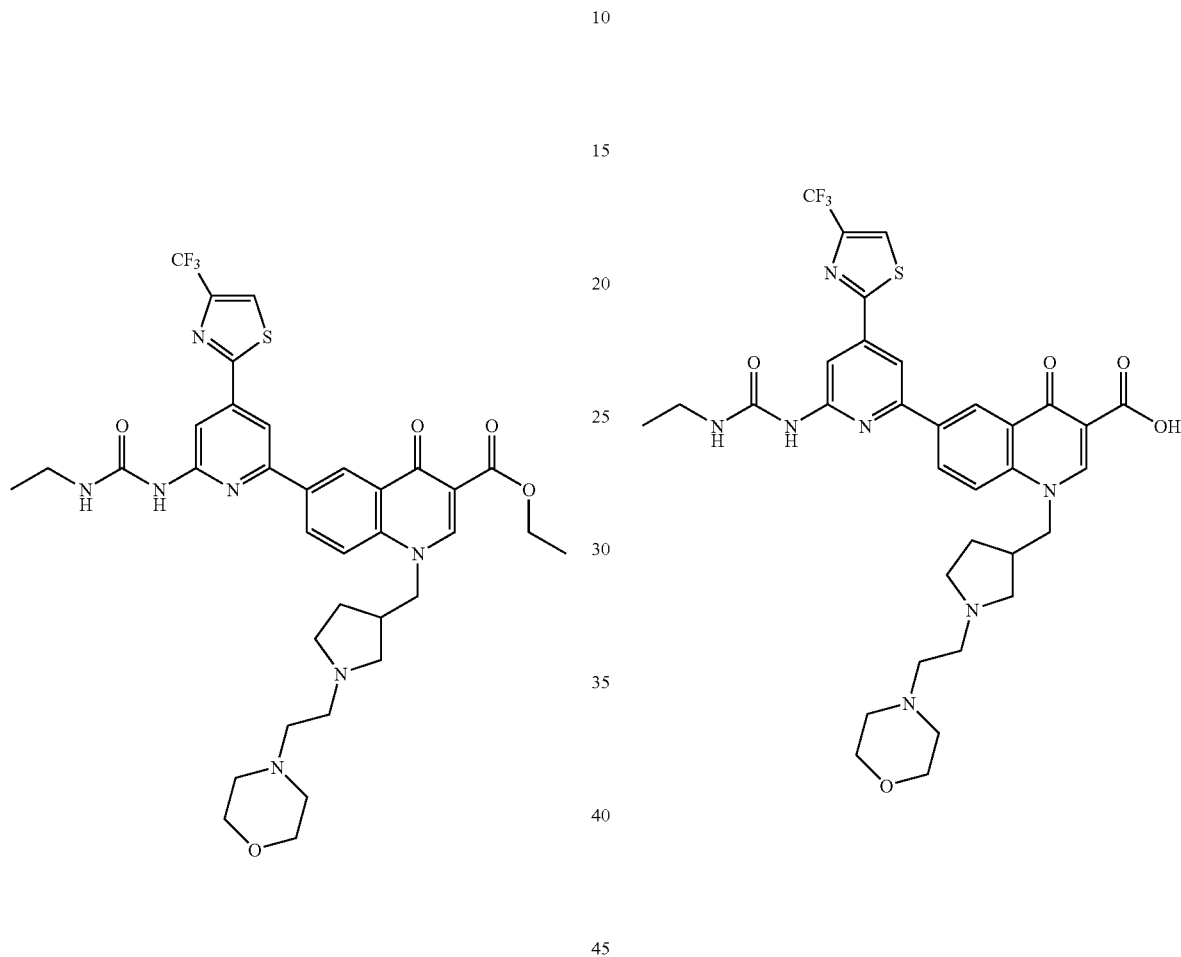

A vial was charged with ethyl 6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylate (Example 239, 700 mg, 1.14 mmol), morpholin-4-yl-acetaldehyde monohydrate hydrochloride (260 mg, 1.39 mmol) and methanol (10 mL). MP-cyanoborohydride beads (730 mg, 1.71 mmol) were added and the resulting mixture was allowed to stir at room temperature overnight. The reaction went to completion based on LC. The mixture was filtered and the beads were washed with methanol. The filtrate was concentrated under reduced pressure and purified by Analogix SF15-24 g column eluting with dichloromethane/methanol system to give a light yellow solid (310 mg, 37.4%).

MS (ESP): 728.1 (MH$^+$) for $C_{35}H_{40}F_3N_7O_5S$.

Ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate (Example 240, 340 mg) was dissolved in methanol (3 mL) and tetrahydrofuran (3 mL). To this solution was added 24 wt % sodium hydroxide (1 mL) and the reaction mixture was stirred at room temperature for 3 h. The solution was concentrated under reduced pressure to remove the organics. Water (7 mL) was added and the aqueous layer was carefully acidified to pH~3 with 1N hydrochloric acid. A solid precipitated, and the mixture was centrifuged to help collect the solid which was then washed with cold water once and dried to give a light yellow solid (270 mg, 81.2%).

MS (ESP): 700.2 (MH$^+$) for $C_{33}H_{36}F_3N_7O_5S$ $^1$H NMR (CD$_3$OD): 1.23 (m, 3H), 1.99-2.1 (br, 1H), 2.25-2.4 (br, 2H), 3.3-3.4 (m, 6H), 3.45-3.6 (m, 4H), 3.7-3.8 (m, 4H), 3.9-4.0 (m, 4H), 4.85-4.9 (br, 2H), 7.85 (d, 1H), 7.90 (s, 1H), 8.12 (d, 1H), 8.23 (s, 1H), 8.37 (s, 1H), 8.47 (s, 1H), 9.11 (s, 1H).

Example 242

(R)-1-((1-piperidin-3-yl)methyl)-6-(6-(3-ethylureido)-4-(4-(trifluoromethyl)thiazol-2-yl)pyridin-3-yl)-4-oxo-1,4-dihydroquinoline-3-carboxylic acid

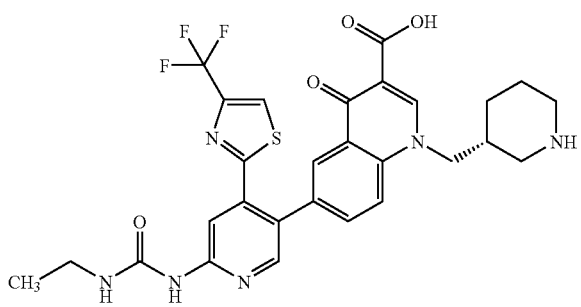

To a solution of (R)-ethyl 6-iodo-4-oxo-1-(piperidin-3-ylmethyl)-1,4-dihydroquinoline-3-carboxylate (Intermediate 108, 200 mg, 0.42 mmol, 1 equiv.) and 6-(3-ethylureido)-4-(4-(trifluoromethyl)thiazol-2-yl)pyridin-3-ylboronic acid (Intermediate 17, 151 mg, 0.42 mmol, 1 equiv.) in 1,4-dioxane (4.5 mL) was added tetrakis(triphenylphosphine)palladium(0) (48.5 mg, 0.04 mmol, 0.1 equiv.) followed by a solution of cesium carbonate (205 mg, 0.63 mmol, 1.5 equiv.) in water (1.5 mL). This was stirred at 100° C. for 2 h. 2 M lithium hydroxide (0.629 mL, 1.26 mmol, 3 equiv.) was then added and the mixture was stirred at 100° C. for 12 h. The reaction mixture was diluted with water, and the precipitate that formed was collected by filtration, washed with water and hexanes and dried under vacuum. Purification via reverse phase HPLC (C18, 0-95% acteonitirile/water gradient) gave (R)-6-(6-(3-ethylureido)-4-(4-(trifluoromethyl)thiazol-2-yl)pyridin-3-yl)-4-oxo-1-(piperidin-3-ylmethyl)-1,4-dihydroquinoline-3-carboxylic acid as a light yellow solid (92.5 mg, 36%).

Calcd for $C_{28}H_{27}F_3N_6O_4S$ [M+H]$^+$: 601.06.

Examples 243-252

The following examples were prepared according to the procedure described in Example 242 from the indicated starting materials.

| Ex | Compound | Data | SM |
| --- | --- | --- | --- |
| 243 | (S)-6-(6-(3-ethylureido)-4-(4-(trifluoromethyl)thiazol-2-yl)pyridin-3-yl)-4-oxo-1-(pyrrolidin-3-ylmethyl)-1,4-dihydroquinoline-3-carboxylic acid | Calcd for $C_{27}H_{25}F_3N_6O_4S$ [M + H]$^+$: 587.02 | Intermediate 109 & Intermediate 17 |
| 244 | (R)-6-(6-(3-ethylureido)-4-(4-(trifluoromethyl)thiazol-2-yl)pyridin-3-yl)-4-oxo-1-(pyrrolidin-3-yl)-1,4-dihydroquinoline-3-carboxylic acid | Calcd for $C_{26}H_{23}F_3N_6O_4S$ [M + H]$^+$: 573.01 | Intermediate 110 & Intermediate 17 |

| Ex | Compound | Data | SM |
|---|---|---|---|
| 245 | (S)-6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylic acid | Calcd for $C_{27}H_{25}F_3N_6O_4S$ [M + H]$^+$: 587.02 | Intermediate 111 & Intermediate 17 |
| 246 | (R)-6-(6-(3-ethylureido)-4-(4-(trifluoromethyl)thiazol-2-yl)pyridin-3-yl)-1-(1-methylpyrrolidin-3-yl)-4-oxo-1,4-dihydroquinoline-3-carboxylic acid | Calcd for $C_{27}H_{25}F_3N_6O_4S$ [M + H]$^+$: 587.02 | Intermediate 101 & Intermediate 17 |
| 247 | (R)-6-(6-(3-ethylureido)-4-(4-(trifluoromethyl)thiazol-2-yl)pyridin-3-yl)-1-((1-methylpiperidin-3-yl)methyl)-4-oxo-1,4-dihydroquinoline-3-carboxylic acid | Calcd for $C_{29}H_{29}F_3N_6O_4S$ [M + H]$^+$: 615.02 | Intermediate 102 & Intermediate 17 |
| 248 | (S)-6-(6-(3-ethylureido)-4-(4-(trifluoromethyl)thiazol-2-yl)pyridin-3-yl)-1-(1-methylpiperidin-3-yl)-4-oxo-1,4-dihydroquinoline-3-carboxylic acid | Calcd for $C_{28}H_{27}F_3N_6O_4S$ [M + H]$^+$: 601.04 | Intermediate 103 & Intermediate 17 |

| Ex | Compound | Data | SM |
|---|---|---|---|
| 249 | (S)-1-((1-ethylpyrrolidin-3-yl)methyl)-6-(6-(3-ethylureido)-4-(4-(trifluoromethyl)thiazol-2-yl)pyridin-3-yl)-4-oxo-1,4-dihydroquinoline-3-carboxylic acid | Calcd for $C_{29}H_{29}F_3N_6O_4S$ [M + H]$^+$: 615.04 | Intermediate 104 & Intermediate 17 |
| 250 | (R)-1-(1-ethylpyrrolidin-3-yl)-6-(6-(3-ethylureido)-4-(4-(trifluoromethyl)thiazol-2-yl)pyridin-3-yl)-4-oxo-1,4-dihydroquinoline-3-carboxylic acid | Calcd for $C_{28}H_{27}F_3N_6O_4S$ [M + H]$^+$: 615.04 | Intermediate 105 & Intermediate 17 |
| 251 | (R)-1-((1-ethylpiperidin-3-yl)methyl)-6-(6-(3-ethylureido)-4-(4-(trifluoromethyl)thiazol-2-yl)pyridin-3-yl)-4-oxo-1,4-dihydroquinoline-3-carboxylic acid | Calcd for $C_{30}H_{31}F_3N_6O_4S$ [M + H]$^+$: 629.06 | Intermediate 106 & Intermediate 17 |
| 252 | (R)-1-(1-ethylpiperidin-3-yl)-6-(6-(3-ethylureido)-4-(4-(trifluoromethyl)thiazol-2-yl)pyridin-3-yl)-4-oxo-1,4-dihydroquinoline-3-carboxylic acid | Calcd for $C_{29}H_{29}F_3N_6O_4S$ [M + H]$^+$: 615.04 | Intermediate 107 & Intermediate 17 |

Example 253

Ethyl 6-(6-(3-ethylureido)-4-(4-(trifluoromethyl)thiazol-2-yl)pyridin-3-yl)-1-(cis-2-hydroxycyclohexyl)-4-oxo-1,4-dihydroquinoline-3-carboxylate

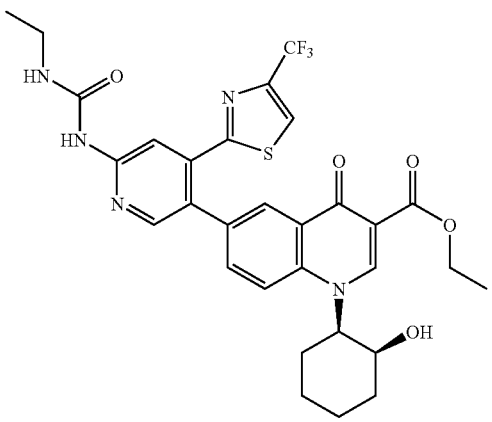

Palladium (II) acetate (0.027 g, 0.12 mmol) and 1,1'-bis(di-t-butylphosphino)ferrocene (0.058 g, 0.12 mmol) were dissolved in 1 ml of acetonitrile. Ethyl 1-(cis-2-hydroxycyclohexyl)-6-iodo-4-oxo-1,4-dihydroquinoline-3-carboxylate (Intermediate 121, 0.539 g, 1.22 mmol) and 6-(3-ethylureido)-4-(4-(trifluoromethyl)thiazol-2-yl)pyridin-3-ylboronic acid (Intermediate 17, 0.444 g, 1.23 mmol) were added along with an additional 2 ml of acetonitrile. Potassium carbonate (0.253 g, 1.83 mmol) was dissolved in water (1.333 mL) then added to the mixture. The reaction was stirred at 100° C. for 30 min, then cooled to room temperature and quenched with water (2 ml). The precipitate was filtered off and washed with water, ethyl acetate and hexanes, then dried in a vacuum oven at 50° C. for 18 h to give 0.606 g (78%) of ethyl 6-(6-(3-ethylureido)-4-(4-(trifluoromethyl)thiazol-2-yl)pyridin-3-yl)-1-(cis-2-hydroxycyclohexyl)-4-oxo-1,4-dihydroquinoline-3-carboxylate as a light brown solid.

MS (ES) (M+H)$^+$: 630 for $C_{30}H_{30}F_3N_5O_5S$.

Examples 254-260

The following Examples were prepared by the procedure described in Example 253 from the starting materials (SM) indicated.

| Ex | Compound | Data | SM |
|---|---|---|---|
| 254 | (R)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylate | MS (ES) (M + H)$^+$: 731 for $C_{34}H_{37}F_3N_6O_7S$ NMR: (300 MHz, DMSO-d$_6$) δ 9.45 (br. s., 1H), 8.53 (s, 2H), 8.31-8.44 (m, 1H), 8.15-8.26 (m, 2H), 7.97-8.14 (m, 1H), 7.61-7.75 (m, 2H), 4.61-4.81 (m, 2H), 4.14-4.32 (m, 2H), 3.96-4.06 (m, 1H), 3.60-3.94 (m, 2H), 3.49-3.60 (m, 1H), 3.38 (d, J = 7.54 Hz, 2H), 3.15-3.27 (m, 2H), 1.21-1.33 (m, 4H), 1.05-1.20 (m, 6H), 0.79-0.90 (m, 6H). | Intermediate 17 and Intermediate 117 |

| Ex | Compound | Data | SM |
|---|---|---|---|
| 255 | (S)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylate | MS (ES) (M + H)$^+$: 731 for C$_{34}$H$_{37}$F$_3$N$_6$O$_7$S NMR: (300 MHz, DMSO-d$_6$) δ 9.46 (br. s., 1H), 8.53 (s, 1H), 8.32-8.45 (m, 1H), 8.15-8.27 (m, 2H), 7.98-8.14 (m, 1H), 7.61-7.75 (m, 2H), 4.64-4.76 (m, 2H), 4.15-4.33 (m, 3H), 3.95-4.14 (m, 2H), 3.73-3.95 (m, 2H), 3.36-3.61 (m, 2H), 3.10-3.29 (m, 2H), 1.21-1.34 (m, 4H), 1.03-1.20 (m, 6H), 0.76-0.90 (m, 6H). | Intermediate 17 and Intermediate 118 |
| 256 | ethyl 1-(2-(dimethylamino)propyl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 617 for C$_{29}$H$_{31}$F$_3$N$_6$O$_4$S NMR: (300 MHz, DMSO-d$_6$) δ 9.44 (s, 1H), 8.56 (s, 1H), 8.51 (s, 1H), 8.33 (s, 1H), 8.22 (s, 1H), 8.14 (d, J = 2.26 Hz, 1H), 7.86 (d, J = 9.04 Hz, 1H), 7.58-7.68 (m, 2H), 4.17-4.42 (m, 4H), 3.15-3.27 (m, 2H), 2.92-3.05 (m, 1H), 2.16 (s, 5H), 1.28 (t, J = 6.78 Hz, 3H), 1.11 (t, J = 7.16 Hz, 3H), 0.96 (d, 3H). | Intermediate 17 and Intermediate 116 |
| 257 | ethyl 6-(6-(3-ethylureido)-4-(4-(trifluoromethyl)thiazol-2-yl)pyridin-3-yl)-1-((1R,2R)-2-hydroxycyclohexyl)-4-oxo-1,4-dihydroquinoline-3-carboxylate | MS (ES) (M + H)$^+$: 630 for C$_{30}$H$_{30}$F$_3$N$_5$O$_5$S NMR: (300 MHz, DMSO-d$_6$) δ 9.43 (s, 1H), 8.59-8.70 (m, 1H), 8.46-8.55 (m, 1H), 8.31 (s, 1H), 8.05-8.25 (m, 3H), 7.56-7.74 (m, 2H), 5.15 (d, J = 5.27 Hz, 1H), 4.50-4.69 (m, 1H), 4.25 (q, J = 6.78 Hz, 2H), 3.94 (br. s., 1H), 3.38 (q, J = 7.28 Hz, 1H), 3.21 (dq, J = 6.78, 6.53 Hz, 2H), 1.89-2.11 (m, 1H), 1.73 (d, J = 9.04 Hz, 2H), 1.39-1.63 (m, 3H), 1.29 (t, J = 7.16 Hz, 3H), 1.10 (q, J = 6.78 Hz, 4H). | Intermediate 17 and Intermediate 119 |

-continued

| Ex | Compound | Data | SM |
|---|---|---|---|
| 258 | ethyl 6-(6-(3-ethylureido)-4-(4-(trifluoromethyl)thiazol-2-yl)pyridin-3-yl)-1-((1R,2R)-2-hydroxycyclohexyl)-4-oxo-1,4-dihydroquinoline-3-carboxylate | MS (ES) (M + H)+: 630 for $C_{30}H_{30}F_3N_5O_5S$ NMR: (300 MHz, DMSO-$d_6$) δ 9.43 (s, 1H), 8.65 (s, 1H), 8.48 (s, 1H), 8.29-8.38 (m, 1H), 8.04-8.26 (m, 2H), 7.60-7.71 (m, 1H), 5.15 (d, J = 5.27 Hz, 1H), 4.59 (br. s., 1H), 4.25 (q, J = 6.78 Hz, 1H), 4.08 (q, J = 5.27 Hz, 1H), 3.86-3.98 (m, 1H), 3.15-3.26 (m, 6H), 1.99 (s, 2H), 1.71 (br. s., 2H), 1.48 (d, J = 9.80 Hz, 2H), 1.29 (t, J = 7.16 Hz, 2H), 1.03-1.18 (m, 3H). | Intermediate 17 and Intermediate 120 |
| 259 | (S)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)+: 630 for $C_{34}H_{37}F_3N_6O_6S$ | Intermediate 17 and Intermediate 122 |

-continued

| Ex | Compound | Data | SM |
|---|---|---|---|
| 260 | (R)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 630 for $C_{34}H_{37}F_3N_6O_6S$ | Intermediate 17 and Intermediate 123 |

Example 261

(S)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate

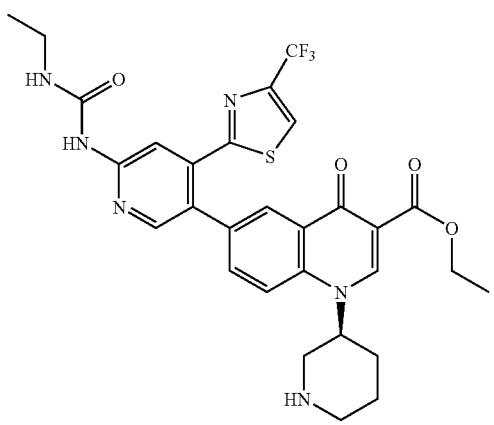

(S)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate (Example 259, 5.00 g, 7.00 mmol) was taken up in dichloromethane (10 mL) and 4M HCl in dioxane (0.486 mL, 13.99 mmol) was added while stirring at RT for 1 h. Removed solvent in vaccuo and residue was taken back up in methanol and water. The reaction was neutralized using NaHCO$_3$ and a precipitate was collected, washed with ether and dried under high vacuum overnight to give (S)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate (3.10 g, 72.1%).

MS (ES) (M+H)$^+$: 615 for $C_{29}H_{29}F_3N_6O_4S$.

Example 262

The following Example was prepared by the procedure described in Example 261 from the starting materials (SM) indicated.

| Int | Compound | Data | SM |
|---|---|---|---|
| 262 | (R)-ethyl 1-(1-(tert-butoxycarbonyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)⁺: 615 for $C_{29}H_{29}F_3N_6O_4S$ | Example 260 |

Example 263

(R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate

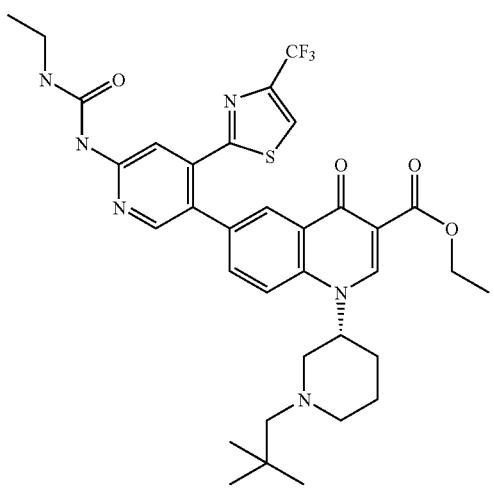

(R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate (Example 262, 0.150 g, 0.24 mmol) was taken up in dichloromethane (5 mL) and added pivalaldehyde (0.030 ml, 0.27 mmol) and stirred at RT for 15 min. Sodium triacetoxyborohydride (0.078 g, 0.37 mmol) was added and reaction was stirred at 60° C. for 18 h. The reaction was then quenched with NaHCO₃ and extracted with DCM 3 times. The organics were combined and dried over Na₂SO₄ then the solvent was removed in vaccuo. The residue was purified by flash column chromatography on silica gel using (dichloromethane-methanol) to give (R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate (0.060 g, 38%).

MS (ES) (M+H)⁺: 685 for $C_{34}H_{39}F_3N_6O_4S$

Examples 264-272

The following Examples were prepared by the procedure described in Example 263 from the starting materials (SM) indicated.

| Ex | Compound | Data | SM |
|---|---|---|---|
| 264 | (S)-ethyl 6-(6-(3-ethylureido)-4-(4-(trifluoromethyl)thiazol-2-yl)pyridin-3-yl)-1-(1-((1-methyl-1H-pyrrol-2-yl)methyl)piperidin-3-yl)-4-oxo-1,4-dihydroquinoline-3-carboxylate | MS (ES) (M + H)$^+$: 708 for $C_{35}H_{36}F_3N_7O_4S$ | Example 261 and 1-methyl-1H-pyrrole-2-carbaldehyde |
| 265 | (R)-ethyl 6-(6-(3-ethylureido)-4-(4-(trifluoromethyl)thiazol-2-yl)pyridin-3-yl)-1-(1-((1-methyl-1H-pyrrol-2-yl)methyl)piperidin-3-yl)-4-oxo-1,4-dihydroquinoline-3-carboxylate | MS (ES) (M + H)$^+$: 708 for $C_{35}H_{36}F_3N_7O_4S$ | Example 262 and 1-methyl-1H-pyrrole-2-carbaldehyde |

-continued

| Ex | Compound | Data | SM |
|---|---|---|---|
| 266 | (R)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydroquinoline-3-carboxylate | MS (ES) (M + H)$^+$: 728 for $C_{35}H_{40}F_3N_7O_5S$ | Example 262 and 2-morpholino-acetaldehyde 2,2,2-trifluoro-acetate |
| 267 | (S)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydroquinoline-3-carboxylate | MS (ES) (M + H)$^+$: 728 for $C_{35}H_{40}F_3N_7O_5S$ | Example 261 and 2-morpholino-acetaldehyde 2,2,2-trifluoro-acetate |

| Ex | Compound | Data | SM |
|---|---|---|---|
| 268 | (S)-ethyl 1-(1-(2,2-dimethyl-3-morpholinopropyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate 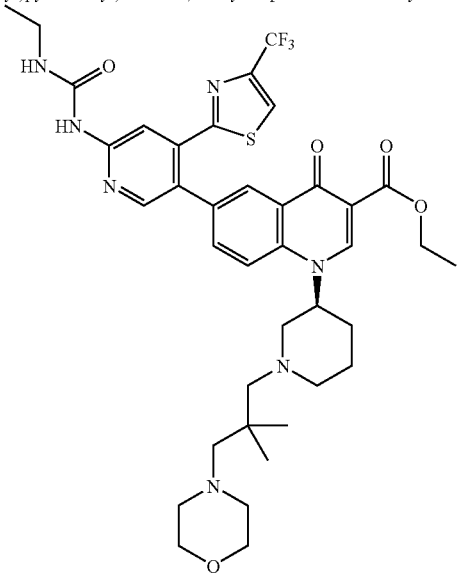 | MS (ES) (M + H)$^+$: 770 for $C_{38}H_{46}F_3N_7O_5S$ | Example 261 and 2,2-dimethyl-3-morpholino-propanal |
| 269 | (R)-ethyl 1-(1-(2,2-dimethyl-3-morpholinopropyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate 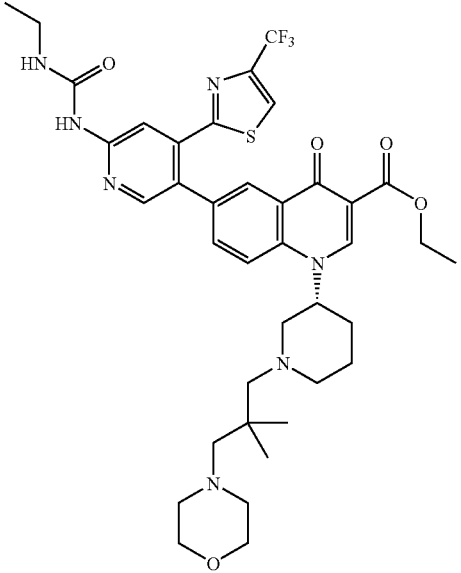 | MS (ES) (M + H)$^+$: 770 for $C_{38}H_{46}F_3N_7O_5S$ | Example 262 and 2,2-dimethyl-3-morpholino-propanal |

-continued

| Ex | Compound | Data | SM |
|---|---|---|---|
| 270 | (S)-ethyl 1-(1-(2-(tert-butyldimethylsilyloxy)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 773 for $C_{37}H_{47}F_3N_6O_5SSi$ | Example 261 and 2-(tert-butyldimethylsilyloxy)acetaldehyde |
| 271 | (R)-ethyl 1-(1-(2-(tert-butyldimethylsilyloxy)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 773 for $C_{37}H_{47}F_3N_6O_5SSi$ | Example 262 and 2-(tert-butyldimethylsilyloxy)acetaldehyde |

Example 272

(R)-ethyl 6-(6-(3-ethylureido)-4-(4-(trifluoromethyl)thiazol-2-yl)pyridin-3-yl)-1-(1-(2-(methylsulfonyl)ethyl)piperidin-3-yl)-4-oxo-1,4-dihydroquinoline-3-carboxylate

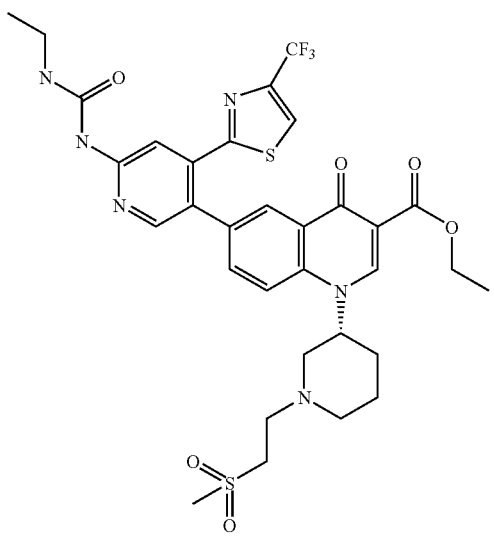

(R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate (Example 262, 0.150 g, 0.24 mmol) was taken up in isopropanol (2 mL) and methyl vinyl sulfone (0.026 mL, 0.29 mmol) was added. The reaction mixture was stirred at 100° C. for 18 h in a sealed vessel, then cooled to room temperature and the solvent was removed in vacuo and loaded directly onto silica. Purified by flash column chromatography on silica gel using (dichloromethane-methanol) gave (R)-ethyl 6-(6-(3-ethylureido)-4-(4-(trifluoromethyl)thiazol-2-yl)pyridin-3-yl)-1-(1-(2-(methylsulfonyl)ethyl)piperidin-3-yl)-4-oxo-1,4-dihydroquinoline-3-carboxylate (0.110 g, 62.5%).

MS (ES) (M+H)$^+$: 721 for $C_{32}H_{35}F_3N_6O_6S_2$

Example 273

The following Example was prepared according to the procedure described in Example 272 from the starting materials indicated.

| Int | Compound | Data | SM |
|---|---|---|---|
| 273 | (S)-ethyl 6-(6-(3-ethylureido)-4-(4-(trifluoromethyl)thiazol-2-yl)pyridin-3-yl)-1-(1-(2-(methylsulfonyl)ethyl)piperidin-3-yl)-4-oxo-1,4-dihydroquinoline-3-carboxylate | MS (ES) (M + H)$^+$: 721 for $C_{32}H_{35}F_3N_6O_6S_2$ | Example 261 and methyl vinyl sulfone |

Example 274

(R)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate

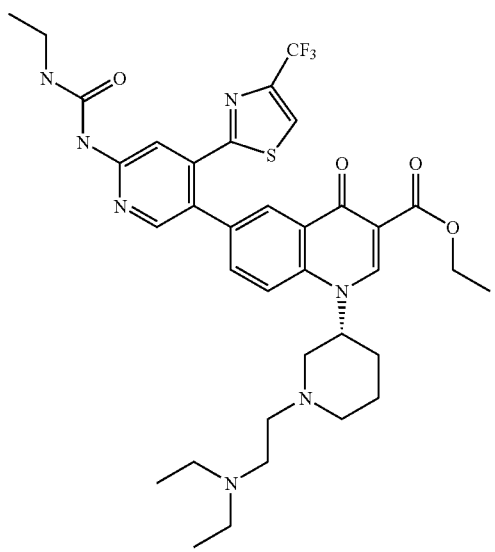

(R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylate (Example 262, 0.100 g, 0.16 mmol) was taken up in DMF (2 mL), $K_2CO_3$ (0.112 g, 0.81 mmol) and 2-chloro-N,N-diethylethanamine hydrochloride (0.031 g, 0.18 mmol) were added. The mixture was heated to 100° C. overnight then the reaction was cooled to room temperature and diluted with EtOAc. The organic layer was washed with brine twice and water twice, then the solvent was removed in vacuo and the residue was purified by flash column chromatography on silica gel using (dichloromethane-methanol) to give (R)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate (0.020 g, 17%).

MS (ES) (M+H)$^+$: 714 for $C_{35}H_{42}F_3N_7O_4S$

Example 275

The following Example was prepared according to the procedure described for Example 274 from the starting material indicated.

| Ex | Compound | Data | SM |
|---|---|---|---|
| 275 | (S)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ES) (M + H)$^+$: 714 for $C_{35}H_{42}F_3N_7O_4S$ | Example 261 and 2-chloro-N,N-diethyl-ethanamine hydrochloride |

Example 276

6-(6-(3-ethylureido)-4-(4-(trifluoromethyl)thiazol-2-yl)pyridin-3-yl)-1-(cis-2-hydroxycyclohexyl)-4-oxo-1,4-dihydroquinoline-3-carboxylic acid

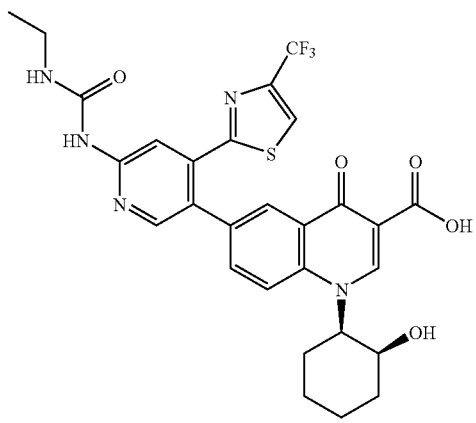

Ethyl 6-(6-(3-ethylureido)-4-(4-(trifluoromethyl)thiazol-2-yl)pyridin-3-yl)-1-(cis-2-hydroxycyclohexyl)-4-oxo-1,4-dihydroquinoline-3-carboxylate (Example 253, 0.240 g, 0.38 mmol) was suspended in MeOH (6 mL) in a microwave vessel (CEM). THF (3.00 mL) was added. A 2.0 M aq solution of LiOH (0.381 mL, 0.76 mmol) was added. The microwave vessel was heated in the microwave at 100° C. for 15 min After cooling to room temperature, the solvent was removed in vacuo to give a residue which was purified by flash column chromatography on silica gel using (dichloromethane-methanol) to give 6-(6-(3-ethylureido)-4-(4-(trifluoromethyl)thiazol-2-yl)pyridin-3-yl)-1-(cis-2-hydroxycyclohexyl)-4-oxo-1,4-dihydroquinoline-3-carboxylic acid (0.113 g, 49%).

MS (ES) (M+H)$^+$: 602 for $C_{28}H_{26}F_3N_5O_5S$.

$^1$H NMR (300 MHz, DMSO-d$_6$) δ 15.10 (s, 1H), 9.48 (s, 1H), 8.87 (s, 1H), 8.53 (s, 1H), 8.36 (s, 2H), 8.29 (d, J=9.80 Hz, 1H), 8.22 (s, 1H), 7.85 (d, J=7.54 Hz, 1H), 7.57-7.65 (m, 1H), 5.20 (d, J=4.52 Hz, 1H), 5.09 (d, J=10.55 Hz, 1H), 3.96 (br. s., 1H), 3.15-3.27 (m, 2H), 2.29 (d, J=11.30 Hz, 1H), 1.74-1.96 (m, 4H), 1.62 (d, J=7.54 Hz, 2H), 1.48 (d, 1H), 1.11 (t, J=7.16 Hz, 3H).

Examples 277-286

The following Examples were prepared according to the procedure described for Example 276 from the indicated starting materials.

| Ex | Compound | Data | SM |
|---|---|---|---|
| 277 | 1-(2-(dimethylamino)propyl)-6-(6-(3-ethylureido)-4-(4-(trifluoromethyl)thiazol-2-yl)pyridin-3-yl)-4-oxo-1,4-dihydroquinoline-3-carboxylic acid | MS (ES) (M + H)$^+$: 589 for $C_{27}H_{27}F_3N_6O_4S$<br>$^1$H NMR (300 MHz, DMSO-d$_6$) δ 14.87 (br. s., 1H), 10.57 (br. s., 1H), 9.48 (s, 1H), 9.16 (s, 1H), 8.55 (s, 1H), 8.34 (d, J = 12.81 Hz, 2H), 8.23 (s, 2H), 7.89 (d, J = 8.29 Hz, 1H), 7.60 (br. s., 1H), 5.06 (br. s., 1H), 4.86 (d, J = 11.30 Hz, 1H), 3.93 (br. s., 1H), 3.17-3.25 (m, 1H), 2.84 (br. s., 6H), 1.05-1.26 (m, 6H). | Example 256 |

-continued

| Ex | Compound | Data | SM |
|---|---|---|---|
| 278 | 6-(6-(3-ethylureido)-4-(4-(trifluoromethyl)thiazol-2-yl)pyridin-3-yl)-1-((1R,2R)-2-hydroxycyclohexyl)-4-oxo-1,4-dihydroquinoline-3-carboxylic acid | MS (ES) (M + H)$^+$: 602 for C$_{28}$H$_{26}$F$_3$N$_5$O$_5$S<br>$^1$H NMR (300 MHz, DMSO-d$_6$) δ 15.15 (s, 1H), 9.47 (s, 1H), 8.98 (s, 1H), 8.51 (s, 1H), 8.35 (d, J = 9.80 Hz, 3H), 8.22 (s, 1H), 7.85 (d, J = 10.55 Hz, 1H), 7.61 (t, J = 4.90 Hz, 1H), 5.21 (d, J = 5.27 Hz, 1H), 4.80 (t, J = 9.04 Hz, 1H), 4.00-4.11 (m, 1H), 3.15-3.27 (m, 2H), 2.01 (d, J = 14.32 Hz, 2H), 1.80-1.94 (m, 1H), 1.72 (br. s., 2H), 1.45-1.64 (m, 3H), 1.11 (t, J = 7.16 Hz, 3H). | Example 257 |
| 279 | 6-(6-(3-ethylureido)-4-(4-(trifluoromethyl)thiazol-2-yl)pyridin-3-yl)-1-((1S,2S)-2-hydroxycyclohexyl)-4-oxo-1,4-dihydroquinoline-3-carboxylic acid | MS (ES) (M + H)$^+$: 602 for C$_{28}$H$_{26}$F$_3$N$_5$O$_5$S<br>$^1$H NMR (300 MHz, DMSO-d$_6$) δ 15.15 (s, 1H), 9.47 (s, 1H), 8.98 (s, 1H), 8.51 (s, 1H), 8.35 (d, J = 9.80 Hz, 3H), 8.22 (s, 1H), 7.85 (dd, J = 9.04, 2.26 Hz, 1H), 7.61 (t, J = 5.27 Hz, 1H), 5.21 (d, J = 5.27 Hz, 1H), 4.75-4.85 (m, 1H), 4.04-4.13 (m, 2H), 3.23 (d, J = 6.78 Hz, 1H), 2.02 (d, J = 13.56 Hz, 2H), 1.85 (d, J = 11.30 Hz, 1H), 1.72 (br. s., 2H), 1.44-1.64 (m, 3H), 1.11 (t, J = 7.16 Hz, 3H). | Example 258 |
| 280 | (S)-ethyl 6-(6-(3-ethylureido)-4-(4-(trifluoromethyl)thiazol-2-yl)pyridin-3-yl)-1-(1-(2-(methylsulfonyl)ethyl)piperidin-3-yl)-4-oxo-1,4-dihydroquinoline-3-carboxylic acid | MS (ES) (M + H)$^+$: 693 for C$_{30}$H$_{31}$F$_3$N$_6$O$_5$S$_2$<br>$^1$H NMR (300 MHz, DMSO-d$_6$) δ 15.01 (br. s., 1H), 9.48 (s, 1H), 9.40 (br. s., 1H), 8.52 (s, 1H), 8.36 (br. s., 2H), 8.13-8.28 (m, 2H), 7.88 (d, J = 9.04 Hz, 1H), 7.60 (d, J = 5.27 Hz, 1H), 5.03 (br. s., 1H), 3.28-3.45 (m, 3H), 3.14-3.28 (m, 3H), 2.99-3.12 (m, 3H), 2.87 (t, J = 6.78 Hz, 3H), 2.70 (d, J = 15.82 Hz, 1H), 1.90-2.14 (m, 2H), 1.72 (br. s., 2H), 1.11 (t, J = 6.78 Hz, 3H). | Example 273 |

-continued

| Ex | Compound | Data | SM |
|---|---|---|---|
| 281 | (R)-ethyl 6-(6-(3-ethylureido)-4-(4-(trifluoromethyl)thiazol-2-yl)pyridin-3-yl)-1-(1-(2-(methylsulfonyl)ethyl)piperidin-3-yl)-4-oxo-1,4-dihydroquinoline-3-carboxylic acid | MS (ES) (M + H)$^+$: 693 for C$_{30}$H$_{31}$F$_3$N$_6$O$_5$S$_2$<br>$^1$H NMR (300 MHz, DMSO-d$_6$) δ 14.99 (br. s., 1H), 9.48 (s, 1H), 9.30-9.45 (m, 1H), 8.53 (s, 1H), 8.35 (br. s., 2H), 8.23 (s, 2H), 7.91 (br. s., 1H), 7.55-7.69 (m, 1H), 5.04 (br. s., 1H), 3.21 (dq, J = 6.78, 6.53 Hz, 3H), 3.06 (br. s., 5H), 2.87 (br. s., 2H), 2.72 (br. s., 1H), 2.06 (br. s., 3H), 1.72 (d, J = 7.54 Hz, 2H), 1.11 (t, J = 7.16 Hz, 3H). | Example 272 |
| 282 | (R)-ethyl 6-(6-(3-ethylureido)-4-(4-(trifluoromethyl)thiazol-2-yl)pyridin-3-yl)-1-(1-(((1-methyl-1H-pyrrol-2-yl)methyl)piperidin-3-yl)-4-oxo-1,4-dihydroquinoline-3-carboxylic acid | MS (ES) (M + H)$^+$: 680 for C$_{33}$H$_{32}$F$_3$N$_7$O$_4$S<br>$^1$H NMR (300 MHz, DMSO-d$_6$) δ 15.04 (br. s., 1H), 9.55 (br. s., 2H), 8.50 (s, 1H), 8.34 (br. s., 2H), 8.24 (s, 1H), 8.08 (d, J = 9.04 Hz, 1H), 7.82 (d, J = 8.29 Hz, 1H), 7.66 (br. s., 1H), 6.67 (br. s., 1H), 5.96 (br. s., 1H), 5.86 (br. s., 1H), 5.08 (br. s., 1H), 3.68 (s, 3H), 3.57 (d, J = 13.56 Hz, 1H), 3.43 (d, J = 13.56 Hz, 1H), 3.12-3.25 (m, 2H), 2.92-3.07 (m, 1H), 2.89 (br. s., 1H), 2.38 (br. s., 1H), 1.96 (d, J = 15.82 Hz, 2H), 1.66 (br. s., 2H), 1.19-1.39 (m, 1H), 1.11 (t, J = 7.16 Hz, 3H). | Example 265 |

| Ex | Compound | Data | SM |
|---|---|---|---|
| 283 | (S)-ethyl 6-(6-(3-ethylureido)-4-(4-(trifluoromethyl)thiazol-2-yl)pyridin-3-yl)-1-(1-((1-methyl-1H-pyrrol-2-yl)methyl)piperidin-3-yl)-4-oxo-1,4-dihydroquinoline-3-carboxylic acid | MS (ES) (M + H)$^+$: 680 for C$_{33}$H$_{32}$F$_3$N$_7$O$_4$S $^1$H NMR (300 MHz, DMSO-d$_6$) δ 14.89 (br. s., 1H), 10.60 (br. s., 1H), 9.49 (s, 1H), 8.97 (s, 1H), 8.55 (s, 2H), 8.35 (br. s., 3H), 8.24 (s, 1H), 7.97 (d, J = 9.04 Hz, 1H), 7.62 (br. s., 1H), 6.88 (br. s., 1H), 6.33 (br. s., 1H), 6.04 (br. s., 1H), 4.37 (br. s., 2H), 3.70 (s, 5H), 3.48-3.57 (m, 1H), 3.22 (ddd, 3H), 1.99-2.34 (m, 3H), 1.12 (t, J = 7.16 Hz, 3H). | Example 264 |
| 284 | (S)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydroquinoline-3-carboxylic acid | MS (ES) (M + H)$^+$: 700 for C$_{33}$H$_{36}$F$_3$N$_7$O$_5$S $^1$H NMR (300 MHz, DMSO-d$_6$) δ 15.01 (br. s., 1H), 9.75 (br. s., 1H), 9.48 (s, 1H), 8.52 (s, 1H), 8.35 (br. s., 2H), 8.22 (s, 1H), 8.12 (d, J = 9.04 Hz, 1H), 7.86 (d, J = 8.29 Hz, 1H), 7.61 (br. s., 1H), 5.04 (br. s., 1H), 3.53 (d, J = 4.52 Hz, 4H), 3.06-3.26 (m, 3H), 2.94 (d, J = 9.80 Hz, 1H), 2.66 (br. s., 1H), 2.38 (br. s., 4H), 1.98 (br. s., 2H), 1.65 (br. s., 2H), 1.11 (t, J = 7.16 Hz, 3H), 0.96 (t, J = 6.78 Hz, 1H). | Example 267 |

| Ex | Compound | Data | SM |
|---|---|---|---|
| 285 | (R)-ethyl 6-(6-(3-ethylureido)-4-(4-(trifluoromethyl)thiazol-2-yl)pyridin-3-yl)-1-(1-(2-morpholinoethyl)piperidin-3-yl)-4-oxo-1,4-dihydroquinoline-3-carboxylic acid | MS (ES) (M + H)$^+$: 700 for $C_{33}H_{36}F_3N_7O_5S$<br>$^1$H NMR (300 MHz, DMSO-d$_6$) δ 14.97 (br. s., 1H), 9.74 (br. s., 1H), 9.49 (s, 1H), 8.52 (s, 1H), 8.35 (br. s., 2H), 8.22 (s, 1H), 8.12 (d, J = 9.04 Hz, 1H), 7.86 (d, J = 9.04 Hz, 1H), 7.61 (br. s., 1H), 5.04 (br. s., 1H), 3.53 (br. s., 4H), 3.07-3.27 (m, 3H), 2.94 (d, J = 10.55 Hz, 1H), 2.66 (br. s., 1H), 2.38 (br. s., 4H), 1.97 (br. s., 2H), 1.65 (br. s., 2H), 1.11 (t, J = 7.16 Hz, 3H), 0.96 (t, 1H). | Example 266 |
| 286 | (R)-ethyl 6-(6-(3-ethylureido)-4-(4-(trifluoromethyl)thiazol-2-yl)pyridin-3-yl)-4-oxo-1-(piperidin-3-yl)-1,4-dihydroquinoline-3-carboxylic acid | MS (ES) (M + H)$^+$: 657 for $C_{32}H_{35}F_3N_6O_4S$<br>$^1$H NMR (300 MHz, DMSO-d$_6$) δ 10.17 (br. s., 1H), 9.51 (s, 1H), 8.97 (s, 1H), 8.41-8.59 (m, 2H), 8.29-8.39 (m, 2H), 8.23 (s, 1H), 7.97 (d, J = 9.04 Hz, 1H), 7.62 (br. s., 1H), 6.00 (br. s., 1H), 3.58-3.79 (m, 5H), 3.12-3.28 (m, 5H), 3.01-3.10 (m, 2H), 2.33-2.42 (m, 2H), 2.18-2.27 (m, 2H), 2.08 (d, J = 8.29 Hz, 2H), 1.03-1.26 (m, 6H). | Example 263 |

Examples 287-292

The following compounds were prepared according to the procedure described in Example 276 and purified by a Gilson HPLC on a C18 column using acetonitrile/water/TFA to yield the TFA salts.

| Ex | Compound | Data | SM |
|---|---|---|---|
| 287 | (S)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylic acid trifluoroacetate | MS (ES) (M + H)+: 686 for $C_{33}H_{38}F_3N_7O_4S$<br>1H NMR (300 MHz, DMSO-$d_6$) δ 9.49 (s, 2H), 8.55 (s, 1H), 8.37 (s, 2H), 8.10-8.26 (m, 2H), 7.89 (d, J = 8.29 Hz, 1H), 7.59 (br. s., 1H), 5.07 (br. s., 1H), 3.21 (q, J = 6.78 Hz, 8H), 3.04 (none, 1H), 2.73 (br. s., 3H), 2.08 (br. s., 2H), 1.74 (br. s., 2H), 1.22 (t, J = 7.16 Hz, 6H), 1.12 (t, J = 7.16 Hz, 3H). | Example 275 |
| 288 | (S)-ethyl 1-(1-(2-(diethylamino)ethyl)piperidin-3-yl)-6-(6-(3-ethylureido)-4-(4-(trifluoromethyl)thiazol-2-yl)pyridin-3-yl)-4-oxo-1,4-dihydroquinoline-3-carboxylic acid trifluoroacetate | MS (ES) (M + H)+: 686 for $C_{33}H_{38}F_3N_7O_4S$<br>1H NMR (300 MHz, DMSO-$d_6$) δ 9.49 (s, 2H), 8.55 (s, 1H), 8.37 (s, 2H), 8.23 (s, 1H), 8.17 (d, J = 9.04 Hz, 1H), 7.89 (d, J = 9.04 Hz, 1H), 7.59 (br. s., 1H), 5.07 (br. s., 1H), 3.56 (br. s., 7H), 3.09-3.31 (m, 8H), 2.92-3.11 (m, 1H), 2.73 (br. s., 2H), 2.06 (br. s., 2H), 1.74 (br. s., 1H), 1.22 (t, J = 7.16 Hz, 6H), 1.12 (t, J = 7.16 Hz, 4H). | Example 274 |

| Ex | Compound | Data | SM |
|---|---|---|---|
| 289 | (S)-1-(1-(2,2-dimethyl-3-morpholinopropyl)piperidin-3-yl)-6-(6-(3-ethylureido)-4-(trifluoromethyl)thiazol-2-yl)pyridin-3-yl)-4-oxo-1,4-dihydroquinoline-3-carboxylic acid | MS (ES) (M + H)$^+$: 742 for C$_{36}$H$_{42}$F$_3$N$_7$O$_5$S<br>$^1$H NMR (300 MHz, DMSO-d$_6$) δ 9.51 (br. s., 2H), 8.51 (s, 1H), 8.35 (br. s., 2H), 8.22 (s, 1H), 8.12 (d, J = 9.04 Hz, 1H), 7.83 (d, J = 7.54 Hz, 1H), 7.63 (br. s., 1H), 5.05 (br. s., 1H), 3.50 (br. s., 4H), 3.18-3.25 (m, 1H), 2.94 (br. s., 2H), 2.60 (d, J = 18.84 Hz, 2H), 2.40 (br. s., 4H), 2.08-2.25 (m, 4H), 2.02 (br. s., 1H), 1.88-1.96 (m, 1H), 1.72 (br. s., 2H), 1.22 (s, 2H), 1.11 (t, J = 6.78 Hz, 3H), 0.85 (s, 6H). | Example 268 |
| 290 | (R)-1-(1-(2,2-dimethyl-3-morpholinopropyl)piperidin-3-yl)-6-(6-(3-ethylureido)-4-(trifluoromethyl)thiazol-2-yl)pyridin-3-yl)-4-oxo-1,4-dihydroquinoline-3-carboxylic acid | MS (ES) (M + H)$^+$: 742 for C$_{36}$H$_{42}$F$_3$N$_7$O$_5$S<br>$^1$H NMR (300 MHz, DMSO-d$_6$) δ 9.49 (br. s., 2H), 8.51 (s, 1H), 8.35 (br. s., 2H), 8.22 (s, 1H), 8.11 (d, J = 8.29 Hz, 1H), 7.83 (d, J = 7.54 Hz, 1H), 7.62 (br. s., 1H), 5.04 (br. s., 1H), 3.51 (br. s., 4H), 3.22 (d, J = 6.78 Hz, 2H), 2.94 (br. s., 2H), 2.41 (br. s., 5H), 1.99-2.26 (m, 6H), 1.90 (br. s., 1H), 1.73 (br. s., 2H), 1.11 (t, J = 6.78 Hz, 3H), 0.85 (br. s., 6H). | Example 269 |

-continued

| Ex | Compound | Data | SM |
|---|---|---|---|
| 291 | (S)-6-(6-(3-ethylureido)-4-(4-(trifluoromethyl)thiazol-2-yl)pyridin-3-yl)-1-(1-(2-hydroxyethyl)piperidin-3-yl)-4-oxo-1,4-dihydroquinoline-3-carboxylic acid | MS (ES) (M + H)+: 631 for $C_{29}H_{29}F_3N_6O_5S$<br>1H NMR (300 MHz, DMSO-d6) δ 9.77 (br. s., 1H), 9.47 (s, 1H), 8.51 (s, 1H), 8.35 (d, J = 3.77 Hz, 2H), 8.22 (s, 1H), 8.14 (d, J = 9.80 Hz, 1H), 7.86 (d, J = 7.54 Hz, 1H), 7.60 (br. s., 1H), 5.04 (br. s., 1H), 4.45 (t, J = 4.90 Hz, 1H), 3.62 (q, J = 5.53 Hz, 2H), 3.17-3.25 (m, 2H), 3.05-3.13 (m, 1H), 2.98 (br. s., 1H), 2.72 (br. s., 1H), 1.97 (br. s., 2H), 1.65 (br. s., 2H), 1.11 (t, J = 6.78 Hz, 3H). | Example 270 |
| 292 | (R)-6-(6-(3-ethylureido)-4-(4-(trifluoromethyl)thiazol-2-yl)pyridin-3-yl)-1-(1-(2-hydroxyethyl)piperidin-3-yl)-4-oxo-1,4-dihydroquinoline-3-carboxylic acid | MS (ES) (M + H)+: 631 for $C_{29}H_{29}F_3N_6O_5S$<br>1H NMR (300 MHz, DMSO-d6) δ 15.04 (s, 1H), 9.78 (br. s., 1H), 9.47 (s, 1H), 8.52 (s, 1H), 8.36 (br. s., 2H), 8.23 (s, 1H), 8.16 (br. s., 1H), 7.87 (d, J = 10.55 Hz, 1H), 7.60 (br. s., 1H), 5.04 (br. s., 1H), 4.45 (br. s., 1H), 3.61 (br. s., 2H), 3.18-3.26 (m, 2H), 2.99 (br. s., 2H), 2.72 (br. s., 1H), 1.98 (br. s., 2H), 1.66 (br. s., 2H), 1.11 (t, J = 6.78 Hz, 3H). | Example 271 |

Example 293

(R)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylic acid

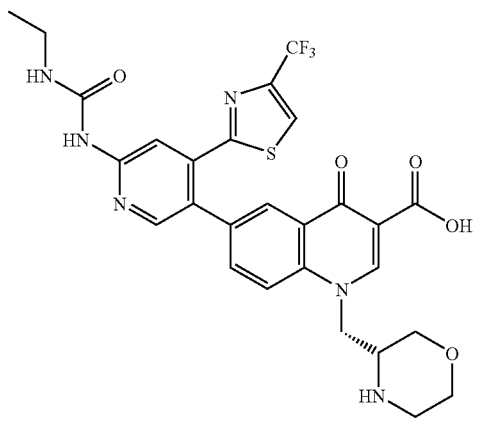

(R)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylate (Example 254, 0.150 g, 0.20 mmol) was suspended in MeOH (6 mL) in a microwave vessel (CEM). THF (3.00 mL) was added. A 2.0 M aq solution of LiOH (0.381 mL, 0.76 mmol) was added. The microwave vessel was heated in the microwave at 100° C. for 15 min After cooling to room temperature solvent was removed in vacuo and residue was taken up in dichloromethane (2 ml) and 4N HCl in dioxane (1 ml) was added. The mixture was stirred at room temperature for 1 h, then diluted with water (3 ml) and neutralized with saturate NaHCO$_3$. The mixture was extracted with DCM three times, and the combined organic layers were dried over Na$_2$SO$_4$ and filtered. The filtrate was concentrated in vacuo, and the residue was purified by flash column chromatography on silica gel using (dichloromethane-methanol) to give (R)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylic acid (0.042 g, 36%).

MS (ES) (M+H)$^+$: 603 for $C_{27}H_{25}F_3N_6O_5S$. NMR:
$^1$H NMR (300 MHz, DMSO-d$_6$) δ 15.06 (br. s., 1H), 9.48 (s, 1H), 8.93 (s, 1H), 8.52 (s, 1H), 8.34 (d, J=17.33 Hz, 2H), 8.10-8.24 (m, 2H), 7.83 (d, J=7.54 Hz, 1H), 7.60 (br. s., 1H), 4.65 (d, J=10.55 Hz, 1H), 4.33 (dd, J=14.69, 8.67 Hz, 1H), 3.86 (d, J=9.04 Hz, 1H), 3.55-3.66 (m, 1H), 3.34-3.44 (m, 1H), 3.21 (t, J=6.40 Hz, 3H), 3.05 (br. s., 1H), 2.68-2.86 (m, 1H), 1.11 (t, J=7.16 Hz, 3H).

Example 294

The following Examples were prepared by the procedure described in Example 293 from the starting materials (SM) indicated.

| Ex | Compound | Data | SM |
|---|---|---|---|
| 294 | (S)-tert-butyl 3-((3-(ethoxycarbonyl)-6-(6-(3-ethylureido)-4-(4-(trifluoromethyl)thiazol-2-yl)pyridin-3-yl)-4-oxoquinolin-1(4H)-yl)methyl)morpholine-4-carboxylic acid | MS (ES) (M + H)$^+$: 603 for $C_{27}H_{25}F_3N_6O_5S$. $^1$H NMR (300 MHz, DMSO-d$_6$) δ 15.07 (br. s., 1H), 9.47 (s, 1H), 8.94 (s, 1H), 8.52 (s, 1H), 8.37 (s, 1H), 8.29-8.35 (m, 2H), 8.13-8.24 (m, 2H), 7.83 (d, J = 7.54 Hz, 1H), 7.60 (br. s., 1H), 4.63 (br. s., 1H), 4.34 (dd, J = 13.56, 9.04 Hz, 1H), 3.86 (d, J = 9.04 Hz, 1H), 3.53-3.73 (m, 2H), 3.37-3.52 (m, 1H), 3.21 (t, J = 6.40 Hz, 3H), 3.05 (br. s., 1H), 2.77 (t, J = 12.43 Hz, 1H), 1.11 (t, J = 7.16 Hz, 3H). | Example 255 |

Another potential method for preparation of the Examples described above is listed below for Example 119.

Example 119

(S)-ethyl 6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylate

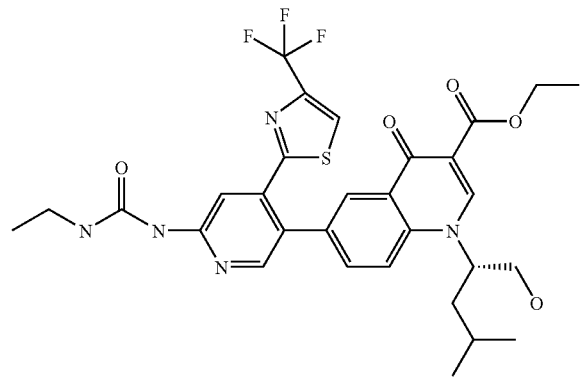

Ethyl 3-(dimethylamino)-2-(5-(6-(3-ethylureido)-4-(4-(trifluoromethyl)thiazol-2-yl)pyridin-3-yl)-2-fluorobenzoyl)acrylate (0.150 g, 0.26 mmol, Intermediate 125) and (S)-2-amino-4-methylpentan-1-ol (0.033 ml, 0.26 mmol) were taken up in THF (2 ml). The mixture was placed in an oil bath and heated to 60° C. for 2 h. Potassium carbonate (0.107 g, 0.78 mmol) was added followed by DMF (1 ml) and the mixture was stirred at 60° C. overnight. Reaction was cooled to room temperature and concentrated in vacuo. The residue was then diluted with water (0.5 mL) and cooled to 0° C. 1N HCl was added drop wise until pH~4. A light yellow solid was collected by filtration, washed with water, and dried in vacuum oven overnight at 50° C. to give (S)-ethyl 6-(6-(3-ethylureido)-4-(4-(trifluoromethyl)thiazol-2-yl)pyridin-3-yl)-1-(1-hydroxy-4-methylpentan-2-yl)-4-oxo-1,4-dihydroquinoline-3-carboxylate (0.072 g, 44%) as a yellow solid.

MS (ES) (M+H)$^+$: 632 for $C_{30}H_{32}F_3N_5O_5S$.

Examples 295-304

The following Examples were prepared according to the general procedure described below.

General Procedure

To a slurry of 6-(3-ethylureido)-4-(4-trifluoromethylthiazol-2-yl)pyridin-3-ylboronic acid (Intermediate 17, 202 mg, 0.56 mmol), the appropriate dihydroquinoline (0.50 mmol) and trans dichlorobis(triphenylphosphine)palladium (II) (33 mg, 0.047 mmol) in 1,4-dioxane (8 mL) was added a solution of potassium carbonate (130 mg, 0.94 mmol) in water (2 mL). The reaction was stirred for 1.5 h at 70° C. The reaction was cooled to room temperature, and ethyl acetate (8 mL) was added to help separate the layers. The water was removed, and the organic phase was washed with water (3 mL). The reaction was then concentrated and the material was either chromatographed on a 4 g Analogix column using 0-10% methanol in dichloromethane or triturated with ethanol for purification.

| Ex | Compound | Data | SM |
|---|---|---|---|
| 295 | ethyl 1-((1-ethylpyrrolidin-3-yl)methyl)-6-(6-(3-ethylureido)-4-(4-(trifluoromethyl)thiazol-2-yl)pyridin-3-yl)-4-oxo-1,4-dihydroquinoline-3-carboxylate | MS (ESP): 643.2 (MH$^+$) for $C_{31}H_{33}F_3N_6O_4S$<br>$^1$H NMR (300 MHz, DMSO-d$_6$): 1.22-1.35 (m, 6H), 1.42 (t, 3H), 3.40-3.52 (m, 2H), 4.09 (q, 2H), 4.41 (q, 2H), 7.27-7.41 (m, 5H), 7.61 (s, 1H), 7.72 (m, 2H), 8.29 (s, 1H), 8.46 (s, 1H), 8.52-8.61 (m, 2H), 9.04 (bs, 1H) | Intermediate 17 and Intermediate 127 |

| Ex | Compound | Data | SM |
|---|---|---|---|
| 296 | ethyl 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylate | MS (ESP): 728.1 (MH+) for $C_{35}H_{40}F_3N_7O_5S$ | Intermediate 17 and Intermediate 128 |
| 297 | ethyl 6-(6-(3-ethylureido)-4-(4-(trifluoromethyl)thiazol-2-yl)pyridin-3-yl)-4-oxo-1-((1-((tetrahydrofuran-2-yl)methyl)pyrrolidin-3-yl)methyl)-1,4-dihydroquinoline-3-carboxylate | MS (ESP): 699.3 (MH+) for $C_{34}H_{37}F_3N_6O_5S$<br>$^1$H NMR (300 MHz, DMSO-d$_6$): 1.11 (t, 3H), 1.28 (t, 3H), 1.69 (m, 1H), 1.75-2.81 (bm, 10H) 3.09-3.26 (m, 2H), 4.19 (q, 2H), 4.36 (d, 2H), 7.52-7.68 (m, 3H), 7.94 (d, 1H), 8.18 (s, 1H), 8.24 (s, 1H), 8.29 (s, 1H), 8.47 (s, 1H), 8.65 (dd, 1H), 9.41 (bs, 1H) | Intermediate 17 and Intermediate 129 |

| Ex | Compound | Data | SM |
|---|---|---|---|
| 298 | ethyl 1-((1-(2-(tert-butyldimethylsilyloxy)ethyl)pyrrolidin-3-yl)methyl)-6-(6-(3-ethylureido)-4-(4-(trifluoromethyl)thiazol-2-yl)pyridin-3-yl)-4-oxo-1,4-dihydroquinoline-3-carboxylate | MS (ESP): 773.4 (M + H$^+$) for C$_{37}$H$_{47}$F$_3$N$_6$O$_5$SSi | Intermediate 17 and Intermediate 130 |
| 299 | ethyl 6-(6-(3-ethylureido)-4-(4-(trifluoromethyl)thiazol-2-yl)pyridin-3-yl)-4-oxo-1-(1-(pyridin-4-ylmethyl)piperidin-3-yl)-1,4-dihydroquinoline-3-carboxylate | MS (ESP): 706.2 (MH$^+$) for C$_{35}$H$_{34}$F$_3$N$_7$O$_4$S | Intermediate 17 and Intermediate 133 |

| Ex | Compound | Data | SM |
|---|---|---|---|
| 300 | Trans-ethyl 1-(1-(tert-butoxycarbonyl)-4-hydroxypyrrolidin-3-yl)-6-(6-(3-ethylureido)-4-(4-(trifluoromethyl)thiazol-2-yl)pyridin-3-yl)-4-oxo-1,4-dihydroquinoline-3-carboxylate | MS (ESP): 717.3 (MH+) for $C_{33}H_{35}F_3N_6O_7S$ | Intermediate 17 and Intermediate 138 |
| 301 | ethyl 6-(6-(3-ethylureido)-4-(4-(trifluoromethyl)thiazol-2-yl)pyridin-3-yl)-1-(1-methylpiperidin-3-yl)-4-oxo-1,4-dihydroquinoline-3-carboxylate | MS (ESP): 629.1 (MH+) for $C_{30}H_{31}F_3N_6O_4S$ | Intermediate 17 and Intermediate 134 |
| 302 | (S)-ethyl 6-(6-(3-ethylureido)-4-(4-(trifluoromethyl)thiazol-2-yl)pyridin-3-yl)-1-(1-methylpyrrolidin-3-yl)-4-oxo-1,4-dihydroquinoline-3-carboxylate | MS (ESP): 615.0 (MH+) for $C_{29}H_{29}F_3N_6O_4S$ | Intermediate 17 and Intermediate 137 |

| Ex | Compound | Data | SM |
|---|---|---|---|
| 303 | ethyl 6-(6-(3-ethylureido)-4-(4-(trifluoromethyl)thiazol-2-yl)pyridin-3-yl)-1-((1-methylpiperidin-3-yl)methyl)-4-oxo-1,4-dihydroquinoline-3-carboxylate | MS (ESP): 643.1 (MH$^+$) for C$_{31}$H$_{33}$F$_3$N$_6$O$_4$S | Intermediate 17 and Intermediate 139 |
| 304 | ethyl 1-((1S,2S)-2-aminocyclohexyl)-6-(6-(3-ethylureido)-4-(4-(trifluoromethyl)thiazol-2-yl)pyridin-3-yl)-4-oxo-1,4-dihydroquinoline-3-carboxylate | MS (ESP): 572.1 (MH$^+$) for C$_{30}$H$_{31}$F$_3$N$_6$O$_4$S | Intermediate 17 and Intermediate 140 |

Examples 305-314

The following Examples were prepared according to the general procedure described below.

General Procedure

The ethyl ester (~110 mg) was dissolved in methanol (3 mL) and tetrahydrofuran (3 mL). To this solution was added 1N sodium hydroxide (3 mL) and the reaction was stirred at room temperature for 3 h. The solution was concentrated to remove the organics. Water (3 mL) was added and the aqueous layer was washed with methyl tert-butyl ether (3 mL). The aqueous phase was filtered then acidified to pH~3 with 1N hydrochloric acid. For compounds Example 308 and Example 310 the aqueous phase was taken to pH 1 and stirred for 3 h to remove the protecting groups then basified back to pH~3 with 1N sodium hydroxide. The acids were extracted with 1:1 ethyl acetate: tetrahydrofuran (3×, 5 mL each). The organic layers were combined, dried over sodium sulfate, and the solvent removed in vacuo.

| Ex | Compound | Data | SM |
|---|---|---|---|
| 305 | 1-((1-ethylpyrrolidin-3-yl)methyl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 615.3 (MH$^+$) for C$_{29}$H$_{29}$F$_3$N$_6$O$_4$S<br>$^1$H NMR (300 MHz, DMSO-d$_6$): 1.12 (t, 3H), 1.21 (t, 3H), 1.60-2.20 (m, 2H), 2.80-3.25 (m, 4H), 3.18-3.25 (m, 2H), 4.73 (brs, 1H), 7.62 (t, 1H), 7.87 (d, 1H), 8.19-8.24 (m, 2H), 8.32 (d, 1H), 8.36 (s, 1H), 8.54 (s, 1H), 9.13 (s, 1H), 9.50 (s, 1H) | Example 295 |
| 306 | 6-(6-(3-ethylureido)-4-(4-(trifluoromethyl)thiazol-2-yl)pyridin-3-yl)-1-((1-(2-morpholinoethyl)pyrrolidin-3-yl)methyl)-4-oxo-1,4-dihydroquinoline-3-carboxylic acid | MS (ESP): 700.2 (MH$^+$) for C$_{33}$H$_{36}$F$_3$N$_7$O$_5$S<br>$^1$H NMR (300 MHz, DMSO-d$_6$): 1.12 (t, 3H), 1.80 (bs, 1H), 2.06 (bs, 1H), 2.38-2.50 (bm, 2H), 2.60-2.70 (bm, 2H), 2.80-3.00 (bm, 1H), 3.18-3.25 (bm, 4H), 3.50-3.62 (bm, 4H), 4.75 (bd, 2H), 7.63 (bt, 1H), 7.89 (dd, 1H), 8.23-8.26 (m, 2H), 8.32 (d, 1H), 8.37 (s, 1H), 8.55 (d, 1H), 9.14 (s, 1H), 9.53 (s, 1H) | Example 296 |

| Ex | Compound | Data | SM |
|---|---|---|---|
| 307 | 6-(6-(3-ethylureido)-4-(4-(trifluoromethyl)thiazol-2-yl)pyridin-3-yl)-4-oxo-1-((1-((tetrahydrofuran-2-yl)methyl)pyrrolidin-3-yl)methyl)-1,4-dihydroquinoline-3-carboxylic acid | MS (ESP): 671.4 (MH+) for $C_{32}H_{33}F_3N_6O_5S$<br>$^1$H NMR (300 MHz, $CD_3OD$): 1.21 (t, 3H), 1.41-1.58 (bm, 1H), 1.62-1.79 (bm, 1H), 1.80-1.92 (bm, 2H), 1.93-2.10 (bm, 2H), 2.62-2.85 (bm, 4H), 2.80-3.00 (bm, 1H), 3.01-3.13 (bm, 1H), 3.31-3.37 (m, 2H), 3.63-3.75 (m, 1H), 3.78-3.89 (bm, 1H), 3.96-4.10 (bm, 1H), 4.53 (bd, 2H), 7.72 (d, 1H), 7.83 (s, 1H), 8.04 (d, 2H), 8.17 (s, 1H), 8.31 (d, 1H), 8.37 (s, 1H), 8.97 (d, 1H) | Example 297 |
| 308 | 6-(6-(3-ethylureido)-4-(4-(trifluoromethyl)thiazol-2-yl)pyridin-3-yl)-1-((1-(2-hydroxyethyl)pyrrolidin-3-yl)methyl)-4-oxo-1,4-dihydroquinoline-3-carboxylic acid hydrochloride | MS (ESP): 631.2 (MH+) for $C_{29}H_{29}F_3N_6O_5S$<br>$^1$H NMR (300 MHz, DMSO-$d_6$): 1.11 (t, 3H), 1.56-1.65 (bs, 1H), 1.83-2.03 (bs, 1H), 2.60-3.20 (bm, 6H), 3.18-3.24 (m, 3H), 3.55-3.62 (m, 2H), 4.65 (bd, 2H), 7.51-7.63 (m, 2H), 7.86 (dd, 1H), 8.20 (d, 1H), 8.22 (s, 2H), 8.32 (d, 1H), 8.38 (s, 1H), 8.54 (s, 1H), 9.11 (s, 1H), 9.52 (s, 1H) | Example 298 |

-continued

| Ex | Compound | Data | SM |
|---|---|---|---|
| 309 | 6-(6-(3-ethylureido)-4-(4-(trifluoromethyl)thiazol-2-yl)pyridin-3-yl)-4-oxo-1-(1-(pyridin-4-ylmethyl)piperidin-3-yl)-1,4-dihydroquinoline-3-carboxylic acid | MS (ESP): 678.3 (MH$^+$) for C$_{33}$H$_{30}$F$_3$N$_7$O$_4$S<br>$^1$H NMR (300 MHz, DMSO-d$_6$): 1.11 (t, 3H), 1.80-2.40 (bm, 4H), 3.21-3.27 (m, 3H), 5.00-5.50 (bs, 1H), 7.63 (t, 1H), 7.90-7.94 (bm, 2H), 8.24 (s, 1H), 8.32-8.34 (m, 2H), 8.54 (d, 1H), 8.74 (bm, 2H), 9.52 (s, 1H) | Example 299 |
| 310 | trans 6-(6-(3-ethylureido)-4-(4-(trifluoromethyl)thiazol-2-yl)pyridin-3-yl)-1-(4-hydroxypyrrolidin-3-yl)-4-oxo-1,4-dihydroquinoline-3-carboxylic acid | MS (ESP): 589.2 (MH$^+$) for C$_{26}$H$_{23}$F$_3$N$_6$O$_5$S<br>$^1$H NMR (300 MHz, DMSO-d$_6$): 1.11 (t, 3H), 3.16-3.22 (m, 3H), 3.58-3.77 (m, 2H), 3.85-4.05 (m, 1H), 4.83 (q, 1H), 5.62 (q, 1H), 7.60-7.71 (m, 1H), 7.96 (dd, 1H), 8.24-8.36 (m, 4H), 8.54 (d, 1H), 9.08 (s, 1H), 9.52-9.56 (m, 2H), 9.79 (bs, 1H) | Example 300 |

| Ex | Compound | Data | SM |
|---|---|---|---|
| 311 | 6-(6-(3-ethylureido)-4-(4-(trifluoromethyl)thiazol-2-yl)pyridin-3-yl)-1-(1-methylpiperidin-3-yl)-4-oxo-1,4-dihydroquinoline-3-carboxylic acid | MS (ESP): 601.2 (MH$^+$) for C$_{28}$H$_{27}$F$_3$N$_6$O$_4$S<br>$^1$H NMR (300 MHz, DMSO-d$_6$): 1.11 (t, 3H), 2.07-2.20 (m, 2H), 2.21-2.48 (m, 2H), 2.79 (d, 3H), 3.02-3.20 (m, 1H), 3.21-3.27 (m, 3H), 3.49-3.71 (m, 2H), 5.51 (t, 1H), 7.66 (t, 1H), 7.97 (dd, 1H), 8.25 (d, 1H), 8.32-8.34 (m, 2H), 8.47 (d, 1H), 8.54 (d, 1H), 8.96 (s, H), 9.52 (s, 1H), 11.28 (bs, 1H) | Example 301 |
| 312 | (S)-6-(6-(3-ethylureido)-4-(4-(trifluoromethyl)thiazol-2-yl)pyridin-3-yl)-1-(1-methylpyrrolidin-3-yl)-4-oxo-1,4-dihydroquinoline-3-carboxylic acid | MS (ESP): 587.1 (MH$^+$) for C$_{22}$H$_{25}$F$_3$N$_6$O$_4$S<br>$^1$H NMR (300 MHz, DMSO-d$_6$): 1.12 (t, 3H), 2.60-3.00 (bm, 2H), 2.94 (bs, 3H), 3.20-4.2 (bm, 4H), 5.6-6.0 (bm, 1H), 7.64 (t, 1H), 7.95 (dd, 1H), 8.10-8.24 (m, 2H), 8.34 (d, 1H), 8.37 (s, 1H), 8.56 (d, 1H), 9.06 (bs, 1H), 9.53 (s, 1H), 10.70-11.15 (bm, 1H) | Example 302 |

| Ex | Compound | Data | SM |
|---|---|---|---|
| 313 | 6-(6-(3-ethylureido)-4-(4-(trifluoromethyl)thiazol-2-yl)pyridin-3-yl)-1-((1-methylpiperidin-3-yl)methyl)-4-oxo-1,4-dihydroquinoline-3-carboxylic acid | MS (ESP): 615.3 (MH$^+$) for C$_{29}$H$_{29}$F$_3$N$_6$O$_4$S<br>$^1$H NMR (300 MHz, DMSO-d$_6$): 1.11 (t, 4H), 1.40-1.90 (bm, 2H), 3.21-3.27 (m, 3H), 4.55 (bm, 4H), 7.64 (t, 1H), 7.86 (bd, 1H), 8.14 (d, 1H), 8.24 (s, 1H), 8.32 (d, 1H), 8.36 (s, 1H), 8.53 (d, 1H), 9.03 (s, 1H), 9.50 (s, 1H) | Example 303 |
| 314 | 1-((1S,2S)-2-aminocyclohexyl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 601.2 (MH$^+$) for C$_{28}$H$_{27}$F$_3$N$_6$O$_4$S<br>$^1$H NMR (300 MHz, CD$_3$OD): 1.20 (t, 3H), 1.58-1.80 (bm, 2H), 1.80-2.03 (bm, 4H), 2.10-2.22 (bm, 1H), 2.49-2.61 (bm, 1H), 3.20-3.40 (bm, 2H), 3.92-4.10 (bm, 1H), 5.00-5.20 (bm, 1H), 7.71 (d, 1H), 7.77 (s, 1H), 8.15 (s, 1H), 8.10-8.30 (bs, 1H), 8.22 (s, 1H), 8.30 (s, 1H), 8.36 (s, 1H), 9.00 (bs, 1H) | Example 304 |

Examples 315-319

The following Examples were prepared according to the general procedure described for Examples 295-304 from the indicated starting materials.

| Ex | Compound | Data | SM |
|---|---|---|---|
| 315 | Ethyl 6-(6-(3-ethylureido)-4-(4-(trifluoromethyl)thiazol-2-yl)pyridin-3-yl)-1-(3-hydroxypropyl)-4-oxo-1,4-dihydroquinoline-3-carboxylate | MS (ESP): 590 (M + 1) for $C_{27}H_{26}F_3N_5O_5S$<br>$^1$H-NMR (DMSO-d$_6$) δ: 1.11 (t, J = 7.20 Hz, 3H); 1.28 (t, J = 7.07 Hz, 3H); 1.87-1.98 (m, 2H); 3.15-3.27 (m, 2H); 3.48 (q, J = 5.56 Hz, 2H); 4.23 (q, J = 6.99 Hz, 2H); 4.45 (t, J = 6.95 Hz, 2H); 4.76 (t, J = 4.67 Hz, 1H); 7.63 (t, J = 5.05 Hz, 1H); 7.71 (dd, J = 8.72, 2.15 Hz, 1H); 7.89 (d, J = 8.84 Hz, 1H); 8.15 (d, J = 2.27 Hz, 1H); 8.23 (s, 1H); 8.32 (s, 1H); 8.48 (s, 1H); 8.69 (s, 1H); 9.44 (s, 1H) | Intermediate 17 and Intermediate 141 |
| 316 | Ethyl 6-(6-(3-ethylureido)-4-(4-(trifluoromethyl)thiazol-2-yl)pyridin-3-yl)-4-oxo-1-(tetrahydro-2H-pyran-4-yl)-1,4-dihydroquinoline-3-carboxylate | MS (ESP): 616.18 (M + 1) for $C_{29}H_{28}F_3N_5O_5S$ | Intermediate 17 and Intermediate 142 |
| 317 | Ethyl 1-cyclohexyl-6-(6-(3-ethylureido)-4-(4-(trifluoromethyl)thiazol-2-yl)pyridin-3-yl)-4-oxo-1,4-dihydroquinoline-3-carboxylate | MS (ESP): 614.17 (M + 1) for $C_{30}H_{30}F_3N_5O_4S$<br>$^1$H-NMR (400 MHz, DMSO-d$_6$) δ: 1.11 (t, J = 7.07 Hz, 3H); 1.21-1.39 (m, 4H); 1.51-1.95 (m, 7H); 1.98-2.13 (m, 2H); 3.14-3.26 (m, 2H); 4.24 (q, J = 6.99 Hz, 2H); 4.59-4.80 (m, 1H); 7.58-7.67 (m, 1H); 7.69 (dd, J = 8.84, 2.27 Hz, 1H); 8.07 (d, J = 9.09 Hz, 1H); 8.19 (d, J = 2.27 Hz, 1H); 8.23 (s, 1H); 8.31 (s, 1H); 8.48 (s, 1H); 8.64 (s, 1H); 9.44 (s, 1H) | Intermediate 17 and Intermediate 143 |

-continued

| Ex | Compound | Data | SM |
|---|---|---|---|
| 318 | Ethyl 6-(6-(3-ethylureido)-4-(4-(trifluoromethyl)thiazol-2-yl)Pyridin-3-yl)-1-(1-methyl piperidin-4-yl)-4-oxo-1,4-dihydro-quinoline-3-carboxylate | MS (ESP): 629.23 (M + 1) for $C_{30}H_{31}F_3N_6O_4S$<br>$^1$H-NMR (400 MHz, DMSO-$d_6$) δ: 1.10 (t, J = 7.20 Hz, 3H); 1.28 (t, J = 7.07 Hz, 3H); 1.92-2.10 (m, 4H); 2.17-2.33 (m, 5H); 2.85-3.00 (m, 2H); 3.13-3.27 (m, 2H); 4.23 (q, J = 7.07 Hz, 2H); 4.62-4.79 (m, 1H); 7.58-7.67 (m, 1H); 7.70 (dd, J = 8.84, 2.27 Hz, 1H); 8.08 (d, J = 9.09 Hz, 1H); 8.18 (d, J = 2.27 Hz, 1H); 8.22 (s, 1H); 8.31 (s, 1H); 8.48 (s, 1H); 8.61 (s, 1H); 9.44 (s, 1H) | Intermediate 17 and Intermediate 144 |
| 319 | Ethyl 1-((5-cyclopropyl-1,2,4-oxadiazol-3-yl)methyl)-6-(6-(3-ethylureido)-4-(4-(trifluoro-methyl)thiazol-2-yl)pyridin-3-yl)-4-oxo-1,4-dihydroquinoline-3-carboxylate | MS (ESP): 654.14 (M + 1) for $C_{30}H_{26}F_3N_7O_5S$<br>$^1$H-NMR (400 MHz, DMSO-$d_6$) δ: 1.00-1.16 (m, 5H); 1.18-1.37 (m, 5H); 2.22-2.43 (m, 1H); 3.21 (dq, J = 6.95, 6.69 Hz, 2H); 4.25 (q, J = 7.07 Hz, 2H); 5.86 (s, 2H); 7.54-7.78 (m, 3H); 8.13 (s, 1H); 8.20 (s, 1H); 8.31 (s, 1H); 8.49 (s, 1H); 8.89 (s, 1H); 9.43 (s, 1H) | Intermediate 17 and Intermediate 145 |

Examples 320-324

The following Examples were prepared according to the procedure described for Example 293 from the indicated starting material.

| Ex | Compound | Data | SM |
|---|---|---|---|
| 320 | 6-(6-(3-Ethylureido)-4-(4-(trifluoromethyl)thiazol-2-yl)pyridin-3-yl)-1-(3-hydroxy-propyl)-4-oxo-1,4-dihydro-quinoline-3-carboxylic acid | MS (ESP): 562 (M + 1) for $C_{25}H_{22}F_3N_5O_5S$<br>$^1$H-NMR (400 MHz, DMSO-d$_6$) δ: 1.11 (t, J = 7.20 Hz, 3H); 1.90-2.04 (m, 2H); 3.13-3.29 (m, J = 6.95, 6.69, 6.57, 6.57 Hz, 2H); 3.48 (q, J = 5.39 Hz, 2H); 4.65 (t, J = 6.82 Hz, 2H); 4.77 (t, J = 4.80 Hz, 1H); 7.60 (br. s., 1H); 7.87 (dd, J = 8.72, 1.89 Hz, 1H); 8.09 (d, J = 8.84 Hz, 1H); 8.22 (s, 1H); 8.31 (d, J = 1.77 Hz, 1H); 8.37 (s, 1H); 8.51 (s, 1H); 9.04 (s, 1H); 9.48 (s, 1H); 15.07 (s, 1H) | Example 315 |
| 321 | 6-(6-(3-Ethylureido)-4-(4-(trifluoromethyl)thiazol-2-yl)-pyridin-3-yl)-4-oxo-1-(tetrahydro-2H-pyran-4-yl)-1,4dihydroquinoline-3-carboxylic acid | MS (ESP): 588.09 (M + 1) for $C_{27}H_{24}F_3N_5O_5S$<br>$^1$H-NMR (400 MHz, DMSO-d$_6$) δ: 1.11 (t, J = 7.20 Hz, 3H); 1.96-2.20 (m, 4H); 3.15-3.27 (m, 2H); 3.60-3.77 (m, 2H); 3.96-4.09 (m, 2H); 5.16 (br. s., 1H); 7.64 (br. s., 1H); 7.83 (br. s., 1H); 8.23 (s, 1H); 8.35 (br. s., 2H); 8.49 (br. s., 1H); 8.90 (br. s., 1H); 9.48 (s, 1H); 15.02 (br. s., 1H) | Example 316 |
| 322 | 1-Cyclohexyl-6-(6-(3-ethylureido)-4-(4-(trifluoro-methyl)thiazol-2-yl)pyridin-3-yl)-4-oxo-1,4-dihydroquinoline-3-carboxylic acid | MS (ESP): 586.36 (M + 1) for $C_{28}H_{26}F_3N_5O_4S$<br>$^1$H-NMR (400 MHz, DMSO-d$_6$) δ: 1.11 (t, J = 7.20 Hz, 3H) 1.27-1.41 (m, 1H) 1.55-1.76 (m, 3H); 1.80-1.97 (m, 4H); 2.02-2.14 (m, 2H); 3.14-3.28 (m, 2H); 4.83-4.99 (m, 1H); 7.62 (d, 1H); 7.86 (d, J = 9.60 Hz, 1H); 8.23 (s, 1H); 8.25-8.31 (m, 1H); 8.33-8.38 (m, 2H); 8.51 (s, 1H); 8.92 (s, 1H); 9.48 (s, 1H) | Example 317 |

| Ex | Compound | Data | SM |
|---|---|---|---|
| 323 | 6-(6-(3-Ethylureido)-4-(4-(trifluoromethyl)thiazol-2-yl)pyridin-3-yl)-1-(1-methyl-piperidin-4-yl)-4-oxo-1,4-dihydro-quinoline-3-carboxylic acid | MS (ESP): 601.22 (M + 1) for $C_{28}H_{27}F_3N_6O_4S$<br>$^1$H-NMR (400 MHz, DMSO-d$_6$) δ: 1.11 (t, J = 7.07 Hz, 3H); 2.00-2.17 (m, 4H); 2.19-2.38 (m, 5H); 2.87-3.05 (m, 2H); 3.14-3.27 (m, 2H); 4.78-4.98 (m, 1H); 7.61 (br. s., 1H); 7.86 (dd, J = 8.97, 1.89 Hz, 1H); 8.23 (s, 1H); 8.28 (d, J = 9.35 Hz, 1H); 8.32-8.40 (m, 2H); 8.51 (s, 1H); 8.85 (s, 1H); 9.48 (s, 1H); 15.01 (br. s., 1H) | Example 318 |
| 324 | 1-((5-Cyclopropyl-1,2,4-oxadiazol-3-yl)methyl)-6-(6-(3-ethylureido)-4-(4-(trifluoromethyl)thiazol-2-yl)pyridin-3-yl)-4-oxo-1,4-dihydroquinoline-3-carboxylic acid | MS (ESP): 626.03 (M+) for $C_{28}H_{22}F_3N_7O_5S$<br>$^1$H-NMR (400 MHz, DMSO-d$_6$) δ: 0.97-1.17 (m, 5H); 1.18-1.33 (m, 2H); 2.18-2.42 (m, J = 8.34, 8.34, 4.42, 4.17 Hz, 1H); 3.11-3.27 (m, 2H); 6.06 (s, 2H) 7.57 (br. s., 1H); 7.77-7.86 (m, 1H); 7.86-7.96 (m, 1H); 8.17-8.26 (m, 1H); 8.24-8.33 (m, 1H); 8.36 (s, 1H); 8.52 (s, 1H); 9.27 (s, 1H); 9.46 (s, 1H); 14.82 (s, 1H) | Example 319 |

Example 325

1-Cyclopropyl-6-(6-(3-ethylureido)-4-(4-(trifluoromethyl)thiazol-2-yl)pyridin-3-yl)-N-(2-methoxyethyl)-4-oxo-1,4-dihydroquinoline-3-carboxamide

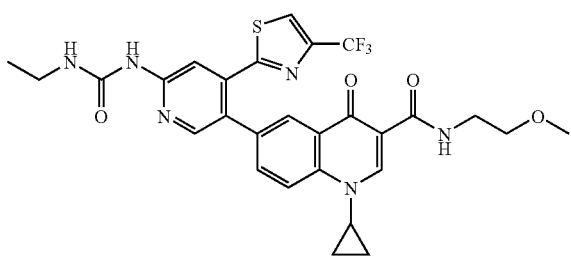

To a solution of 1-cyclopropyl-6-(6-(3-ethylureido)-4-(4-(trifluoromethyl)thiazol-2-yl)pyridin-3-yl)-4-oxo-1,4-dihydroquinoline-3-carboxylic acid (Example 20, 80 mg, 0.15 mmol) in DMF (3 mL) was added HATU (112 mg, 0.29 mmol), DIEA (0.051 mL, 0.29 mmol) followed by 2-methoxyethanamine (22.11 mg, 0.29 mmol). After 1 h stirring, LC-MS shows completion of reaction. DMF removed under vacuum, and the residue was purified by ISCO column using MeOH—CH$_2$Cl$_2$ (0-20%) to give white solid (47.3 mg, 53.5%).

MS (ESP): 601.22 (M+1) for $C_{28}H_{27}F_3N_6O_4S$ $^1$H-NMR (400 MHz, DMSO-d$_6$) δ: 1.11 (t, J=7.07 Hz, 3H); 1.20-1.37 (m, 4H); 3.15-3.25 (m, 2H); 3.40-3.54 (m, 4H); 3.73-3.85 (m, 1H); 7.56-7.67 (m, 1H); 7.80 (dd, J=8.84, 2.27 Hz, 1H); 8.14-8.29 (m, 3H); 8.33 (s, 1H); 8.48 (s, 1H); 8.75 (s, 1H); 9.45-9.99 (m, 1H).

Examples 326-329

The following Examples were prepared according to the procedure described for Example 325 from the indicated starting materials.

| Ex | Compound | Data | SM |
|---|---|---|---|
| 326 | N,1-Dicyclopropyl-6-(6-(3-ethylureido)-4-(4-(trifluoromethyl)thiazol-2-yl)pyridin-3-yl)-4-oxo-1,4-dihydroquinoline-3-carboxamide | MS (ESP): 583.20 (M + 1) for $C_{28}H_{25}F_3N_6O_3S$<br>$^1$H-NMR (400 MHz, DMSO-d$_6$) δ: 0.45-0.58 (m, 2H); 0.65-0.80 (m, 2H); 1.03-1.17 (m, 5H); 1.24-1.38 (m, 2H); 2.78-2.92 (m, 1H); 3.15-3.27 (m, 2H); 3.71-3.87 (m, 1H); 7.62 (br. s., 1H); 7.81 (dd, J = 8.72, 2.15 Hz, 1H); 8.21 (s, 1H); 8.22-8.26 (m, 1H); 8.31 (s, 1H); 8.49 (s, 1H); 8.75 (s, 1H); 9.45 (s, 1H); 9.82 (d, 1H) | Example 20 and cyclopropylamine |
| 327 | 1-Cyclopropyl-N-(1,3-dimethoxy-propan-2-yl)-6-(6-(3-ethylureido)-4-(4-(trifluoromethyl)thiazol-2-yl)pyridin-3-yl)-4-oxo-1,4-dihydroquinoline-3-carboxamide | MS (ESP): 645.27 (M + 1) for $C_{30}H_{31}F_3N_6O_5S$<br>$^1$H-NMR (400 MHz, DMSO-d$_6$) δ: 1.03-1.19 (m, 5H); 1.25-1.39 (m, 2H); 3.15-3.26 (m, 2H); 3.28 (s, 6H); 3.36-3.50 (m, 4H); 3.73-3.86 (m, 1H); 4.22-4.33 (m, 1H); 7.62 (br. s., 1H); 7.80 (dd, J = 8.97, 1.89 Hz, 1H); 8.22 (d, J = 8.84 Hz, 1H); 8.26 (s, 2H); 8.32 (s, 1H); 8.48 (s, 1H); 8.75 (s, 1H); 9.45 (s, 1H); 9.99 (d, J = 8.34 Hz, 1H); | Example 20 and 1,3-dimethoxy-2-aminopropane |
| 328 | 1-Cyclopropyl-N-(2,3-dihydroxy-propyl)-6-(6-(3-ethylureido)-4-(4-(trifluoromethyl)thiazol-2-yl)pyridin-3-yl)-4-oxo-1,4-dihydroquinoline-3-carboxamide | MS (ESP): 617.19 (M + 1) for $C_{28}H_{27}F_3N_6O_5S$<br>$^1$H-NMR (400 MHz, DMSO-d$_6$) δ: 0.97-1.21 (m, 5H); 1.24-1.43 (m, 2H); 3.11-3.47 (m, 5H); 3.47-3.65 (m, 2H); 3.69-3.91 (m, 1H); 4.63 (t, J = 5.68 Hz, 1H); 4.91 (d, 1H); 7.63 (br. s., 1H); 7.80 (dd, J = 8.72, 1.89 Hz, 1H); 8.13-8.29 (m, 3H); 8.32 (s, 1H); 8.48 (s, 1H); 8.75 (s, 1H); 9.45 (s, 1H); 9.93 (br. s., 1H) | Example 20 and 2,3-dihydroxypropanamine |

-continued

| Ex | Compound | Data | SM |
|---|---|---|---|
| 329 | 1-((5-Cyclopropyl-1,2,4-oxadiazol-3-yl)methyl)-6-(6-(3-ethylureido)-4-(4-(trifluoromethyl)thiazol-2-yl)pyridin-3-yl)-N-(2-hydroxyethyl)-4-oxo-1,4-dihydroquinoline-3-carboxamide | MS (ESP): 669.11 (M + 1) for $C_{30}H_{27}F_3N_8O_5S$<br>$^1$H-NMR (400 MHz, DMSO-$d_6$) δ: 0.99-1.15 (m, 5H); 1.17-1.27 (m, J = 7.64, 4.04, 3.76, 3.76 Hz, 2H); 2.26-2.39 (m, 1H); 3.21 (quin, J = 6.76 Hz, 2H); 3.35-3.47 (m, 2H); 3.53 (q, J = 5.39 Hz, 2H); 4.80 (t, J = 5.05 Hz, 1H); 5.97 (s, 2H); 7.60 (br. s., 1H); 7.67-7.76 (m, 1H); 7.80 (d, 1H); 8.18-8.27 (m, 2H); 8.33 (s, 1H); 8.49 (s, 1H); 9.06 (s, 1H); 9.44 (s, 1H); 9.90 (t, 1H) | Example 324 2-hydroxyethanamine |

Examples 330-379

The following Examples were prepared according to the procedure described for Example 33 from the indicated starting materials.

| Ex | Compound | Data | SM |
|---|---|---|---|
| 330 | 1-Ethyl-7-{6-[(ethylcarbamoyl)amino]-4-[4-(trifluoromethyl)-1,3-thiazol-2-yl]pyridin-3-yl}-N-(2-hydroxyethyl)-4-oxo-1,4-dihydroquinoline-3-carboxamide | $^1$H NMR (400 MHz, DMSO-$d_6$): δ 1.08 (t, 3H), 1.15 (t, 3H), 3.21 (q, 2H), 3.41 (t, 2H), 3.56 (t, 2H), 4.41 (q, 2H), 4.80 (s, 1H), 7.42 (d, 1H), 7.61 (s, 1H), 7.86 (s, 1H), 8.22 (s, 1H), 8.34 (m, 2H), 8.48 (s, 1H), 8.88 (s, 1H), 9.46 (s, 1H), 10.06 (s, 1H).<br>LC-MS: m/z 575.2 (M + H) | Example 42 and 3-aminoethanol |

-continued

| Ex | Compound | Data | SM |
|---|---|---|---|
| 331 | 1-Ethyl-7-{6-[(ethylcarbamoyl)amino]-4-[4-(trifluoromethyl)-1,3-thiazol-2-yl]pyridin-3-yl}-N-(3-hydroxypropyl)-4-oxo-1,4-dihydroquinoline-3-carboxamide | $^1$H NMR (400 MHz, DMSO-d$_6$): δ 1.08 (t, 3H), 1.15 (t, 3H), 1.64 (m, 2H), 3.21 (q, 2H), 3.38 (q, 2H), 3.44 (q, 2H), 4.21 (m, 3H), 7.39 (d, 1H), 7.58 (s, 1H), 7.84 (s, 1H), 8.21 (s, 1H), 8.37 (m, 2H), 8.43 (s, 1H), 8.84 (s, 1H), 9.42 (s, 1H), 9.98 (t, 1H). LC-MS: m/z 589.3 (M + H) | Example 42 and 3-amino-propanol |
| 332 | N-[2-(dimethylamino)ethyl]-1-ethyl-7-{6-[(ethylcarbamoyl)amino]-4-[4-(trifluoromethyl)-1,3-thiazol-2-yl]pyridin-3-yl}-4-oxo-1,4-dihydroquinoline-3-carboxamide | $^1$H NMR (400 MHz, DMSO-d$_6$): δ 1.08 (t, 3H), 1.14 (t, 3H), 2.78 (s, 5H), 3.21 (m, 4H), 3.67 (d, 2H), 4.23 (q, 2H), 7.42 (d, 1H), 7.56 (m, 2H), 7.92 (s, 1H), 8.21 (s, 1H), 8.35 (d, 1H), 8.42 (s, 1H), 8.52 (s, 1H), 8.91 (s, 1H), 9.48 (s, 1H), 10.16 (t, 1H). LC-MS: m/z 602.3 (M + H) | Example 42 2-(N,N-dimethyl-amino)-ethanamine |
| 333 | 1-Ethyl-7-{6-[(ethylcarbamoyl)amino]-4-[4-(trifluoromethyl)-1,3-thiazol-2-yl]pyridin-3-yl}-N-[2-(morpholin-4-yl)ethyl]-4-oxo-1,4-dihydroquinoline-3-carboxamide | $^1$H NMR (400 MHz, DMSO-d$_6$): δ 1.08 (t, 3H), 1.14 (t, 3H), 3.18 (m, 4H), 3.61 (m, 6H), 4.02 (m, 2H), 4.22 (q, 2H), 7.42 (d, 1H), 7.58 (s, 1H), 7.86 (s, 1H), 8.21 (s, 1H), 8.38 (m, 2H), 8.51 (s, 1H), 8.91 (s, 1H), 9.42 (s, 1H), 9.44 (s, 1H), 10.18 (s, 1H). LC-MS: m/z 644.2 (M + H) | Example 42 and 2-morpholino-ethylamine |

| Ex | Compound | Data | SM |
|---|---|---|---|
| 334 | 1-Ethyl-7-{6-[(ethylcarbamoyl)amino]-4-[4-(trifluoromethyl)-1,3-thiazol-2-yl]pyridin-3-yl}-N-[2-(4-methylpiperazin-1-yl)ethyl]-4-oxo-1,4-dihydroquinoline-3-carboxamide | $^1$H NMR (400 MHz, DMSO-d$_6$): δ 1.08 (q, 3H), 1.12 (t, 3H), 2.19 (m, 4H), 2.28 (m, 7H), 3.21 (q, 2H), 3.42 (d, 2H), 4.22 (d, 2H), 7.22 (m, 7H), 7.84 (s, 1H), 8.21 (s, 1H), 8.37 (m, 3H), 8.82 (s, 1H), 9.46 (s, 1H), 9.96 (s, 1H).<br>LC-MS: m/z 657.4 (M + H) | Example 42 and 2-(4-methyl-piperazino)-ethanamine |
| 335 | 7-{6-[(ethylcarbamoyl)amino]-4-[4-(trifluoromethyl)-1,3-thiazol-2-yl]pyridin-3-yl}-N-methyl-1-(3-methylbutyl)-4-oxo-1,4-dihydroquinoline-3-carboxamide | $^1$H NMR (400 MHz, DMSO-d$_6$): δ 0.85 (d, 6H), 1.14 (t, 3H), 1.38 (d, 2H), 1.54 (m, 1H), 2.86 (d, 3H), 3.19 (q, 2H), 4.21 (s, 1H), 7.52 (d, 1H), 7.60 (s, 1H), 7.79 (s, 1H), 8.24 (s, 1H), 8.41 (d, 2H), 8.51 (s, 1H), 8.86 (s, 1H), 9.48 (s, 1H), 9.78 (d, 1H).<br>LC-MS: m/z 587.4 (M + H) | Example 63 and methylamine |
| 336 | 7-{6-[(ethylcarbamoyl)amino]-4-[4-(trifluoromethyl)-1,3-thiazol-2-yl]pyridin-3-yl}-N-(2-hydroxyethyl)-1-(3-methylbutyl)-4-oxo-1,4-dihydroquinoline-3-carboxamide | $^1$H NMR (400 MHz, DMSO-d$_6$): δ 0.84 (d, 6H), 1.15 (t, 3H), 1.41 (q, 2H), 1.52 (m, 1H), 3.21 (q, 4H), 3.42 (d, 2H), 3.58 (q, 2H), 4.42 (t, 2H), 4.82 (s, 1H), 7.48 (d, 1H), 7.58 (s, 1H), 7.78 (s, 1H), 8.24 (s, 1H), 8.39 (d, 2H), 8.48 (s, 1H), 8.84 (s, 1H), 9.42 (s, 1H), 10.06 (s, 1H)<br>LC-MS: m/z 617.3 (M + H) | Example 63 and ethanolamine |

| Ex | Compound | Data | SM |
|---|---|---|---|
| 337 | 7-{6-[(ethylcarbamoyl)amino]-4-[4-(trifluoromethyl)-1,3-thiazol-2-yl]pyridin-3-yl}-N-(3-hydroxypropyl)-1-(3-methylbutyl)-4-oxo-1,4-dihydroquinoline-3-carboxamide | $^1$H NMR (400 MHz, DMSO-d$_6$): δ 0.84 (d, 6H), 1.15 (t, 3H), 1.38 (t, 2H), 1.52 (m, 1H), 1.68 (q, 2H), 3.20 (q, 2H), 3.39 (t, 2H), 3.45 (t, 2H), 4.38 (t, 2H), 4.49 (s, 1H), 7.46 (d, 1H), 7.58 (s, 1H), 7.78 (s, 1H), 8.24 (s, 1H), 8.39 (d, 2H), 8.49 (s, 1H), 8.85 (s, 1H), 9.43 (s, 1H), 9.96 (s, 1H)<br>LC-MS: m/z 631.3 (M + H) | Example 63 and 3-amino-propanol |
| 338 | N-[2-(dimethylamino)ethyl]-7-{6-[(ethylcarbamoyl)amino]-4-[4-(trifluoromethyl)-1,3-thiazol-2-yl]pyridin-3-yl}-1-(3-methylbutyl)-4-oxo-1,4-dihydroquinoline-3-carboxamide | $^1$H NMR (400 MHz, DMSO-d$_6$): δ 0.82 (d, 6H), 1.12 (t, 3H), 1.39 (q, 2H), 1.48 (m, 1H), 2.29 (s, 6H), 2.44 (s, 2H), 3.21 (q, 2H), 3.44 (t, 2H), 4.41 (t, 2H), 7.45 (d, 1H), 7.6 (s, 1H), 7.80 (s, 1H), 8.22 (s, 1H), 8.41 (d, 2H), 8.52 (s, 1H), 8.85 (s, 1H), 9.48 (s, 1H), 10.0 (t, 1H)<br>LC-MS: m/z 643.74 (M + H) | Example 63 and 2-(N,N-dimethyl-amino)-ethanamine |
| 339 | 7-{6-[(ethylcarbamoyl)amino]-4-[4-(trifluoromethyl)-1,3-thiazol-2-yl]pyridin-3-yl}-1-(3-methylbutyl)-N-[2-(morpholin-4-yl)ethyl]-4-oxo-1,4-dihydroquinoline-3-carboxamide | $^1$H NMR (400 MHz, DMSO-d$_6$): δ 0.84 (d, 6H), 1.14 (t, 3H), 1.38 (d, 2H), 1.54 (m, 1H), 3.21 (q, 4H), 3.60 (m, 6H), 3.96 (s, 2H), 4.40 (s, 2H), 7.52 (d, 2H), 7.79 (s, 1H), 8.22 (s, 1H), 8.39 (d, 2H), 8.54 (s, 1H), 8.88 (s, 1H), 9.44 (s, 1H), 10.18 (s, 1H).<br>LC-MS: m/z 686.3 (M + H) | Example 63 and 2-morpholino-ethanamine |

| Ex | Compound | Data | SM |
|---|---|---|---|
| 340 | 7-{6-[(ethylcarbamoyl)amino]-4-[4-(trifluoromethyl)-1,3-thiazol-2-yl]pyridin-3-yl}-1-(3-methylbutyl)-N-[2-(4-methylpiperazin-1-yl)ethyl]-4-oxo-1,4-dihydroquinoline-3-carboxamide | $^1$H NMR (400 MHz, DMSO-d$_6$): δ 0.89 (d, 6H), 1.08 (t, 3H), 1.38 (m, 4H), 2.19 (s, 4H), 2.26 (m, 5H), 3.21 (m, 3H), 3.42 (m, 3H), 4.40 (s, 2H), 7.21 (m, 8H), 7.64 (m, 3H), 7.79 (s, 1H), 8.21 (s, 1H), 8.38 (s, 1H), 8.54 (s, 1H), 8.81 (s, 1H), 9.43 (s, 1H) 9.95 (s, 1H). LC-MS: m/z 699.9 (M + H) | Example 63 and 2-(4-methyl-piperazino)-ethanamine |
| 341 | 7-{6-[(ethylcarbamoyl)amino]-4-[4-(trifluoromethyl)-1,3-thiazol-2-yl]pyridin-3-yl}-N-methyl-1-(2-methylpropyl)-4-oxo-1,4-dihydroquinoline-3-carboxamide | $^1$H NMR (400 MHz, DMSO-d$_6$): δ 0.73-0.75 (d, 6H), 1.11 (t, 3H), 1.63 (m, 1H), 2.86-2.89 (m, 3H), 3.19 (t, 2H), 4.21-4.23 (d, 2H), 7.51-7.54 (m, 1H), 7.60 (m, 1H), 7.78 (s, 1H), 8.18 (s, 1H), 8.39 (t, 2H), 8.51 (s, 1H), 8.80 (s, 1H), 9.48 (s, 1H), 9.78-9.79 (m, 1H). LC-MS: m/z 573.3 (M + H) | Example 64 and methylamine |
| 342 | 7-{6-[(ethylcarbamoyl)amino]-4-[4-(trifluoromethyl)-1,3-thiazol-2-yl]pyridin-3-yl}-N-(2-hydroxyethyl)-1-(2-methylpropyl)-4-oxo-1,4-dihydroquinoline-3-carboxamide | $^1$H NMR (400 MHz, DMSO-d$_6$): δ 0.75 (d, 6H), 1.11 (t, 3H), 1.63 (m, 1H), 3.21 (m, 2H), 3.41 (m, 2H), 3.54 (m, 2H), 4.22 (d, 2H), 4.81 (t, 1H), 7.52 (d, 1H), 7.60 (br s, 1H), 7.78 (s, 1H), 8.18 (s, 1H), 8.38-8.40 (m, 2H), 8.52 (s, 1H), 8.81 (s, 1H), 9.48 (s, 1H), 10.05 (t, 1H). LC-MS: m/z 603.3 (M + H) | Example 64 and ethanolamine |

| Ex | Compound | Data | SM |
|---|---|---|---|
| 343 | 7-{6-[(ethylcarbamoyl)amino]-4-[4-(trifluoromethyl)-1,3-thiazol-2-yl]pyridin-3-yl}-N-(3-hydroxypropyl)-1-(2-methylpropyl)-4-oxo-1,4-dihydroquinoline-3-carboxamide | $^1$H NMR (400 MHz, DMSO-d$_6$): δ 0.74-0.75 (m, 6H), 1.11 (t, 3H), 1.65-1.71 (m, 3H), 3.17-3.24 (m, 2H), 3.37-3.49 (m, 2H), 3.49-3.51 (m, 2H), 4.20-4.22 (m, 2H), 4.51 (br s, 1H), 7.34-7.45 (m, 2H), 7.78 (s, 1H), 8.18 (s, 1H), 8.37-8.39 (m, 2H), 8.50 (s, 1H), 8.79 (s, 1H), 9.48 (s, 1H), 9.95 (s, 1H). LC-MS: m/z 617.2 (M + H) | Example 64 and 3-amino-propanol |
| 344 | N-[2-(dimethylamino)ethyl]-7-{6-[(ethylcarbamoyl)amino]-4-[4-(trifluoromethyl)-1,3-thiazol-2-yl]pyridin-3-yl}-1-(2-methylpropyl)-4-oxo-1,4-dihydroquinoline-3-carboxamide | $^1$H NMR (400 MHz, DMSO-d$_6$): δ 0.75 (d, 6H), 1.11 (t, 3H), 1.61 (m, 1H), 2.76 (br s, 6H), 3.19 (m, 4H), 3.68 (m, 2H), 4.22 (d, 2H), 7.51 (m, 2H), 7.82 (s, 1H), 8.11 (s, 1H), 8.31-8.42 (m, 2H), 8.55 (s, 1H), 8.87 (s, 1H), 9.41 (s, 1H), 10.12 (t, 1H). LC-MS: m/z 630.4 (M + H) | Example 64 and 2-(N,N-dimethyl-amino)-ethanamine |
| 345 | 7-{6-[(ethylcarbamoyl)amino]-4-[4-(trifluoromethyl)-1,3-thiazol-2-yl]pyridin-3-yl}-1-(2-methylpropyl)-N-[2-(morpholin-4-yl)ethyl]-4-oxo-1,4-dihydroquinoline-3-carboxamide | $^1$H NMR (400 MHz, DMSO-d$_6$): δ 0.75 (d, 6H), 1.12 (m, 4H), 1.64 (m, 2H), 2.47 (m, 4H), 3.24 (m, 2H), 3.49 (m, 2H), 3.61 (m, 4H), 4.22 (d, 2H), 7.53 (m, 1H), 7.61 (t, 1H), 7.78 (s, 1H), 8.18 (s, 1H), 8.40 (m, 2H), 8.52 (s, 1H), 8.79 (s, 1H), 9.49 (s, 1H), 10.02 (t, 1H). LC-MS: m/z 672.3 (M + H) | Example 64 and 2-morpholino-ethanamine |

-continued

| Ex | Compound | Data | SM |
|---|---|---|---|
| 346 | 7-{6-[(ethylcarbamoyl)amino]-4-[4-(trifluoromethyl)-1,3-thiazol-2-yl]pyridin-3-yl}-N-[2-(4-methylpiperazin-1-yl)ethyl]-1-(2-methylpropyl)-4-oxo-1,4-dihydroquinoline-3-carboxamide | $^1$H NMR (400 MHz, CD$_3$OD): δ 0.91 (d, 6H), 1.12 (t, 3H), 1.82 (m, 1H), 2.18 (s, 3H), 2.65 (m, 8H), 3.19 (q, 2H), 3.59 (q, 2H), 4.18 (d, 2H), 7.54 (d, 1H), 7.69 (s, 1H), 7.81 (s, 1H), 8.22 (s, 1H), 8.40 (s, 1H), 8.51 (d, 1H), 8.79 (s, 1H). LC-MS: m/z 685.3 (M + H) | Example 65 and 2-(4-methyl-piperazino)-ethanamine |
| 347 | 7-{6-[(ethylcarbamoyl)amino]-4-[4-(trifluoromethyl)-1,3-thiazol-2-yl]pyridin-3-yl}-N-methyl-4-oxo-1-propyl-1,4-dihydroquinoline-3-carboxamide | $^1$H NMR (400 MHz, DMSO-d$_6$): δ 0.78 (t, 3H), 1.11 (t, 3H), 1.52 (m, 2H), 2.87 (m, 3H), 3.19 (m, 2H), 4.31 (t, 2H), 7.41 (d, 1H), 7.62 (br s, 1H), 7.82 (s, 1H), 8.21 (s, 1H), 8.36-8.39 (m, 2H), 8.49 (s, 1H), 8.87 (s, 1H), 9.42 (s, 1H), 9.79-9.78 (m, 1H). LC-MS: m/z 559.3 (M + H) | Example 65 and methylamine |
| 348 | 7-{6-[(ethylcarbamoyl)amino]-4-[4-(trifluoromethyl)-1,3-thiazol-2-yl]pyridin-3-yl}-N-(2-hydroxyethyl)-4-oxo-1-propyl-1,4-dihydroquinoline-3-carboxamide | $^1$H NMR (400 MHz, DMSO-d$_6$): δ 0.78 (t, 3H), 1.10 (t, 3H), 1.50-1.55 (m, 2H), 3.19-3.22 (m, 2H), 3.40-3.42 (m, 2H), 3.52-3.53 (m, 2H), 4.37 (m, 2H), 4.81 (br s, 1H), 7.47-7.51 (m, 1H), 7.71 (br s, 1H), 7.84 (s, 1H), 8.22 (m, 1H), 8.36-8.39 (m, 2H), 8.49 (s, 1H), 8.84 (s, 1H), 9.58 (s, 1H), 10.03 (s, 1H). LC-MS: m/z 589.19 (M + H) | Example 65 and ethanolamine |

-continued

| Ex | Compound | Data | SM |
|---|---|---|---|
| 349 | 7-{6-[(ethylcarbamoyl)amino]-4-[4-(trifluoromethyl)-1,3-thiazol-2-yl]pyridin-3-yl}-N-(3-hydroxypropyl)-4-oxo-1-propyl-1,4-dihydroquinoline-3-carboxamide | $^1$H NMR (400 MHz, DMSO-d$_6$): δ 0.78 (t, 3H), 1.11 (t, 3H), 1.50-1.55 (m, 2H), 1.66-1.69 (m, 2H), 3.21 (t, 2H), 3.41 (m, 2H), 3.47-3.51 (m, 2H), 4.37 (t, 2H), 4.55 (t, 1H), 7.47-7.49 (d, 1H), 7.61 (br s, 1H), 7.85 (s, 1H), 8.20 (s, 1H), 8.36-8.39 (m, 2H), 8.49 (s, 1H), 8.83 (s, 1H), 9.48 (s, 1H), 9.91 (t, 1H). LC-MS: m/z 603.3 (M + H) | Example 65 and 3-amino-propanol |
| 350 | N-[2-(dimethylamino)ethyl]-7-{6-[(ethylcarbamoyl)amino]-4-[4-(trifluoromethyl)-1,3-thiazol-2-yl]pyridin-3-yl}-4-oxo-1-propyl-1,4-dihydroquinoline-3-carboxamide | $^1$H NMR (400 MHz, DMSO-d$_6$): δ 0.782 (t, 3H), 1.09 (t, 3H), 1.49-1.55 (m, 2H), 2.20 (s, 6H), 2.41 (t, 2H), 3.18-3.24 (m, 2H), 3.42-3.45 (m, 2H), 4.37 (t, 2H), 7.31 (m, 1H), 7.61 (m, 1H), 7.84 (s, 1H), 8.21 (s, 1H), 8.36-8.40 (m, 2H), 8.49 (s, 1H), 8.84 (s, 1H), 9.48 (s, 1H), 9.91 (t, 1H). LC-MS: m/z 616 (M + H) | Example 65 and 2-(N,N-dimethyl-amino)-ethanamine |
| 351 | 7-{6-[(ethylcarbamoyl)amino]-4-[4-(trifluoromethyl)-1,3-thiazol-2-yl]pyridin-3-yl}-N-[2-(morpholin-4-yl)ethyl]-4-oxo-1-propyl-1,4-dihydroquinoline-3-carboxamide | $^1$H NMR (400 MHz, DMSO-d$_6$): δ 0.782 (t, 3H), 1.11 (t, 3H), 1.50-1.55 (m, 2H), 2.43-2.41 (m, 4H), 3.18-3.22 (m, 2H), 3.44-3.49 (m, 3H), 3.59-3.61 (m, 5H), 4.37 (t, 2H), 7.46-7.49 (d, 1H), 7.61 (br s, 1H), 7.85 (s, 1H) 8.20 (s, 1H), 8.36-8.40 (m, 2H), 8.49 (s, 1H), 8.84 (s, 1H), 9.48 (s, 1H), 10.07 (t, 1H). LC-MS: m/z 658.3 (M + H) | Example 65 and 2-morpholino-ethanamine |

| Ex | Compound | Data | SM |
|---|---|---|---|
| 352 | 7-{6-[(Ethylcarbamoyl)amino]-4-[4-(trifluoromethyl)-1,3-thiazol-2-yl]pyridin-3-yl}-N-[2-(4-methylpiperazin-1-yl)ethyl]-4-oxo-1-propyl-1,4-dihydroquinoline-3-carboxamide | $^1$H NMR (400 MHz, CD$_3$OD): δ 0.92 (q, 3H), 1.11 (q, 3H), 1.64 (q, 2H), 2.38 (s, 3H), 2.61 (m, 8H), 3.14 (q, 2H), 3.59 (t, 2H), 4.29 (t, 2H), 7.48 (d, 1H), 7.78 (s, 1H), 7.84 (s, 1H), 8.21 (s, 1H), 8.41 (s, 1H), 8.42 (d, 1H), 8.83 (s, 1H). LC-MS: m/z 671.4 (M + H) | Example 65 and 2-(4-methylpiper-azino)-ethanamine |
| 353 | 1-Benzyl-7-{6-[(ethylcarbamoyl)amino]-4-[4-(trifluoromethyl)-1,3-thiazol-2-yl]pyridin-3-yl}-N-methyl-4-oxo-1,4-dihydroquinoline-3-carboxamide | $^1$H NMR (400 MHz, DMSO-d$_6$): δ 1.10 (t, 3H), 2.88-2.89 (m, 3H), 3.16-3.23 (m, 2H), 5.74 (s, 2H), 7.10-7.08 (m, 2H), 7.19-7.25 (m, 3H), 7.40-7.42 (m, 1H), 7.51-7.53 (br s, 1H), 7.79 (s, 1H), 8.16 (s, 1H), 8.22 (s, 1H), 8.32 (s, 1H), 8.37-8.38 (s, 1H), 9.07 (s, 1H). 9.42 (s, 1H). 9.75-9.77 (m, 1H). LC-MS: m/z 607.3 (M + H) | Example 66 and methylamine |
| 354 | 1-Benzyl-7-{6-[(ethylcarbamoyl)amino]-4-[4-(trifluoromethyl)-1,3-thiazol-2-yl]pyridin-3-yl}-N-(2-hydroxyethyl)-4-oxo-1,4-dihydroquinoline-3-carboxamide | $^1$H NMR (400 MHz, DMSO-d$_6$): δ 1.1 (t, 3H), 3.16-3.23 (m, 2H), 3.41-3.45 (m, 2H), 3.53-3.57 (m, 2H), 5.74 (s, 1H), 7.08-7.10 (m, 2H), 7.19-7.42 (m, 1H), 7.51-7.25 (m, 3H), 7.40-7.42 (m, 1H), 7.53 (br s, 1H), 7.79 (s, 1H), 8.17 (s, 1H), 8.22 (s, 1H), 8.32 (s, 1H). 8.36-8.38 (s, 1H). 9.07 (s, 1H). 9.42 (s, 1H). 10.02 (m, 1H). LC-MS: m/z 637.3 (M + H) | Example 66 and ethanolamine |

| Ex | Compound | Data | SM |
|---|---|---|---|
| 355 | 1-Benzyl-7-{6-[(ethylcarbamoyl)amino]-4-[4-(trifluoromethyl)-1,3-thiazol-2-yl]pyridin-3-yl}-N-(3-hydroxypropyl)-4-oxo-1,4-dihydroquinoline-3-carboxamide | $^1$H NMR (400 MHz, DMSO-d$_6$): δ 1.08-1.11 (t, 3H), 1.66-1.73 (m, 2H), 3.16-3.23 (m, 2H), 3.39-3.51 (m, 2H), 3.48-3.53 (m, 2H), 4.54 (t, 1H), 7.08-7.10 (m, 2H), 7.19-7.25 (m, 3H), 7.40-7.42 (m, 1H), 7.51-7.53 (br s, 1H), 7.79 (s, 1H), 8.17 (s, 1H), 8.23 (s, 1H), 8.32-8.38 (m, 2H). 9.06 (s, 1H). 9.42 (s, 1H). 9.94 (t, 1H). LC-MS: m/z 651.3 (M + H) | Example 66 and 3-amino-propanol |
| 356 | 1-Benzyl-N-[2-(dimethylamino)ethyl]-7-{6-[(ethylcarbamoyl)amino]-4-[4-(trifluoromethyl)-1,3-thiazol-2-yl]pyridin-3-yl}-4-oxo-1,4-dihydroquinoline-3-carboxamide | $^1$H NMR (400 MHz, DMSO-d$_6$): δ 1.09 (t, 3H), 3.21 (s, 6H), 2.43 (m, 2H), 3.16-3.29 (m, 2H), 3.43-3.47 (m, 2H), 5.73 (s, 2H), 7.08-7.10 (m, 2H), 7.19-7.25 (m, 3H), 7.40-7.42 (m, 1H), 7.52 (br s, 1H), 7.78 (s, 1H), 8.17 (s, 1H), 8.22 (s, 1H), 8.33-8.38 (m, 2H). 9.65 (s, 1H). 9.42 (s, 1H). 9.95 (m, 1H). LC-MS: m/z 664.4 (M + H) | Example 66 and 2-(N,N-dimethyl-amino)-ethanamine |
| 357 | 1-Benzyl-7-{6-[(ethylcarbamoyl)amino]-4-[4-(trifluoromethyl)-1,3-thiazol-2-yl]pyridin-3-yl}-N-[2-(morpholin-4-yl)ethyl]-4-oxo-1,4-dihydroquinoline-3-carboxamide | $^1$H NMR (400 MHz, DMSO-d$_6$): δ 1.10 (t, 3H), 2.32 (m, 4H), 3.20 (q, 2H), 3.48 (d, 2H), 3.61 (s, 4H), 5.74 (s, 2H), 7.10 (d, 2H), 7.21 (d, 3H), 7.39 (d, 1H), 7.41 (s, 1H), 7.79 (s, 1H), 8.17 (d, 2H), 8.32 (m, 2H), 9.06 (s, 1H), 9.43 (s, 1H), 9.99 (s, 1H). LC-MS: m/z 706.3 (M + H) | Example 66 and 2-morpholino-ethanamine |

| Ex | Compound | Data | SM |
|---|---|---|---|
| 358 | 1-Benzyl-7-{6-[(ethylcarbamoyl)amino]-4-[4-(trifluoromethyl)-1,3-thiazol-2-yl]pyridin-3-yl}-N-[2-(4-methylpiperazin-1-yl)ethyl]-4-oxo-1,4-dihydroquinoline-3-carboxamide | $^1$H NMR (400 MHz, DMSO-$d_6$): δ 1.09 (t, 3H), 2.16 (s, 3H), 2.31-2.34 (m, 4H), 3.16-3.23 (m, 2H), 3.44-3.48 (q, 2H), 5.73 (s, 2H), 7.08-7.10 (m, 2H), 7.19-7.24 (m, 2H), 7.39-7.41 (d, 1H), 7.53 (m, 1H), 7.79 (s, 1H), 8.17 (s, 1H), 8.23 (s, 1H), 8.31 (s, 1H), 8.37-8.39 (d, 1H), 9.05 (s, 1H), 9.43 (s, 1H), 9.94-9.96 (t, 1H). LC-MS: m/z 719.89 (M + H) | Example 66 and 2-(4-methylpiperazino)-ethanamine |
| 359 | 7-{6-[(ethylcarbamoyl)amino]-4-[4-(trifluoromethyl)-1,3-thiazol-2-yl]pyridin-3-yl}-N-(3-hydroxypropyl)-4-oxo-1-(pyridin-3-ylmethyl)-1,4-dihydroquinoline-3-carboxamide | $^1$H NMR (400 MHz, DMSO-$d_6$): δ 1.10 (t, 3H), 1.70 (m, 2H), 3.21 (q, 2H), 3.40 (m, 5H), 4.57 (s, 1H), 5.80 (s, 2H), 7.22 (m, 1H), 7.42 (d, 2H), 7.58 (s, 1H), 7.84 (s, 1H), 8.19 (d, 2H), 8.33 (m, 4H), 9.12 (s, 1H), 9.46 (s, 1H), 9.93 (t, 1H). LC-MS: m/z 652 (M + H) | Example 67 and 3-amino-propanol |
| 360 | N-[2-(dimethylamino)ethyl]-7-{6-[(ethylcarbamoyl)amino]-4-[4-(trifluoromethyl)-1,3-thiazol-2-yl]pyridin-3-yl}-4-oxo-1-(pyridin-3-ylmethyl)-1,4-dihydroquinoline-3-carboxamide | $^1$H NMR (400 MHz, CD$_3$OD): δ 1.19 (t, 3H), 2.69 (s, 6H), 3.73 (q, 2H), 5.73 (s, 2H), 7.31 (m, 9H), 7.69 (s, 1H), 7.86 (s, 1H), 8.04 (s, 1H), 8.20 (s, 1H), 8.40 (m, 2H), 8.48 (d, 1H), 9.08 (s, 1H). LC-MS: m/z 665.4 (M + H) | Example 67 and 2-(N,N-dimethyl-amino)-ethanamine |

| Ex | Compound | Data | SM |
|---|---|---|---|
| 361 | 7-{6-[(ethylcarbamoyl)amino]-4-[4-(trifluoromethyl)-1,3-thiazol-2-yl]pyridin-3-yl}-N-[2-(morpholin-4-yl)ethyl]-4-oxo-1-(pyridin-3-ylmethyl)-1,4-dihydroquinoline-3-carboxamide | $^1$H NMR (400 MHz, DMSO-$d_6$): δ 1.08 (t, 3H), 2.33 (m, 6H), 3.18 (q, 2H), 3.48 (d, 2H), 3.61 (s, 4H), 5.80 (s, 2H), 7.22 (m, 2H), 7.36 (m, 4H), 7.56 (s, 2H), 7.84 (s, 1H), 8.19 (d, 2H), 8.40 (m, 4H), 9.11 (s, 1H), 9.45 (s, 1H), 9.99 (s, 1H). LC-MS: m/z 707.4 (M + H) | Example 67 and 2-morpholino-ethanamine |
| 362 | 7-{6-[(ethylcarbamoyl)amino]-4-[4-(trifluoromethyl)-1,3-thiazol-2-yl]pyridin-3-yl}-N-[2-(4-methylpiperazin-1-yl)ethyl]-4-oxo-1-(pyridin-3-ylmethyl)-1,4-dihydroquinoline-3-carboxamide | $^1$H NMR (400 MHz, CD$_3$OD): δ 1.19 (t, 3H), 2.46 (s, 2H), 2.68 (m, 4H), 2.76 (m, 4H), 3.60 (q, 2H), 5.74 (s, 2H), 7.30 (m, 8H), 7.69 (s, 1H), 7.86 (s, 1H), 8.03 (s, 1H), 8.20 (s, 1H), 8.41 (s, 2H), 8.49 (d, 1H), 9.08 (s, 1H). LC-MS: m/z 720.45 (M + H) | Example 67 and 2-(4-methylpiper-azino)-ethnamine |
| 363 | 7-{6-[(Ethylcarbamoyl)amino]-4-[4-(trifluoromethyl)-1,3-thiazol-2-yl]pyridin-3-yl}-1-(2-hydroxyethyl)-N-methyl-4-oxo-1,4-dihydroquinoline-3-carboxamide | $^1$H NMR (400 MHz, DMSO-$d_6$): δ 1.09-1.12 (t, 3H), 2.86-2.87 (m, 3H), 3.19-3.22 (m, 2H), 3.59-3.60 (m, 2H), 4.49 (br s, 1H), 4.95-4.98 (t, 1H), 7.39-7.41 (d, 1H), 7.63 (br s, 1H), 7.98 (s, 1H), 8.24 (s, 1H), 8.34-8.37 (m, 2H), 8.48 (s, 1H), 8.87 (s, 1H), 9.48 (s, 1H), 9.79-9.80 (d, 1H). LC-MS: m/z 561.3 (M + H) | Example 68 and methylamine |

-continued

| Ex | Compound | Data | SM |
|---|---|---|---|
| 364 | 7-{6-[(Ethylcarbamoyl)amino]-4-[4-(trifluoromethyl)-1,3-thiazol-2-yl]pyridin-3-yl}-N,1-bis(2-hydroxyethyl)-4-oxo-1,4-dihydroquinoline-3-carboxamide | $^1$H NMR (400 MHz, DMSO-d$_6$): δ 1.11 (t, 3H), 3.19-3.22 (m, 2H), 3.40-3.42 (m, 2H), 3.52-3.60 (m, 4H), 4.83 (t, 1H), 4.97 (t, 1H), 7.40-7.42 (d, 1H), 7.6 (br s, 1H), 7.97 (s, 1H), 8.24 (s, 1H), 8.33-8.38 (m, 2H). 8.4 (s, 1H). 8.78 (s, 1H), 9.48 (s, 1H). 10.06 (s, 1H).<br>LC-MS: m/z 591.3 (M + H) | Example 68 and ethanolamine |
| 365 | 7-{6-[(ethylcarbamoyl)amino]-4-[4-(trifluoromethyl)-1,3-thiazol-2-yl]pyridin-3-yl}-1-(2-hydroxyethyl)-N-(3-hydroxypropyl)-4-oxo-1,4-dihydroquinoline-3-carboxamide | $^1$H NMR (400 MHz, DMSO-d$_6$): δ 1.12 (t, 3H), 1.7 (m, 2H), 3.21-3.22 (m, 2H), 3.40-3.42 (m, 2H), 3.49-3.52 (m, 2H), 3.6 (br s, 2H), 4.49 (br s, 2H), 4.54-4.57 (t, 1H), 4.9 (t, 1H), 7.4-7.42 (d, 1H). 7.6 (br s, 1H). 7.9 (s, 1H), 8.24 (s, 1H). 8.33-8.37 (m, 2H) 8.48 (s, 1H), 8.78 (s, 1H), 9.48 (s, 1H), 9.98 (t, 1H).<br>LC-MS: m/z 605.2 (M + H) | Example 68 and 3-amino-propanol |
| 366 | N-[2-(dimethylamino)ethyl]-7-{6-[(ethylcarbamoyl)amino]-4-[4-(trifluoromethyl)-1,3-thiazol-2-yl]pyridin-3-yl}-1-(2-hydroxyethyl)-4-oxo-1,4-dihydroquinoline-3-carboxamide | $^1$H NMR (400 MHz, DMSO-d$_6$): δ 1.10 (t, 3H), 2.67-2.73 (m, 6H), 3.21 (m, 4H), 3.60-3.66 (m, 4H), 4.50 (s, 1H), 4.98 (t, 1H), 7.41-7.43 (m, 1H), 7.59 (br s, 2H), 7.99 (s, 1H), 8.24 (s, 1H), 8.34-8.38 (m, 1H), 8.50 (s, 1H), 8.79 (s, 1H), 9.49 (s, 1H), 10.12 (br s, 1H).<br>LC-MS: m/z 618.2 (M + H) | Example 68 and 2-(N,N-dimethyl-amino)-ethanamine |

-continued

| Ex | Compound | Data | SM |
|---|---|---|---|
| 367 | 7-{6-[(ethylcarbamoyl)amino]-4-[4-(trifluoromethyl)-1,3-thiazol-2-yl]pyridin-3-yl}-1-(2-hydroxyethyl)-N-[2-(morpholin-4-yl)ethyl]-4-oxo-1,4-dihydroquinoline-3-carboxamide | $^1$H NMR (400 MHz, DMSO-d$_6$): δ 1.11 (br s, 3H), 2.43 (m, 4H), 3.21 (br s, 3H), 3.46-3.60 (m, 9H), 7.39-7.41 (s, 1H), 7.61 (br s, 1H), 7.91 (s, 1H), 8.24 (s, 1H), 8.34-8.37 (m, 3H), 8.77 (s, 1H), 9.48 (s, 1H), 10.11 (br s, 1H). LC-MS: m/z 660.2 (M + H) | Example 68 and 2-morpholino-ethanamine |
| 368 | 7-{6-[(Ethylcarbamoyl)amino]-4-[4-(trifluoromethyl)-1,3-thiazol-2-yl]pyridin-3-yl}-1-(2-hydroxyethyl)-N-[2-(4-methylpiperazin-1-yl)ethyl]-4-oxo-1,4-dihydroquinoline-3-carboxamide | $^1$H NMR (400 MHz, CD$_3$OD): δ 1.21 (t, 3H), 2.45 (s, 3H), 2.67 (m, 8H), 3.59 (s, 2H), 3.79 (s, 2H), 4.49 (s, 2H), 7.43 (d, 1H), 7.88 (s, 2H), 8.16 (s, 1H), 8.41 (m, 2H), 8.86 (s, 1H). LC-MS: m/z 673.3 (M + H) | Example 68 and 2-(4-methylpiper-azino)-ethanamine |
| 369 | 7-{6-[(Ethylcarbamoyl)amino]-4-[4-(trifluoromethyl)-1,3-thiazol-2-yl]pyridin-3-yl}-1-(2-methoxyethyl)-N-methyl-4-oxo-1,4-dihydroquinoline-3-carboxamide | $^1$H NMR (400 MHz, DMSO-d$_6$): δ 1.12 (t, 3H), 2.83 (s, 3H), 3.18 (m, 5H), 3.46 (s, 2H), 4.59 (s, 2H), 7.41 (d, 1H), 7.58 (s, 1H), 7.95 (s, 1H), 8.22 (s, 1H), 8.34 (d, 2H), 8.48 (s, 1H), 8.78 (s, 1H), 9.42 (s, 1H), 9.76 (s, 1H). LC-MS: m/z 575.3 (M + H) | Example 69 and methylamine |

-continued

| Ex | Compound | Data | SM |
|---|---|---|---|
| 370 | 7-{6-[(Ethylcarbamoyl)amino]-4-[4-(trifluoromethyl)-1,3-thiazol-2-yl]pyridin-3-yl}-N-(2-hydroxyethyl)-1-(2-methoxyethyl)-4-oxo-1,4-dihydroquinoline-3-carboxamide 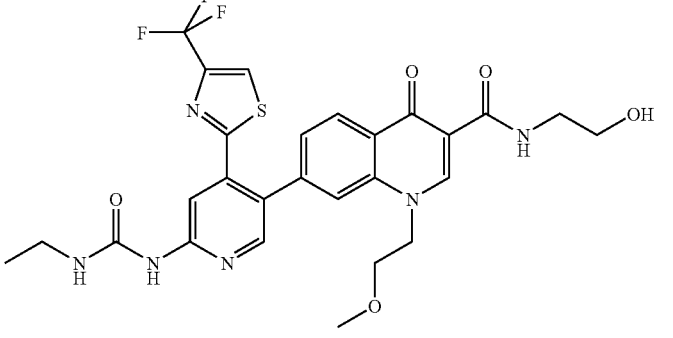 | $^1$H NMR (400 MHz, DMSO-d$_6$): δ 1.12 (t, 3H), 3.18 (s, 3H), 3.19 (m, 2H), 5.45 (m, 6H), 4.58 (s, 2H), 4.69 (s, 1H), 7.41 (d, 1H), 7.56 (s, 1H), 7.91 (s, 1H), 8.21 (s, 1H), 8.38 (m, 2H), 8.44 (s, 1H), 8.79 (s, 1H), 9.39 (s, 1H), 9.99 (s, 1H).<br>LC-MS: m/z 605.3 (M + H) | Example 69 and ethanolamine |
| 371 | 7-{6-[(Ethylcarbamoyl)amino]-4-[4-(trifluoromethyl)-1,3-thiazol-2-yl]pyridin-3-yl}-N-(3-hydroxypropyl)-1-(2-methoxyethyl)-4-oxo-1,4-dihydroquinoline-3-carboxamide | $^1$H NMR (400 MHz, DMSO-d$_6$): δ 1.11 (t, 3H), 1.65 (s, 2H), 3.18 (s, 3H), 3.39 (m, 6H), 4.22 (s, 2H), 4.58 (s, 1H), 7.38 (m, 2H), 7.92 (s, 1H), 8.22 (s, 1H), 8.38 (m, 3H), 8.78 (s, 1H), 9.38 (s, 1H), 9.98 (s, 1H).<br>LC-MS: m/z 619.3 (M + H) | Example 69 and 3-amino-propanol |
| 372 | N-[2-(dimethylamino)ethyl]-7-{6-[(ethylcarbamoyl)amino]-4-[4-(trifluoromethyl)-1,3-thiazol-2-yl]pyridin-3-yl}-1-(2-methoxyethyl)-4-oxo-1,4-dihydroquinoline-3-carboxamide 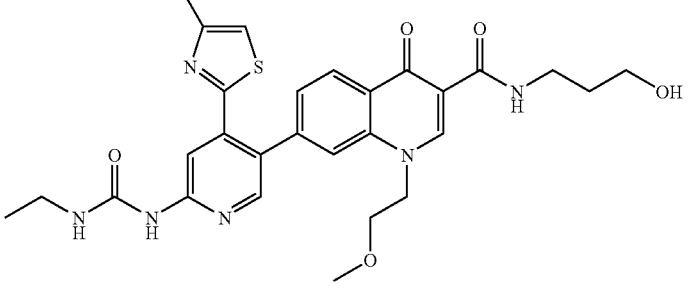 | $^1$H NMR (400 MHz, DMSO-d$_6$): δ 1.11 (t, 3H), 2.45 (s, 6H), 2.96 (s, 2H), 3.18 (s, 3H), 3.21 (q, 2H), 3.46 (s, 2H), 3.62 (s, 2H), 4.58 (s, 2H), 7.38 (m, 2H), 7.94 (s, 1H), 8.22 (s, 1H), 8.35 (m, 2H), 8.45 (s, 1H), 8.78 (s, 1H), 9.40 (s, 1H), 10.02 (s, 1H).<br>LC-MS: m/z 632.3 (M + H) | Example 69 and 2-(N,N-dimethyl-amino)-ethanamine |

-continued

| Ex | Compound | Data | SM |
|---|---|---|---|
| 373 | 7-{6-[(Ethylcarbamoyl)amino]-4-[4-(trifluoromethyl)-1,3-thiazol-2-yl]pyridin-3-yl}-1-(2-methoxyethyl)-N-[2-(4-methylpiperazin-1-yl)ethyl]-4-oxo-1,4-dihydroquinoline-3-carboxamide | $^1$H NMR (400 MHz, CD$_3$OD): δ 1.12 (t, 3H), 2.78 (s, 2H), 2.86 (s, 3H), 3.21 (s, 3H), 3.38 (m, 4H), 3.59 (s, 4H), 4.58 (s, 2H), 7.26 (s, 1H), 7.84 (s, 1H), 8.21 (s, 1H), 8.38 (m, 2H), 8.82 (s, 1H). LC-MS: m/z 687.30 (M + H) | Example 69 and 2-(4-methylpiper-azino)-ethanamine |
| 374 | 1-(Cyclopropylmethyl)-7-{6-[(ethylcarbamoyl)amino]-4-[4-(trifluoromethyl)-1,3-thiazol-2-yl]pyridin-3-yl}-N-methyl-4-oxo-1,4-dihydroquinoline-3-carboxamide | $^1$H NMR (400 MHz, DMSO-d$_6$): δ 0.39 (dd, 4H), 1.02 (m, 4H), 2.82 (d, 3H), 3.21 (q, 2H), 4.38 (d, 2H), 7.41 (m, 3H), 7.61 (s, 2H), 7.99 (s, 1H), 8.21 (s, 1H), 8.36 (m, 3H), 8.88 (s, 1H), 9.48 (s, 1H), 9.79 (s, 1H). LC-MS: m/z 571.4 (M + H) | Example 70 and methylamine |
| 375 | 1-(Cyclopropylmethyl)-7-{6-[(ethylcarbamoyl)amino]-4-[4-(trifluoromethyl)-1,3-thiazol-2-yl]pyridin-3-yl}-N-(2-hydroxyethyl)-4-oxo-1,4-dihydroquinoline-3-carboxamide | $^1$H NMR (400 MHz, DMSO-d$_6$): δ 0.38 (d, 4H), 1.05 (m, 1H), 1.16 (t, 3H), 3.21 (t, 2H), 3.39 (t, 2H), 3.51 (t, 2H), 4.29 (d, 2H), 4.81 (t, 1H), 7.48 (d, 1H), 7.61 (s, 1H), 7.98 (s, 1H), 8.24 (s, 1H), 8.38 (m, 2H), 8.48 (s, 1H), 8.91 (s, 1H), 9.48 (s, 1H), 10.4 (s, 1H). LC-MS: m/z 601.2 (M + H) | Example 70 and ethanolamine |

| Ex | Compound | Data | SM |
|---|---|---|---|
| 376 | 1-(Cyclopropylmethyl)-7-{6-[(ethylcarbamoyl)amino]-4-[4-(trifluoromethyl)-1,3-thiazol-2-yl]pyridin-3-yl}-N-(3-hydroxypropyl)-4-oxo-1,4-dihydroquinoline-3-carboxamide | $^1$H NMR (400 MHz, DMSO-d$_6$): δ 0.38 (d, 4H), 1.04 (m, 4H), 164 (s, 2H), 3.21 (q, 2H), 3.41 (dd, 4H), 4.28 (m, 2H), 4.52 (s, 1H), 7.44 (d, 1H), 7.51 (s, 1H), 7.96 (s, 1H), 8.21 (s, 1H), 8.36 (m, 3H), 8.86 (s, 1H), 9.46 (s, 1H), 9.94 (s, 1H) LC-MS: m/z 615.2 (M + H) | Example 70 and 3-amino-propanol |
| 377 | 1-(Cyclopropylmethyl)-N-[2-(dimethylamino)ethyl]-7-{6-[(ethylcarbamoyl)amino]-4-[4-(trifluoromethyl)-1,3-thiazol-2-yl]pyridin-3-yl}-4-oxo-1,4-dihydroquinoline-3-carboxamide | $^1$H NMR (400 MHz, DMSO-d$_6$): δ 0.38 (d, 4H), 0.94 (s, 1H), 1.14 (t, 3H), 2.68 (s, 2H), 2.96 (d, 3H), 3.18 (m, 4H), 3.46 (m, 10H), 4.18 (d, 2H), 6.98 (s, 2H), 7.38 (d, 1H), 7.61 (s, 1H), 7.94 (d, 1H), 8.22 (s, 1H), 8.26-8.54 (m, 5H), 9.48 (s, 1H). LC-MS: m/z 628.3 (M + H) | Example 70 and 2-(N,N-dimethyl-amino)-ethanamine |
| 378 | 1-(Cyclopropylmethyl)-7-{6-[(ethylcarbamoyl)amino]-4-[4-(trifluoromethyl)-1,3-thiazol-2-yl]pyridin-3-yl}-N-[2-(morpholin-4-yl)ethyl]-4-oxo-1,4-dihydroquinoline-3-carboxamide | $^1$H NMR (400 MHz, DMSO-d$_6$): δ 0.38 (d, 4H), 0.94 (s, 1H), 1.14 (t, 3H), 3.19 (s, 3H), 3.49 (q, 2H), 3.60 (s, 3H), 4.31 (t, 2H), 7.43 (d, 1H), 7.58 (s, 1H), 7.98 (s, 1H), 8.21 (s, 1H), 8.38 (m, 2H), 8.48 (s, 1H), 8.90 (s, 1H), 9.48 (s, 1H), 10.06 (s, 1H). LC-MS: m/z 670.2 (M + H) | Example 70 and 2-morpholino-ethanamine |

| Ex | Compound | Data | SM |
|---|---|---|---|
| 379 | 1-(Cyclopropylmethyl)-7-{6-[(ethylcarbamoyl)amino]-4-[4-(trifluoromethyl)-1,3-thiazol-2-yl]pyridin-3-yl}-N-[2-(4-methylpiperazin-1-yl)ethyl]-4-oxo-1,4-dihydroquinoline-3-carboxamide 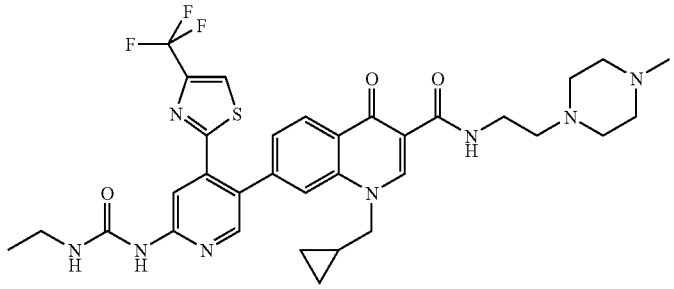 | $^1$H NMR (400 MHz, DMSO-d$_6$): δ 0.37-0.43 (m, 4H), 1.01 (m, 1H), 1.11 (t, 3H), 2.24-2.33 (m, 4H), 3.18-3.24 (m, 3H), 3.43-3.36 (m, 2H), 4.30-4.32 (d, 2H), 7.46-7.48 (d, 1H), 7.61 (br s, 1H), 7.97 (s, 1H), 8.21 (s, 1H), 8.36-8.48 (m, 3H), 8.88 (s, 1H), 9.49 (s, 1H), 9.97-9.99 (t, 1H). | Example 70 and 2-(4-methylpiperazino)-ethanamine |

Intermediate 1

Methyl 5-bromo-2-(3-ethylureido)isonicotinate

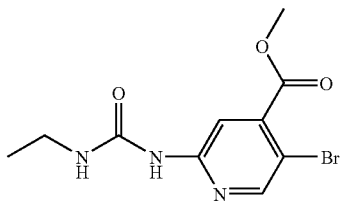

A solution of methyl 2-amino-5-bromoisonicotinate (50 g, 216.5 mmol) in chloroform (500 mL) was placed into a sealed tube. Ethyl isocyanate (51 mL, 649.4 mmol) was then added in two parts over the course of 6 hours. The sealed tube was insulated and heated at 40° C. for 3 d. The reaction mixture was then cooled to room temperature, concentrated under reduced pressure, and extracted with ethyl acetate (3 L) and water (1 L). The ethyl acetate layer was then dried with sodium sulfate, filtered, and concentrated under reduced pressure to yield 68.4 g of a pale yellow solid (96%).

MS (ESP): 302 (M+H$^+$) for C$_{10}$H$_{12}$BrN$_3$O$_3$ $^1$H NMR (CDCl$_3$): δ 1.22 (t, 3H), 3.41 (q, 2H), 7.22 (s, 1H), 7.30 (s, 1H), 8.38 (s, 1H), 8.70 (s, 1H), 9.42 (s, 1H)

Intermediate 2

5-Bromo-2-(3-ethylureido)isonicotinamide

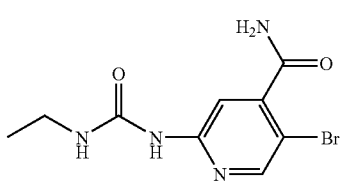

A solution of methyl 5-bromo-2-(3-ethylureido)isonicotinate (Intermediate 1, 56.22 g, 186.0 mmol) in 7N ammonia in methanol (1 L) was allowed to stir at room temperature in a sealed flask for 1½ d. The precipitate that formed was collected by filtration, rinsed with acetonitrile (500 mL), and then dried on the high vacuum pump overnight, yielding 50.8 g of a solid (95.1%).

MS (ESP): 287 (M+H$^+$) for C$_9$H$_{11}$BrN$_4$O$_2$ $^1$H NMR (DMSO-d$_6$): δ 1.1 (t, 3H), 3.18 (q, 2H), 7.40 (s, 1H), 7.60 (s, 1H), 7.80 (s, 1H), 8.1 (s, 1H), 8.38 (s, 1H), 9.39 (s, 1H)

Intermediate 3

5-Bromo-2-(3-ethylureido)pyridine-4-carbothioamide

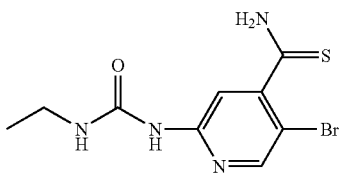

A solution of 5-bromo-2-(3-ethylureido)isonicotinamide (Intermediate 2, 52.17 g, 181.73 mmol), Lawesson's Reagent (73.50 g, 181.73 mmol), and tetrahydrofuran (840 mL) was prepared and stirred with heating at reflux overnight. After approximately 12 h, it was confirmed by LCMS that the reaction had gone to completion; therefore, stirring was stopped and a bright yellow precipitate was allowed to settle to ease filtration. The precipitate was then filtered and subsequently washed with 500 mL of additional tetrahydrofuran. The solid was then dried in the vacuum oven at 50° C. for 30 min, yielding 51 g of a bright yellow solid (92.5%).

MS (ESP): 304 (M+H$^+$) for C$_9$H$_{11}$BrN$_4$OS $^1$H NMR (DMSO-d$_6$): δ 1.1 (t, 3H), 3.18 (q, 2H), 7.38 (s, 1H), 7.50 (s, 1H), 8.28 (s, 1H), 9.25 (s, 1H), 9.80 (s, 1H), 10.28 (s, 1H)

Intermediate 4

Diethyl 2-((4-iodophenylamino)methylene)malonate

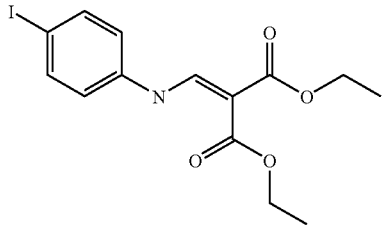

A mixture of ethoxymethylene malonic acid diethyl ester (20.1 mL, 0.10 mol) and 4-iodoaniline (22 g, 0.10 mole) in toluene (300 ml) was heated to reflux for 1 h. After this period of time, solvents were removed under vacuum, and the crude material was precipitated in methyl tert-butyl ether and the resulting white solid was filtered, and dried under vacuum to give 30 g product.

MS (ESP): 390 (M+H$^+$) for C$_{14}$H$_{16}$INO$_4$

Intermediate 5

Ethyl 6-iodo-4-oxo-1,4-dihydroquinoline-3-carboxylate

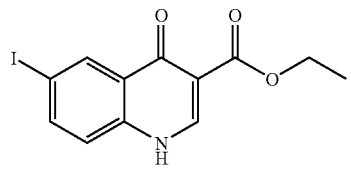

Method A: Diethyl 2-((4-iodophenylamino)methylene)malonate (Intermediate 4, 10 g, 25 mmol) was added to a round-bottom flask that was equipped with thermocouple and stirrer, then Eaton's reagent (26 ml) was added to the flask. The reaction mixture was stirred at 95° C. for 6 h under nitrogen. After this period of time, the reaction mixture was cooled to 5° C. and slowly transferred into an excess of saturated sodium carbonate solution (50 ml) that was cooled to 10° C. The precipitated solid was filtered, washed with water (~20 ml) and dried under vacuum to give product (80% yield).

Method B: Phenyl ether (70 ml) was heated with stirring to 240° C., then diethyl 2-((4-iodophenylamino)methylene)malonate (Intermediate 4, 10 g, 25 mmol) was gradually added and the resulting mixture was refluxed at 280° C. for 1 hour. After cooling the reaction to room temperature, the resulting solid was collected by filtration, washed with methyl tert-butyl ether and dichloromethane to give a white solid (30% yield)

MS (ESP): 344 (M+H$^+$) for C$_{12}$H$_{10}$INO$_3$.

Intermediate 6

Ethyl 1-ethyl-6-iodo-4-oxo-1,4-dihydroquinoline-3-carboxylate

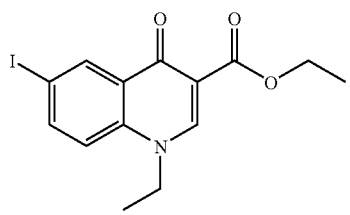

To ethyl 6-iodo-4-oxo-1,4-dihydroquinoline-3-carboxylate (Intermediate 5, 5 g, 0.013 mol) in dimethylformamide (26 ml, 0.2M) were added potassium carbonate (4.50 g, 0.033 mole) and ethyl bromide (5.71 g, 0.053 mole). The reaction was stirred at 90° C. overnight then the solvent was removed in vacuo. The residue was taken up in ethyl acetate washed with water, brine, and dried over sodium sulfate. Solvents were removed under vacuum and the residue was purified by flash column chromatography on silica gel using (dichloromethane-ethyl acetate) to give the desired quinolone product (90%) and trace of O-alkylated impurity.

MS (ESP): 372 (M+H$^+$) for C$_{14}$H$_{14}$INO$_3$

Intermediate 7

Diethyl 2-((3-iodophenylamino)methylene)malonate

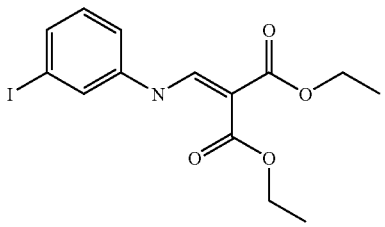

A mixture of ethoxymethylene malonic acid diethyl ester (13.72 g, 0.068 mol) and 3-iodoaniline (15 g, 0.068 mole) in toluene (230 ml) was refluxed for 1 h. After this period of time, solvents were removed under vacuum, and the crude material was precipitated in methyl tert-butyl ether and the resulting white solid was filtered, and dried under vacuum (24.3 g, 93%).

MS (ESP): 390 (M+H$^+$) for C$_{14}$H$_{16}$INO$_4$

Intermediate 8

Ethyl 7-iodo-4-oxo-1,4-dihydroquinoline-3-carboxylate

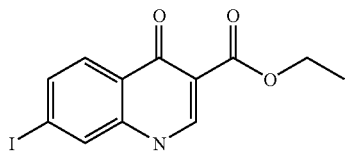

Method A: Diethyl 2-((3-iodophenylamino)methylene)malonate (Intermediate 7, 10 g, 25 mmol) was added to a round-bottom flask that was equipped with thermocouple and stirrer, then Eaton's reagent (26 ml) was added to the flask. The reaction mixture was stirred at 95° C. for 6 h under nitrogen. After this period of time, the reaction mixture was cooled to 5° C. and slowly transferred into an excess of saturated sodium carbonate solution (50 ml) that was cooled to 10° C. The precipitated solid was filtered, washed with water (~20 ml) and dried under vacuum to give product (80% yield).

Method B: Phenyl ether (70 ml) was heated with stirring to 240° C., then diethyl 2-((3-iodophenylamino)methylene)malonate (Intermediate 7, 10 g, 25 mmol) was gradually added and the resulting mixture was refluxed at 280° C. for 1 hour. After cooling the reaction to room temperature, the resulting solid was collected by filtration, washed with methyl tert-butyl ether and dichloromethane to give a white solid (30% yield).

MS (ESP): 344 (M+H$^+$) for $C_{12}H_{10}INO_3$

Intermediate 9

Ethyl 1-ethyl-7-iodo-4-oxo-1,4-dihydroquinoline-3-carboxylate

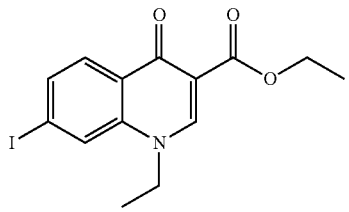

To ethyl 6-iodo-4-oxo-1,4-dihydroquinoline-3-carboxylate (Intermediate 8, 5 g, 0.013 mol) in dimethylformamide (26 ml, c=0.2M) were added potassium carbonate (4.50 g, 0.033 mole) and ethyl bromide (5.71 g, 0.053 mole). The reaction was stirred at 90° C. overnight then the solvent was removed in vacuo. The residue was taken up in ethyl acetate washed with water, brine, and dried over sodium sulfate. Solvents were removed under vacuum and the crude was purified by flash column chromatography on silica gel using (dichloromethane-ethyl acetate) to give the desired quinolone (90%)

MS (ESP): 372 (M+H$^+$) for $C_{14}H_{14}INO_3$.

Intermediate 10

2-((2-Fluoro-4-iodophenylamino)methylene)malonate

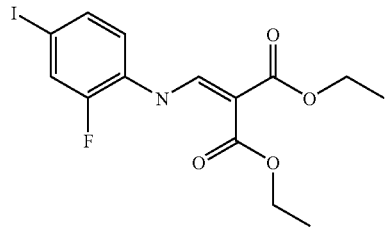

A solution of 2-fluoro-4-iodoaniline (15 g, 63.29 mmol) and diethyl ethoxymethylene malonate (41.05 g, 0.19 mol) in toluene (75 mL) was heated to reflux with a Dean-Stark condenser for 7 h. The mixture was cooled, concentrated and washed with methyl tert-butyl ether (500 ml). The methyl tert-butyl ether layer was then concentrated and the residue was washed with heptane (500 ml), yielding a white solid that precipitated out of the yellow solution. This solid was then collected, yielding 23.6 g (91%) of diethyl 2-((2-fluoro-4-iodophenylamino)methylene)malonate.

MS (ESP): 407 (M+H$^+$) for $C_{14}H_{15}FINO_4$ $^1$H NMR (CDCl$_3$): δ 1.40 (t, 6H), 4.30 (q, 4H), 7.03 (t, 1H), 7.51 (d, 1H), 8.42 (d, 1H), 11.02 (d, 1H).

Intermediate 11

Ethyl 8-fluoro-6-iodo-4-oxo-1,4-dihydroquinoline-3-carboxylate

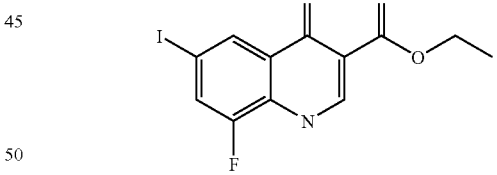

Diethyl 2-((2-fluoro-4-iodophenylamino)methylene)malonate (Intermediate 10, 13.45 g, 33.05 mmol) was placed in a 250 mL round bottom flask with Eaton's Reagent (55 mL, 0.29 mol) and aged while stirring at 90° C. for 4-5 days. The reaction was then cooled to 5° C. and was slowly quenched with saturated sodium carbonate solution (500 ml) at 10° C. to form a clumpy brownish-yellow solid. The precipitate was vacuum filtered and washed with water (300 ml). The collected solid was dried under vacuum at 50° C. for 16 h, resulting in 10.7 g (90%) of light tan solid.

MS (ESP): 362 (M+H$^+$) for $C_{12}H_9FINO_3$ $^1$H NMR (CDCl$_3$): δ 1.37 (t, 3H), 4.18 (q, 2H), 6.59 (d, 1H), 7.20 (d, 1H), 7.30 (d, 1H), 7.64 (d, 1H)

Intermediate 12

Ethyl 8-fluoro-1-(2-hydroxyethyl)-6-iodo-4-oxo-1,4-dihydroquinoline-3-carboxylate

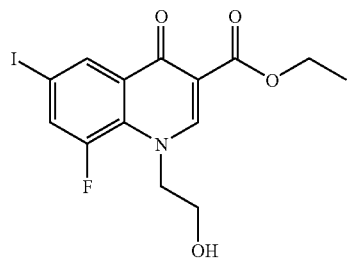

Ethyl 8-fluoro-6-iodo-4-oxo-1,4-dihydroquinoline-3-carboxylate (Intermediate 11, 7.22 g, 20 mmol) was dissolved in dimethylformamide (35 ml). Powdered potassium carbonate (8.28 g, 60 mmol) and 2-iodoethanol (11.3 ml, 145 mmol) were then added and the reaction mixture was allowed to stir at 90° C. for 1 h. The reaction mixture was cooled to room temperature and poured into brine (300 ml) then water (50 ml) was added to dissolve the material. This solution was extracted with 9:1 tetrahydrofuran:methyl tert-butyl ether (5×200 ml). The organic extracts were combined washed with brine (2×200 ml), dried over sodium sulfate, and concentrated under reduced pressure to give a dark yellow oil of ethyl 8-fluoro-1-(2-hydroxyethyl)-6-iodo-4-oxo-1,4-dihydroquinoline-3-carboxylate that was carried on to the next reaction without any further purification.

MS (ESP): 405 (M+H$^+$) for C$_{14}$H$_{13}$FINO$_4$

Intermediate 13

Ethyl 9-iodo-7-oxo-3,7-dihydro-2H-[1,4]oxazino[2,3,4-ij]quinoline-6-carboxylate

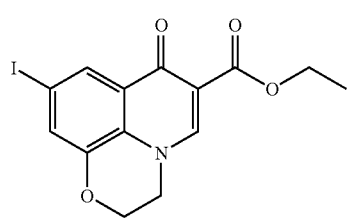

A solution of ethyl 8-fluoro-1-(2-hydroxyethyl)-6-iodo-4-oxo-1,4-dihydroquinoline-3-carboxylate (Intermediate 12, 20 mmol) in DMF (30 mL) was treated with 1.8-diazabicyclo[5.4.0]undec-7-ene (5.6 ml, 40 mmol) and the reaction mixture was stirred at 100° C. for 24 h. The solvent was then removed in vacuo and the residue was chromatographed on silica gel using 0-5% (0.2N ammonia in methanol) in dichloromethane to give 1.4 g (18%) of ethyl 9-iodo-7-oxo-3,7-dihydro-2H-[1,4]oxazino[2,3,4-ij]quinoline-6-carboxylate as a white solid.

MS (ESP): 386 (M+H$^+$) for C$_{14}$H$_{12}$INO$_4$

Intermediate 14

1-(5-Bromo-4-(4-ethylthiazol-2-yl)pyridin-2-yl)-3-ethylurea

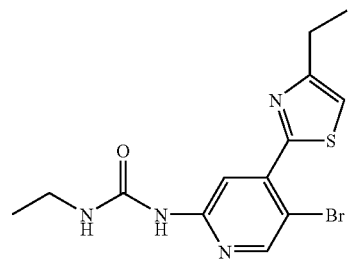

5-Bromo-2-(3-ethylureido)pyridine-4-carbothioamide (Intermediate 3, 6.06 g, 20 mmol) was suspended in acetonitrile (150 ml). 1-Bromobutan-2-one (30 mmol) was added and the reaction mixture was heated at reflux for 16 h. The reaction was cooled to 0° C. and the suspension was filtered. The solid was washed with acetonitrile (50 ml), collected, and dried in a vacuum oven at 50° C. for 4 hours to give an off white solid.

MS (ESP): 356 (MH$^+$) for C$_{13}$H$_{15}$BrN$_4$OS
$^1$H NMR (d$_6$-DMSO): δ 0.91 (t, 3H), 1.28 (t, 3H), 3.83 (q, 2 H), 3.18 (q, 2H), 7.31 (bs, 1H), 7.66 (s, 1 H), 8.37 (s, 1H), 8.47 (s, 1H), 9.37 (s, 1H).

Intermediates 15-16

The following Intermediates were prepared by the procedure described for the preparation of Intermediate 14 from the starting materials (SM) indicated.

| Int | Compound | Data | SM |
|---|---|---|---|
| 15 | 1-(5-bromo-4-(4-phenylthiazol-2-yl)pyridin-2-yl)-3-ethylurea | MS (ESP): 504 (MH$^+$) for C$_{17}$H$_{15}$BrN$_4$OS<br>$^1$H NMR: 1.10 (t, 3H), 3.19 (q, 2H), 7.24-7.40 (m, 2H), 7.41-7.50 (m, 2H), 8.04 (d, 1H), 8.43-8.53 (m, 3H), 9.39 (s, 1H) | Intermediate 3 and 2-bromo-1-phenylethanone |
| 16 | 1-(5-bromo-4-(4-trifluoromethylthiazol-2-yl)pyridin-2-yl)-3-ethylurea | MS (ESP): 395 (M + H$^+$) for C$_{12}$H$_{10}$BrF$_3$N$_4$OS<br>$^1$H NMR: 1.1 (t, 3H), 3.20 (q, 2H), 7.23 (s, 1H), 8.40 (s, 1H), 8.60 (s, 1H), 8.83 (s, 1H), 9.40 (s, 1H) | Intermediate 3 and 3-bromo-1,1,1,-trifluoro-acetone |

Intermediate 17

1-Ethyl-3-(5-(4,4,5,5-tetramethyl-1,3,2-dioxaborolan-2-yl)-4-(4-(trifluoromethyl)thiazol-2-yl)pyridin-2-yl)urea

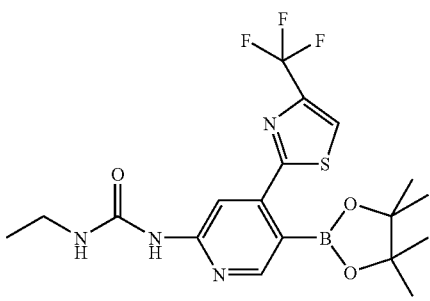

1-(5-Bromo-4-(4-(trifluoromethyl)thiazol-2-yl)pyridin-2-yl)-3-ethylurea (Intermediate 16, 200 mg, 0.51 mmol), 4,4,4',4',5,5,5',5'-octamethyl-2,2'-bi(1,3,2-dioxaborolane) (386 mg, 1.52 mmol), potassium acetate (149 mg, 1.52 mmol), and 1,1'-bis(diphenylphosphino)ferrocene-palladium dichloride (20.72 mg, 0.03 mmol) were taken in a microwave vial and degassed with argon. DMSO (4 mL) was added to the vial and the solution was heated at 90° C. for 5 h. The reaction mixture was partitioned between water and ethyl acetate. The layers were separated and the organic layer was back extracted three times with ethyl acetate. The organic layers were combined and washed with water and brine, then dried over magnesium sulfate and concentrated under reduced pressure to give a light brown solid that was a mixture of the title compound (35%), {6-{[(ethylamino)carbonyl]amino}-4-[4-(trifluoromethyl)-1,3-thiazol-2-yl]pyridin-3-yl}boronic acid (25%) and N-ethyl-N'-{4-[4-(trifluoromethyl)-1,3-thiazol-2-yl]pyridin-2-yl}urea (25%). The crude mixture was taken to the next step without further purification.

MS (ESP): 361 (MH$^+$) for C$_{12}$H$_{12}$BF$_3$N$_4$O$_3$S $^1$H NMR (d$_6$-DMSO): δ 1.11 (t, 3H), 3.16-3.22 (q, 2 H), 7.71 (bt, 1H), 7.89 (d, 1 H), 8.16 (s, 1H), 8.28 (s, 1H), 8.63 (s, 1H), 9.26 (s, 1H).

Intermediate 18

The following Intermediate was prepared by the procedure described in Intermediate 17 from the starting materials (SM) indicated.

| Int | Compound | Data | SM |
|---|---|---|---|
| 18 | 6-(3-ethylureido)-4-(4-ethylthiazol-2-yl)pyridin-3-ylboronic acid | MS (ESP): 321 (MH$^+$) for $C_{13}H_{17}BN_4O_3S$<br>$^1$H NMR (d$_6$-DMSO): δ 1.16 (t, 3H), 1.23 (t, 3H), 2.78 (q, 2H), 3.18-3.23 (m, 2H), 7.48 (s, 1H), 7.78 (bt, 1H), 7.91 (s, 1H), 8.26 (s, 1H), 9.40 (s, 1H) | Intermediate 14 |

Intermediate 19

6-(3-Ethylureido)-4-(4-phenylthiazol-2-yl)pyridin-3-ylboronic acid

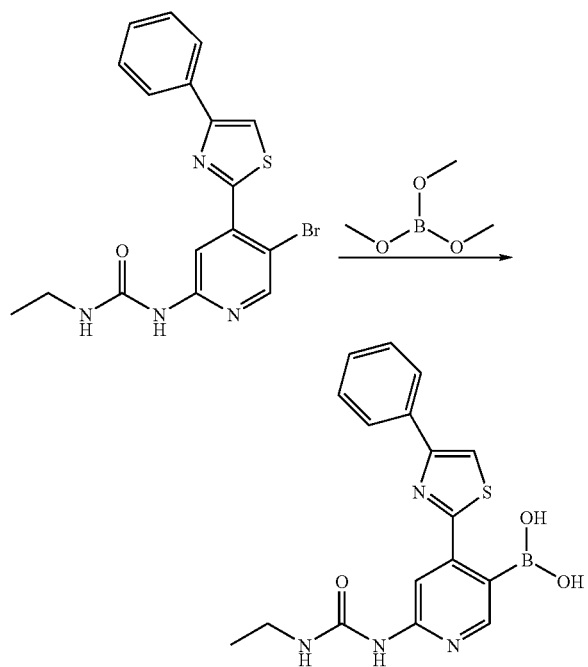

A solution of 1-(5-bromo-4-(4-phenylthiazol-2-yl)pyridin-2-yl)-3-ethylurea (2.97 g, 7.36 mmol, Intermediate 15) in THF (25 mL) was cooled to −78° C. Isopropylmagnesium chloride (2.0M in THF; 8.84 mL, 17.67 mmol, Aldrich) was added slowly and the reaction was slowly warmed to −15° C. before being cooled back down to −78° C. N-Butyllithium (2.5M in hexanes; 14.73 mL, 36.82 mmol, Aldrich) was then added and the reaction was stirred at −78° C. for 1 hour. Trimethyl borate (8.21 mL, 73.64 mmol, Aldrich) was added all at once and an exotherm was observed. Following the exotherm, the reaction mixture was allowed to warm to room temperature and stir for 3 h. The reaction mixture was then cooled to 0° C. and 20 mL of water was added slowly followed by 10 mL of 6N HCl. The reaction mixture was allowed to warm to room temperature and stir for 30 min The reaction mixture was concentrated under reduced pressure to remove THF. The aqueous portion was diluted with 1N NaOH and diethylether. The impurities went into the ether layer (yellow) and the remaining white solid was filtered, washed with water and dried. The solid was then triturate with dilute acid (pH 4.5) to remove salts. The solid was dried overnight to yield product as a white solid (1.60 g).

MS (ES) (M+H)$^+$: 369 for $C_{17}H_{17}BN_4O_3S$
NMR: 1.10 (t, 3H), 3.20 (q, 2H), 7.37-7.51 (m, 3H), 7.79 (m, 1H), 7.93 (s, 1H), 8.06 (d, 2H), 8.28 (d, 2H), 9.30 (s, 1H).

Intermediate 20

Ethyl 6-iodo-1-(2-methoxyethyl)-4-oxo-1,4-dihydroquinoline-3-carboxylate

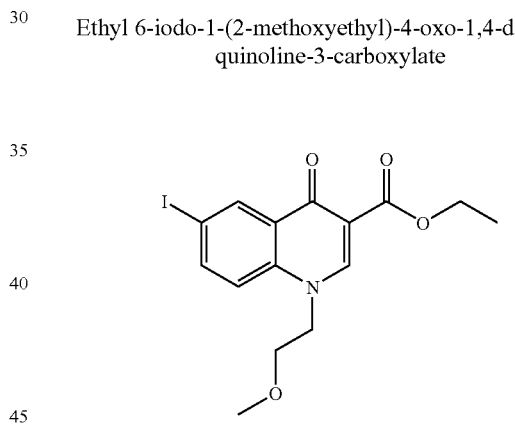

(Z)-Ethyl 3-(dimethylamino)-2-(2-fluoro-5-iodobenzoyl)acrylate (0.428 g, 1.09 mmol, Intermediate 24) and 2-methoxyethanamine (0.082 g, 1.09 mmol, Acros) were combined in DMF (3.0 mL). Potassium carbonate (0.151 g, 1.09 mmol, Fisher) was added and the reaction was heated in the microwave at 90° C. for 30 min After 30 minutes, LC/MS indicated that the reaction was complete. The reaction mixture was cooled to room temperature and slowly poured into water. The resulting precipitate was filtered, washed with water and dried overnight to yield a white solid (0.277 g).

MS (ES) (M+H)$^+$: 402 for $C_{15}H_{16}INO_4$;
NMR: 1.28 (t, 3H), 3.21 (s, 3H), 3.65 (t, 2H), 4.21 (q, 2H), 4.55 (t, 2H), 7.68 (d, 1H), 8.04 (d, 1H), 8.50 (s, 1H), 8.60 (s, 1H).

Intermediates 21-23

The following Intermediates were prepared by the procedure described in Intermediate 20 from the starting materials (SM) indicated.

| Int | Compound | Data | SM |
|---|---|---|---|
| 21 | ethyl 6-iodo-4-oxo-1-(3-(2-oxopyrrolidin-1-yl)propyl)-1,4-dihydroquinoline-3-carboxylate | MS (ES) (M + H)$^+$: 469 for $C_{19}H_{21}IN_2O_4$ | Intermediate 24 and 1-(3-aminopropyl)pyrrolidin-2-one (Acros) |
| 22 | ethyl 1-(1,3-dimethoxypropan-2-yl)-6-iodo-4-oxo-1,4-dihydroquinoline-3-carboxylate | MS (ES) (M + H)$^+$: 446 for $C_{17}H_{20}INO_5$ NMR: 1.28 (t, 3H), 3.24 (s, 6H), 3.73-3.84 (m, 4H), 4.22 (q, 2H), 5.27 (q, 1H), 7.81 (d, 1H), 8.04 (d, 1H), 8.51 (s, 1H), 8.72 (s, 1H). | Intermediate 24 and 1,3-dimethoxy-propan-2-amine (Tyger) |
| 23 | ethyl 6-iodo-1-(3-methoxypropyl)-4-oxo-1,4-dihydroquinoline-3-carboxylate | MS (ES) (M + H)$^+$: 416 for $C_{16}H_{18}INO_4$ NMR: 1.28 (t, J = 8 Hz, 3H), 1.97 (m, 2H), 3.34 (m, 5H), 4.21 (q, J = 8 Hz, 2H), 4.39 (m, 2H), 7.62 (d, J = 9 Hz, 1H), 8.06 (d, J = 9 Hz, 1H), 8.51 (s, 1H), 8.63 (s, 1H). | Intermediate 24 and 3-methoxypropylamine |

Intermediate 24

(Z)-Ethyl 3-(dimethylamino)-2-(2-fluoro-5-iodobenzoyl)acrylate

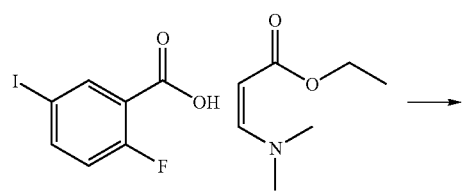 → 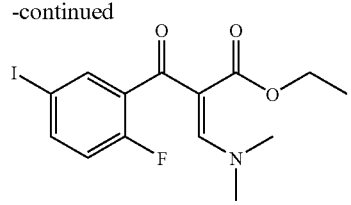

2-Fluoro-5-iodobenzoic acid (5.20 g, 19.55 mmol, Aldrich) was suspended in thionyl chloride (1.427 mL, 19.55 mmol, Aldrich) and heated to reflux for 30 min The reaction mixture was cooled to room temperature and concentrated under reduced pressure to a tan solid. The solid was dissolved in toluene (30 mL) and concentrated under reduced pressure again. To a solution of the resulting solid (5.20 g, 19.55 mmol) in toluene (30 mL) was added triethylamine (2.72 mL, 19.55 mmol, Acros) and (Z)-ethyl 3-(dimethylamino)acrylate (3.64 mL, 25.41 mmol, Acros) and the reaction mixture was heated to 90° C. for 1 h. The reaction mixture was diluted with water and extracted three times with ethyl acetate. The combined organic extracts were dried over magnesium sulfate, filtered and concentrated under reduced pressure. Purification by Isco column (0%-100% ethyl acetate/dichloromethane) afforded the desired compound as a yellow solid (6.51 g).

MS (ES) (M+H)$^+$: 392 for $C_{14}H_{15}FINO_3$

NMR: 0.88 (t, 3H), 2.78 (s, 3H), 3.33 (s, 3H), 3.85 (q, 2H), 7.03 (dd, 1H), 7.65 (dd, 1H), 7.77 (s, 2H).

Intermediates 25-26

The following Intermediates were prepared by the procedure described in Intermediate 9 from the starting materials (SM) indicated.

| Int | Compound | Data | SM |
|---|---|---|---|
| 25 | Ethyl 7-iodo-1-methyl-4-oxo-1,4-dihydroquinoline-3-carboxylate | MS (ESP): 358 (M + 1) for $C_{13}H_{12}INO_3$; $^1$H-NMR (DMSO-d$_6$) δ: 1.28 (t, 3H); 3.90 (s, 3H); 4.22 (q, J = 7.07 Hz, 2H); 7.83 (dd, 1H); 7.94 (d, J = 8.59 Hz, 1H); 8.10 (s, 1H); 8.64 (s, 1H) | Intermediate 8 and iodomethane |
| 26 | Ethyl 7-iodo-1-isopropyl-4-oxo-1,4-dihydroquinoline-3-carboxylate | MS (ESP): 386 (M + 1) for $C_{15}H_{16}INO_3$; $^1$H-NMR (DMSO-d$_6$): 1.29 (d, J = 6.06 Hz, 6H); 1.36 (t, J = 7.07 Hz, 3H); 4.39 (q, J = 7.07 Hz, 2H); 4.58-4.70 (m, 1H); 7.96 (dd, 1H) 8.03 (d, 1H); 8.45 (d, J = 1.26 Hz, 1H); 9.04 (s, 1H) | Intermediate 8 and 2-iodopropane |

Intermediates 27-31

The following Intermediates were prepared by the procedure described in Intermediate 20 from the starting materials (SM) indicated.

| Int | Compound | Data | SM |
|---|---|---|---|
| 27 | Ethyl 1-cyclopropyl-6-iodo-4-oxo-1,4-dihydroquinoline-3-carboxylate | MS (ESP): 384 (M + 1) for $C_{15}H_{14}INO_3$; $^1$H-NMR (DMSO-d$_6$): 1.05-1.13 (m, 2H); 1.20-1.32 (m, 5H); 3.60-3.69 (m, 1H); 4.22 (q, J = 7.07 Hz, 2H); 7.89 (d, J = 8.84 Hz, 2H); 8.12 (dd, J = 8.84, 2.02 Hz, 1H); 8.47 (d, J = 2.02 Hz, 1H); 8.49 (s, 1H) | Intermediate 24 and cyclopropylamine |
| 28 | Ethyl 6-iodo-1-isopropyl-4-oxo-1,4-dihydroquinoline-3-carboxylate | MS (ESP): 386 (M + 1) for $C_{15}H_{16}INO_3$; $^1$H-NMR (DMSO-d$_6$): 1.29 (t, J = 7.07 Hz, 3H): 1.49 (d, J = 6.57 Hz, 6H): 4.23 (q, J = 7.07 Hz, 2H): 5.00-5.10 (m, 1H); 7.80 (d, J = 9.35 Hz, 1H): 8.07 (dd, J = 9.09, 2.27 Hz, 1H) 8.53 (d, J = 2.02 Hz, 1H): 8.61 (s, 1H) | Intermediate 24 and propan-2-amine |

-continued

| Int | Compound | Data | SM |
|---|---|---|---|
| 29 | Ethyl 1-(2-(dimethylamino)ethyl)-6-iodo-4-oxo-1,4-dihydroquinoline-3-carboxylate | MS (ESP): 415 (M + 1) for $C_{16}H_{19}IN_2O_3$<br>$^1$H-NMR (DMSO-d$_6$): 1.28 (t, J = 7.20 Hz, 3H); 2.18 (s, 6H); 2.58 (t, J = 5.94 Hz, 2H); 4.23 (q, J = 7.24 Hz, 2H); 4.44 (t, J = 5.81 Hz, 2H); 7.65 (d, J = 8.84 Hz, 1H); 8.06 (dd, J = 8.84, 2.27 Hz, 1H); 8.51 (d, J = 2.02 Hz, 1H); 8.63 (s, 1H) | Intermediate 24 and 2-(N,N-dimethylamino)-ethanamine |
| 30 | Ethyl 1-(2-hydroxyethyl)-6-iodo-4-oxo-1,4-dihydroquinoline-3-carboxylate | MS (ESP) 388 (M + 1) for $C_{14}H_{14}INO_4$<br>$^1$H-NMR (DMSO-d$_6$): 1.28 (t, J = 7.06 Hz, 3H); 3.63-3.76 (m, 2H); 4.22 (q, J = 6.97 Hz, 2H); 4.36-4.46 (m, 2H); 5.02 (t, J = 5.46 Hz, 1H); 7.67 (d, J = 9.04 Hz, 1H); 8.04 (dd, J = 9.04, 1.88 Hz, 1H); 8.51 (d, J = 1.88 Hz, 1H); 8.59 (s, 1H) | Intermediate 24 and 2-aminoethanol |
| 31 | Ethyl 6-iodo-1-(1-methylazetidin-3-yl)-4-oxo-1,4-dihydroquinoline-3-carboxylate | MS (ESP): 413 (M + 1) for $C_{16}H_{17}IN_2O_3$<br>$^1$H NMR (DMSO-d$_6$): 1.29 (t, J = 7.06 Hz, 3H); 2.31 (s, 3H); 3.25-3.39 (m, 2H); 3.85 (t, 2H); 4.25 (q, J = 7.03 Hz, 2H); 5.01-5.16 (m, 1H); 7.45 (d, J = 8.85 Hz, 1H); 8.03 (dd, J = 8.85, 2.07 Hz, 1H); 8.50 (d, J = 2.07 Hz, 1H); 8.60 (s, 1H) | Intermediate 24 and 1-methylazetidin-3-amine |

Intermediate 32

Diethyl {[(3-bromophenyl)amino]methylidene}propanedioate

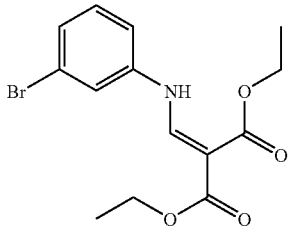

A mixture of 3-bromoaniline (10.0 g, 58.1 mmol) and diethyl(ethoxymethylidene)propanedioate (13.9 mL, 63.9 mmol) were heated to 110° C. for 1 h. After completion of the reaction, the reaction mixture was cooled to room temperature. The obtained solid was filtered and dried to afford 16.0 g 78% of diethyl {[(3-bromophenyl)amino]methylidene}propanedioate.

$^1$H NMR (400 MHz, CDCl$_3$): 1.37 (m, 6H), 4.25 (m, 4H), 7.05 (d, 1H), 7.25 (m, 2H), 8.44 (d, 1H), 10.95 (d, 1H).

Intermediate 33

Ethyl 7-bromo-4-oxo-1,4-dihydroquinoline-3-carboxylate

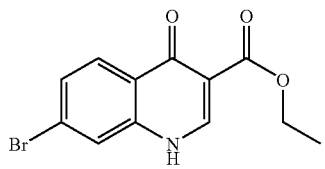

Dowtherm (50 mL) was taken in double neck round bottom flask (100 mL) and heated to 250° C. in sand bath. At this temperature diethyl {[(3-bromophenyl)amino]methylidene}propanedioate (Intermediate 32, 10.0 g, 29.2 mmol) was added and the reaction temperature was maintained for another 1 h at 250° C. After completion of the reaction, the reaction mixture was cooled to room temperature, a white solid was collected by filtration and dried to yield 6.0 g (69.3%) ethyl 7-bromo-4-oxo-1,4-dihydroquinoline-3-carboxylate.

$^1$H NMR (400 MHz, DMSO-d$_6$): 1.07 (t, 3H), 1.22 (s, 12H), 3.16 (q, 2H), 7.29 (m, 1H), 7.31 (d, 2H), 7.61 (s, 1H), 7.88 (s, 1H), 8.31 (s, 1H), 8.65 (s, 1H), 9.44 (s, 1H).

Intermediates 34-41

The following Intermediates were prepared by the procedure described in Intermediate 9 from the starting materials (SM) indicated.

| Int | Compound | Data | SM |
|-----|----------|------|-----|
| 34 | Ethyl 7-bromo-1-(3-methylbutyl)-4-oxo-1,4-dihydroquinoline-3-carboxylate | $^1$H NMR (400 MHz, CDCl$_3$): 1.04 (d, 6H), 1.41 (t, 3H), 1.78 (q, 3H), 4.14 (q, 2H), 4.40 (q, 2H), 7.52 (s, 1H), 7.56 (d, 1H), 8.39 (s, 1H), 8.42 (d, 1H). | Intermediate 33 and 1-bromo-3-methylbutane |
| 35 | Ethyl 7-bromo-1-(2-methylpropyl)-4-oxo-1,4-dihydroquinoline-3-carboxylate | $^1$H NMR (400 MHz, CDCl$_3$): 1.02 (d, 6H), 1.39 (t, 3H), 2.27 (m, 1H), 3.93 (d, 2H), 4.41 (q, 2H), 4.53 (d, 2H), 8.40 (d, 2H). | Intermediate 33 and 1-bromo-2-methylpropane |

| Int | Compound | Data | SM |
|---|---|---|---|
| 36 | Ethyl 7-bromo-4-oxo-1-propyl-1,4-dihydroquinoline-3-carboxylate | $^1$H NMR (400 MHz, DMSO-d$_6$): 0.90 (t, 3H), 1.75 (q, 2H), 4.24 (q, 2H), 4.35 (q, 2H), 7.63 (d, 1H), 8.07 (s, 1H), 8.14 (d, 1H), 8.66 (s, 1H). | Intermediate 33 and 1-bromopropane |
| 37 | Ethyl 1-benzyl-7-bromo-4-oxo-1,4-dihydroquinoline-3-carboxylate | $^1$H NMR (400 MHz, DMSO-d$_6$): 1.24 (t, 3H), 2.83 (s, 1H), 4.22 (q, 2H), 4.57 (s, 1H), 5.67 (s, 2H), 7.22 (m, 2H), 7.33 (m, 2H), 7.56 (m, 2H), 7.85 (s, 1H), 8.12 (d, 1H), 8.86 (s, 1H). | Intermediate 33 and benzyl bromide |
| 38 | Ethyl 7-bromo-4-oxo-1-(pyridin-3-ylmethyl)-1,4-dihydroquinoline-3-carboxylate | $^1$H NMR (400 MHz, DMSO-d$_6$): 1.29 (t, 3H), 4.25 (q, 2H), 5.74 (s, 2H), 7.37 (d, 1H), 7.61 (d, 2H), 7.91 (s, 1H), 8.14 (d, 1H), 8.42 (d, 1H), 8.58 (d, 1H), 8.91 (s, 1H). | Intermediate 33 and 3-(bromomethyl)pyridine |
| 39 | Ethyl 7-bromo-1-(2-hydroxyethyl)-4-oxo-1,4-dihydroquinoline-3-carboxylate | $^1$H NMR (400 MHz, DMSO-d$_6$): 1.28 (t, 3H), 3.71 (d, 2H), 4.23 (q, 2H), 4.42 (s, 2H), 4.48 (s, 2H), 4.99 (m, 1H), 7.62 (d, 1H), 8.10 (s, 1H), 8.14 (d, 1H), 8.56 (s, 1H). | Intermediate 33 and 2-bromoethanol |

| Int | Compound | Data | SM |
|---|---|---|---|
| 40 | Ethyl 7-bromo-1-(2-methoxyethyl)-4-oxo-1,4-dihydroquinoline-3-carboxylate | $^1$H NMR (400 MHz, DMSO-$d_6$): 1.33 (t, 3H), 3.22 (s, 3H), 3.65 (m, 2H), 4.22 (q, 2H), 4.58 (m, 2H), 7.62 (d, 1H), 8.15 (m, 2H), 8.49 (s, 1H). | Intermediate 33 and 1-bromo-2-methoxy-ethane |
| 41 | Ethyl 7-bromo-1-(cyclopropylmethyl)-4-oxo-1,4-dihydroquinoline-3-carboxylate | $^1$H NMR (400 MHz, CDCl$_3$): 0.48 (d, 2H), 0.79 (m, 2H), 1.39 (m, 1H), 1.42 (t, 3H), 3.98 (d, 2H), 4.42 (q, 2H), 7.53 (d, 1H), 7.65 (s, 1H), 8.40 (d, 1H), 8.54 (s, 1H). | Intermediate 33 and (bromomethyl)cyclopropyl |

Intermediate 42 methyl 5-bromo-2-(3-propylureido)isonicotinate

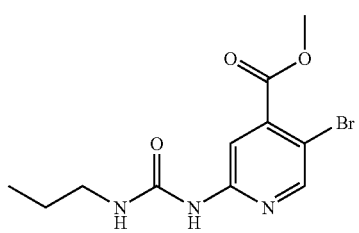

Methyl 2-amino-5-bromoisonicotinate (100 g, 433 mmol) was dissolved in chloroform (600 mL) and placed into a 1 L sealed tube. Propyl isocyanate (122.5 mL, 1.29 mol) was then added. The reactor was heated at 55° C. for 72 h at which time the reaction was determined to be complete. The mixture was then cooled to room temperature, concentrated under reduced pressure, and the solid was dissolved in 2:1 ethyl acetate: tetrahydrofuran (3 L). This solution was washed with water (2×200 mL), and the water was back extracted with ethyl acetate (300 mL). The organic layers were then dried with sodium sulfate, filtered, and concentrated yielding 129 g (95%) of methyl 5-bromo-2-(3-propylureido)isonicotinate as a dark yellow solid.

MS (ESP): 316.1 (MH$^+$) for C$_{11}$H$_{14}$BrN$_3$O$_3$ $^1$H NMR (300 MHz, CDCl$_3$): δ 0.88 (t, 3H), 1.45 (m, 2H), 3.11 (m, 2H), 3.90 (s, 3H), 7.21 (bt, 1H), 8.02 (s, 1H), 8.46 (s, 1H), 9.40 (s, 1H)

Intermediate 43

5-bromo-2-(3-propylureido)isonicotinamide

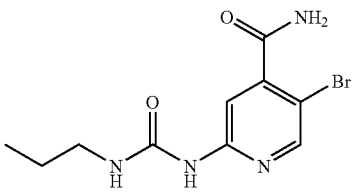

A solution of methyl 5-bromo-2-(3-propylureido)isonicotinate (Intermediate 42, 128 g, 405 mmol) and 7N ammonia in methanol (1 L) was allowed to stir at room temperature for 3 d. Stirring for the reaction was then stopped and the solids were allowed to settle. The precipitated was then vacuum filtered, rinsed with methanol (2×500 mL), and then dried on the high vacuum pump overnight, yielding 123 g (quant) of 5-bromo-2-(3-propylureido)isonicotinamide as a white solid.

MS (ESP): 301.1 (MH$^+$) for C$_{10}$H$_{13}$BrN$_4$OS

¹H NMR (300 MHz, DMSO-d₆): δ 0.88 (t, 3H), 1.46 (m, 2H), 3.18 (q, 2H), 7.41 (bs, 1H), 7.58 (s, 1H), 7.78 (bs, 1H), 8.08 (bs, 1H), 8.33 (s, 1H), 9.31 (s, 1H)

Intermediate 44

5-bromo-2-(3-propylureido)pyridine-4-carbothioamide

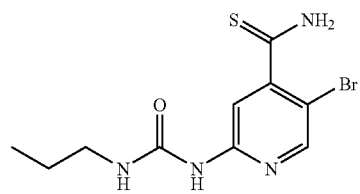

A suspended mixture of 5-bromo-2-(3-propylureido)isonicotinamide (Intermediate 43, 123 g, 407 mmol), Lawesson's Reagent (131.6 g, 326 mmol), and tetrahydrofuran (1.55 L) was stirred at 70° C. for 18 h. Stirring was stopped and a bright yellow precipitate was allowed to settle. The precipitate was then vacuum filtered and washed with methyl tert-butyl ether (2×500 L). This solid was then dried in the vacuum oven at 50° C. for 12 hours to give 50 g of product solid. The mother liquor was concentrated and the residue was suspended in toluene (300 mL). The solid thus obtained was filtered and combined with the previous solid. The combined totaled 110 g (85%) of 5-bromo-2-(3-propylureido)pyridine -4-carbothioamide as an off white solid MS (ESP): 317.2 (MH⁺) for $C_{10}H_{13}BrN_4OS$ ¹H NMR (300 MHz, CDCl₃): δ 0.88 (t, 3H), 1.42 (m, 2H), 3.13 (m, 2H), 7.38 (s, 1H), 7.50 (s, 1H), 8.28 (s, 1H), 9.25 (s, 1H), 9.80 (s, 1H), 10.28 (s, 1H)

Intermediate 45

1-(5-bromo-4-(4-hydroxy-4-(trifluoromethyl)-4,5-dihydrothiazol-2-yl)pyridin-2-yl)-3-propylurea

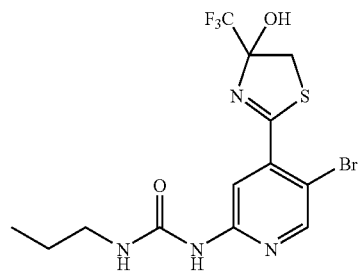

A suspension of 5-bromo-2-(3-propylureido)pyridine-4-carbothioamide (Intermediate 44, 100 g, 315 mmol), 3-bromo-1,1,1-trifluoroacetone (64 mL, 630 mmol) in acetonitrile (1.5 L) was heated at 80° C. for 20 hours. The solution was then cooled down and was concentrated under reduced pressure. This gave an orange oil that was carried on without further purification.

MS (ESP): 426.9 (MH⁺) for $C_{13}H_{14}BrF_3N_4O_2S$

¹H NMR (300 MHz, DMSO-d₆): δ 0.88 (t, 3H), 1.48 (m, 2H), 3.11 (m, 2H), 3.62 (d, 1H), 3.92 (d, 1H), 7.30 (bs, 1H), 7.98 (s, 1H), 8.46 (s, 1H), 9.42 (s, 1H).

Intermediate 46

1-(5-bromo-4-(4-(trifluoromethyl)thiazol-2-yl)pyridin-2-yl)-3-propylurea

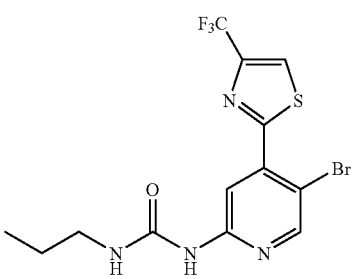

A solution of 1-(5-bromo-4-(4-hydroxy-4-(trifluoromethyl)-4,5-dihydrothiazol-2-yl)pyridin-2-yl)-3-propylurea (Intermediate 45, 315 mmol) and triethylamine (217 mL, 1.57 mol) in tetrahydrofuran (1.3 L) was prepared and stirred at room temperature. Methane sulfonyl chloride (61 mL, 787 mmol) was added dropwise over the course of 1 h. This mixture was stirred at 26° C. for 4 h. Stirring was then stopped and the solids were filtered, washed with tetrahydrofuran (3×200 mL), and discarded. The combined tetrahydrofuran layers were concentrated to a viscous, yellow semi-solid which was then triturated with methanol (1 L). The solid was filtered and washed with methanol (2×300 mL). The solid was then dried in the vacuum oven at 50° C. for 12 h. This gave 99.4 g (76%) of 1-(5-bromo-4-(4-(trifluoromethyl)thiazol-2-yl)pyridin-2-yl)-3-propylurea as an off-white solid.

MS (ESP): 409.1 (MH⁺) for $C_{13}H_{12}BrF_3N_4OS$

¹H NMR (300 MHz, DMSO-d₆): δ 0.89 (t, 3H), 1.47 (m, 2H), 3.16 (m, 2H), 7.25 (s, 1H), 8.41 (s, 1H), 8.57 (s, 1H), 8.82 (s, 1H), 9.39 (s, 1H).

Intermediate 47

6-(3-propylureido)-4-(4-(trifluoromethyl)thiazol-2-yl)pyridin -3-ylboronic acid

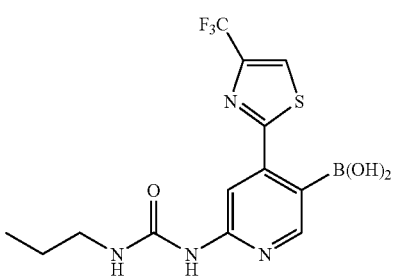

A suspension of 1-(5-bromo-4-(4-(trifluoromethyl)thiazol-2-yl)pyridin-2-yl)-3-propylurea (Intermediate 46, 50 g, 123 mmol) in tetrahydrofuran (1.25 L) was prepared and stirred at −50° C. 2.0M isopropyl magnesium chloride in tetrahydrofuran (183 mL, 368 mmol) was added dropwise over 45 min so that the temperature never rose above −35° C.

The reaction mixture was stirred for a further hour at −40° C. then was cooled to −78° C. 2.5M n-Butyl lithium in hexanes (295 mL, 735 mmol) was then added dropwise to the reaction solution over the course of 1 h so that the temperature never rose above −65° C. This mixture was then allowed to react at −78° C. for 1.5 h. Boron methoxide (164 mL, 1.47 mol) was added in 1 portion and the cold bath was removed. The reaction was allowed to warm to room temperature and stirred for 1 h. 3N Hydrochloric acid (500 mL) was then added slowly to minimize foaming and the reaction was stirred at room temperature for 30 min so that all of the solids dissolved. The reaction was concentrated to remove the tetrahydrofuran and water (1 L) was added. The solution was basified to pH 10 with 24% sodium hydroxide and the total volume was increased to 2 L with water. The aqueous solution was extracted with methyl tert-butyl ether (3×650 mL). The layers were slow to separate. The organic layers were combined and extracted with 5% sodium hydroxide (100 mL). The aqueous phases were combined and acidified to pH 5.5 with 6N hydrochloric acid when a suspension formed. This suspension was extracted with 2:1 ethyl acetate: THF (5×400 mL) ensuring all solid dissolved in the organic phase. The organic phases were combined and back washed with water (1 L). The organics were concentrated and triturated with methyl tert-butyl ether (1 L). The solid obtained was dried in a vacuum oven at 50° C. for 18 h. This gave 25 g (55%) of 6-(3-propylureido)-4-(4-(trifluoromethyl)thiazol-2-yl)pyridin-3-ylboronic acid as an off-white solid.

MS (ESP): 375.0 (MH+) for $C_{13}H_{14}BF_3N_4O_3S$ $^1$H NMR (300 MHz, DMSO-$d_6$): δ 0.90 (t, 3H), 1.45-1.52 (m, 2H), 3.07-3.16 (m, 2H), 7.81 (bt, 1H), 7.91 (s, 1H), 8.20 (br, 2H), 8.31 (d, 1H), 8.65 (m, 1H), 9.32 (s, 1H).

Intermediate 48 ethyl 1-[(1R)-2-hydroxy-1-methylethyl]-6-iodo-4-oxo-1,4-dihydroquinoline-3-carboxylate

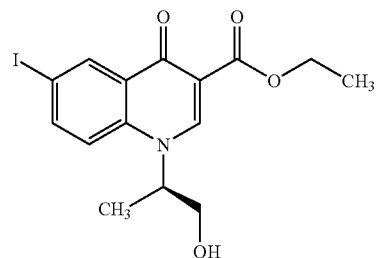

To a solution of ethyl 3-(dimethylamino)-2-(2-fluoro-5-iodobenzoyl)acrylate (Intermediate 24, 1 g, 2.56 mmol) dissolved in THF (10 mL) was added (R)-2-aminopropan-1-ol (300 mg, 2.56 mmol). The reaction mixture was stirred at 60° C. for 2 h. The reaction mixture was concentrated under reduced pressure, and the resulting residue was suspended in DMF (10 mL). Potassium carbonate was added (1.06 g, 7.67 mmol, 3 equiv.), and the reaction mixture was stirred at 70° C. for 18 h. The reaction mixture was cooled down to room temperature and quenched with 1 N HCl. The precipitate that formed was collected by filtration, washed with water and hexanes to provide (R)-ethyl 1-(1-hydroxypropan-2-yl)-6-iodo-4-oxo-1,4-dihydroquinoline-3-carboxylate (446 mg, 39%).

MS (ESP): 402 for $C_{15}H_{16}INO_4$.
NMR ($d_6$-DMSO) δ 8.65 (s, 1H), 8.53 (d, 1H), 8.07 (dd, 1H), 7.82 (d, 1H), 5.23 (s, 1H), 5.05-4.98 (m, 1H), 4.27-4.2 (m, 2H), 3.74.

Intermediates 49-68

The following examples were prepared by the procedure described in Intermediate 48 from the indicated starting material.

| Int | Compound | Data | SM |
|---|---|---|---|
| 49 | (S)-ethyl 1-(1-hydroxypropan-2-yl)-6-iodo-4-oxo-1,4-dihydroquinoline-3-carboxylate | MS (ESP): 402 for $C_{15}H_{16}INO_4$ NMR ($d_6$-DMSO) δ 8.65 (s, 1H), 8.54 (d, 1H), 8.07 (dd, 1H), 7.82 (d, 1H), 5.19 (s, 1H), 5.03-4.98 (m, 1H), 4.27-4.2 (m, 2H), 3.74 (d, 2H), 1.48 (d, 3H), 1.28 (t, 3H) | Intermediate 24 & (S)-2-aminopropan-1-ol |

| Int | Compound | Data | SM |
|---|---|---|---|
| 50 | Ethyl 1-((2R,3R)-1,3-dihydroxybutan-2-yl)-6-iodo-4-oxo-1,4-dihydroquinoline-3-carboxylate | MS (ESP): 432 for $C_{16}H_{16}INO_5$ NMR ($d_6$-DMSO) δ 8.88 (s, 1H), 8.52 (d, 1H), 8.03 (dd, 1H), 7.84 (d, 1H), 5.2 (s, 2H), 4.8-4.76 (m, 1H), 4.26-4.19 (m, 2H), 4.25-4.14 (m, 2H), 3.92-3.79 (m, 2H), 1.27 (t, 3H), 1.1 (d, 3H) | Intermediate 24 & (2R, 3R)-2-aminobutane-1,3-diol |
| 51 | (S)-ethyl 1-(1-hydroxy-3-phenylpropan-2-yl)-6-iodo-4-oxo-1,4-dihydroquinoline-3-carboxylate | MS (ESP): 478 for $C_{21}H_{20}INO_4$ NMR ($d_6$-DMSO) δ 8.7 (s, 1H), 8.44 (d, 1H), 7.98 (dd, 1H), 7.78 (d, 1H), 7.23-7.16 (m, 5H), 7.14-7.09 (m, 1H), 5.38-5.27 (m, 2H), 4.29-4.18 (m, 2H), 3.81 (d, 2H), 3.27-3.15 (m, 2H), 1.29 (t, 3H) | Intermediate 24 & (S)-2-amino-3-phenylpropan-1-ol |
| 52 | Ethyl 1-(1,3-dihydroxypropan-2-yl)-6-iodo-4-oxo-1,4-dihydroquinoline-3-carboxylate | MS (ESP): 418 for $C_{15}H_{16}INO_5$ NMR ($d_6$-DMSO) δ 8.65 (s, 1H), 8.53 (d, 1H), 8.07 (dd, 1H), 7.82 (d, 1H), 5.23 (s, 1H), 5.04-4.98 (m, 1H), 4.27-4.2 (m, 2H), 3.74 (d, 2H), 1.48 (d, 3H), 1.28 (t, 3H) | Intermediate 24 & 2-aminopropan-1,3-diol |
| 53 | (S)-ethyl 1-(1-hydroxy-3-methylbutan-2-yl)-6-iodo-4-oxo-1,4-dihydroquinoline-3-carboxylate | MS (ESP): 430 for $C_{17}H_{20}INO_4$ NMR ($d_6$-DMSO) δ 8.69 (s, 1H), 8.53 (d, 1H), 8.04 (dd, 1H), 7.9 (d, 1H), 5.25-5.15 (m, 1H), 4.65-4.58 (m, 1H), 4.26-4.19 (m, 2H), 3.92-3.86 (m, 1H), 3.77-3.72 (m, 1H), 2.4-2.3 (m, 1H), 1.27 (t, 3H), 1.1 (d, 3H), 0.71 (d, 3H) | Intermediate 24 & (S)-2-amino-3-methylbutan-1-ol |

-continued

| Int | Compound | Data | SM |
|---|---|---|---|
| 54 | (R)-ethyl 1-(1-hydroxy-4-methylpentan-2-yl)-6-iodo-4-oxo-1,4-dihydroquinoline-3-carboxylate | MS (ESP): 444 for $C_{18}H_{22}INO_4$ NMR ($d_6$-DMSO) δ 8.6 (s, 1H), 8.53 (d, 1H), 8.07 (dd, 1H), 7.89 (d, 1H), 5.23 (s, 1H), 4.94 (s, 1H), 4.26-4.19 (m, 2H), 3.71 (d, 2H), 1.87-1.77 (m, 1H), 1.74-1.69 (m, 1H), 1.46-1.38 (m, 1H), 1.27 (t, 3H), 0.89 (d, 3H), 0.84 (t, 3H) | Intermediate 24 & (R)-2-amino-4-methylpentan-1-ol |
| 55 | (S)-ethyl 1-(1-hydroxy-3,3-dimethylbutan-2-yl)-6-iodo-4-oxo-1,4-dihydroquinoline-3-carboxylate | MS (ESP): 443 for $C_{18}H_{22}INO_4$ $H^1$NMR ($d_6$-DMSO) δ 8.62 (s, 1H), 8.53 (s, 1H), 8.01 (s, 1H), 5.07-4.99 (m, 1H), 4.92-4.85 (m, 1H), 4.26-4.20 (m, 2H), 4.02-3.95 (m, 2H), 1.28 (t, 3H), 0.95 (s, 9H) | Intermediate 24 & (S)-2-amino-3,3-dimethylbutan-1-ol |
| 56 | (R)-ethyl 1-(1-hydroxy-3-methylbutan-2-yl)-6-iodo-4-oxo-1,4-dihydroquinoline-3-carboxylate | MS (ESP): 430 for $C_{17}H_{20}INO_4$ $H^1$NMR ($d_6$-DMSO) δ 8.69 (s, 1H), 8.53 (d, 1H), 8.04 (dd, 1H), 7.91 (t, 1H), 4.65-4.59 (m, 1H), 4.26-4.19 (m, 2H), 3.92-3.86 (m, 1H), 3.76-3.72 (m, 1H), 2.31-2.21 (m, 1H), 1.27 (t, 3H), 1.1 (d, 3H), 0.71 (d, 3H) | Intermediate 24 & (R)-2-amino-3-methylbutan-1-ol |
| 57 | (R)-ethyl 1-(1-hydroxy-3-methylbutan-2-yl)-6-iodo-4-oxo-1,4-dihydroquinoline-3-carboxylate | MS (ESP): 416 for $C_{16}H_{18}INO_4$ NMR ($d_6$-DMSO) δ 8.62 (s, 1H), 8.53 (s, 1H), 8.03 (dd, 1H), 7.85 (d, 1H), 4.83 (s, 1H), 4.26-4.19 (m, 2H), 3.77-3.73 (m, 2H), 1.99-1.83 (m, 2H), 1.28 (t, 3H), 0.84 (t, 3H) | Intermediate 24 & (R)-2-aminobutan-1-ol |

-continued

| Int | Compound | Data | SM |
|---|---|---|---|
| 58 | (S)-ethyl 1-(1-hydroxy-3-methylbutan-2-yl)-6-iodo-4-oxo-1,4-dihydroquinoline-3-carboxylate | MS (ESP): 416 for $C_{16}H_{18}INO_4$ NMR ($d_6$-DMSO) δ 8.62 (s, 1H), 8.53 (s, 1H), 8.06 (d, 1H), 7.85 (d, 1H), 4.83 (s, 1H), 4.25-4.2 (m, 2H), 3.78-3.71 (m, 2H), 1.99-1.84 (m, 2H), 1.27 (t, 3H), 0.84 (t, 3H) | Intermediate 24 & (S)-2-aminobutan-1-ol |
| 59 | Ethyl 1-(2-hydroxy-1-(tetrahydro-2H-pyran-4-yl)ethyl)-6-iodo-4-oxo-1,4-dihydroquinoline-3-carboxylate | MS (ESP): 472 for $C_{19}H_{22}INO_5$ [NMR ($d_6$-DMSO) δ 8.75 (s, 1H), 8.52 (s, 1H), 8.05 (d, 1H), 7.94 (d, 1H), 5.22-5.17 (m, 1H), 4.75 (s, 1H), 4.27-4.2 (m, 2H), 3.91-3.88 (m, 2H), 3.81-3.78 (m, 2H), 3.28-3.16 (m, 1H), 2.27-2.23 (m, 1H), 1.77-1.72 (m, 1H), 1.59-1.52 (m, 1H), 1.28 (t, 3H), 1.17 (t, 3H), 1.1-1.02 (1H) | Intermediate 24 & 2-amino-2-(tetrahydro-2H-pyran-4-yl)ethanol |
| 60 | (S)-ethyl 1-(1-hydroxy-3,3-dimethylbutan-2-yl)-6-iodo-4-oxo-1,4-dihydroquinoline-3-carboxylate | MS (ESP): 444 for $C_{18}H_{22}INO_5$ $H^1$NMR ($d_6$-DMSO) δ 8.69 (s, 1H), 8.53 (d, 1H), 8.07 (dd, 1H), 7.89 (d, 1H), 4.95-4.91 (m, 1H), 4.26-4.19 (m, 2H), 3.71 (d, 2H), 1.86-1.8 (m, 1H), 1.75-1.72 (m, 1H), 1.46-1.39 (m, 1H), 1.27 (t, 3H), 0.89 (d, 3H), 0.84 (d, 3H) | Intermediate 24 & (S)-2-amino-4-methylpentan-1-ol |
| 61 | (S)-ethyl 6-iodo-4-oxo-1-((tetrahydrofuran-2-yl)methyl)-1,4-dihydroquinoline-3-carboxylate | MS (ESP): 428 for $C_{17}H_{18}INO_4$ NMR ($d_6$-DMSO) δ 8.62 (s, 1H), 8.5 (d, 1H), 8.06 (dd, 1H), 7.74 (d, 1H), 4.6 (dd, 1H), 4.3-4.27 (m, 1H), 4.25-4.21 (m, 2H), 4.17-4.12 (m, 1H), 3.82-3.75 (m, 1H), 3.65-3.61 (m, 1H), 2.06-1.9 (m, 1H), 1.87-1.8 (m, 2H), 1.63-1.57 (m, 1H), 1.28 (t, 3H) | Intermediate 24 & (S)-(tetrahydrofuran-2-yl)methan-amine |

| Int | Compound | Data | SM |
|---|---|---|---|
| 62 | Ethyl 6-iodo-4-oxo-1-((tetrahydro-2H-pyran-4-yl)methyl)-1,4-dihydroquinoline-3-carboxylate | MS (ESP): 442d for $C_{18}H_{20}INO_4$ NMR ($d_6$-DMSO) δ 8.66 (s, 1H), 8.51 (d, 1H), 8.07 (dd, 1H), 7.74 (d, 1H), 4.33-4.19 (m, 4H), 3.84 (d, 2H), 3.23-3.15 (m, 2H), 2.08-2.02 (m, 1H), 1.42-1.37 (m, 4H), 1.28 (t, 3H) | Intermediate 24 & (tetrahydro-2H-pyran-4-yl)methan-amine |
| 63 | Ethyl 1-((2S,3S)-1,3-dihydroxypentan-2-yl)-6-iodo-4-oxo-1,4-dihydroquinoline-3-carboxylate | MS (ESP): 444 for $C_{18}H_{22}INO_4$ $H^1$NMR ($d_6$-DMSO) δ 8.69 (S, 1H), 8.53 (d, 1H), 8.05 (d, 1H), 7.89 (d, 1H), 5.16-5.13 (m, 1H), 4.68 (s, 1H), 4.26-4.19 (m, 2H), 3.94-3.87 (m, 1H), 3.78-3.72 (m, 1H), 2.13-2.08 (m, 1H), 1.28 (t, 3H), 1.16-0.95 (m, 2H), 1.07 (d, 2H), 0.73 (t, 3H) | Intermediate 24 & (2S,3S)-2-amino-3-methylpentan-1-ol |
| 64 | Ethyl 1-(1-hydroxybutan-2-yl)-6-iodo-4-oxo-1,4-dihydroquinoline-3-carboxylate | MS (ESP): 416 for $C_{16}H_{18}INO_4$ NMR ($d_6$-DMSO) δ 8.62 (s, 1H), 8.53 (s, 1H0, 8.06 (dd, 1H), 7.85 (d, 1H), 5.18-5.13 (m, 1H), 4.83 (s, 1H), 4.27-4.2 (m, 2H), 3.76-3.72 (m, 2H), 1.97-1.82 (m, 2H), 1.28 (t, 3H), 0.84 (t, 3H) | Intermediate 24 & 2-aminobutan-1-ol |
| 65 | Ethyl 6-iodo-1-((1-methylpiperidin-4-yl)methyl)-4-oxo-1,4-dihydroquinoline-3-carboxylate | MS (ESP): 455 for $C_{19}H_{23}IN_2O_3$ NMR ($d_6$-DMSO) δ 8.65 (s, 1H), 8.5 (d, 1H), 8.07 (dd, 1H), 7.71 (d, 1H), 4.27-4.19 (m, 2H), 2.74-2.7 (m, 2H), 2.09 (s, 3H), 1.72-1.66 (m, 3H), 1.45-1.42 (m, 2H), 1.28 (t, 3H) | Intermediate 24 & (1-methylpiper-idin-4-yl)methan-amine |

| Int | Compound | Data | SM |
|---|---|---|---|
| 66 | (R)-ethyl 1-(1-hydroxy-3,3-dimethylbutan-2-yl)-6-iodo-4-oxo-1,4-dihydroquinoline-3-carboxylate | MS (ESP): 444 for $C_{18}H_{22}INO_4$ NMR ($d_6$-DMSO) δ 8.62 (s, 1H), 8.53 (s, 1H), 8.01 (s, 2H), 5.08-5.04 (m, 1H), 4.89-4.84 (m, 1H), 4.26-4.22 (m, 2H), 4.02-3.98 (m, 2H), 1.28 (t, 3H), 0.95 (s, 9H) | Intermediate 24 & (R)-2-amino-3,3-dimethylbutan-1-ol |
| 67 | (R)-ethyl 1-(1-hydroxy-3-(4-hydroxyphenyl)propan-2-yl)-6-iodo-4-oxo-1,4-dihydroquinoline-3-carboxylate | MS (ESP): 494 for $C_{21}H_{20}INO_5$ NMR ($d_6$-DMSO) δ 8.64 (s, 1H), 8.45 (d, 1H), 7.99 (dd, 1H), 7.76 (d, 1H), 6.98 (d, 2H), 6.56 (d, 2H), 5.18 (s, 1H), 4.29-4.19 (m, 2H), 3.78 (d, 2H), 3.13-3.09 (m, 2H), 1.29 (t, 3H) | Intermediate 24 & (R)-4-(2-amino-3-hydroxypropyl)-phenol |
| 68 | (S)-ethyl 1-(1-cyclohexyl-2-hydroxyethyl)-6-iodo-4-oxo-1,4-dihydroquinoline-3-carboxylate | MS (ESP): 470 for $C_{20}H_{24}INO_4$ NMR ($d_6$-DMSO) δ 8.71 (s, 1H), 8.53 (d, 1H), 8.04 (dd, 1H), 7.9 (t, 1H), 5.15 (s, 1H), 4.68 (s, 1H), 4.27-4.2 (m, 2H), 3.92-3.89 (m, 1H), 3.77-3.74 (m, 1H), 1.98-1.9 (m, 2H), 1.82-1.74 (m, 1H), 1.61-1.55 (m, 2H), 1.28 (t, 3H), 1.25-1.2 (m, 2H), 1.09-1.05 (m, 2H), 0.92-0.86 (m, 1H) | Intermediate 24 & (S)-2-amino-2-cyclohexyl-ethanol |

Intermediate 69 ethyl 6-iodo-1-[2-(1-methylpiperidin-4-yl)ethyl]-4-oxo-1,4-dihydroquinoline-3-carboxylate

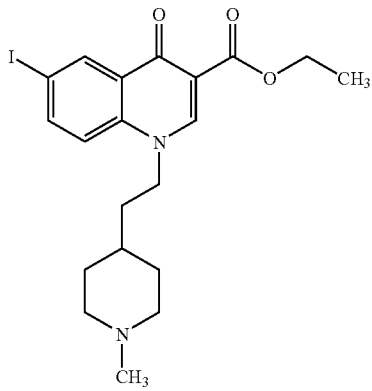

To a solution of ethyl 3-(dimethylamino)-2-(2-fluoro-5-iodobenzoyl)acrylate (Intermediate 24, 1 g, 2.56 mmol) dissolved in THF (5.5 mL) was added 2-(1-methylpiperidin-4-yl-ethanamine (0.406 mL, 2.56 mmol). The reaction mixture was stirred at 60° C. for 2 h. Potassium carbonate was added (1.06 g, 7.67 mmol), and the reaction was stirred for 18 h and cooled down to room temperature. The reaction was quenched with 1 N HCl and partitioned between dichloromethane (10 mL) and water (20 mL). The aqueous layer was extracted with dichloromethane (2×10 mL), and the organics were dried over sodium sulfate and concentrated to give ethyl 6-iodo-1-(2-(1-methylpiperidin-4-yl)ethyl)-4-oxo-1,4-dihydroquinoline-3-carboxylate as a light yellow solid (1.08 g, 90%).

MS (ESP): 469 for $C_{20}H_{25}IN_2O_4$.

NMR ($d_6$-DMSO) δ 8.7 (s, 1H), 8.5 (d, 1H), 8.089 (dd, 1H), 7.6 (d, 1H), 4.4-4.35 (m, 1H), 4.26-4.19 (m, 2H), 2.75-2.7 (m, 2H), 2.12 (s, 3H), 1.83-1.74 (m, 2H), 1.69-1.61 (m, 4H), 1.28 (t, 3H), 1.25-1.13 (m, 2H).

Intermediate 70 ethyl 6-iodo-1-[1-(methoxymethyl)-2-methylpropyl]-4-oxo-1,4-dihydroquinoline-3-carboxylate

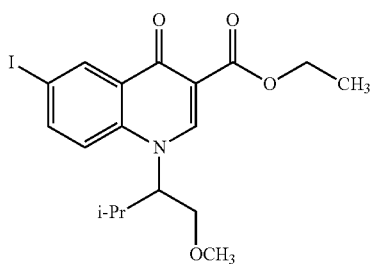

To a solution of ethyl 3-(dimethylamino)-2-(2-fluoro-5-iodobenzoyl)acrylate (Intermediate 24, 1 g, 2.56 mmol) dissolved in THF (10 mL) was added 1-methoxy-3-methylbutan-2-amine hydrochloride (366 mg, 2.38 mmol) followed by potassium carbonate. The reaction mixture was stirred at 60° C. for 2 d. The reaction mixture was concentrated under reduced pressure and the residue was resuspended in DMF (10 mL). Potassium carbonate was added (978 mg, 7.08 mmol), and the reaction mixture was stirred at 70° C. for 2 h. The reaction mixture was cooled down to room temperature and quenched with 1 N HCl. The reaction mixture was partitioned between water (20 mL) and ethyl acetate (20 mL). The aqueous layer was extracted with ethyl acetate, and the organics were dried and concentrated to provide ethyl 6-iodo-1-(1-methoxy-3-methylbutan-2-yl)-4-oxo-1,4-dihydroquinoline-3-carboxylate (623 mg, 60%).

MS (ESP): 444 for $C_{18}H_{22}INO_4$.

NMR ($d_6$-DMSO) δ 8.69 (s, 1H), 8.53 (d, 1H), 8.05 (d, 1H), 7.94 (d, 1H), 4.83-4.78 (m, 1H), 4.26-4.2 (m, 2H), 3.9-3.74 (m, 1H), 3.71-3.68 (m, 1H), 3.46-3.4 (m, 1H), 2.3-2.26 (m, 1H), 1.28 (t, 3H), 1.11 (d, 3H), 0.92-0.85 (m, 2H), 0.71 (d, 3H).

Intermediates 71-77

The following compounds were prepared according to either of the procedures described below from the starting materials indicated.

General Procedures

Procedure A: (Z)-Ethyl 3-(dimethylamino)-2-(2-fluoro-5-iodobenzoyl)acrylate (Intermediate 24, eq, 2.5 mmol) and the appropriate amine (1.1-1.2 eq) were diluted with THF (10 mL) and heated to 60° C. for 1 h. After cooling to RT, the mixture was conconcentrated in vacuo. Potassium carbonate (3 eq) and DMF (5 mL) were added and the mixture was then heated to 70° C. overnight. The mixture was cooled to 0° C. and acidified to approx. pH 4 with 1 N aq HCl. The resultant solid was collected and used without additional purification.

Procedure B: (Z)-Ethyl 3-(dimethylamino)-2-(2-fluoro-5-iodobenzoyl)acrylate (Intermediate 24, 1 eq, 2.5 mmol) and the appropriate amine hydrochloride salt (1.1-1.2 eq) were diluted with THF (10 mL). Potassium carbonate (1.2 eq) was added and the mixture was heated to 60° C. for 1 h. After cooling to room temperature, the mixture was concentrated in vacuo. Additional potassium carbonate (3 eq) and DMF (5 mL) were added and the mixture was then heated to 70° C. overnight. The mixture was cooled to 0° C. and acidified to approx. pH 4 with 1 N aq HCl. The resultant solid was collected and used without additional purification

| Int | Compound | Data | SM |
|---|---|---|---|
| 71 | ethyl 1-(4-(hydroxymethyl)tetrahydro-2H-pyran-4-yl)-6-iodo-4-oxo-1,4-dihydroquinoline-3-carboxylate | LC/MS (ES⁺)[(M + H)⁺]: 458 for $C_{18}H_{20}INO_5$<br>NMR (DMSO-$d_6$): δ 8.71 (s, 1H); 8.57 (d, 1H); 8.05 (m, 1H); 7.94 (dd, 1H); 5.36 (br s, 1H); 4.23 (q, 2H); 4.17 (s, 2H); 3.68 (m, 4H); 2.35 (m, 4H); 1.27 (t, 3H). | (4-amino-tetrahydro-2H-pyran-4-yl)methanol |
| 72 | ethyl 1-((1-(tert-butoxycarbonyl)piperidin-2-yl)methyl)-6-iodo-4-oxo-1,4-dihydroquinoline-3-carboxylate | LC/MS (ES⁺)[(M + H)⁺]: 541 for $C_{23}H_{29}IN_2O_5$<br>¹H NMR (DMSO-$d_6$): δ 8.50 (d, 1H); 8.47 (s, 1H); 8.06 (d, 1H); 7.73 (d, 1H); 4.70 (m, 1H); 4.47 (m, 2H); 4.21 (m, 2H); 3.91 (m, 1H); 3.14 (m, 1H); 1.87 (m, 1H); 1.59 (m, 4H); 1.26 (m, 4H); 1.10 (br s, 3H); 0.75 (br s, 6H). | 2-(Aminomethyl)-1-N-Boc-piperidine |
| 73 | ethyl 6-iodo-4-oxo-1-(pyridin-4-ylmethyl)-1,4-dihydroquinoline-3-carboxylate | LC/MS (ES⁺)[(M + H)⁺]: 435 for $C_{18}H_{15}IN_2O_3$<br>¹H NMR (DMSO-$d_6$): δ 8.92 (s, 1H); 8.51 (m, 3H); 7.95 (dd, 1H); 7.31 (d, 1H); 7.17 (m, 2H); 5.72 (s, 2H); 4.24 (q, 2H); 1.28 (t, 3H). | 4-Aminomethyl pyridine |
| 74 | ethyl 1-(1-(dimethylamino)propan-2-yl)-6-iodo-4-oxo-1,4-dihydroquinoline-3-carboxylate, hydrochloride salt | LC/MS (ES⁺)[(M + H)⁺]: 429 for $C_{17}H_{21}IN_2O_3$<br>¹H NMR (DMSO-$d_6$): δ 10.23 (br s, 1H); 8.53 (s, 1H); 8.45 (d, 1H); 8.03 (m, 1H); 7.88 (m, 1H); 5.42 (br s, 1H); 4.17 (q, 2H); 3.72 (m, 1H); 3.59 (m, 1H); 2.70 (br s, 6H); 1.50 (m, 3H); 1.21 (t, 3H). | 1-Dimethyl-amino-2-propylamine |

| Int | Compound | Data | SM |
|---|---|---|---|
| 75 | ethyl 6-iodo-1-((1-methylpiperidin-2-yl)methyl)-4-oxo-1,4-dihydroquinoline-3-carboxylate, hydrochloride salt | LC/MS (ES⁺)[(M + H)⁺]: 455 for $C_{19}H_{23}IN_2O_3$ | (1-Methyl-piperidin-2-yl)methan-amine |
| 76 | ethyl 6-iodo-1-((1-methyl-1H-imidazol-4-yl)methyl)-4-oxo-1,4-dihydroquinoline-3-carboxylate | LC/MS (ES⁺)[(M + H)⁺]: 438 for $C_{17}H_{16}IN_3O_3$<br>¹H NMR (DMSO-d₆): δ 8.82 (s, 1H); 8.47 (d, 1H); 8.00 (dd, 1H); 7.79 (d, 1H); 7.51 (s, 1H); 7.21 (s, 1H); 5.41 (s, 2H); 4.23 (q, 2H); 3.58 (s, 3H); 1.28 (t, 3H). | (1-Methyl-1H-imidazol-4-yl)methan-amine |
| 77 | (S)-ethyl 1-(1-tert-butoxy-3-methyl-1-oxobutan-2-yl)-6-iodo-4-oxo-1,4-dihydroquinoline-3-carboxylate | LC/MS (ES⁺)[(M + H)⁺]: 500 for $C_{21}H_{26}INO_5$<br>¹H NMR (DMSO-d₆): δ 8.66 (m, 1H); 8.53 (d, 1H); 8.10 (dd, 1H); 7.95 (m, 1H); 5.26 (d, 1H); 4.24 (q, 2H); 2.60 (m, 1H); 1.36 (br s, 9H); 1.28 (t, 3H); 1.15 (m, 3H); 0.78 (br s, 3H). | L-valine tert-butyl ester hydrochloride |

Intermediate 78

1-(1,3-dimethoxypropan-2-yl)-6-iodo-4-oxo-1,4-dihydroquinoline-3-carboxylic acid

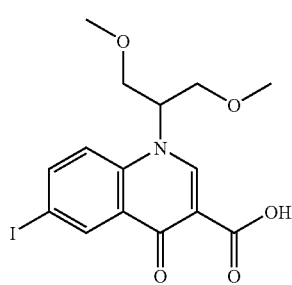

Ethyl 1-(1,3-dimethoxypropan-2-yl)-6-iodo-4-oxo-1,4-dihydroquinoline-3-carboxylate (Intermediate 22, 270 mg, 0.60 mmol) was dissolved in tetrahydrofuran (20 mL) and water (5 mL). Lithium hydroxide (56 mg, 2.42 mmol) was added and the mixture was stirred for 10 min at room temperature. The reaction mixture was then refluxed at 80° C. for 1 h. The reaction mixture was concentrated under reduced pressure and water (10 mL) was added. The pH was adjusted to 2 with hydrochloric acid (2N) and the solid that precipitated was collected by filtration and dried to afford 185 mg (75%) of 1-(1,3-dimethoxypropan-2-yl)-6-iodo-4-oxo-1,4-dihydroquinoline-3-carboxylic acid.

¹H NMR (400 MHz, DMSO-d₆): δ 3.22 (s, 6H), 3.62 (q, 2H), 3.72 (q, 2H), 4.68 (m, 1H), 7.81 (d, 1H), 8.14 (d, 1H), 8.78 (s, 1H), 9.14 (s, 1H)

LC-MS: m/z 417.8 (M+H).

Intermediate 79

Tert-butyl 4-{[1-(1,3-dimethoxypropan-2-yl)-6-iodo-4-oxo-1,4-dihydroquinolin-3-yl]carbonyl}piperazine-1-carboxylate

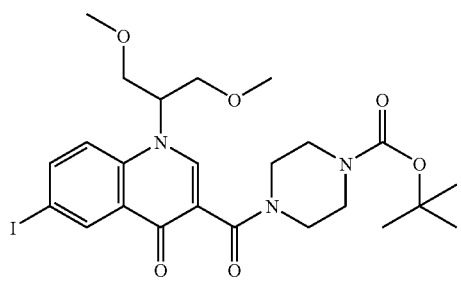

To a solution of 1-(1,3-dimethoxypropan-2-yl)-6-iodo-4-oxo-1,4-dihydroquinoline-3-carboxylic acid (Intermediate 78, 500 mg, 1.12 mmol) and tert-butyl piperazine-1-carboxylate (312 mg, 1.67 mmol) in dichloromethane (50 mL) was added hydroxybenzotriazole (HOBT) (183 mg, 1.12 mmol) and N-methyl morpholine (484 mg, 4.79 mmol). The reaction mixture was stirred for 1 h at room temperature and 1-ethyl-3-(3-dimethylaminopropyl)carbodiimide hydrochloride (EDCI HCl) (390. mg, 2.15 mmol) was added. The resulting reaction mixture was stirred for room temperature overnight. The reaction mixture was quenched with dilute hydrochloric acid (2N, 30 mL) and the layers were separated. The organic layer was washed with saturated sodium bicarbonate solution (40 mL), water (60 mL) and finally with brine successively and dried over anhydrous sodium sulphate, filtered, concentrated under vacuum to afford tert-butyl 4-{[1-(1,3-dimethoxypropan-2-yl)-6-iodo-4-oxo-1,4-dihydroquinolin-3-yl]carbonyl}piperazine-1-carboxylate 400 mg (57%) as thick oil.

$^1$H NMR (400 MHz, DMSO-$d_6$): δ 1.40 (s, 9H), 3.08-3.28 (m, 12H), 3.22-3.72 (m, 8H), 3.79 (m, 1H), 4.52 (m, 1H), 7.82 (d, 1H), 8.08 (d, 1H), 8.78 (2s, 2H).

MASS (APCI+ve Scan): m/z 586.1 (M+H).

Intermediate 80

1-(1,3-dimethoxypropan-2-yl)-6-iodo-3-[(4-methylpiperazin-1-yl)carbonyl]quinolin-4(1H)-one

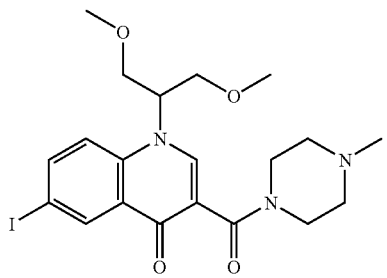

To a solution of 1-(1,3-dimethoxypropan-2-yl)-6-iodo-4-oxo-1,4-dihydroquinoline-3-carboxylic acid (Intermediate 78, 300 mg, 0.72 mmol) and 1-methylpiperazine (100 mg, 1.00 mmol) in dichloromethane (50 mL) was added hydroxybenzotriazole (HOBT) (110 mg, 0.72 mmol) and N-methylmorpholine (290 mg, 2.87 mmol). The reaction mixture was stirred for 1 h at room temperature and 1-ethyl-3-(3-dimethylaminopropyl)carbodiimide hydrochloride (EDC HCl) (234 mg, 1.29 mmol) was added. The resulting reaction mixture was stirred at room temperature over night. The reaction mixture was quenched with 2N hydrochloric acid (30 mL) and the layers were separated. The organic layer was washed with saturated sodium bicarbonate solution (40 mL), water (60 mL) and finally with brine successively and dried over anhydrous sodium sulphate, filtered and concentrated under vacuum to afford 1-(1,3-dimethoxypropan-2-yl)-6-iodo-3-[(4-methylpiperazin-1-yl)carbonyl]quinolin-4(1H)-one 300 mg (80%) as thick oil.

$^1$H NMR (400 MHz, DMSO-$d_6$): δ 2.17 (s, 2H), 2.21 (s, 3H), 3.21-3.46 (m, 4H), 3.16-3.31 (s, 6H), 3.41-3.72 (m, 5H), 3.85 (s, 1H), 4.57 (m, 1H), 7.81 (d, 1H), 8.07 (d, 1H), 8.74 (2s, 2H).

MASS (APCI+ve Scan): m/z 500 (M+H).

Intermediates 81-82

The following compounds were prepared according to the procedure described for Intermediate 80 from the starting material listed in the table.

| Int | Compound | Data | SM |
| --- | --- | --- | --- |
| 81 | 3-[(4-acetylpiperazin-1-yl)carbonyl]-1-(1,3-dimethoxypropan-2-yl)-6-iodoquinolin-4(1H)-one | $^1$H NMR (400 MHz, DMSO-$d_6$): δ 1.96-2.20 (m, 3H), 2.10 (s, 3H), 2.35 (m, 3H), 3.18-3.30 (m, 6H), 3.79 (m, 1H), 4.56 (m, 1H), 7.82 (d, 1H), 8.09 (d, 1H), 8.78 (m, 2H). MASS (APCI + ve Scan): m/z 528.1 (M + H) | Intermediate 78 and 3-(4-acetyl)piperazine |

-continued

| Int | Compound | Data | SM |
|---|---|---|---|
| 82 | 1-(1,3-dimethoxypropan-2-yl)-6-iodo-3-{[4-(methylsulfonyl)piperazin-1-yl]carbonyl}quinolin-4(1H)-one | $^1$H NMR (400 MHz, DMSO-$d_6$): δ 2.97 (s, 3H), 3.11-3.40 (m, 14H), 3.45 (m, 1H), 3.56 (m, 4H), 4.04 (m, 1H), 4.53 (m, 1H), 7.81 (d, 1H), 8.12 (d, 1H), 8.78 (br s, 2H). MASS (APCI + ve Scan): m/z 564.0 (M + H) | Intermediate 78 and 3-(4-methane-sulfonyl)pi-perazine |

Intermediate 83

Methyl 2-(bis(tert-butoxycarbonyl)amino)-5-bromoisonicotinate

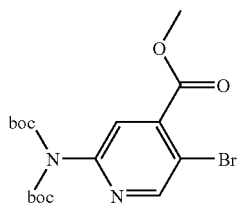

To a 5 L round bottom flask was charged methyl 2-amino-5-bromoisonicotinate (200 g, 866 mmol) and tert-butanol (3000 mL). The reaction mixture was kept at 30° C., then 4-dimethylaminopyridine (DMAP, 6.3 g, 52 mmol) and di-tert-butyl dicarbonate (566 g, 2.6 mol) were added, the resulting mixture was slowly heated to 60° C. for 2 h. The reaction mixture was concentrated under reduced pressure to one-fourth volume. A yellow needle-like solid precipitated which was collected by filtration and washed by ethanol. After drying under vacuum overnight at 25° C., the first crop was obtained as 282 g pale yellow needle-like solid.

MS (ESP): 277.1 (M+H$^+$-Boc-tBu) for $C_{17}H_{23}BrN_2O_6$ $^1$H NMR (300 MHz, CDCl$_3$): δ 1.5 (s, 18H), 4.0 (s, 32H), 7.7 (s, 1H), 8.7 (s, 1H).

Intermediate 84 tert-butyl 5-bromo-4-carbamoylpyridin-2-ylcarbamate

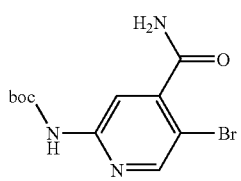

A solution of methyl 2-(bis(tert-butoxycarbonyl)amino)-5-bromoisonicotinate (Intermediate 83, 100 g, 232 mmol) in 7 N ammonia in methanol (600 mL) was allowed to stir at 50° C. in a 1 L sealed tube overnight. The resulting mixture was evaporated to dryness and the crude product was directly used for the next step without further purification.

MS (ESP): 339.9 (M+Na$^+$) for $C_{11}H_{14}BrN_3O_3$ $^1$H NMR (300 MHz, dmso-$d_6$): δ 1.47 (s, 9H), 7.82 (d, 2H), 8.07 (s, 1H), 8.41 (d, 1H), 10.2 (s, 1H).

Intermediate 85 tert-butyl 5-bromo-4-carbamothioylpyridin-2-ylcarbamate

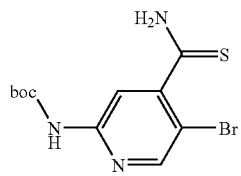

The crude tert-butyl 5-bromo-4-carbamoylpyridin-2-ylcarbamate (Intermediate 84, 232 mmol) was treated with Lawesson's Reagent (94 g, 232 mmol, 1 eq) and tetrahydrofuran (700 mL), the resulting mixture was heated at reflux for 1 h, then it was allowed to stir at room temperature over the weekend. The mixture was concentrated to dryness in vacuo and toluene (~300 mL) was added. A bright yellow solid precipitated formed which was collected by filtration and washed with toluene, then dried in the vacuum oven at 50° C. for 4 h, yielding 75 g of a bright yellow solid (97%).

MS (ESP): 354.2 (M+Na$^+$) for $C_{11}H_{14}BrN_3O_2S$

¹H NMR (300 MHz, CDCl₃): δ 1.53 (s, 9H), 7.03 (br, 1H), 7.61 (br, 1H), 7.74 (br, 1H), 8.2 (s, 1H), 8.35 (s, 1H).

Intermediate 86 tert-butyl 5-bromo-4-(4-hydroxy-4-(trifluoromethyl)-4,5-dihydrothiazol-2-yl)pyridin-2-ylcarbamate

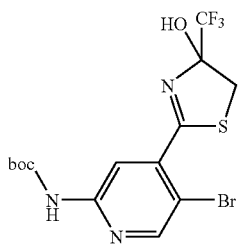

To a 2 L round bottom flask was charged tert-butyl 5-bromo-4-carbamothioylpyridin-2-ylcarbamate (Intermediate 85, 50 g, 151 mmol) in tetrahydrofuran (800 mL), then solid sodium bicarbonate (25.4 g, 302 mmol) was added followed by 1,1,1-trifluoro-3-bromoacetone (31 mL, 290 mmol). The resulting mixture (yellow suspension) was allowed to stir at room temperature overnight. The white suspension was filtered and the solid was washed with water (2.2~2.5 L). The white solid was dried under vacuum to give 56.8g of white powder (85%)

MS (ESP): 386.0 (M-t-Bu) for $C_{14}H_{15}BrF_3N_3O_3S$

¹H NMR (300 MHz, CDCl₃): δ 1.6 (s, 9H), 3.3 (br, 2H), 3.6 (d, 1H), 3.9 (d, 1H), 8.5 (s, 1H).

Intermediate 87 tert-butyl 5-bromo-4-(4-(trifluoromethyl)thiazol-2-yl)pyridin-2-ylcarbamate

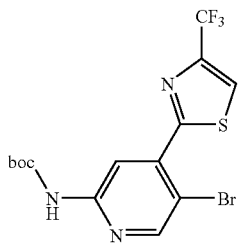

To a 2 L round bottom flask was charged tert-butyl 5-bromo-4-(4-hydroxy-4-(trifluoromethyl)-4,5-dihydrothiazol-2-yl)pyridin-2-ylcarbamate (Intermediate 86, 56.8 g, 128 mmol) and dimethoxyethane (800 mL). The reaction mixture was chilled in an ice-water bath, then trifluoroacetic anhydride (69 mL, 514 mmol) and 2,6-lutidine (133 mL, 1.15 mol) were added simultaneously over 1 h. An orange/yellow solution which resulted was allowed to stir in the ice-water bath for 30 min, then the solution was warmed to room temperature. The orange solution was concentrated under reduced pressure to dryness, and the resulting residue was triturated with methanol. The solid was collected by filtration and washed with more methanol, dried under vacuum overnight, yielding 49 g of white solid.

MS (ESP): 368.0 (M-t-Bu) for $C_{14}H_{13}BrF_3N_3O_2S$

¹H NMR (300 MHz, CDCl₃): δ 1.6 (s, 9H), 8.0 (s, 1H), 8.2 (br, 1H), 8.55 (s, 1H), 8.65 (s, 1H).

Intermediate 88

1-(5-bromo-4-(4-(trifluoromethyl)thiazol-2-yl)pyridin-2-yl)-3-isopropylurea

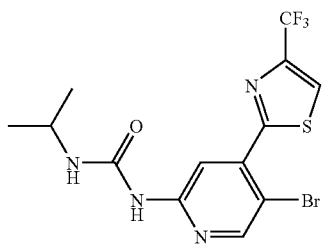

A mixture of tert-butyl 5-bromo-4-(4-(trifluoromethyl)thiazol-2-yl)pyridin-2-ylcarbamate (Intermediate 87, 25 g, 59 mmol), isopropyl amine (250 mL) and acetonitrile (100 mL) was heated at 130° C. in a Parr Bomb apparatus for 50 h (~150 PSI). The reaction mixture was cooled to room temperature and the reaction filtered through Celite, and the filtrate was washed with tetrahydrofuran (~300 mL). The solvents were evaporated and the residue was triturated with methanol (200 mL), filtered and the solid was dried to give 14.6 g of product.

MS (ESP): 410 (MH⁺) for $C_{13}H_{12}BrF_3N_4OS$.

Intermediate 89

6-(3-isopropylureido)-4-(4-(trifluoromethyl)thiazol-2-yl)pyridin-3-ylboronic acid

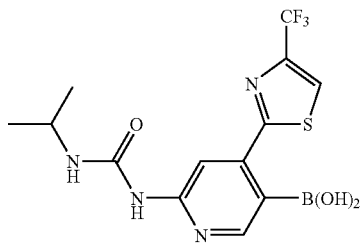

A suspension of 1-(5-bromo-4-(4-(trifluoromethyl)thiazol-2-yl)pyridin-2-yl)-3-isopropylurea (Intermediate 88, 14.6 g, 35 7 mmol) in tetrahydrofuran (400 mL) was prepared and stirred at −50° C. 2.0M Isopropyl magnesium chloride in tetrahydrofuran (53.6 mL, 107 mmol) was added dropwise over 45 min so that the temperature never rose above −35° C. The reaction mixture was stirred for 1 h at −40° C. then was cooled to −78° C. 2.5M n-Butyl lithium in hexanes (85.8 mL, 215 mmol) was then added dropwise to the reaction solution so that the temperature never rose above −65° C. This reaction mixture was then allowed to react at −78° C. for 1.5 h. Boron methoxide (44 mL, 394 mmol) was added in 1 portion and the cold bath was removed. The reaction mixture was allowed to warm to room temperature and stir for 1 h. 3N Hydrochloric acid (500 mL) was then added slowly to minimize foaming and the reaction was stirred at room temperature for 30 min The reaction mixture was concentrated under high vacuum to remove the tetrahydrofuran and water (1 L). The solution was basified to pH 10 with 24% sodium hydroxide and the total volume was increased to 2 L with water. The aqueous solution was extracted with methyl tert-butyl ether (3×300 mL). The organic layers were combined and extracted with 5% sodium hydroxide (100 mL). The aqueous phases were combined and acidified to pH 5.5 with 6 N hydrochloric acid when a suspension formed. This suspension was extracted with 2:1 ethyl acetate: THF (5×400 mL). The organic phases were combined and back washed with water (1 L). The organics were concentrated and triturated with methyl tert-butyl ether (1 L). The solid obtained was dried in a vacuum oven at 50° C. to give 10.4 g of product.

MS (ESP): 375.0 (MH$^+$) for $C_{13}H_{14}BF_3N_4O_3S$
$^1$H NMR (300 MHz, DMSO-d$_6$): δ 1.24 (d, 6H), 3.98 (m, 1H), 7.80 (bt, 1H), 7.91 (s, 1H), 8.20 (br, 2H), 8.31 (d, 1H), 8.63 (m, 1H), 9.32 (s, 1H).

Intermediate 90 ethyl 6-iodo-1-(2-morpholinoethyl)-4-oxo-1,4-dihydroquinoline-3-carboxylate

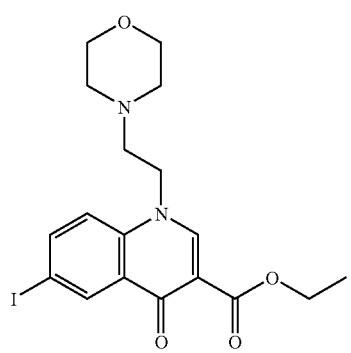

2-Morpholinoethanamine (0.88 g, 6.7 mmol) was added to the stock solution of (Z)-ethyl 3-(dimethylamino)-2-(3-iodobenzoyl)acrylate (Intermediate 24, 0.38M, 18 mL, 7 mmol) and the mixture was heated at 40° C. for 3 h. The solvent was removed in vacuo and the resulting residue was dried in a vacuum oven for 1.5 h. The residue was then dissolved in dimethyl formamide (5 mL) and potassium carbonate powder (1.2 g, 10 mmol) was added. The reaction was heated at 70° C. for a further 3 h then cooled to room temperature. The crude reaction mixture was placed into a fridge for a 3 h. The solid precipitate that formed was collected by filtration, washed with a small amount of dimethylformamide, followed by water, then dried under high vacuum.

MS (ESP): 457 (M+H$^+$) for $C_{18}H_{21}IN_2O_4$ $^1$H NMR (300 MHz, DMSO-d$_6$): δ 1.28 (t, 3H), 2.42 (brs, 4H), 2.61 (brs, 2H), 3.50 (br, 4H), 4.23 (q, 2H), 4.46 (br, 2H), 7.67 (d, 1H), 8.05 (d, 1H), 8.50 (s, 1H), 8.64 (s, 1H).

Intermediates 91-94

The following compounds were prepared according to the procedure described for Intermediate 90 from the starting materials indicated.

| Int | Compound | Data | SM |
|---|---|---|---|
| 91 | ethyl 6-iodo-4-oxo-1-(tetrahydro-2H-pyran-4-yl)-1,4-dihydroquinoline-3-carboxylate | MS (ESP): 428.1 (M + H$^+$) for $C_{17}H_{18}INO_4$<br>$^1$H NMR (300 MHz, DMSO-d$_6$): δ 1.29 (t, 3H), 2.00 (brs, 4H), 3.64 (m, 2H), 4.00 (d, 2H), 4.23 (q, 2H), 4.95 (m, 1H), 7.92 (d, 1H), 8.06 (d, 1H), 8.53 (s, 1H), 8.60 (s, 1H) | Intermediate 24 and tetrahydro-2H-pyran-4-amine |

| Int | Compound | Data | SM |
|---|---|---|---|
| 92 | ethyl 6-iodo-1-(2-(4-methylpiperazin-1-yl)ethyl)-4-oxo-1,4-dihydroquinoline-3-carboxylate | MS (ESP): 470.1 (M + H$^+$) for C$_{19}$H$_{24}$IN$_3$O$_3$<br>$^1$H NMR (300 MHz, DMSO-d$_6$): δ 1.29 (t, 3H), 2.10 (s, 3H), 2.22 (br, 4H), 2.41 (br, 4H), 2.60 (t, 2H), 4.22 (q, 2H), 4.43 (t, 2H), 7.66 (d, 1H), 8.03 (d, 1H), 8.50 (s, 1H), 8.59 (s, 1H). | Intermediate 24 and 2-(4-methyl-piperazino)-ethanamine |
| 93 | ethyl 6-iodo-4-oxo-1-(2-(pyrrolidin-1-yl)ethyl)-1,4-dihydroquinoline-3-carboxylate | MS (ESP): 441.1 (M + H$^+$) for C$_{18}$H$_{21}$IN$_2$O$_3$<br>$^1$H NMR (300 MHz, dmso-d$_6$): δ 1.28 (t, 3H), 1.65 (br, 4H), 2.48 (m, 4H), 2.75 (br, 2H), 4.20 (q, 2H), 4.45 (m, 2H), 7.64 (d, 1H), 8.04 (d, 1H), 8.63 (s, 1H), 8.65 (s, 1H) | Intermediate 24 and 2-pyrrolidino-ethanamine |
| 94 | ethyl 6-iodo-4-oxo-1-(2-(tetrahydro-2H-pyran-4-yl)ethyl)-1,4-dihydroquinoline-3-carboxylate | MS (ESP): 456.1 (M + H$^+$) for C$_{19}$H$_{22}$INO$_4$<br>$^1$H NMR (300 MHz, CDCl$_3$): δ 1.22 (m, 1H), 1.28 (t, 3H), 1.67 (m, 4H), 3.27 (t, 2H), 3.34 (m, 2H), 3.84 (d, 2H), 4.22 (q, 2H), 4.40 (m, 2H), 7.59 (d, 1H), 8.08 (d, 1H), 8.50 (s, 1H), 8.72 (s, 1H) | Intermediate 24 and 2-(tetrahydro-2H-pyran-4-yl)-ethanamine |

Intermediate 95

(R)-ethyl 1-((1-(tert-butoxycarbonyl)pyrrolidin-3-yl)methyl)-6-iodo-4-oxo-1,4-dihydroquinoline-3-carboxylate

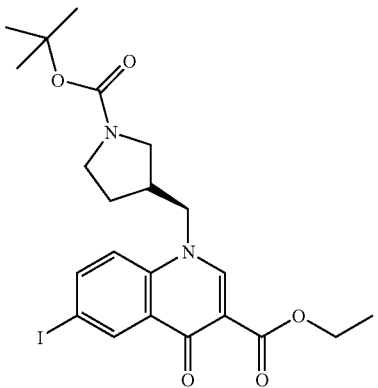

(R)-3-(Aminomethyl)-1-N-Boc-pyrrolidine (994 mg, 4.86 mmol) was added to the stock solution of (Z)-ethyl 3-(dimethylamino)-2-(3-iodobenzoyl)acrylate (Intermediate 24, 0.34M, 13 mL, 4.42 mmol). The reaction mixture was stirred at room temperature overnight. The solvent was removed in vacuo and the residue was dried in a vacuum oven for 1.5 h. The resulting residue was then dissolved in dimethylformamide (8 mL) and potassium carbonate powder (670 mg, 4.86 mmol) was added. The reaction mixture was heated at 60° C. for overnight then cooled to room temperature. Water (50 mL) was added and the suspension was extracted with ethyl acetate (3×50 mL). The organic layers were dried over sodium sulfate, and the solvent was removed in vacuo to give quantitative (R)-ethyl 1-((1-(tert-butoxycarbonyl)pyrrolidin-3-yl)methyl)-6-iodo-4-oxo-1,4-dihydroquinoline-3-carboxylate as a brown sticky solid.

MS (ESP): 527.1 (M+H$^+$) for $C_{22}H_{27}IN_2O_5$ $^1$H NMR (300 MHz, DMSO-d$_6$): δ 1.42 (t, 3H), 1.46 (s, 9H), 1.71 (m, 1H), 2.02 (bm, 1H), 2.78 (bs, 1H), 3.12 (bs, 1H), 3.25-3.62 (bm, 3H), 3.96-4.40 (bm, 2H), 4.42 (q, 2H), 7.19 (d, 1H), 7.92 (dd, 1H), 8.40 (s, 1H), 8.83 (s, 1H).

Intermediate 96

(S)-ethyl 1-((1-(tert-butoxycarbonyl)pyrrolidin-3-yl)methyl)-6-iodo-4-oxo-1,4-dihydroquinoline-3-carboxylate

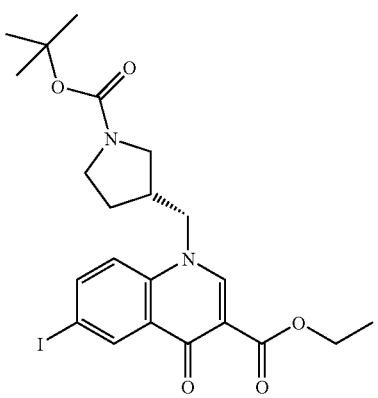

(S)-3-(Aminomethyl)-1-N-Boc-pyrrolidine (994 mg, 4.86 mmol) was added to the stock solution of (Z)-ethyl 3-(dimethylamino)-2-(3-iodobenzoyl)acrylate (Intermediate 24, 0.34M, 13 mL, 4.42 mmol). The reaction mixture was stirred at room temperature overnight. The solvent was removed in vacuo and the residue was dried in a vacuum oven for 1.5 h. The resulting residue was then dissolved in dimethylformamide (8 mL) and potassium carbonate powder (670 mg, 4.86 mmol) was added. The reaction mixture was heated at 60° C. for overnight then cooled to room temperature. Water (50 mL) was added and the suspension was extracted with ethyl acetate (3×50 mL). The organic layers were dried over sodium sulfate, and the solvent was removed in vacuo to give quantitative (S)-ethyl 1-((1-(tert-butoxycarbonyl)pyrrolidin-3-yl)methyl)-6-iodo-4-oxo-1,4-dihydroquinoline-3-carboxylate as a brown sticky solid.

MS (ESP): 527.1 (M+H$^+$) for $C_{22}H_{27}IN_2O_5$ $^1$H NMR (300 MHz, DMSO-d$_6$): δ 1.42 (t, 3H), 1.46 (s, 9H), 1.71 (m, 1H), 2.02 (bm, 1H), 2.78 (bs, 1H), 3.12 (bs, 1H), 3.25-3.62 (bm, 3H), 3.96-4.40 (bm, 2H), 4.42 (q, 2H), 7.19 (d, 1H), 7.92 (dd, 1H), 8.40 (s, 1H), 8.83 (s, 1H).

Intermediate 97

(R)-ethyl 6-iodo-4-oxo-1-(pyrrolidin-3-ylmethyl)-1,4-dihydroquinoline-3-carboxylate hydrochloride

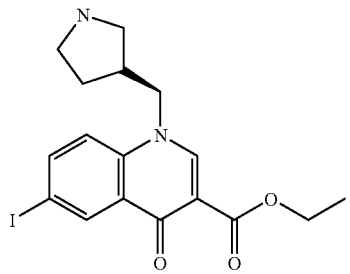

The crude (R)-ethyl 1-((1-(tert-butoxycarbonyl)pyrrolidin-3-yl)methyl)-6-iodo-4-oxo-1,4-dihydroquinoline-3-carboxylate (Intermediate 95, ~4.4 mmol) was dissolved in 1,4-dioxane (20 mL) and 4.0M hydrogen chloride in 1,4-dioxane (20 mL) was added. The reaction mixture was stirred at room temperature for 1 h, and the solvent was removed in vacuo. The solid was then dried in a vacuum oven at 40° C. for 18 h to give 2.3 g (quant. yield) of (R)-ethyl-6-iodo-4-oxo-1-(pyrrolidin-3-ylmethyl)-1,4-dihydroquinoline-3-carboxylate hydrochloride as a yellow solid.

MS (ESP): 427.1 (M+H$^+$) for $C_{17}H_{19}IN_2O_3$

Intermediate 98

(S)-ethyl 6-iodo-4-oxo-1-(pyrrolidin-3-ylmethyl)-1,4-dihydroquinoline-3-carboxylate hydrochloride

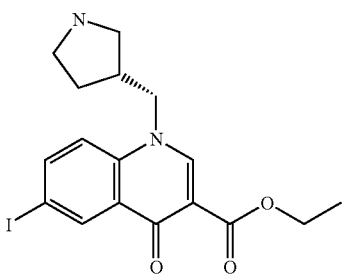

The crude (S)-ethyl 1-((1-(tert-butoxycarbonyl)pyrrolidin-3-yl)methyl)-6-iodo-4-oxo-1,4-dihydroquinoline-3-carboxylate (Intermediate 96, ~4.4 mmol) was dissolved in 1,4-dioxane (20 mL) and 4.0M hydrogen chloride in 1,4-dioxane (20 mL) was added. The reaction mixture was stirred at room temperature for 1 h, and the solvent was removed in vacuo. The solid was then dried in a vacuum oven at 40° C. for 18 h to give 2.3 g (quant. yield) of (S)-ethyl 6-iodo-4-oxo-1-(pyrrolidin-3-ylmethyl)-1,4-dihydroquinoline-3-carboxylate hydrochloride as a yellow solid.

MS (ESP): 427.1 (M+H$^+$) for $C_{17}H_{19}IN_2O_3$

Intermediate 99 ethyl 1-((1-(tert-butoxycarbonyl)pyrrolidin-3-yl)methyl)-6-iodo-4-oxo-1,4-dihydroquinoline-3-carboxylate

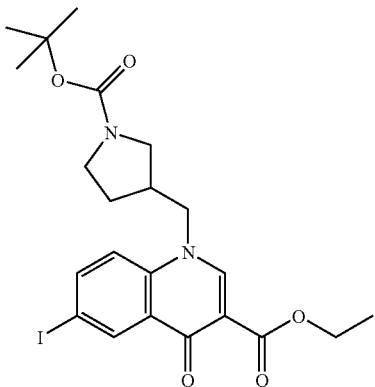

3-(Aminomethyl)-1-N-Boc-pyrrolidine (2.5 g, 12.5 mmol) was added to the stock solution of (Z)-ethyl 3-(dimethylamino)-2-(3-iodobenzoyl)acrylate (Intermediate 24, 0.34M, 34 mL, 11.3 mmol). The reaction mixture was heated at 50° C. for 3 h. The solvent was removed in vacuo and the resulting residue was dried in a vacuum oven for 1.5 h. The residue was then dissolved in dimethylformamide (20 mL) and potassium carbonate powder (2.2 g, 15.8 mmol) was added. The reaction mixture was heated at 70° C. for 3 h then cooled to room temperature. Water (100 mL) was added and the suspension was extracted with 1:1 ethyl acetate: methyl tert-butyl ether (3×50 mL). The organic layers were dried over sodium sulfate, and the solvent was removed in vacuo. The residue was suspended in methyl tert-butyl ether (20 mL) and stirred at 40° C. for 1 h. The suspension was filtered and the solid dried to give 4.15 g (70% yield) of ethyl 1-((1-(tert-butoxycarbonyl)pyrrolidin-3-yl)methyl)-6-iodo-4-oxo-1,4-dihydroquinoline-3-carboxylate as a yellowish powder.

MS (ESP): 527.1 (M+H$^+$) for $C_{22}H_{27}IN_2O_5$ $^1$H NMR (300 MHz, DMSO-d$_6$): δ ppm 1.42 (t, 3H), 1.46 (s, 9H), 1.71 (m, 1H), 2.02 (bm, 1H), 2.78 (bs, 1H), 3.12 (bs, 1H), 3.25-3.62 (bm, 3H), 3.96-4.40 (bm, 2H), 4.42 (q, 2H), 7.19 (d, 1H), 7.92 (dd, 1H), 8.40 (s, 1H), 8.83 (s, 1H)

Intermediate 100 ethyl 6-iodo-4-oxo-1-(pyrrolidin-3-ylmethyl)-1,4-dihydroquinoline-3-carboxylate hydrochloride

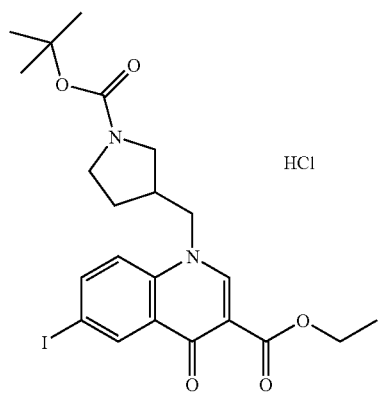

Ethyl 1-((1-(tert-butoxycarbonyl)pyrrolidin-3-yl)methyl)-6-iodo-4-oxo-1,4-dihydroquinoline-3-carboxylate (Intermediate 99, 3.0 g, 5.7 mmol) was dissolved in 1,4-dioxane (15 mL) and 4.0M hydrogen chloride in 1,4-dioxane (10 mL) was added. The reaction was stirred at 23° C. for 3 hours, and the solvent was removed in vacuo. The solid was then dried in a vacuum oven at 50° C. for 18 h to give 2.61 (quant. yield) of ethyl 6-iodo-4-oxo-1-(pyrrolidin-3-ylmethyl)-1,4-dihydroquinoline-3-carboxylate hydrochloride as a yellow solid.

MS (ESP): 427.1 (M+H$^+$) for $C_{17}H_{19}IN_2O_3$

Intermediate 101

(R)-ethyl 6-iodo-4-oxo-1-(1-methyl-pyrrolidin-3-yl)-1,4-dihydroquinoline-3-carboxylate

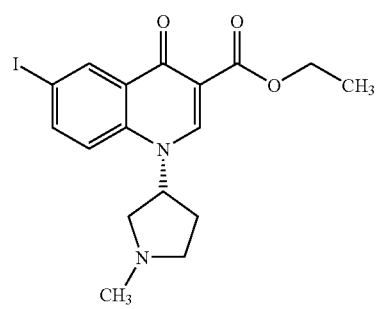

To a solution of (R)-ethyl 6-iodo-4-oxo-1-(pyrrolidin-3-yl)-1,4-dihydroquinoline-3-carboxylate (Intermediate 110, 282 mg, 0.68 mmol, 1 equiv.) in THF (7 mL) was added iodomethane (0.0471 mL, 0.75 mmol, 1.1 equiv.) followed by potassium carbonate (378 mg, 2.74 mmol, 4 equiv.). This was stirred at 60° C. for 1 d. The reaction mixture was cooled to room temperature and partitioned between ethyl acetate (10 mL) and water (10 mL). The aqueous layer was extracted with ethyl acetate (2×10 mL), and the organics were concentrated to provide (R)-ethyl 6-iodo-1-(1-methylpyrrolidin-3-yl)-4-oxo-1,4-dihydroquinoline-3-carboxylate as a light yellow solid (282 mg, >99%).

NMR (d$_6$-DMSO) δ 8.97 (s, 1H), 8.51 (s, 1H), 8.13 (dd, 1H), 7.86 (d, 1H), 5.46-4.38 (m, 1H), 4.28-4.18 (m, 2H), 3.59-3.54 (m, 1H), 3.24-3.1 (m, 3H), 2.6-2.54 (m, 2H), 2.36 (s, 3H), 2.26-2.14 (m, 2H), 1.28 (t, 3H).

Intermediates 102-107

The following Intermediates were prepared according to the procedure described for Intermediate 101 from the indicated starting materials.

| Int | Compound | Data | SM |
|---|---|---|---|
| 102 | (R)-ethyl 6-iodo-1-((1-methylpiperidin-3-yl)methyl)-4-oxo-1,4-dihydroquinoline-3-carboxylate | Calcd for C$_{19}$H$_{23}$IN$_2$O$_3$ [M + H]$^+$: 454.96 | Iodomethane and Intermediate 108 |
| 103 | (R)-ethyl 6-iodo-1-(1-methylpiperidin-3-yl)-4-oxo-1,4-dihydroquinoline-3-carboxylate | Calcd for C$_{18}$H$_{21}$IN$_2$O$_3$ [M + H]$^+$: 440.91 | Iodomethane & Intermediate 111 |
| 104 | (S)-ethyl 1-((1-ethylpyrrolidin-3-yl)methyl)-6-iodo-4-oxo-1,4-dihydroquinoline-3-carboxylate | Calcd for C$_{19}$H$_{23}$IN$_2$O$_3$ [M + H]$^+$: 455.01 | Iodoethane & Intermediate 109 |

-continued

| Int | Compound | Data | SM |
|---|---|---|---|
| 105 | (R)-ethyl 1-(1-ethylpyrrolidin-3-yl)-6-iodo-4-oxo-1,4-dihydroquinoline-3-carboxylate 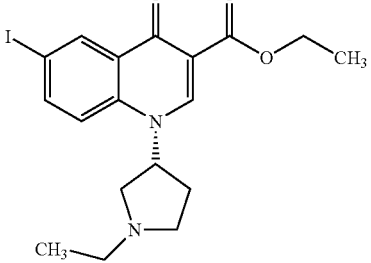 | Calcd for $C_{18}H_{21}IN_2O_3$ $[M + H]^+$: 441.0 | Iodoethane & Intermediate 110 |
| 106 | (R)-ethyl 1-((1-ethylpiperidin-3-yl)methyl)-6-iodo-4-oxo-1,4-dihydroquinoline-3-carboxylate 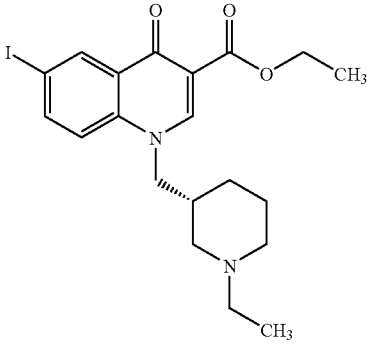 | Calcd for $C_{20}H_{25}IN_2O_3$ $[M + H]^+$: 469.11 | Iodoethane & Intermediate 108 |
| 107 | (R)-ethyl 1-(1-ethylpiperidin-3-yl)-6-iodo-4-oxo-1,4-dihydroquinoline-3-carboxylate 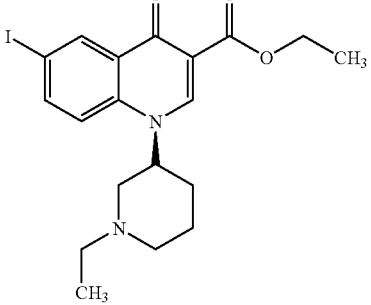 | Calcd for $C_{19}H_{23}IN_2O_3$ $[M + H]^+$: 454.66 | Iodoethane & Intermediate 111 |

Intermediate 108

(S)-ethyl 1-(1-piperidin-3-yl)-6-iodo-4-oxo-1,4-dihydroquinoline-3-carboxylate

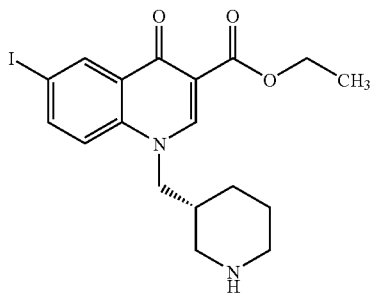

To a solution of (S)-ethyl 1-((1-(tert-butoxycarbonyl)piperidin-3-yl)methyl)-6-iodo-4-oxo-1,4-dihydroquinoline-3-carboxylate (Intermediate 112, 2.47 g, 4.57 mmol, 1 equiv.) in dichloromethane (18 mL) was added 4 N hydrogen chloride (4.57 mL, 18.28 mmol, 4 equiv.). This was stirred at room temperature for 12 h. The precipitate was washed with diethyl ether and dried to provide (R)-ethyl 6-iodo-4-oxo-1-(piperidin-3-ylmethyl)-1,4-dihydroquinoline-3-carboxylate as a light yellow solid (2.1 g, >99%).

Calcd for $C_{18}H_{21}IN_2O_3$ $[M+H]^+$: 440.95.

Intermediates 109-111

The following Intermediates were prepared according to the procedures described for Intermediate 108 from the indicated starting materials.

| Int | Compound | Data | SM |
|---|---|---|---|
| 109 | (S)-ethyl 6-iodo-4-oxo-1-(pyrrolidin-3-ylmethyl)-1,4-dihydroquinoline-3-carboxylate | Calcd for $C_{17}H_{19}IN_2O_3$ $[M + H]^+$: 426.94 | Intermediate 113 |
| 110 | (R)-ethyl 6-iodo-4-oxo-1-(pyrrolidin-3-yl)-1,4-dihydroquinoline-3-carboxylate | Calcd for $C_{16}H_{17}IN_2O_3$ $[M + H]^+$: 412.92 | Intermediate 114 |
| 111 | (S)-ethyl 6-iodo-4-oxo-1-(piperidin-3-yl)-1,4-dihydroquinoline-3-carboxylate | Calcd for $C_{17}H_{19}IN_2O_3$ $[M + H]^+$: 426.95 | Intermediate 115 |

Intermediates 112-115

The following Intermediates were prepared according to the procedure described for Intermediate 96 from the starting materials indicated.

| Int | Compound | Data | SM |
| --- | --- | --- | --- |
| 112 | (S)-ethyl 1-((1-(tert-butoxycarbonyl)piperidin-3-yl)methyl)-6-iodo-4-oxo-1,4-dihydroquinoline-3-carboxylate | Calcd for $C_{23}H_{29}IN_2O_5$ $[M + H]^+$: 541.07 | (S)-tert-butyl 3-(aminomethyl)-piperidine-1-carboxylate & Intermediate 24 |
| 113 | (R)-ethyl 1-((1-(tert-butoxycarbonyl)pyrrolidin-3-yl)methyl)-6-iodo-4-oxo-1,4-dihydroquinoline-3-carboxylate | Calcd for $C_{22}H_{27}IN_2O_5$ $[M + H]^+$: 527.03 | (R)-tert-butyl 3-aminomethyl pyrrolidine-1-carboxylate & Intermediate 24 |
| 114 | (R)-ethyl 1-(1-(tert-butoxycarbonyl)pyrrolidin-3-yl)-6-iodo-4-oxo-1,4-dihydroquinoline-3-carboxylate | Calcd for $C_{21}H_{25}IN_2O_5$ $[M + H]^+$: 512.99 | (R)-tert-butyl 3-amino-pyrrolidine-1-carboxylate & Intermediate 24 |

-continued

| Int | Compound | Data | SM |
|---|---|---|---|
| 115 | (S)-ethyl 1-(1-(tert-butoxycarbonyl)piperidin-3-yl)-6-iodo-4-oxo-1,4-dihydroquinoline-3-carboxylate 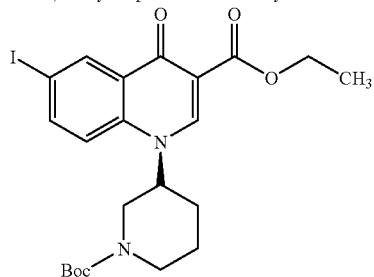 | Calcd for $C_{22}H_{27}IN_2O_5$ [M + H]$^+$: 527.01 | (S)-tert-butyl 3-amino-piperidine-1-carboxylate & Intermediate 24 |

Intermediate 116

Ethyl 1-(2-(dimethylamino)propyl)-6-iodo-4-oxo-1,4-dihydroquinoline-3-carboxylate

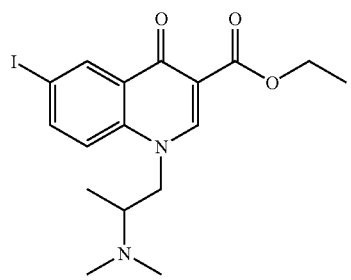

(Z)-Ethyl 3-(dimethylamino)-2-(2-fluoro-5-iodobenzoyl)acrylate (0.500 g, 1.28 mmol, Intermediate 24), N2,N2-dimethylpropane-1,2-diamine hydrochloride (0.177 g, 1.28 mmol), and potassium carbonate (0.194 g, 1.41 mmol) were combined in THF (10.0 mL). The reaction was heated at 60° C. for 2 hrs. After 2 h, DMF (5.0 mL) was added followed by potassium carbonate (0.530 g, 3.83 mmol). The reaction was heated at 90° C. for 6 h. The reaction mixture was cooled to 0° C. and 1N HCl was slowly added until pH was around 4. The resulting precipitate was filtered, washed with water and dried overnight to yield a light yellow solid (0.428 g).

MS (ES) (M+H)$^+$: 429 for $C_{17}H_{21}IN_2O_3$;

NMR: 10.99 (br. s., 1 H), 8.73 (br. s., 1 H), 8.51 (s, 1H), 8.07 (dd, J=8.67, 1.88 Hz, 1H), 7.83-7.97 (m, 1H), 4.92 (d, J=12.06 Hz, 1H), 4.59 (t, J=11.30 Hz, 1H), 4.24 (q, J=7.54 Hz, 2H), 3.70-3.89 (m, 1H), 2.68-2.86 (m, 6H), 1.29 (t, J=7.16 Hz, 4H), 1.15 (d, J=3.77 Hz, 3H).

Intermediates 117-123

The following Intermediates were prepared by the procedure described in Intermediate 116 from the starting materials (SM) indicated.

| Int | Compound | Data | SM |
|---|---|---|---|
| 117 | (R)-tert-butyl 3-((3-(ethoxycarbonyl)-6-iodo-4-oxoquinolin-1(4H)-yl)methyl)morpholine-4-carboxylate 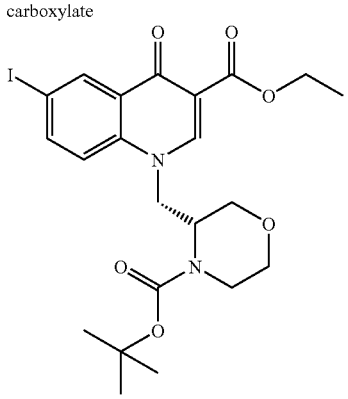 | MS (ES) (M + H)$^+$: 543 for $C_{22}H_{27}IN_2O_6$<br>NMR: 8.45-8.56 (m, 2H), 8.06 (d, J = 7.54 Hz, 1H), 7.79 (d, J = 9.04 Hz, 1H), 4.56-4.76 (m, 2H), 4.20 (d, J = 7.54 Hz, 3H), 3.94-4.06 (m, 1H), 3.74-3.92 (m, 2H), 3.44-3.68 (m, 2H), 1.21-1.43 (m, 4H), 1.12 (s, 3H), 0.77 (s, 6H). | Intermediate 24 and (R)-tert-butyl 3-(aminomethyl)-morpholine-4-carboxylate |

-continued

| Int | Compound | Data | SM |
|---|---|---|---|
| 118 | (S)-tert-butyl 3-((3-(ethoxycarbonyl)-6-iodo-4-oxoquinolin-1(4H)-yl)methyl)morpholine-4-carboxylate | MS (ES) (M + H)$^+$: 543 for $C_{22}H_{27}IN_2O_6$ NMR: 8.42-8.56 (m, 2H), 8.06 (d, J = 8.29 Hz, 1H), 7.79 (d, J = 8.29 Hz, 1H), 4.53-4.79 (m, 2H), 4.20 (d, J = 6.78 Hz, 3H), 3.94-4.09 (m, 1H), 3.72-3.94 (m, 2H), 3.45-3.70 (m, 2H), 1.19-1.43 (m, 4H), 1.12 (s, 3H), 0.77 (s, 6H). | Intermediate 24 and (S)-tert-butyl 3-(aminomethyl)-morpholine-4-carboxylate |
| 119 | ethyl 1-((1R,2R)-2-hydroxycyclohexyl)-6-iodo-4-oxo-1,4-dihydroquinoline-3-carboxylate | MS (ES) (M + H)$^+$: 442 for $C_{18}H_{20}INO_4$ NMR: 8.62 (s, 1H), 8.52 (s, 1H), 8.03 (d, J = 9.04 Hz, 1H), 7.84-7.93 (m, 1H), 5.10 (d, J = 4.52 Hz, 1H), 4.51 (t, J = 8.67 Hz, 1H), 4.24 (q, J = 6.78 Hz, 2H), 3.87 (d, J = 4.52 Hz, 1H), 1.86-2.09 (m, 2H), 1.71 (br. s., 3H), 1.41-1.60 (m, 3H), 1.29 (t, J = 7.16 Hz, 3H). | Intermediate 24 and (1R,2R)-2-aminocyclo-hexanol hydrochloride |
| 120 | ethyl 1-((1S,2S)-2-hydroxycyclohexyl)-6-iodo-4-oxo-1,4-dihydroquinoline-3-carboxylate | MS (ES) (M + H)$^+$: 442 for $C_{18}H_{20}INO_4$ | Intermediate 24 and (1S,2S)-2-aminocyclo-hexanol hydrochloride |
| 121 | ethyl 1-(cis-2-hydroxycyclohexyl)-6-iodo-4-oxo-1,4-dihydroquinoline-3-carboxylate | MS (ES) (M + H)$^+$: 442 for $C_{18}H_{20}INO_4$ NMR: 1.21-1.35 (m, 3H), 1.39-1.67 (m, 3H), 1.67-1.95 (m, 4H), 2.15-2.31 (m, 1H), 3.94 (br. s., 1H), 4.24 (q, J = 6.78 Hz, 2H), 4.72-4.85 (m, 1H), 5.12 (d, J = 5.27 Hz, 1H), 7.83 (d, J = 9.04 Hz, 1H), 8.05 (dd, J = 9.04, 2.26 Hz, 1H), 8.55 (d, J = 2.26 Hz, 1H), 8.64 (s, 1H). | Intermediate 24 and cis-2-aminocyclo-hexanol hydrochloride |

-continued

| Int | Compound | Data | SM |
|---|---|---|---|
| 122 | (S)-ethyl 1-(1-(tert-butoxycarbonyl)piperidin-3-yl)-6-iodo-4-oxo-1,4-dihydroquinoline-3-carboxylate | MS (ES) (M + H)⁺: 527 for $C_{22}H_{27}IN_2O_5$ | Intermediate 24 and (S)-tert-butyl 3-amino-piperidine-1-carboxylate |
| 123 | (R)-ethyl 1-(1-(tert-butoxycarbonyl)piperidin-3-yl)-6-iodo-4-oxo-1,4-dihydroquinoline-3-carboxylate | MS (ES) (M + H)⁺: 527 for $C_{22}H_{27}IN_2O_5$ | Intermediate 24 and (R)-tert-butyl 3-amino-piperidine-1-carboxylate |

Intermediate 124

5-(6-(3-ethylureido)-4-(4-(trifluoromethyl)thiazol-2-yl)pyridin-3-yl)-2-fluorobenzoic acid

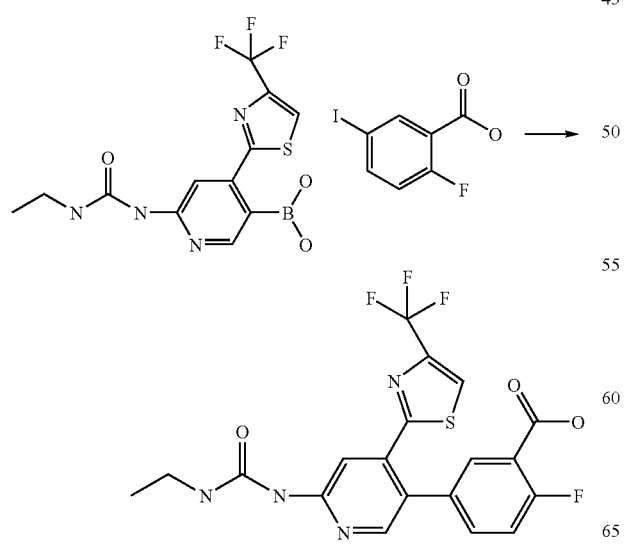

6-(3-ethylureido)-4-(4-(trifluoromethyl)thiazol-2-yl)pyridin-3-ylboronic acid (Intermediate 17, 0.261 g, 0.72 mmol, Intermediate 17) and 2-fluoro-5-iodobenzoic acid (0.175 g, 0.66 mmol, aldrich) were combined in dioxane (1 ml). A solution of cesium carbonate (0.364 g, 1.12 mmol) in water (0.658 ml) was added followed by tetrakis(triphenylphosine) palladium(0) (0.076 g, 0.07 mmol, strem) and additional dioxane (2.63 ml). The flask was placed in an oil bath preheated to 100° C. and was heated for 1h., then cooled to 0° C. and 1 N HCl was added until the pH was ~3. EtOAc (5 ml) was added and a solid crashed out and was collected by filtration and washed with EtOAc, then dried to give a grey solid 5-(6-(3-ethylureido)-4-(4-(trifluoromethyl)thiazol-2-yl)pyridin-3-yl)-2-fluorobenzoic acid (0.180 g, 60.2%).

MS (ES) (M+H)⁺: 455 for $C_{19}H_{14}F_4N_4O_3S$ NMR:

¹H NMR (300 MHz, DMSO-d₆) δ 13.38 (br. s., 1H), 9.43 (s, 1H), 8.53 (s, 1H), 8.28 (s, 1H), 8.21 (s, 1H), 7.76 (d, J=6.78

Hz, 1H), 7.59 (d, J=3.77 Hz, 2H), 7.35-7.47 (m, 1H), 3.18-3.25 (m, 2H), 1.10 (t, J=7.16 Hz, 3H).

Intermediate 125 ethyl 3-(dimethylamino)-2-(5-(6-(3-ethylureido)-4-(4-(trifluoromethyl)thiazol-2-yl)pyridin-3-yl)-2-fluorobenzoyl)acrylate

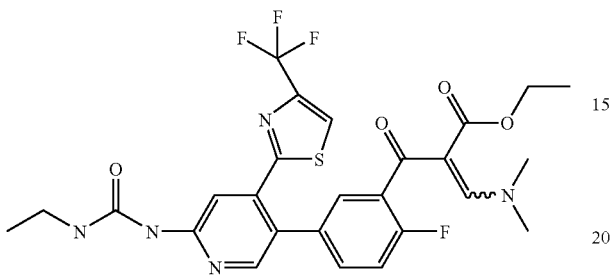

5-(6-(3-ethylureido)-4-(4-(trifluoromethyl)thiazol-2-yl) pyridin-3-yl)-2-fluorobenzoic acid (0.180 g, 0.40 mmol, Intermediate 124) was suspended in toluene (3 mL). Thionyl chloride (0.145 mL, 1.98 mmol, Aldrich) and 1drop of DMF were added and the mixture was heated to 45° C. for 15 min After cooling to room temperature, the mixture was concentrated in vacuo, and toluene was added, then the mixture was concentrated in vacuo again to give a dark yellow residue. After drying under high vacuum overnight the oil turned into a dark yellow film. This film was taken up in THF (2 mL). In separate flask ethyl 3-(dimethylamino)acrylate (0.074 g, 0.51 mmol, Acros) and triethylamine (0.082 mL, 0.59 mmol, Acros) were dissolved in THF (5 ml). The solution of the acid chloride in THF (2 ml) was added dropwise to acrylate solution, then the flask was placed in an oil bath preheated to 72° C. and stirred for 1 h. After cooling to room temperature, the mixture was diluted with EtOAc(10 mL) and water (10 mL). The layers were separated and the organic layer was washed with 1 N HCl, twice with water, once with brine, then dry over $Na_2SO_4$, filter and concentrated in vacuo to give crude product as an orange oil.

MS (ES) (M+H)$^+$: 580 for $C_{26}H_{25}F_4N_5O_4S$.

Intermediate 126 ethyl 6-iodo-4-oxo-1-(pyrrolidin-3-ylmethyl)-1,4-dihydroquinoline-3-carboxylate hydrochloride

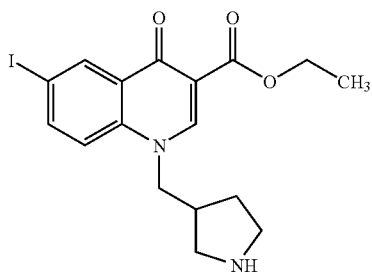

Ethyl 1-((1-(tert-butoxycarbonyl)pyrrolidin-3-yl)methyl)-6-iodo-4-oxo-1,4-dihydroquinoline-3-carboxylate (Intermediate 100, 3.0 g, 5.7 mmol) was dissolved in 1,4-dioxane (15 mL) and 4.0M hydrogen chloride in 1,4-dioxane (10 mL) was added. The reaction was stirred at 23° C. for 3 h, and the solvent was removed in vacuo. The solid was then dried in a vacuum oven at 50° C. for 18 h to give 2.61 (quant. yield) of ethyl 6-iodo-4-oxo-1-(pyrrolidin-3-ylmethyl)-1,4-dihydroquinoline-3-carboxylate hydrochloride as a yellow solid.

MS (ESP): 427.1 (M+H$^+$) for $C_{17}H_{19}IN_2O_3$

Intermediate 127 ethyl 1-((1-ethylpyrrolidin-3-yl)methyl)-6-iodo-4-oxo-1,4-dihydroquinoline-3-carboxylate

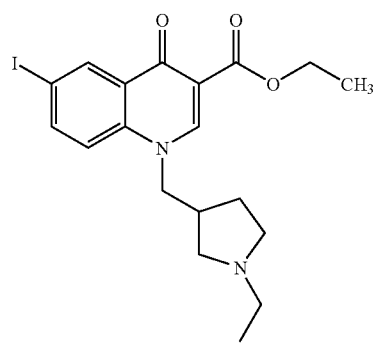

Ethyl 6-iodo-4-oxo-1-(pyrrolidin-3-ylmethyl)-1,4-dihydroquinoline-3-carboxylate hydrochloride (Intermediate 126, 500 mg, 1.08 mmol) was suspended in methanol (15 mL) then acetaldehyde (300 µl, 5.4 mmol) and sodium cyanoborohydride (612 mg, 9.7 mmol) were added. The reaction was stirred at 23° C. for 16 h. The volume of the reaction was reduced by half and water (25 mL) was added. The suspension was extracted with 2:1 ethyl acetate: tetrahydrofuran (3×10 mL). The organic phases were combined, dried over sodium sulfate, and the solvent was removed in vacuo. The residue was passed through a plug of silica gel (2 g) eluting with 10% methanol in dichloromethane to remove any remaining borohydride. The solid was then dried in a vacuum oven at 50° C. for 18 h to give 378 mg (77% yield) of ethyl 1-((1-ethylpyrrolidin-3-yemethyl)-6-iodo-4-oxo-1,4-dihydroquinoline-3-carboxylate as an off white solid.

MS (ESP): 455.1 (M+H$^+$) for $C_{18}H_{21}IN_2O_3$

Intermediate 128 ethyl 6-iodo-1-((1-(2-morpholinoethyl)pyrrolidin-3-yl)methyl)-4-oxo-1,4-dihydroquinoline-3-carboxylate

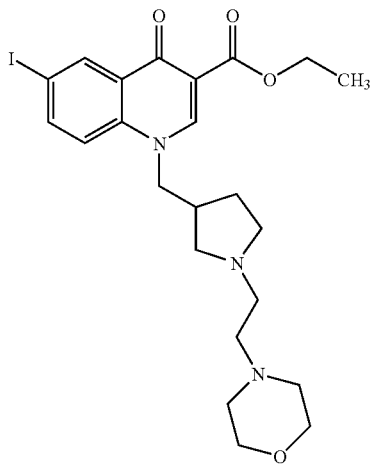

Ethyl 6-iodo-4-oxo-1-(pyrrolidin-3-ylmethyl)-1,4-dihydroquinoline-3-carboxylate hydrochloride (Intermediate 127, 500 mg, 1.08 mmol) was suspended in methanol (15 mL) then morpholine-4-ylacetaldehyde monohydrate hydrochloride (1 g, 5.4 mmol) and sodium cyanoborohydride (612 mg, 9.7 mmol) were added. The reaction was stirred at 23° C. for 16 h. The volume of the reaction was reduced by half and water (25 mL) was added. The suspension was extracted with 2:1 ethyl acetate: tetrahydrofuran (3×10 mL). The organic phases were combined, dried over sodium sulfate, and the solvent was removed in vacuo. The residue was passed through a plug of silica gel (2 g) eluting with 10% methanol in dichloromethane to remove any remaining borohydride. The solid was then dried in a vacuum oven at 50° C. for 18 h to give 225 mg (38% yield) of ethyl 6-iodo-1-((1-(2-morpholinoethyl)pyrrolidin-3-yl)methyl)-4-oxo-1,4-dihydroquinoline-3-carboxylate as an off white solid.

MS (ESP): 540.0 (M+H$^+$) for $C_{23}H_{30}IN_3O_4$

Intermediate 129 ethyl 6-iodo-4-oxo-1-((1-((tetrahydrofuran-2-yl)methyl)pyrrolidin-3-yl)methyl)-1,4-dihydroquinoline-3-carboxylate

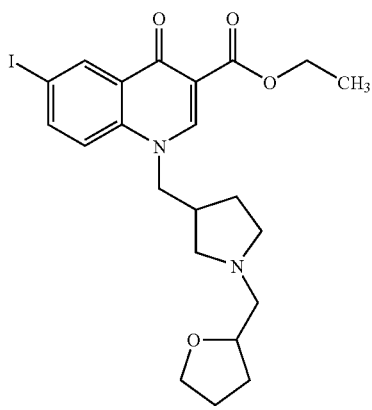

Ethyl 6-iodo-4-oxo-1-(pyrrolidin-3-ylmethyl)-1,4-dihydroquinoline-3-carboxylate hydrochloride (Intermediate 126, 500 mg, 1.08 mmol) was suspended in dimethyl formamide (3 mL) then tetrahydrofurfuryl chloride (1 mL) and potassium carbonate powder (400 mg, 22.2 mmol) were added. The reaction was stirred at 70° C. for 36 h. Water (15 mL) was added and the suspension was extracted with ethyl acetate (3×10 mL). The organic phases were combined, dried over sodium sulfate, and the solvent was removed in vacuo. The residue was chromatographed on a 4 g Analogix column using 0-10% methanol in dichloromethane. The solid was then dried in a vacuum oven at 50° C. for 18 h to give 181 mg (32% yield) of ethyl 6-iodo-4-oxo-1-((1-((tetrahydrofuran-2-yl)methyl)pyrrolidin-3-yl)methyl)-1,4-dihydroquinoline-3-carboxylate as an off white solid.

MS (ESP): 511.1 (M+H$^+$) for $C_{22}H_{27}IN_2O_4$ $^1$H NMR (300 MHz, CDCl$_3$): δ 1.38 (t, 3H), 1.42-1.61 (m, 2H), 1.81-2.08 (m, 4H), 2.38-2.81 (m, 6H), 2.84-2.96 (m, 1H), 3.71-4.28 (m, 6H), 4.38 (q, 2H), 7.28(dd, 1H), 7.93 (dd, 1H), 8.49 (s, 1H), 8.83 (d, 1H).

Intermediate 130 ethyl 1-((1-(2-(tert-butyldimethylsilyloxy)ethyl)pyrrolidin-3-yl)methyl)-6-iodo-4-oxo-1,4-dihydroquinoline-3-carboxylate

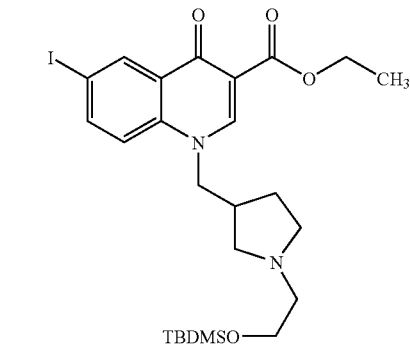

Ethyl 6-iodo-4-oxo-1-(pyrrolidin-3-ylmethyl)-1,4-dihydroquinoline-3-carboxylate hydrochloride (Intermediate 126, 500 mg, 1.08 mmol) was suspended in methanol (15 mL) then (tert-butyldimethylsilyloxy)acetaldehyde (1 mL, 5.4 mmol) and sodium cyanoborohydride (612 mg, 9.7 mmol) were added. The reaction was stirred at 23° C. for 16 h. The volume of the reaction was reduced by half and water (25 mL) was added. The suspension was extracted with 2:1 ethyl acetate: tetrahydrofuran (3×, 10 mL). The organic phases were combined, dried over sodium sulfate, and the solvent was removed in vacuo. The residue was chromatographed on a 4 g Analogix column eluting with 0-10% methanol in dichloromethane. The solid was then dried in a vacuum oven at 50° C. for 18 h to give 253 mg (39% yield) of ethyl 1-((1-(2-(tert-butyldimethylsilyloxy)ethyl)pyrrolidin-3-yl)methyl)-6-iodo-4-oxo-1,4-dihydroquinoline-3-carboxylate as an off white solid.

MS (ESP): 585.2 (M+H$^+$) for $C_{25}H_{28}IN_2O_4Si$

Intermediate 131 ethyl 1-(1-(tert-butoxycarbonyl)piperidin-3-yl)-6-iodo-4-oxo-1,4-dihydroquinoline-3-carboxylate

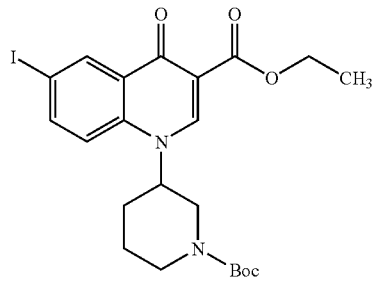

3-Amino-1-N-Boc-piperidine (2.5 g, 12.5 mmol) was added to the solution of (Z)-ethyl 3-(dimethylamino)-2-(3-iodobenzoyl)acrylate (Intermediate 24, 0.34M, 34 mL, 11 3 mmol) and heated at 50° C. for 3 h. The solvent was removed in vacuo and the residue was dried in a vacuum oven for 1.5 h. The residue was then dissolved in dimethyl formamide (20 mL) and potassium carbonate powder (2.2 g, 15.8 mmol) was added. The reaction was heated at 70° C. for 3 h then cooled to room temperature. Water (100 mL) was added and the suspension was extracted with 1:1 ethyl acetate:methyl tert-butyl ether (3×, 50 mL). The organic layers were dried over sodium sulfate, and the solvent was removed in vacuo. The residue was suspended in methyl tert-butyl ether (20 mL) and stirred at 40° C. for 1 h. The suspension was filtered and the solid dried to give 4.93 g (82% yield) of ethyl 1-(1-(tert-butoxycarbonyl)piperidin-3-yl)-6-iodo-4-oxo-1,4-dihydroquinoline-3-carboxylate as a yellowish powder.

MS (ESP): 527.1 (M+H$^+$) for $C_{22}H_{27}IN_2O_5$ $^1$H NMR (300 MHz, DMSO-d$_6$): δ 1.24 (t, 3H), 1.45 (s, 9H), 1.61-1.90 (bm, 4H), 2.18 (bs, 2H), 2.94 (bs, 1H), 3.20 (bs, 1H), 3.83 (bd, 1H), 4.08 (bd, 1H), 4.23 (q, 2H), 4.62 (bs, 1H), 7.77 (bd, 1H), 8.08 (d, 1H), 8.52 (d, 1H), 8.61 (s, 1H).

Intermediate 132 ethyl 6-iodo-4-oxo-1-(piperidin-3-yl)-1,4-dihydroquinoline-3-carboxylate hydrochloride

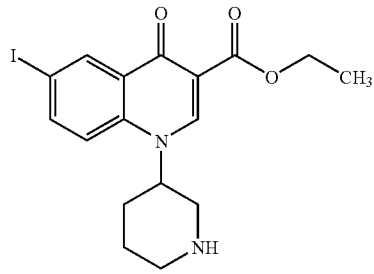

Ethyl 1-((1-(tert-butoxycarbonyl)pyrrolidin-3-yl)methyl)-6-iodo-4-oxo-1,4-dihydroquinoline-3-carboxylate (Intermediate 131, 3.0 g, 5.7 mmol) was dissolved in 1,4-dioxane (15 mL) and 4.0M hydrogen chloride in 1,4-dioxane (10 mL) was added. The reaction was stirred at 23° C. for 3 h, and the solvent was removed in vacuo. The solid was then dried in a vacuum oven at 50° C. for 18 h to give 2.64 g (quant. yield) of ethyl 6-iodo-4-oxo-1-(piperidin-3-yl)-1,4-dihydroquinoline-3-carboxylate hydrochloride as a yellow solid.

MS (ESP): 427.0 (M+H$^+$) for $C_{22}H_{27}IN_2O_5$

Intermediate 133 ethyl 6-iodo-4-oxo-1-(1-(pyridin-4-ylmethyl)piperidin-3-yl)-1,4-dihydroquinoline-3-carboxylate

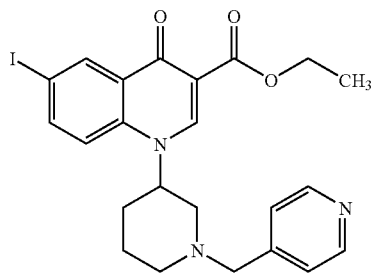

Ethyl 6-iodo-4-oxo-1-(piperidin-3-yl)-1,4-dihydroquinoline-3-carboxylate hydrochloride (Intermediate 132, 500 mg, 1.08 mmol) was suspended in methanol (15 mL) then 4-pyridinecarboxaldehyde (520 μl, 5.4 mmol) and sodium cyanoborohydride (612 mg, 9.7 mmol) were added. The reaction was stirred at 23° C. for 16 h. The volume of the reaction was reduced by half and water (25 mL) was added. The suspension was extracted with 2:1 ethyl acetate: tetrahydrofuran (3×, 10 mL). The organic phases were combined, dried over sodium sulfate, and the solvent was removed in vacuo. The residue was passed through a plug of silica gel (2 g) eluting with 10% methanol in dichloromethane to remove any remaining borohydride. The solid was then dried in a vacuum oven at 50° C. for 18 h to give 460 mg (82% yield) of ethyl 6-iodo-4-oxo-1-(1-(pyridin-4-ylmethyl)piperidin-3-yl)-1,4-dihydroquinoline-3-carboxylate as an off white solid.

MS (ESP): 706.2 (M+H$^+$) for $C_{12}H_{10}BrF_3N_4OS$.

Intermediate 134 ethyl 6-iodo-1-(1-methylpiperidin-3-yl)-4-oxo-1,4-dihydroquinoline-3-carboxylate

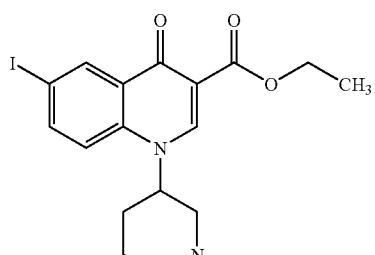

Ethyl 6-iodo-4-oxo-1-(piperidin-3-yl)-1,4-dihydroquinoline-3-carboxylate hydrochloride (Intermediate 132, 500 mg, 1.08 mmol) was suspended in methanol (15 mL) then 37% formaldehyde in water (405 μl, 5.4 mmol) and sodium cyanoborohydride (612 mg, 9.7 mmol) were added. The reaction was stirred at 23° C. for 16 h. The volume of the reaction was reduced by half and water (25 mL) was added. The suspension was extracted with 2:1 ethyl acetate: tetrahydrofuran (3×10 mL). The organic phases were combined, dried over sodium sulfate, and the solvent was removed in vacuo. The residue was passed through a plug of silica gel (2 g) eluting with 10% methanol in dichloromethane to remove any remaining borohydride. The solid was then dried in a vacuum oven at 50° C. for 18 h to give 386 mg (81% yield) of ethyl 6-iodo-1-(1-methylpiperidin-3-yl)-4-oxo-1,4-dihydroquinoline-3-carboxylate as an off white solid.

MS (ESP): 441.0 (M+H$^+$) for $C_{18}H_{21}IN_2O_3$

Intermediate 135

(S)-ethyl 1-(1-(tert-butoxycarbonyl)pyrrolidin-3-yl)-6-iodo-4-oxo-1,4-dihydroquinoline-carboxylate

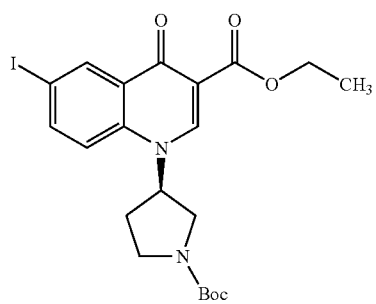

(S)-3-Amino-1-N-Boc-pyrrolidine (1 g, 5.36 mmol) was added to the solution of (Z)-ethyl 3-(dimethylamino)-2-(3-iodobenzoyl)acrylate (Intermediate 24, 0.34M, 14.3 mL, 4.88 mmol) and heated at 50° C. for 3 h. The solvent was removed in vacuo and the residue was dried in a vacuum oven for 1.5 h. The residue was then dissolved in dimethyl formamide (8 mL) and potassium carbonate powder (1.0 g, 6.83 mmol) was added. The reaction was heated at 70° C. for 3 h then cooled to room temperature. Water (40 mL) was added and the suspension was extracted with 1:1 ethyl acetate:methyl tert-butyl ether (3×, 30 mL). The organic layers were dried over sodium sulfate, and the solvent was removed in vacuo. The residue was suspended in methyl tert-butyl ether (20 mL) and stirred at 40° C. for 1 hour. The suspension was filtered and the solid dried to give 1.76 g (71% yield) of (R)-ethyl 1-(1-(tert-butoxycarbonyl)pyrrolidin-3-yl)-6-iodo-4-oxo-1,4-dihydroquinoline-3-carboxylate as a yellowish powder.

MS (ESP): 513.0 (M+H$^+$) for $C_{21}H_{25}IN_2O_5$ $^1$H NMR (300 MHz, DMSO-d$_6$): δ 1.23 (t, 3H), 1.42 (s, 9H), 2.22 (bs, 2H), 2.48 (bs, 2H), 3.40 (bd, 2H), 3.73 (bm, 2H), 4.18 (q, 2H), 5.31 (bs, 1H), 7.78 (d, 1H), 8.07 (dd, 1H), 8.41 (bd, 1H), 8.52 (s, 1H).

Intermediate 136

(S)-ethyl 6-iodo-4-oxo-1-(pyrrolidin-3-yl)-1,4-dihydroquinoline-3-carboxylate hydrochloride

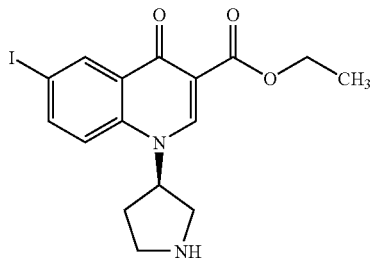

(S)-Ethyl 1-(1-(tert-butoxycarbonyl)pyrrolidin-3-yl)-6-iodo-4-oxo-1,4-dihydroquinoline-3-carboxylate (1.2 g, 1.08 mmol) was dissolved in 1,4-dioxane (10 mL) and 4.0M hydrogen chloride in 1,4-dioxane (4 mL) was added. The reaction was stirred at 23° C. for 3 hours, and the solvent was removed in vacuo. The solid was then dried in a vacuum oven at 50° C. for 18 hours to give 1.03 g (quant. yield) of (R)-ethyl 6-iodo-4-oxo-1-(pyrrolidin-3-yl)-1,4-dihydroquinoline-3-carboxylate hydrochloride as a yellow solid.

MS (ESP): 412.9 (M+H$^+$) for $C_{16}H_{17}IN_2O_3$

Intermediate 137

(S)-ethyl 6-iodo-1-(1-methylpyrrolidin-3-yl)-4-oxo-1,4-dihydroquinoline-3-carboxylate

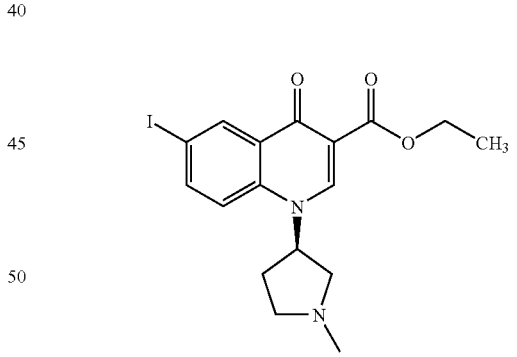

(S)-Ethyl 6-iodo-4-oxo-1-(pyrrolidin-3-yl)-1,4-dihydroquinoline-3-carboxylate hydrochloride (Intermediate 136, 484 mg, 1.08 mmol) was suspended in methanol (15 mL) then 37% formaldehyde in water (405 µl, 5.4 mmol) and sodium cyanoborohydride (612 mg, 9 7 mmol) were added. The reaction was stirred at 23° C. for 16 h. The volume of the reaction was reduced by half and water (25 mL) was added. The suspension was extracted with 2:1 ethyl acetate: tetrahydrofuran (3×, 10 mL). The organic phases were combined, dried over sodium sulfate, and the solvent was removed in vacuo. The residue was passed through a plug of silica gel (2 g) eluting with 10% methanol in dichloromethane to remove any remaining borohydride. The solid was then dried in a vacuum oven at 50° C. for 18 h to give 379 mg (82% yield) of (S)-ethyl 6-iodo-1-(1-methylpyrrolidin-3-yl)-4-oxo-1,4-dihydroquinoline-3-carboxylate as an off white solid.

MS (ESP): 426.9 (M+H$^+$) for $C_{17}H_{19}IN_2O_3$

Intermediate 138

Trans-ethyl 1-(1-(tert-butoxycarbonyl)-4-hydroxypyrrolidin-3-yl)-6-iodo-4-oxo-1,4-dihydroquinoline-3-carboxylate

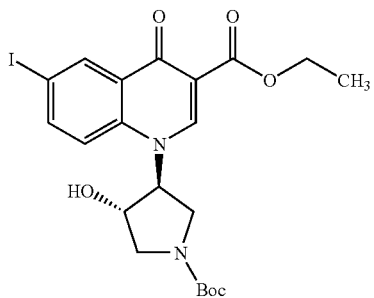

Trans-tert-butyl 3-amino-4-hydroxypyrrolidine-1-carboxylate (500 mg, 2.47 mmol) was added to the solution of (Z)-ethyl 3-(dimethylamino)-2-(3-iodobenzoyl)acrylate (Intermediate 24, 0.34M, 6.7 mL, 2.25 mmol) and the mixture was heated at 50° C. for 3 hour. The solvent was removed in vacuo and the residue was dried in a vacuum oven for 1.5 hours. The residue was then dissolved in dimethyl formamide (5 mL) and potassium carbonate powder (435 mg, 3.15 mmol) was added. The reaction was heated at 70° C. for 3 h then cooled to room temperature. Water (30 mL) was added and the suspension was extracted with 1:1 ethyl acetate:methyl tert-butyl ether (3×50 mL). The organic layers were dried over sodium sulfate, and the solvent was removed in vacuo. The residue was suspended in methyl tert-butyl ether (20 mL) and stirred at 40° C. for 1 h. The suspension was filtered and the solid dried to give 751 mg (64% yield) of racemic trans-ethyl 1-(1-(tert-butoxycarbonyl)-4-hydroxypyrrolidin-3-yl)-6-iodo-4-oxo-1,4-dihydroquinoline-3-carboxylate as a yellowish powder.

MS (ESP): 528.9 (M+H$^+$) for $C_{21}H_{25}IN_2O_6$

Intermediate 139 ethyl 6-iodo-1-((1-methylpiperidin-3-yl)methyl)-4-oxo-1,4-dihydroquinoline-3-carboxylate

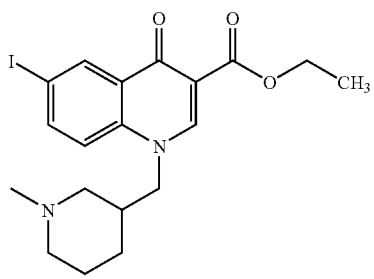

1-(1-Methylpiperidine-3-yl)methanamine (500 mg, 3.9 mmol) was added to the solution of (Z)-ethyl 3-(dimethylamino)-2-(3-iodobenzoyl)acrylate (Intermediate 24, 0.34M, 10.4 mL, 2.25 mmol) and the mixture was heated at 50° C. for 3 h. The solvent was removed in vacuo and the residue was dried in a vacuum oven for 1.5 h. The residue was then dissolved in dimethyl formamide (7 mL) and potassium carbonate powder (695 mg, 5.1 mmol) was added. The reaction was heated at 70° C. for 3 h then cooled to room temperature. Water (30 mL) was added and the suspension was extracted with 1:1 ethyl acetate:methyl tert-butyl ether (3×50 mL). The organic layers were dried over sodium sulfate, and the solvent was removed in vacuo. The residue was suspended in methyl tert-butyl ether (20 mL) and stirred at 40° C. for 1 h. The suspension was filtered and the solid dried to give 1.12 mg (69% yield) of ethyl 6-iodo-1-((1-methylpiperidin-3-yl)methyl)-4-oxo-1,4-dihydroquinoline-3-carboxylate as a yellowish powder.

MS (ESP): 455.2 (M+H$^+$) for $C_{19}H_{23}IN_2O_3$ $^1$H NMR (300 MHz, DMSO-d$_6$): δ 1.12 (m, 1H), 1.28 (t, 3H), 1.29-1.60 (m, 2H), 1.68 (m, 1H), 1.79 (m, 1H), 1.98-2.19 (m, 2H), 2.17 (s, 3H), 2.20-2.42 (m, 2H), 3.38 (m, 1H), 4.26 (q, 2H), 4.20-4.41 (m, 2H), 7.69 (d, 1H), 8.05 (dd, 1H), 8.52 (d, 1H), 8.63 (s, 1H).

Intermediate 140 ethyl 1-((1S,2S)-2-aminocyclohexyl)-6-iodo-4-oxo-1,4-dihydroquinoline-3-carboxylate

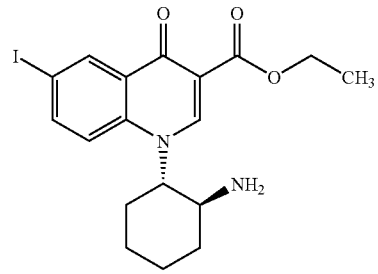

(1S,2S)-(+)-1,2-Diaminocyclohexane (500 mg, 4.3 mmol) was added to the solution of (Z)-ethyl-3-(dimethylamino)-2-(3-iodobenzoyl)acrylate (Intermediate 24, 0.34M, 11.7 mL, 3.9 mmol) and the mixture was heated at 50° C. for 3 h. The solvent was removed in vacuo and the residue was dried in a vacuum oven for 1.5 h. The residue was then dissolved in dimethyl formamide (7 mL) and potassium carbonate powder (753 mg, 5.5 mmol) was added. The reaction was heated at 70° C. for 3 h then cooled to room temperature. Water (30 mL) was added and the suspension was extracted with 1:1 ethyl acetate:methyl tert-butyl ether (3×50 mL). The organic layers were dried over sodium sulfate, and the solvent was removed in vacuo. The residue was suspended in methyl tert-butyl ether (20 mL) and stirred at 40° C. for 1 h. The suspension was filtered and the solid dried to give 724 mg (42% yield) of ethyl 1-((1S ,2S)-2-aminocyclohexyl)-6-iodo-4-oxo-1,4-dihydroquinoline-3-carboxylate as a yellowish powder that was contaminated with about 40% bis dihydroquinoline. This material was used as is in the coupling step.

MS (ESP): 441.0 (M+H$^+$) for $C_{18}H_{21}IN_2O_3$

Intermediates 141-145

The following Intermediates were prepared according to the procedure described for Intermediate 140 from the indicated starting materials.

| Int | Compound | Data | SM |
|---|---|---|---|
| 141 | Ethyl 1-(3-hydroxypropyl)-6-iodo-4-oxo-1,4-dihydroquinoline-3-carboxylate | MS (ESP): 402 (M + 1) for $C_{15}H_{16}INO_4$<br>$^1$H-NMR (400 MHz, DMSO-d$_6$) δ: 1.28 (t, J = 7.07 Hz, 3H); 1.79-1.97 (m, 2H); 3.44 (q, J = 5.64 Hz, 2H); 4.22 (q, J = 7.07 Hz, 2H); 4.39 (t, J = 7.07 Hz, 2H); 4.72 (t, J = 4.93, Hz, 1H); 7.65 (d, J = 9.09 Hz, 1H); 8.07 (dd, J = 8.97, 2.15 Hz, 1H); 8.50 (d, J = 2.27 Hz, 1H); 8.66 (s, 1H). | Intermediate 24 and 3-aminopropan-1ol |
| 142 | Ethyl 6-iodo-4-oxo-1-(tetrahydro-2H-pyran-4-yl)-1,4-dihydroquinoline-3-carboxylate | MS (ESP): 427.98 (M+) for $C_{17}H_{18}INO_4$<br>$^1$H-NMR (400 MHz, CHLOROFORM-d) δ: 1.43 (t, J = 7.07 Hz, 3H); 2.06-2.24 (m, 4H); 3.68 (td, J = 11.56, 2.15 Hz, 2H); 4.24 (dd, J = 11.49, 3.66 Hz, 2H); 4.42 (q, J = 7.16 Hz, 2H); 4.61-4.73 (m, 1H); 7.39 (d, J = 8.84 Hz, 1H); 7.96 (dd, J = 8.97, 2.15 Hz, 1H); 8.66 (s, 1H); 8.88 (d, J = 2.02 Hz, 1H). | Intermediate 24 and tetrahydro-2H-pyran-4-amine |
| 143 | Ethyl 1-cyclohexyl-6-iodo-4-oxo-1,4-dihydroquinoline-3-carboxylate | MS (ESP): 426.03 (M + 1) for $C_{18}H_{20}INO_3$<br>$^1$H-NMR (400 MHz, CHLOROFORM-d) δ: 1.43 (t, J = 7.20 Hz, 3H); 1.50-1.64 (m, 2H); 1.71-1.94 (m, 4H); 2.00-2.11 (m, 2H); 2.13-2.22 (m, 2H); 4.31-4.48 (m, 3H); 7.34 (d, J = 9.09 Hz, 1H); 7.96 (dd, J = 8.97, 2.15 Hz, 1H); 8.68 (s, 1H); 8.89 (d, J = 2.02 Hz, 1H). | Intermediate 24 and cyclohexyl-amine |
| 144 | Ethyl 6-iodo-1-(1-methylpiperidin-4-yl)-4-oxo-1,4-dihydroquinoline-3-carboxylate | MS (ESP): 441.13 (M + 1) for $C_{18}H_{21}IN_2O_3$<br>$^1$H-NMR (400 MHz, DMSO-d$_6$) δ: 1.28 (t, J = 7.07 Hz, 3H); 1.90-2.04 (m, 4H); 2.16-2.30 (m, 5H); 2.85-2.99 (m, 2H); 4.22 (q, J = 7.07 Hz, 2H); 4.54-4.71 (m, 1H); 7.84 (d, J = 9.35 Hz, 1H); 8.06 (dd, J = 9.09, 2.27 Hz, 1H); 8.52 (d, J = 2.27 Hz, 1H); 8.58 (s, 1H). | Intermediate 24 and 1-methylpiper-idin-4-amine |

-continued

| Int | Compound | Data | SM |
|---|---|---|---|
| 145 | Ethyl 1-((5-cyclopropyl-1,2,4-oxadiazol-3-yl)methyl)-6-iodo-4-oxo-1,4-dihydroquinoline-3-carboxylate 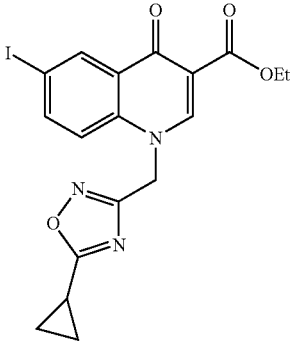 | MS (ESP): 465.95 (M+) for $C_{18}H_{16}IN_3O_4$<br>$^1$H-NMR (400 MHz, DMSO-$d_6$) δ: 1.02-1.10 (m, 2H); 1.17-1.26 (m, 2H); 1.29 (t, J = 7.07 Hz, 3H); 2.26-2.38 (m, 1H); 4.24 (q, J = 7.07 Hz, 2H); 5.81 (s, 2H); 7.48 (d, J = 9.09 Hz, 1H); 8.00-8.08 (m, 1H); 8.49 (d, J = 2.27 Hz, 1H); 8.87 (s, 1H). | Intermediate 24 and 5-cyclopropyl-1,2,4-oxadiazol-3-yl methylamine |

The invention claimed is:
1. A compound of formula (I'):

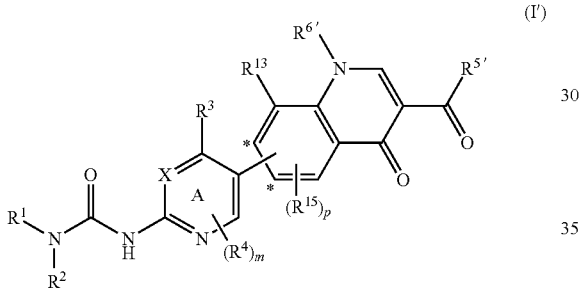

or a pharmaceutically acceptable salt thereof, wherein:
Ring A is attached to one of the carbon atoms indicated by "*";
X is N, CH or $CR^4$;
$R^1$ is selected from $C_{1-6}$alkyl, $C_{2-6}$alkenyl, $C_{2-6}$alkynyl or $C_{3-6}$cycloalkyl; wherein $R^1$ may be optionally substituted on carbon by one or more $R^7$;
$R^2$ is selected from hydrogen or $C_{1-6}$alkyl; wherein said $C_{1-6}$alkyl may be optionally substituted by one or more groups independently selected from halo, cyano, hydroxy, nitro and amino;
or $R^1$ and $R^2$ together with the nitrogen to which they are attached form a heterocyclyl; wherein said heterocyclyl may be optionally substituted on one or more carbon atoms with one or more $R^8$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^9$;
$R^3$ is a $C_{3-14}$carbocyclyl or a heterocyclyl; wherein the carbocyclyl or heterocyclyl may be optionally substituted on one or more carbon atoms by one or more $R^{10}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{11}$;
$R^4$ and $R^{15}$, for each occurrence, are independently selected from the group consisting of halo, nitro, cyano, hydroxy, amino, mercapto, $C_{1-6}$alkyl, $C_{2-6}$alkenyl, $C_{2-6}$alkynyl, $C_{1-6}$alkoxy, N—($C_{1-6}$alkyl)amino, N,N—($C_{1-6}$alkyl)$_2$amino, and $C_{1-6}$alkylsulfanyl; wherein R4 and $R^{15}$ independently of each other may be optionally substituted on one or more carbon by one or more one or more $R^{12}$;
$R^{5'}$ is —OH, a $C_{1-6}$alkoxy, $C_{3-14}$cycloalkoxy, or —$NR^aR^b$; wherein the $C_{1-6}$alkoxy group may be optionally substituted on one or more carbon atoms with one or more, independently selected $R^{14}$; and wherein $R^a$ and $R^b$ are each independently, hydrogen, a $C_{1-6}$alkyl, or a $C_{3-14}$carbocycle, or $R^a$ and $R^b$, together with the nitrogen to which they are attached form a heterocycle, wherein $R^a$ and $R^b$ may be optionally substituted on one or more carbon atoms with one or more, independently selected $R^{14}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{22}$;
$R^{6'}$, for each occurrence, is independently selected from the group consisting of hydrogen, $C_{1-6}$alkyl, $C_{1-6}$alkylsulfanyl, carboxy, carbamoyl, N—($C_{1-6}$alkyl)carbamoyl, N,N—($C_{1-6}$alkyl)2carbamoyl, $C_{3-14}$carbocyclyl-L-, and heterocyclyl-L-; wherein $R^6$ is optionally substituted on one or more carbon atoms with one or more $R^{16}$; and wherein if said heterocyclyl contains an =N— or a —S— moiety that nitrogen may be optionally substituted by one oxo group and that sulfur may be optionally substituted by one or two oxo groups; and wherein if said heterocyclyl contains an —NH— moiety that nitrogen may be optionally substituted by a group selected from $R^{17}$;
$R^{13}$ is selected from the group consisting of hydrogen, halo, nitro, cyano, hydroxy, amino, mercapto, $C_{1-6}$alkyl, $C_{2-6}$alkenyl, $C_{2-6}$alkynyl, $C_{1-6}$alkoxy, N—($C_{1-6}$alkyl)amino, N,N—($C_{1-6}$alkyl)$_2$amino, and $C_{1-6}$alkylsulfanyl; wherein $R^{13}$ may be optionally substituted on one or more carbon by one or more one or more $R^{16}$; or R$^{6'}$ and R$^{13}$ together with the intervening ring atoms may form a fused heterocyclyl, wherein the fused heterocyclyl may be optionally substituted on one or more carbon atoms with one or more independently selected R$^{16}$; and wherein if said fused heterocyclyl contains an =N— or a —S— moiety that nitrogen may be optionally substituted by one oxo group and that sulfur may be optionally substituted by one or two oxo groups; and wherein if said fused heterocyclyl contains an —NH— moiety that nitrogen may be optionally substituted by a group selected from R$^{17'}$;

m is 0 or 1;

p is 0, 1, or 2;

L, for each occurrence, is independently a direct bond or a $C_{1-6}$alkylene;

R$^7$, R$^8$, R$^{10}$, R$^{12}$, R$^{14}$ and R$^{16}$ are substituents on carbon which, for each occurrence, are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$— wherein a is 0, 1 or 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{3-6}$carbocyclyl or heterocyclyl; wherein R$^7$, R$^8$, R$^{10}$, R$^{12}$, R$^{14}$ and R$^{16}$ independently of each other may be optionally substituted on one or more carbon by one or more R$^{19}$; and wherein if said heterocyclyl contains an —NH— moiety that nitrogen may be optionally substituted by a group selected from R$^{20}$; and wherein if said heterocyclyl contains an =N— or a —S— moiety that nitrogen may be optionally substituted by one oxo group and that sulfur may be optionally substituted by one or two oxo groups;

R$^9$, R$^{11}$, and R$^{20}$, for each occurrence, are independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N—($C_{1-6}$alkyl)$_2$carbamoyl, benzyl, benzyloxycarbonyl, benzoyl and phenylsulphonyl; wherein R$^9$, R$^{11}$, and R$^{20}$ independently of each other may be optionally substituted on carbon by one or more R$^{23}$;

R$^{17'}$, for each occurrence, is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl, phenylsulphonyl, $C_{3-14}$carbocyclyl-L-, and heterocyclyl-L-; wherein each R$^{17'}$, independently, may be optionally substituted on carbon by one or more R$^{24}$; and wherein if said heterocyclyl contains an —NH— moiety that nitrogen may be optionally substituted by a group selected from R$^{25}$; and wherein if said heterocyclyl contains an =N— or a —S— moiety that nitrogen may be optionally substituted by one oxo group and that sulfur may be optionally substituted by one or two oxo groups;

R$^{22}$, for each occurrence is independently selected from $C_{1-6}$alkyl, $C_{3-6}$cycloalkyl, $C_{1-6}$alkanoyl, $C_{1-6}$alkylsulphonyl, $C_{1-6}$alkoxycarbonyl, carbamoyl, N,N—($C_{1-6}$alkyl)$_2$sulfamoyl, N—($C_{1-6}$alkyl)carbamoyl, N,N—($C_{1-6}$alkyl)$_2$carbamoyl, benzyl, benzyloxycarbonyl, benzoyl and phenylsulphonyl; wherein R$^{22}$ for each occurrence may be independently optionally substituted on carbon by one or more R$^{23}$;

R$^{19}$ and R$^{23}$, for each occurrence, are independently selected from halo, nitro, cyano, hydroxy, trifluoromethoxy, trifluoromethyl, amino, carboxy, carbamoyl, mercapto, sulphamoyl, $C_{1-6}$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

R$^{24}$, for each occurrence, are independently selected from halo, nitro, cyano, hydroxy, oxo, trifluoromethoxy, trifluoromethyl, amino, carboxy, carbamoyl, mercapto, sulphamoyl, $C_{1-6}$ $_6$alkyl, $C_{1-6}$alkoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and R$^{25}$, for each occurrence is independently selected from a $C_{1-6}$alkyl, provided that the compound is not one of the following compounds:

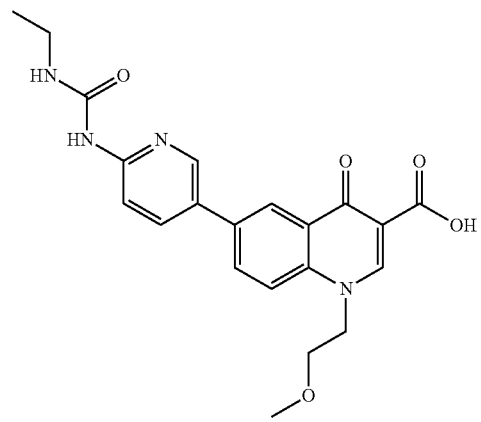

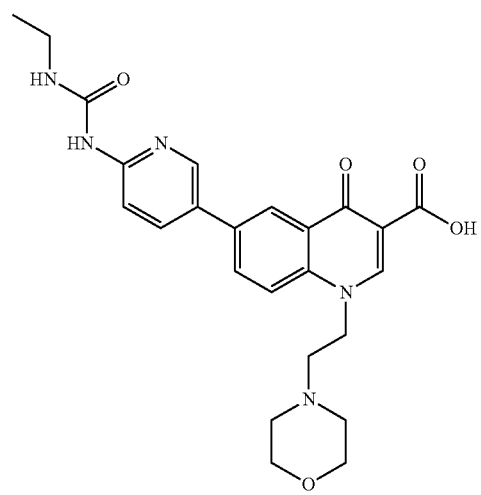

-continued

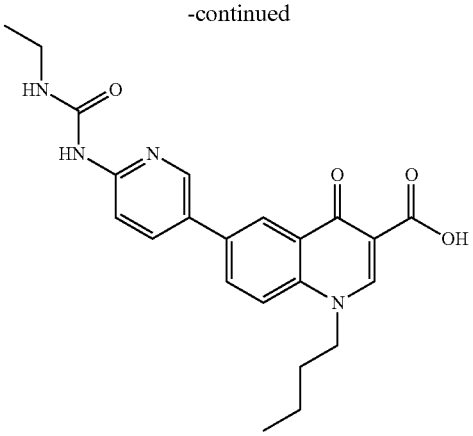

2. The compound of claim 1, wherein the compound is represented by formula (Ia'):

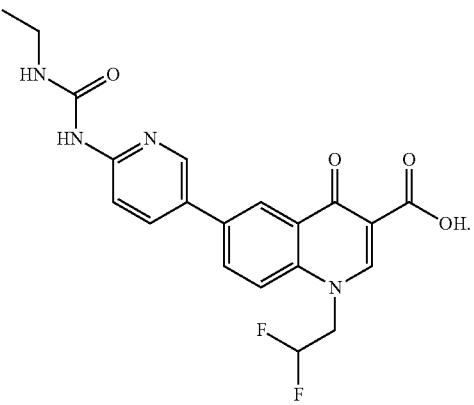

or a pharmaceutically acceptable salts thereof.

3. The compound of claim 1, wherein the compound is represented by formula (Ib):

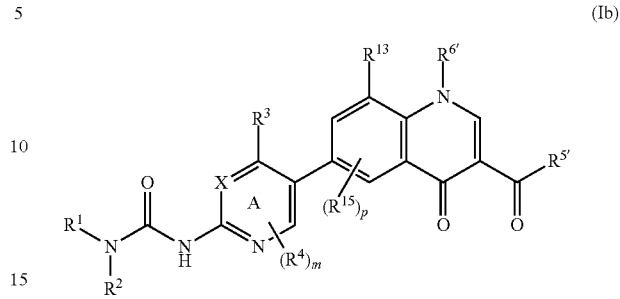

or a pharmaceutically acceptable salts thereof.

4. The compound of claim 1, or a pharmaceutically acceptable salt thereof, wherein X is CH.

5. The compound of claim 4, or a pharmaceutically acceptable salt thereof, wherein $R^1$ is a $C_{1-6}$alkyl.

6. The compound of claim 5, or a pharmaceutically acceptable salt thereof, wherein $R^2$ is hydrogen.

7. The compound of claim 6, or a pharmaceutically acceptable salt thereof, wherein $R^3$ is 4-trifluouromethyl-thiazole-2-yl, 4-ethyl-thiazole-2-yl, or 4-phenyl-thiazole-2-yl.

8. The compound of claim 7, or a pharmaceutically acceptable salt thereof, wherein $R^{5'}$ is selected from the group consisting of —OH, ethoxy, N-methylamino, and N-ethylamino.

9. The compound of claim 8, or a pharmaceutically acceptable salt thereof, wherein $R^{6'}$ is a $C_{1-6}$alkyl which is substituted on one or more carbon atoms with one or more independently selected $R^{16}$.

10. The compound of claim 9, or a pharmaceutically acceptable salt thereof, wherein $R^{16}$, for each occurrence, is independently selected from the group consisting of —OH, fluoro, N-methylamino, N,N-dimethylamino, methoxy, ethoxy, methylsulfanyl, methylsulfonyl, piperidinyl, piperazinyl, morpholinyl, pyrrolidinyl, 2-oxopyrrolidinyl, pyrrolyl, imidazolyl, triazolyl, phenyl which may be optionally substituted with one or more halo, isoxazolyl, pyridinyl, and cyclopropyl.

11. The compound of claim 8, or a pharmaceutically acceptable salt thereof, wherein $R^{6'}$ is selected from the group consisting of methyl, ethyl, propan-1-yl, propan-2-yl, 1-hydroxy-4-methyl-pentan-2-yl, 2-methyl-propan-1-yl, 3-methyl-butan-1-yl, 2-hydroxyethyl, 2-methoxyethyl, cyclopropyl, cyclopropylmethyl, benzyl, pyridin-3-ylmethyl, 3-methoxypropan-1-yl, 2-(N,N-dimethyl)-ethyl, 3-(2-oxopyrrolidin-1-yl)-propan-1-yl, 1,3-dimethoxy-propan-2-yl, and 1-methyl-azetidine-3-yl.

12. The compound of claim 9, or a pharmaceutically acceptable salt thereof, wherein $R^{13}$ is hydrogen.

13. The compound of claim 12, or a pharmaceutically acceptable salt thereof, wherein m is 0 and p is 0.

14. A pharmaceutical composition comprising a compound of claim 1, or a pharmaceutically acceptable salt thereof, and a pharmaceutically acceptable excipient or carrier.

15. A method of inhibiting bacterial DNA gyrase and/or bacterial topoisomerase IV in a warm-blooded animal in need of such treatment, comprising administering to the animal an effective amount of a compound of claim 1, or a pharmaceutically acceptable salt thereof.

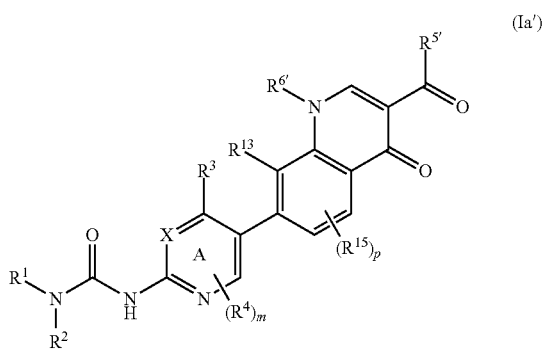

16. A method of producing an antibacterial effect in a warm-blooded animal in need of such treatment, comprising administering to the animal an effective amount of claim 1, or a pharmaceutically acceptable salt thereof.

17. A method of treating a bacterial infection in a warm-blooded animal in need thereof, comprising administering to the animal an effective amount of a compound of claim 1, or a pharmaceutically acceptable salt thereof.

18. The method of claim 17, wherein the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae,* methicillin-resistant *Staphylococcus aureus,* methicillin-resistant *Staphylococcus epidermidis* and Vancomycin-Resistant Enterococci.

19. The method of claim 17, wherein the warm-blooded animal is a human.

* * * * *